(12) United States Patent
Patterson

(10) Patent No.: US 11,518,796 B2
(45) Date of Patent: Dec. 6, 2022

(54) ENGINEERED PLATELETS FOR TARGETED DELIVERY OF A THERAPEUTIC AGENT

(71) Applicant: JPV01 LTD., London (GB)

(72) Inventor: James Patterson, Cambridge (GB)

( * ) Notice: Subject to any disclaimer, the term of this patent is extended or adjusted under 35 U.S.C. 154(b) by 0 days.

(21) Appl. No.: 17/731,748

(22) Filed: Apr. 28, 2022

(65) Prior Publication Data

US 2022/0251165 A1 Aug. 11, 2022

Related U.S. Application Data

(60) Division of application No. 17/508,178, filed on Oct. 22, 2021, which is a continuation of application No. PCT/GB2020/053247, filed on Dec. 16, 2020.

(30) Foreign Application Priority Data

Dec. 17, 2019 (GB) .................................. 1918586

(51) Int. Cl.
*C07K 14/705* (2006.01)
*C07K 16/28* (2006.01)
*C07K 14/735* (2006.01)

(52) U.S. Cl.
CPC ........ *C07K 14/705* (2013.01); *C07K 16/2803* (2013.01); *C07K 14/7056* (2013.01); *C07K 14/70535* (2013.01); *C07K 14/70546* (2013.01); *C07K 2317/622* (2013.01); *C07K 2319/33* (2013.01); *C12Y 503/99005* (2013.01)

(58) Field of Classification Search
None
See application file for complete search history.

(56) References Cited

U.S. PATENT DOCUMENTS

2019/0376034 A1  12/2019  Kahvejian et al.
2021/0393692 A1  12/2021  Scheinberg et al.

FOREIGN PATENT DOCUMENTS

| WO | WO-2013/151666 A1 | 10/2013 |
| WO | WO-2013/176772 A1 | 11/2013 |
| WO | WO-2019/055946 A1 | 3/2019 |
| WO | WO-2019/119822 A1 | 6/2019 |
| WO | WO-2020/072471 A1 | 4/2020 |

OTHER PUBLICATIONS

Aguilar et al., Combined deficiency of RAB32 and RAB38 in the mouse mimics Hermansky-Pudlak syndrome and critically impairs thrombosis. *Blood Adv.* 3(15): 2368-80 (2019).
Bender et al., Combined in vivo depletion of glycoprotein VI and C-type lectin-like receptor 2 severely compromises hemostasis and abrogates arterial thrombosis in mice. *Arterioscler. Thromb. Vasc. Biol.* 33(5): 926-34 (2013).
Berge et al., Pharmaceutical Salts. *Journal of Pharmaceutical Science.* 66(1): 1-19 (1977).
Boulaftali et al., Platelet ITAM signaling is critical for vascular integrity in inflammation. *J. Clin. Invest.* 123(2): 908-16 (2013).
Boulaftali et al., Platelet ITAM signaling and vascular integrity. *Cir. Res.* 28: 1174-84 (2014).
Chronos et al., Aspirin does not affect the flow cytometric detection of fibrinogen binding to, or release of alpha-granules or lysosomes from, human platelets. *Clin. Sci. (Lond).* 87(5): 575-80 (1994).
Collins, Tackling cancer metastasis with engineered blood platelets. *NIH Director's Blog,* https://directorsblog.nih.gov/2020/08/27/tackling-cancer-metastasis-with-engineered-blood-platelets/ (2020).
Cornelissen et al., Roles and interactions among protease-activated receptors and P2ryl2 in hemostasis and thrombosis. *Pros. Natl. Acad. Sci. USA,* 107(43): 18605-10 (2010).
Crescente et al., Platelet COX-1 knockout mouse as a model of the effects of aspirin in the cardiovascular system. *Heart,* 103(5): 108-9, abstract 147 (2017).
Dalby, Forward programming of human pluripotent stem cells to a megakaryocyte-erythrocyte bi-potent progenitor population: an in vitro system for the production of platelets and red blood cells for transfusion medicine. *Doctoral Thesis, University of Cambridge* (2018).
Dicker et al., Fas-ligand (CD178) and TRAIL synergistically induce apoptosis of CD40-activated chronic lymphocytic leukemia B cells. *Blood.* 105(8): 3193-8 (2005).
Durrant et al., Integrin a IIb β 3 outside-in signaling. *Blood,* 130(14): 1607-19 (2017).
Ellebrecht et al., Reengineering chimeric antigen receptor T cells for targeted therapy of autoimmune disease. *Science.* 353(6295): 179-84 (2016).
Feng et al., Scalable Generation of Universal Platelets from Human Induced Pluripotent Stem Cells. *Stem Cell Reports,* 3(5): 817-31 (2014).
Fu et al., CLEC-2 and podoplanin, partners again. *Blood,* 127(13): 1629-30 (2016).
Gardner et al., The mouse pale ear (ep) mutation is the homologue of human Hermansky-Pudlak syndrome. *Proc. Natl. Acad. Sci. USA* 94(17): 9238-43 (1997).
Golli et al., Evidence for a granule targeting sequence within platelet factor 4. *J. Biol. Chem.* 280(34): 30329-35 (2005).
Hayter et al., Updated assessment of the prevalence, spectrum and case definition of autoimmune disease. *Autoimmunity Reviews.* 11: 754-65 (2012).
Henn et al., CD40 ligand on activated platelets triggers an inflammatory reaction of endothelial cells. *Nature,* 391(6667): 591-4 (1998).

(Continued)

*Primary Examiner* — Michael D Burkhart
(74) *Attorney, Agent, or Firm* — RinLaures LLC; Li-Hsien Rin-Laures; Kristen A. Dola

(57) ABSTRACT

The present invention provides engineered platelets with chimeric platelet receptors (CPR) with a desired target specificity. Additionally, the engineered platelets may comprise cargo which may be released upon activation of the platelet. Additionally, the platelets may be generated in vitro from megakaryocytes engineered to generate non-thrombogemc platelets.

15 Claims, 25 Drawing Sheets

Figure 1:
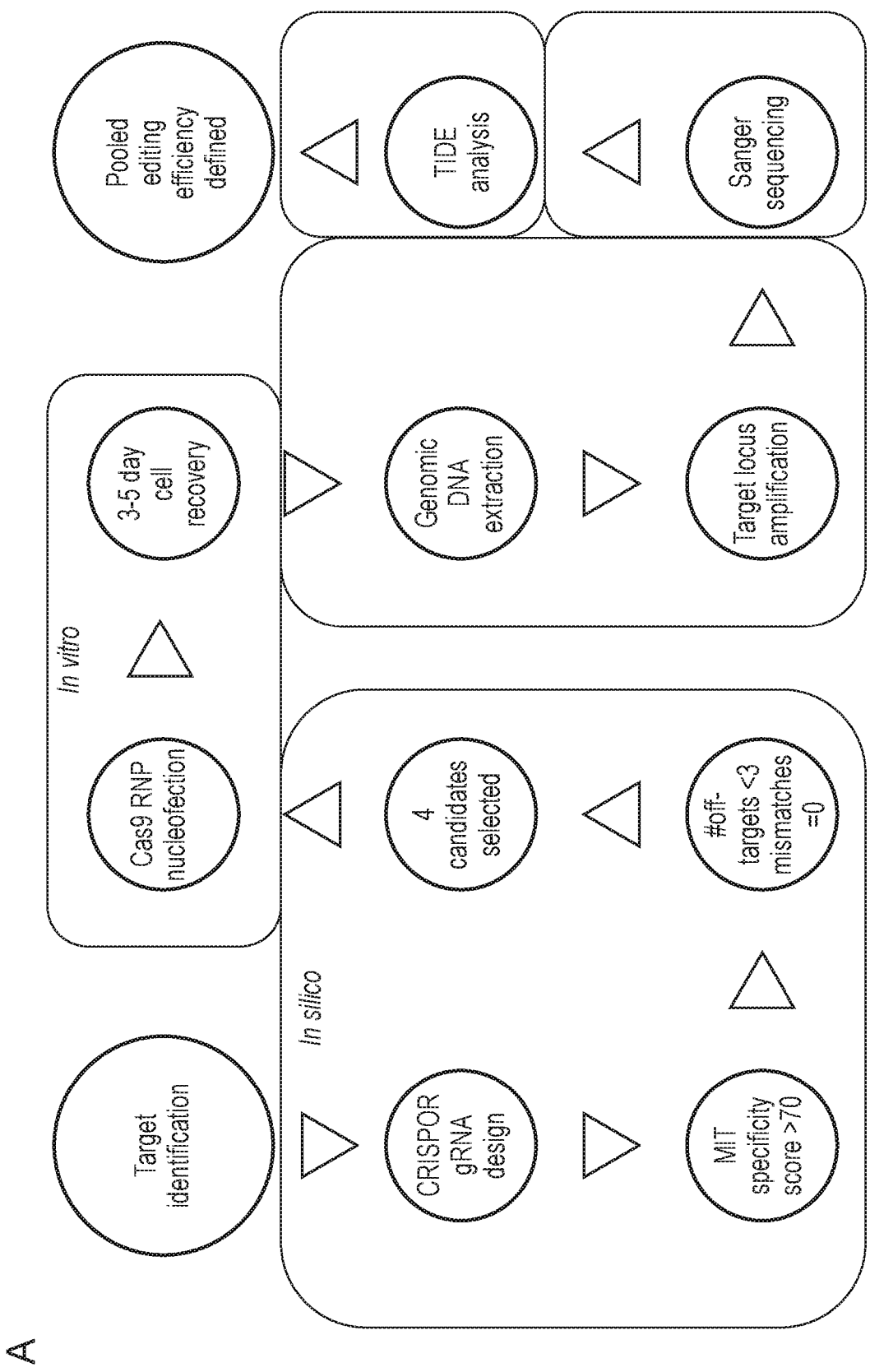
Figure 1:
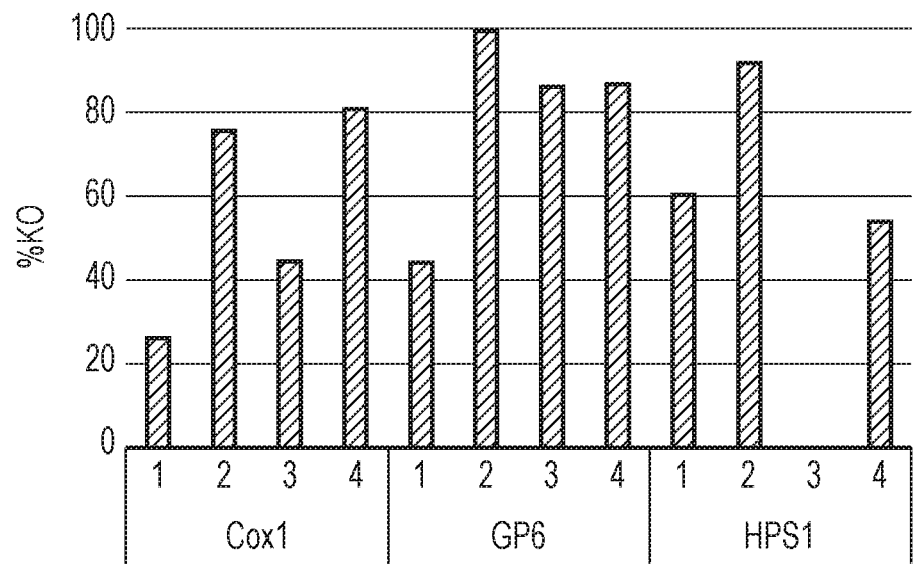
Figure 1:
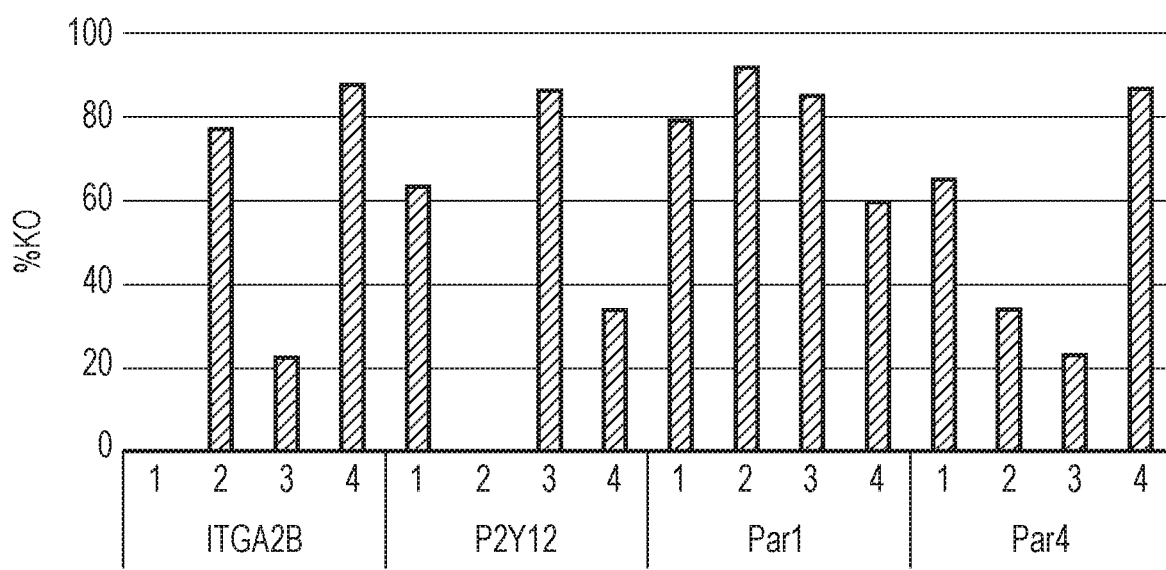
Figure 1:
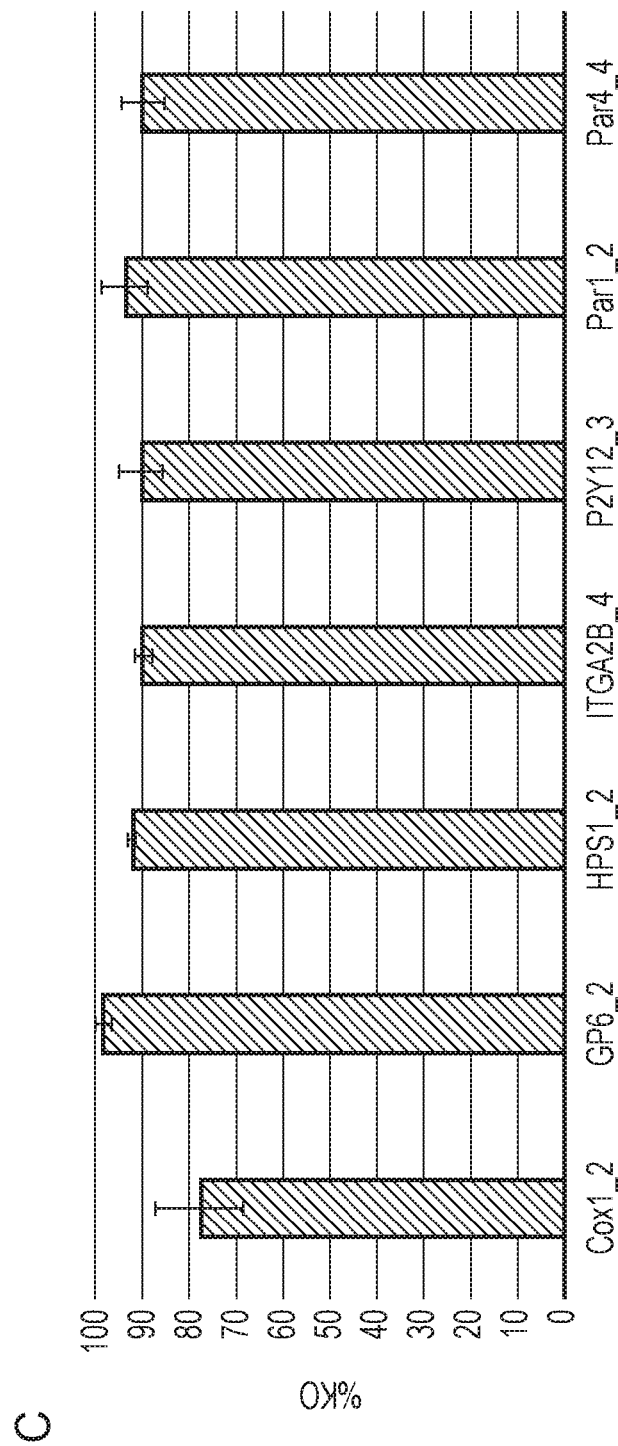

Specification includes a Sequence Listing.

(56) References Cited

OTHER PUBLICATIONS

Hodivala-Dilke et al., Beta3-integrin-deficient mice are a model for Glanzmann thrombasthenia showing placental defects and reduced survival. *J. Clin. Invest.* 103(2): 229-38 (1999).

Hu et al., Modeling Glanzmann thrombasthenia using patient specific iPSCs and restoring platelet aggregation function by CD41 overexpression. *Stem Cell Res.* 20: 14-20. (2017).

Hyslop et al., Undercover Agents: Targeting tumours with modified platelets. *Trends Cancer.,* 3(3): 235-246 (2017).

Ito et al., Turbulence activates platelet biogenesis to enable clinical scale ex vivo production. *Cell,* 174(3): 636-48.e18 (2018).

James et al., Tuning ITAM multiplicity on T cell receptors can control potency and selectivity to ligand density. *Sci. Signal,* 11(531): eaan1088 (2018).

Jinek et al., A programmable dual-RNA—guided DNA endonuclease in adaptive bacterial immunity. *Science.* 337(6096): 816-21 (2012).

Kanaji et al., Amelioration of the macrothrombocytopenia associated with the murine Bernard-Soulier syndrome. *Blood,* 100(6): 2102-7 (2002).

Koupenova et al., Thrombosis and platelets: An update. *Eur. Heart J.* 38(11): 785-91 (2017).

Kuriri et al., Molecular mechanisms of immunoreceptors in platelets. *Thromb. Res.* 176: 108-14 (2019).

Lee et al., Platelet immunoreceptor tyrosine-based activation motif (ITAM) and hemITAM signaling and vascular integrity in inflammation and development. *J. Thromb. Haemost.* 14: 645-54 (2016).

Li et al., Genetic engineering of platelets to neutralize circulating tumor cells. *J. Control. Release,* 228: 38-47 (2016).

Li et al., Targeted drug delivery to circulating tumor cells via platelet membrane-functionalized particles. *Biomaterials* 76: 52-65 (2016).

Liang et al., Engineered exosome-mediated delivery of functionally active miR-26a and its enhanced suppression effect in HepG2 cells. *Int. J. Nanomedicine.* 13: 585-99 (2018).

Lockyer et al., GPVI-deficient mice lack collagen responses and are protected against experimentally induced pulmonary thromboembolism. *Thromb. Res.* 118(3): 371-80 (2006).

Marriot, Engineering platelets for tumour targeting. *Aging.* 8(8): 1572 (2016).

Moreau et al., Forward Programming Megakaryocytes from Human Pluripotent Stem Cells. *BBTS Annual Conference Glasgow* 2017 (2017).

Moreau et al., Large-scale production of megakaryocytes from human pluripotent stem cells by chemically defined forward programming. *Nat. Commun.,* 7(7): 11208 (2016).

Mori et al., G6b-B inhibits constitutive and agonist-induced signaling by glycoprotein VI and CLEC-2. *J Biol. Chem.* 283(51): 35419-27 (2008).

Perez et al., Selective immunotargeting of diabetogenic CD4 T cells by genetically redirected T cells. *Immunology.* 143: 609-17 (2014).

Saeterdal et al., Frameshift-mutation-derived peptides as tumor-specific antigens in inherited and spontaneous colorectal cancer *PNAS.* 98(23): 13255-60 (2001).

Schleicher et al., Platelets induce apoptosis via membrane-bound FasL. *Blood.* 126(12): 1483-93 (2015).

Slitcher et al., Treatment of bleeding in severely thrombocytopenic patients with transfusion of dimethyl sulfoxide (DMSO) cryopreserved platelets (CPP) is safe—Report of a phase 1 dose escalation safety trial. *Blood.* 128(22): 1030 (2016).

Synbiobeta., Platelet BioGenesis and scaled biolabs to collaborate to optimize platelet production platform. *SynBioBeta Press Release.* https://synbiobeta.com/platelet-biogenesis-and-scaled-biolabs-to-collaborate-to-optimize-platelet-production-platform/ (2018).

Verheul et al., Platelets take up the monoclonal antibody bevacizumab. *Clin. Cancer Res.* 13(18 Pt 1): 5341-7 (2007).

Weyrich et al., Signal-dependent translation of a regulatory protein, Bcl-3, in activated human platelets. *Proc. Natl. Acad. Sci. USA,* 95(10): 5556-61 (1998).

Wilcox, Megakaryocyte-and megakaryocyte precursor-related gene therapies. *Blood.* 127(10): 1260-8 (2016).

Xu et al., Doxorubicin-loaded platelets as a smart drug delivery system: An improved therapy for lymphoma. *Sci. Rep.* 7:42632 (2017).

Xu et al., Doxorubicin-loaded platelets conjugated with anti-CD22 mAbs: a novel targeted delivery system for lymphoma treatment with cardiopulmonary avoidance. *Oncotarget.* 8(35): 58322-58337 (2017).

Zetsche et al., Cpf1 is a single RNA-guided endonuclease of a class 2 CRISPR-Cas system. *Cell.* 163(3): 759-71 (2015).

Zhang et al., Engineering PD-1-presenting platelets for cancer immunotherapy. *Nano Lett.* 18(9): 5716-5725 (2018).

Cornelissen et al., Roles and interactions among protease-activated receptors and P2ry12 in hemostasis and thrombosis. *Pros. Natl. Acad. Sci. USA,* 107(43): 18605-10 (2010).

Ito et al., Turbulence activates platelet biogenesis to enable clinical scale ex vivo production. *Cell,* 174(3): 636-48.e18 (2018).

Zetche et al., Cpf1 is a single RNA-guided endonuclease of a class 2 CRISPR-Cas system. *Cell.* 163(3): 759-71 (2015).

B

A     Sequencing round 1:

| | GP6 | Par1 | Par4 | HPS1 | P2Y12 | ITGA2B | Cox1 |
|---|---|---|---|---|---|---|---|
| 1 | | | | 99 | | 99 | |
| 2 | 100 | | | 99 | 100 | 97 | 97 |
| 3 | 100 | 1 | 49 | 97 | 98 | 99 | 96 |
| 4 | 100 | 96 | 11 | 88 | 49 | 91 | |
| 5 | 86 | 94 | | 100 | 95 | 62 | 43 |
| 6 | 100 | 89 | 99 | 99 | | 99 | |
| 7 | 100 | 95 | 99 | 99 | | 99 | |
| 8 | | | 95 | 4 | | 100 | |
| 9 | 52 | 99 | 99 | | 100 | 99 | |
| 10 | 100 | 0 | 95 | 97 | 98 | 39 | 0 |
| 11 | 95 | 96 | 99 | 47 | 30 | 99 | 100 |
| 12 | 100 | 96 | 47 | 99 | 98 | 99 | 3 |
| 13 | 100 | 94 | 89 | 96 | 49 | 93 | |
| 14 | 100 | 38 | 99 | 99 | 99 | 94 | |
| 15 | 100 | 96 | 96 | 90 | 98 | 100 | 100 |
| 16 | 100 | 99 | 96 | 90 | 49 | 91 | 53 |
| 17 | 100 | 38 | 95 | 53 | 97 | 99 | |
| 18 | 51 | 93 | 96 | 42 | 15 | 63 | |
| 19 | 100 | 99 | 99 | 96 | 94 | 94 | |
| 20 | 100 | 99 | 17 | 99 | 96 | 94 | 95 |
| 21 | 96 | 46 | 99 | 96 | 96 | 50 | 99 |
| 22 | 100 | 52 | 68 | 97 | 38 | 96 | 0 |

| | GP6 | Par1 | Par4 | HPS1 | P2Y12 | ITGA2B | Cox1 |
|---|---|---|---|---|---|---|---|
| 23 | 97 | 97 | 99 | 99 | 99 | 92 | 6 |
| 24 | 100 | 97 | | 97 | 98 | 96 | 0 |
| 25 | 96 | 99 | 99 | 97 | 72 | 100 | 84 |
| 26 | 100 | 97 | | 99 | 98 | 92 | 100 |
| 27 | 100 | 51 | 99 | 97 | 16 | 28 | |
| 28 | 100 | 96 | 99 | 98 | 48 | 99 | 0 |
| 29 | 100 | 28 | 95 | 95 | 89 | 41 | 47 |
| 30 | 100 | 99 | 100 | 99 | 97 | 99 | 0 |
| 31 | 100 | 0 | 73 | 99 | 97 | 99 | 47 |
| 32 | 96 | 86 | 95 | 47 | 98 | 90 | 100 |
| 33 | 56 | 96 | 32 | 97 | 98 | 99 | 0 |
| 34 | 100 | 99 | 96 | 99 | 99 | 99 | |
| 35 | 97 | 99 | 67 | 99 | 94 | 99 | |
| 36 | 100 | 93 | 22 | 89 | 54 | | 95 |
| 37 | 10 | 95 | 95 | 99 | 52 | 49 | 43 |
| 38 | 100 | 1 | 99 | 98 | 89 | 48 | |
| 39 | 49 | 99 | 100 | 47 | 98 | 50 | 0 |
| 40 | 100 | 99 | 26 | 97 | 98 | 99 | 54 |
| 41 | 1 | 99 | 100 | | 98 | | |
| 42 | 42 | 96 | | 85 | 48 | 99 | |
| 43 | 49 | 98 | | 99 | 51 | 43 | 81 |
| 44 | 100 | 99 | | 96 | 98 | 91 | |

B     Sequencing round 2:

| clone ID | GP6 | Par1 | Par4 | HPS1 | P2Y12 | ITGA2B | Cox1 |
|---|---|---|---|---|---|---|---|
| 1 | | 0 | 98 | 99 | 0 | 99 | 100 |
| 2 | 100 | | 95 | 99 | 100 | 97 | 97 |
| 5 | 86 | 92 | | 100 | 95 | 99 | 43 |
| 6 | 100 | 89 | 99 | 99 | 100 | 99 | 90 |
| 7 | 100 | 95 | 99 | 99 | | 99 | |
| 8 | 99 | 2 | 95 | 100 | 100 | 100 | |
| 9 | 100 | 99 | 99 | 99 | 100 | 99 | |
| 12 | 100 | 96 | 48 | 99 | 98 | 99 | 3 |
| 14 | 100 | 39 | 99 | 99 | 99 | 94 | 100 |
| 17 | 100 | 26 | 95 | 99 | 97 | 99 | |
| 19 | 100 | 99 | 99 | 96 | 97 | 94 | |

| clone ID | GP6 | Par1 | Par4 | HPS1 | P2Y12 | ITGA2B | Cox1 |
|---|---|---|---|---|---|---|---|
| 20 | 100 | 99 | 20 | 99 | 96 | 94 | 95 |
| 23 | 97 | 97 | 99 | 99 | 99 | 92 | 6 |
| 26 | 100 | 97 | 79 | 99 | 98 | 92 | 100 |
| 29 | 100 | 12 | 95 | 99 | 90 | 100 | 47 |
| 34 | 100 | 99 | 96 | 99 | 99 | 99 | 100 |
| 35 | 97 | 99 | 67 | 99 | 100 | 99 | 100 |
| 38 | 100 | 1 | 99 | 98 | 89 | 99 | |
| 40 | 100 | 99 | 26 | 97 | 98 | 99 | 50 |
| 41 | 20 | 99 | 100 | 97 | 98 | 48 | 100 |
| 44 | 100 | 99 | 100 | 96 | 98 | 99 | 50 |

FIG. 3

Unedited

7xKO Pool

B

Unedited

7xKO pool

A

ENGINEERED PLATELETS FOR TARGETED DELIVERY OF A THERAPEUTIC AGENT

SEQUENCE LISTING

The present application is being filed along with a Sequence Listing in electronic format. The Sequence Listing file, entitled SEQLIST.txt, was created on Dec. 14, 2020, and is 46,300 bytes in size. The information in electronic format of the Sequence Listing is incorporated herein by reference in its entirety.

FIELD OF THE INVENTION

The invention relates to engineered platelets for targeted therapeutic delivery systems.

BACKGROUND OF THE INVENTION

Platelets are small and enucleated and cannot divide or reproduce. In the human body, they perform the important function of recognising injured tissue and releasing their contents to reduce or prevent bleeding. Thrombopoietin from the kidneys and liver contact a myeloid stem cell causing differentiation into a megakaryoblasorphant, and additional signals result in differentiation of the megakaryoblast into a progenitor megakaryocyte. Progenitor megakaryocytes are large cells with platelet precursor extensions that bud off fragments as they divide and proliferate to create platelets.

Mitochondria, microtubules, and vesicles are contained within the platelets, and the platelets have a life span of about 10 days before clearance by macrophages. Platelets have a volume of about 7 μm$^3$ and a diameter of 300 nm. They are metabolically active and can alter gene expression through post-transcriptional control of preloaded mRNA expression (e.g. by miRNAs). On activation, granulation is stimulated to alter the shape and release the contents of the intracellular vesicles.

Platelets respond to a variety of extra cellular signals through a diverse set of signaling pathway receptors. Receptors act both to trigger intracellular signaling cascades resulting in platelet degranulation and effector release and to cause platelet aggregation and adhesion. glycoprotein VI platelet (GPVI) signaling functions analogously to many immune cell receptors—such as the TCR. Interestingly, platelets also express toll-like receptors (TLRs) and can mediated targeted killing of bacteria via peptide secretion and immune system activation.

A huge variety of products are released on platelet degranulation. Vesicles are released by exocytosis. Platelets contain three primary subtypes of vesicles: α-granules (50 to 80 per platelet), dense granules (3 to 8 per platelet), and large dense core vesicles (LDCV) (about 10,000 per platelet). Different mutations can selectively disrupt the biogenesis of each vesicle subtype.

α-granules have a diameter of about 200 to 500 nm and make up about 10% of the platelet's volume. Most effector proteins are found in α-granules. For example, effector proteins released from α-granules include: integral membrane proteins, such as P-selectin, αIIbβ, and GPIbα; coagulants/anticoagulants and fibrinolytic proteins, such as factor V, factor IX, and plasminogen; adhesion proteins, such as fibrinogen and von Willebrand Factor (vWF); chemokines, such as CXCL4 (cytokine (C-X-C motif) ligand 4), also known as platelet factor 4 or PF4, and CXCL12 (cytokine (C-X-C motif) ligand 12), also known as stromal cell-derived factor 1 alpha or SDF-1α; growth factors, such as elongation growth factor (EGF) and insulin-like growth factor 1 (IGF); angiogenic factors/inhibitors, such as vascular endothelial growth factor (VEGF), platelet-derived growth factor (PDGF), and angiostatins; and immune mediators, such as immunoglobulin G (IgG) and complement precursors.

Dense granules have a diameter of about 150 nm and make up about 1% of the platelet's volume. Effector proteins released from dense granules include cations, such as $Ca^{2+}$ and $Mg^{2+}$; polyphosphates; bioactive amines, such as serotonin and histamine; and nucleotides, such as adenosine diphosphate (ADP) and adenosine triphosphate (ATP).

LDCVs have a diameter in the range of about 150 nm to about 300 nm and make up about 13.5% of the platelet's volume. Effector proteins released from LDCVs include structural proteins (e.g., granins and glycoproteins); vasco-regulators (e.g., cateholamines, vasostatins, renin-angiotensin); paracrine signaling factors (e.g., guanylin, neurotensin, chromogranin B); immune mediators (e.g., enkelytin and ubiquitin); opiods (e.g., enkephalins and endorphins); ions (e.g., $Ca^{2+}$, Na+, Cl—), and nucleotides and polyphosphates (e.g., adenosine monophosphate (AMP), guanosine diphosphate (GDP), uridine-5'-triphosphate (UTP)).

Current cell therapies based on engineered chimeric antigen receptor T cells (CAR-T cells) have shown promise treating cancer; however, concerns regarding their safety, specifically oncogenic transformation in the patient, and the limited ability to generate a generic or universal therapeutic product have restricted their use to a small number of patients. There is a long felt need in the art for a new type of therapy with the potential to treat cancer, autoimmune conditions, and infections, free from the safety, cost, and patient matching issues which plague current cell therapeutic products.

SUMMARY OF THE INVENTION

Various embodiments of the invention described herein provide a chimeric platelet receptor (CPR) comprising:
a) an intracellular domain that is a platelet stimulation domain and comprises domains from an immunoreceptor tyrosine-based activation motif (ITAM) receptor; and
b) a heterologous targeting domain that recognizes and binds a target.
By a heterologous targeting domain we mean that the targeting domain is heterologous to the intracellular platelet stimulation domain i.e. the targeting domain is not the usual extracellular domain associated with the intracellular domain. The heterologous targeting domain may bind to an endogenous target, for example may bind to a tumour antigen that is endogenous to a subject but, by virtue of the CPR being chimeric, the targeting domain is heterologous to the internal platelet stimulation domain.

The invention described herein also provides a chimeric platelet receptor (CPR) comprising:
a first region encoded by a nucleic acid sequence selected from the group consisting of SEQ ID NO: 1-19, 24-47, and 52-55; and a second region selected from the group consisting of: (i) a linker or a targeting domain encoded by a nucleic acid sequence selected from the group consisting of SEQ ID NO: 48-51; (ii) at least a portion of a protein selected from the group consisting of; myelin oligodendrocyte glycoprotein (MOG), glutamic acid decarboxylase 2 (GAD65), myelin associated glycoprotein (MAG), peripheral myelin protein 22 (PMP22), thyroid peroxidase (TPO), voltage-gated potassium channel (VGKC), proteolipid protein (PLP), acetylcholine receptor (AChR), tribbles pseudokinase 2 (TRIB2), N-methyl-D-aspartate (NMDA)-type glutamate receptor (GluR), glutamate decarboxylase 2 (GAD2), Armadillo repeat containing 9 (ARMC9), Cytochrome P450 Family 21 Subfamily A Member 2 (CYP21A2), calcium sensing receptor (CASR), nuclear autoantigenic sperm protein (NASP), insulin, thyroid stimulating hormone receptor (TSHR), thyroperoxidase, asioglycoprotein receptor, Cytochrome P450 Family 2 Subfamily D Member 6 (CYP2D6), lactoferrin (LF), tissue trans-glutaminase (TTG), H/K ATP-ase, Factor XIII (F8), beta2-glycoprotein I (Beta2-GPI), erythrocyte I/I, B2 integrin (ITGB2), granulocyte-colony stimulating factor (G-CSF), glycoprotein (GP) IIb/IIIa, collagen II (COLII), fibrinogen (FBG) βα, myeloperoxidase (MPO), cardiac myosin (CYO), proteinase 3 (PRTN3), trichohyalin (TCHH), bullous pemphigoid associated (BP), glycoprotein 1 (GPI), laminin-332 (LM332), transglutaminase (TGM), type VII collagen (COLVII), P80 Coilin (COIL), Desmoglein I (DSG1), Desmoglein III (DSG3), SRY-Box 10 (SOX10), small nuclear ribonucleoprotein U1 subunit (70SNRNP70), S-antigen (SAG), and Collagen alpha-3(IV) chain (α3(IV) NC1 collagen); (iii) an antibody or an antibody fragment selected from the group consisting of: 3F8, 8H9, Abagovomab, Abciximab, Abituzumab, Abrezekimab, Abrilumab, Actoxumab, Adalimumab, Adecatumumab, Atidortoxumab, Aducanumab, Afasevikumab, Afelimomab, Alacizumab pego, Alemtuzumab, Alirocumab, Altumomab pentetate, Amatuximab, Anatumomab mafenatox, Andecaliximab, Anetumab ravtansine, Anifrolumab, Anrukinzumab, Apolizumab, Aprutumab ixadotin, Arcitumomab, Ascrinvacumab, Aselizumab, Atezolizumab, Atinumab, Atorolimumab, Avelumab, Azintuxizumab vedotin, Bapineuzumab, Basiliximab, Bavituximab, BCD-100, Bectumomab, Begelomab, Belantamab mafodotin, Belimumab, Bemarituzumab, Benralizumab, Berlimatoxumab, Bermekimab, Bersanlimab, Bertilimumab, Besilesomab, Bevacizumab, Bezlotoxumab, Biciromab, Bimagrumab, Bimekizumab, Birtamimab, Bivatuzumab mertansine, Bleselumab, Blinatumomab, Blontuvetmab, Blosozumab, Bococizumab, Brazikumab, Brentuximab vedotin, Briakinumab, Brodalumab, Brolucizumab, Brontictuzumab, Burosumab, Cabiralizumab, Camidanlumab tesirine, Camrelizumab, Canakinumab, Cantuzumab mertansine, Cantuzumab ravtansine, Caplacizumab, Capromab pendetide, Carlumab, Carotuximab, Catumaxomab, cBR96-doxorubicin immunoconjugate, Cedelizumab, Cemiplimab, Cergutuzumab amunaleukin, Certolizumab pegol, Cetrelimab, Cetuximab, Cibisatamab, Cirmtuzumab, Citatuzumab bogatox, Cixutumumab, Clazakizumab, Clenoliximab, Clivatuzumab tetraxetan, Codrituzumab, Cofetuzumab pelidotin, Coltuximab ravtansine, Conatumumab, Concizumab, Cosfroviximab, Crenezumab, Crizanlizumab, Crotedumab, CR6261, Cusatuzumab, Dacetuzumab, Daclizumab, Dalotuzumab, Dapirolizumab pegol, Daratumumab, Dectrekumab, Demcizumab, Denintuzumab mafodotin, Denosumab, Depatuxizumab mafodotin, Derlotuximab biotin, Detumomab, Dezamizumab, Dinutuximab, Diridavumab, Domagrozumab, Dorlimomab aritox, Dostarlimab, Drozitumab, DS-8201, Duligotuzumab, Dupilumab, Durvalumab, Dusigitumab, Duvortuxizumab, Ecromeximab, Eculizumab, Edobacomab, Edrecolomab, Efalizumab, Efungumab, Eldelumab, Elezanumab, Elgemtumab, Elotuzumab, Elsilimomab, Emactuzumab, Emapalumab, Emibetuzumab, Emicizumab, Enapotamab vedotin, Enavatuzumab, Enfortumab vedotin, Enlimomab pegol, Enoblituzumab, Enokizumab, Enoticumab, Ensituximab, Epitumomab cituxetan, Epratuzumab, Eptinezumab, Erenumab, Erlizumab, Ertumaxomab, Etaracizumab, Etigilimab, Etrolizumab, Evinacumab, Evolocumab, Exbivirumab, Fanolesomab, Faralimomab, Faricimab, Farletuzumab, Fasinumab, FBTA05, Felvizumab, Fezakinumab, Fibatuzumab, Ficlatuzumab, Figitumumab, Firivumab, Flanvotumab, Fletikumab, Flotetuzumab, Fontolizumab, Foralumab, Foravirumab, Fremanezumab, Fresolimumab, Frovocimab, Frunevetmab, Fulranumab, Futuximab, Galcanezumab, Galiximab, Gancotamab, Ganitumab, Gantenerumab, Gatipotuzumab, Gavilimomab, Gedivumab, Gemtuzumab ozogamicin, Gevokizumab, Gilvetmab, Gimsilumab, Girentuximab, Glembatumumab vedotin, Golimumab, Gomiliximab, Gosuranemab, Guselkumab, Ianalumab, Ibalizumab, IBI308, Ibritumomab tiuxetan, Icrucumab, Idarucizumab, Ifabotuzumab, Igovomab, Iladatuzumab vedotin, IMAB362, Imalumab, Imaprelimab, Imciromab, Imgatuzumab, Inclacumab, Indatuximab ravtansine, Indusatumab vedotin, Inebilizumab, Infliximab, Intetumumab, Inolimomab, Inotuzumab ozogamicin, Ipilimumab, Iomab-B, Iratumumab, Isatuximab, Iscalimab, Istiratumab, Itolizumab, Ixekizumab, Keliximab, Labetuzumab, Lacnotuzumab, Ladiratuzumab vedotin, Lampalizumab, Lanadelumab, Landogrozumab, Laprituximab emtansine, Larcaviximab, Lebrikizumab, Lemalesomab, Lendalizumab, Lenvervimab, Lenzilumab, Lerdelimumab, Leronlimab, Lesofavumab, Letolizumab, Lexatumumab, Libivirumab, Lifastuzumab vedotin, Ligelizumab, Loncastuximab tesirine, Losatuxizumab vedotin, Lilotomab satetraxetan, Lintuzumab, Lirilumab, Lodelcizumab, Lokivetmab, Lorvotuzumab mertansine, Lucatumumab, Lulizumab pegol, Lumiliximab, Lumretuzumab, Lupartumab amadotin, Lutikizumab, Mapatumumab, Margetuximab, Marstacimab, Maslimomab, Mavrilimumab, Matuzumab, Mepolizumab, Metelimumab, Milatuzumab, Minretumomab, Mirikizumab, Mirvetuximab soravtansine, Mitumomab, Modotuximab, Mogamulizumab, Monalizumab, Morolimumab, Mosunetuzumab, Motavizumab, Moxetumomab pasudotox, Muromonab-CD3, Nacolomab tafenatox, Namilumab, Naptumomab estafenatox, Naratuximab emtansine, Narnatumab, Natahzumab, Navicixizumab, Navivumab, Naxitamab, Nebacumab, Necitumumab, Nemolizumab, NEOD001, Nerelimomab, Nesvacumab, Netakimab, Nimotuzumab, Nirsevimab, Nivolumab, Nofetumomab merpentan, Obiltoxaximab, Obinutuzumab, Ocaratuzumab, Ocrelizumab, Odulimomab, Ofatumumab, Olaratumab, Oleclumab, Olendalizumab, Olokizumab, Omalizumab, Omburtamab, OMS721, Onartuzumab, Ontuxizumab, Onvatilimab, Opicinumab, Oportuzumab monatox, Oregovomab, Orticumab, Otelixizumab, Otilimab, Otlertuzumab, Oxelumab, Ozanezumab, Ozoralizumab, Pagibaximab, Palivizumab, Pamrevlumab, Panitumumab, Pankomab, Panobacumab, Parsatuzumab, Pascolizumab, Pasotuxizumab, Pateclizumab, Patritumab, PDR001, Pembrolizumab, Pemtumomab, Perakizumab, Pertuzumab, Pexelizumab, Pidilizumab, Pinatuzumab vedotin, Pintumomab, Placulumab, Plozalizumab, Pogalizumab, Polatuzumab vedotin, Ponezumab, Porgaviximab, Prasinezumab, Prezalizumab, Priliximab, Pritoxaximab, Pritumumab, PRO 140, Quilizumab, Racotumomab, Radretumab, Rafivirumab, Ralpancizumab, Ramucirumab, Ranevetmab, Ranibizumab, Raxibacumab, Ravagalimab, Ravulizumab, Refanezumab, Regavirumab, Relatlimab, Remtolumab, Reslizumab, Rilotumumab, Rinucumab, Risankizumab, Rituximab, Rivabazumab pegol, Robatumumab, Rmab, Roledumab, Romilkimab, Romosozumab, Rontalizumab, Rosmantuzumab, Rovalpituzumab tesirine, Rovelizumab, Rozanolixizumab, Ruplizumab, SA237, Sacituzumab govitecan, Samalizumab, Samrotamab vedotin, Sarilumab, Satralizumab, Satumomab pendetide, Secukinumab, Selicrelumab, Seribantumab, Setoxaximab, Setrusumab, Sevirumab, Sibrotuzumab, SGN-CD19A, SHP647, Sifalimumab, Siltuximab, Simtuzumab, Siplizumab, Sirtratumab vedotin, Sirukumab, Sofituzumab vedotin, Solanezumab, Solitomab, Sonepcizumab, Sontuzumab, Spartalizumab, Stamulumab, Sulesomab, Suptavumab, Sutimlimab, Suvizumab, Suvratoxumab, Tabalumab, Tacatuzumab tetraxetan, Tadocizumab, Talacotuzumab, Talizumab, Tamtuvetmab, Tanezumab, Taplitumomab paptox, Tarextumab, Tavolimab, Tefibazumab, Telimomab aritox, Telisotuzumab vedotin, Tenatumomab, Teneliximab, Teplizumab, Tepoditamab, Teprotumumab, Tesidolumab, Tetulomab, Tezepelumab, TGN1412, Tibulizumab, Tildrakizumab, Tigatuzumab, Timigutuzumab, Timolumab, Tiragotumab, Tislelizumab, Tisotumab vedotin, TNX-650, Tocilizumab, Tomuzotuximab, Toralizumab, Tosatoxumab, Tositumomab, Tovetumab, Tralokinumab, Trastuzumab, Trastuzumab emtansine, TRBS07, Tregalizumab, Tremelimumab, Trevogrumab, Tucotuzumab celmoleukin, Tuvirumab, Ublituximab, Ulocuplumab, Urelumab, Urtoxazumab, Ustekinumab, Utomilumab, Vadastuximab talirine, Vanalimab, Vandortuzumab vedotin, Vantictumab, Vanucizumab, Vapaliximab, Varisacumab, Varlilumab, Vatelizumab, Vedolizumab, Veltuzumab, Vepalimomab, Vesencumab, Visilizumab, Vobarilizumab, Vociximab, Vonlerolizumab, Vopratelimab, Vorsetuzumab mafodotin, Votumumab, Vunakizumab, Xentuzumab, XMAB-5574, Zalutumumab, Zanolimumab, Zatuximab, Zenocutuzumab, Ziralimumab, Zolbetuximab, Zolimomab aritox; and (iv) a major histocompatibility complex (MHC) class 1 receptor or a major histocompatibility complex (MHC) class 2 receptor, wherein the MHC class 1 receptor is bound to a peptide derived from a tumor antigen, a neoantigen, or an autoantigen or the MHC class 2 receptor is bound to a peptide derived from a tumor antigen, a neoantigen, or an autoantigen.

In some embodiments, the chimeric platelet receptor binds at least one antigen. In some embodiments, the chimeric platelet receptor binds a tissue in the body of a subject. In some embodiments, the chimeric platelet receptor inhibits platelet activation. In some embodiments, the chimeric platelet receptor is an ITIM-containing receptor. In some embodiments, the chimeric platelet receptor stimulates platelet activation. In some embodiments, the chimeric platelet receptor is an ITAM-containing receptor. In some embodiments the chimeric platelet receptor binds to at least one antigen that is an endogenous antigen, for example is an endogenous host or subject antigen. By an endogenous host or subject antigen we include the meaning that the antigen is present within a host or subject into which the chimeric platelet receptor is administered or into which cells such as megakaryocytes or platelets that comprise the CPR of the invention are administered. For example the antigen may be an antigen that is present on tissue, or on a particular subset of tissue, or in plasma or blood of a subject, for example a human subject. The antigen may be an antigen that is expressed at abnormal levels, for example at abnormally high levels, on a tissue that does not normally express a high level of the antigen, or that does not normally express the antigen at all.

In some embodiments, the chimeric platelet receptor is not, or does not comprise, a GPCR or a protease-activated receptor.

The invention also provides a nucleic acid encoding the chimeric platelet receptor of the invention. In preferred instances, the chimeric platelet receptor is not a naturally occurring receptor, and so the nucleic acid encoding said receptor is not a naturally occurring nucleic acid. In some embodiments the nucleic acid encodes the CPR of the invention and also comprises a heterologous nucleic acid sequence. In some instances the nucleic acid is operatively linked to an expression control sequence. Expression control sequences are considered to include component such as enhancers and promoters. In one embodiment the nucleic acid of the invention comprises a heterologous promoter. In the same or different embodiment the nucleic acid of the invention comprises a heterologous enhancer sequence.

In some embodiments the nucleic acid is DNA. In some embodiments the nucleic acid is RNA for example is an mRNA. In some embodiments the nucleic acid comprises a megakaryocyte-specific promoter or a platelet-specific promoter. The terms megakaryocyte-specific promoter and platelet-specific promoter are used synonymously. The skilled person will understand what is meant by the terms megakaryocyte-specific promoter and platelet-specific promoter.

The invention also provides a vector that comprises a nucleic acid that encodes the CPR By vector we include the meaning of plasmid. In some embodiments the vector also comprises a heterologous nucleic acid. In some embodiments the vector comprises a megakaryocyte-specific promoter. In some embodiments the vector comprises a platelet-specific promoter.

The invention also provides a viral particle, or viral vector, comprising any one or more of the nucleic acids of the invention.

The invention also provides a nucleic acid encoding a cargo protein or peptide which comprises sequences suitable for driving expression in a megakaryocyte and/or platelet. For example, in some embodiments the nucleic acid encoding the cargo protein, cargo peptide or cargo RNA is operatively linked to a heterologous expression control sequence such as a promoter. In some embodiments the nucleic acid encodes a cargo protein or peptide and also comprises a megakaryocyte specific promoter or a platelet specific promoter. In some embodiments the nucleic acid encodes a cargo protein or peptide and comprises a heterologous sequence, such as a megakaryocyte specific promoter or a platelet specific promoter.

Various embodiments of the invention described herein provide a therapeutic delivery system comprising: an engineered platelet presenting the chimeric platelet receptor previously described; and at least one therapeutic agent selected from the group consisting of: a toxin, a protein, a small molecule drug, and a nucleic acid packaged within a vesicle inside the platelet.

In some embodiments, the engineered platelet is produced from an iPSC progenitor. In some embodiments, the nucleic acid is a mRNA, a miRNA, shRNA, and a clustered regularly interspaced short palindromic repeats (CRISPR) sequence. In some embodiments, the protein is selected from the group consisting of an antibody, an enzyme, a cytokine, and a CRISPR associated protein 9 (Cas9). In an aspect, the enzyme is a nuclease.

In some embodiments, the nuclease is a transcription activator-like effector nuclease (TALEN). In some embodiments, the antibody binds a target such as, but not limited to, a tumor antigen or a neoantigen. In some embodiments, the therapeutic agent is released from the platelet following activation of the platelet by an antigen recognized by the chimeric platelet receptor.

Various methods are provided for delivering a cargo to a subject in need thereof. As described herein, the cargo may be a therapeutic drug or a toxin. The cargo may be a protein or peptide, or may be a nucleic acid such as a therapeutic RNA or an mRNA. Preferences for the cargo are as described elsewhere herein. The invention provides a method of delivering a cargo comprising administering an effective amount of any one or more of an engineered megakaryocyte, engineered platelet, and/or CPR according to any of the preceding claims. The invention also provides a therapeutic delivery system. The invention also provides a non-therapeutic delivery system. The invention also provides a method of targeted cargo delivery to a target tissue or site in the body wherein the method comprises administering an effective amount of any one or more of an engineered megakaryocyte, engineered platelet, and/or CPR according to any of the preceding claims wherein the targeting domain of the CPR binds to the target tissue or site in the body.

Various embodiments of the invention described herein provide a method of treating a disease, disorder, or condition in a subject, the method comprising: administering to the subject the previously described therapeutic delivery system, wherein the chimeric receptor is specific to an antigen associated with the disease, disorder, or condition.

In some embodiments, the disease, disorder, or condition may be, but is not limited to, a cancer, an autoimmunity, and an infection. In some embodiments, the cancer is selected from the group consisting of: Acute granulocytic leukemia, Acute lymphocytic leukemia, Acute myelogenous leukemia, Adenocarcinoma, Adenosarcoma, Adrenal cancer, Adrenocortical carcinoma, Anal cancer, Anaplastic astrocytoma, Angiosarcoma, Appendix cancer, Astrocytoma, Basal cell carcinoma, B-Cell lymphoma), Bile duct cancer, Bladder cancer, Bone cancer, Bowel cancer, Brain cancer, Brain stem glioma, Brain tumor, Breast cancer, Carcinoid tumors, Cervical cancer, Cholangiocarcinoma, Chondrosarcoma, Chronic lymphocytic leukemia, Chronic myelogenous leukemia, Colon cancer, Colorectal cancer, Craniopharyngioma, Cutaneous lymphoma, Cutaneous melanoma, Diffuse astrocytoma, Ductal carcinoma in situ, Endometrial cancer, Ependymoma, Epithelioid sarcoma, Esophageal cancer, Ewing sarcoma, Extrahepatic bile duct cancer, Eye cancer, Fallopian tube cancer, Fibrosarcoma, Gallbladder cancer, Gastric cancer, Gastrointestinal cancer, Gastrointestinal carcinoid cancer, Gastrointestinal stromal tumors, General, Germ cell tumor, Glioblastoma multiforme, Glioma, Hairy cell leukemia, Head and neck cancer, Hemangioendothelioma, Hodgkin lymphoma, Hodgkin's disease, Hodgkin's lymphoma, Hypopharyngeal cancer, Infiltrating ductal carcinoma, Infiltrating lobular carcinoma, Inflammatory breast cancer, Intestinal Cancer, Intrahepatic bile duct cancer, Invasive/infiltrating breast cancer, Islet cell cancer, Jaw cancer, Kaposi sarcoma, Kidney cancer, Laryngeal cancer, Leiomyosarcoma, Leptomeningeal metastases, Leukemia, Lip cancer, Liposarcoma, Liver cancer, Lobular carcinoma in situ, Low-grade astrocytoma, Lung cancer, Lymph node cancer, Lymphoma, Male breast cancer, Medullary carcinoma, Medulloblastoma, Melanoma, Meningioma, Merkel cell carcinoma, Mesenchymal chondrosarcoma, Mesenchymous, Mesothelioma, Metastatic breast cancer, Metastatic melanoma, Metastatic squamous neck cancer, Mixed gliomas, Mouth cancer, Mucinous carcinoma, Mucosal melanoma, Multiple myeloma, Nasal cavity cancer, Nasopharyngeal cancer, Neck cancer, Neuroblastoma, Neuroendocrine tumors, Non-Hodgkin lymphoma, Non-Hodgkin's lymphoma, Non-small cell lung cancer, Oat cell cancer, Ocular cancer, Ocular melanoma, Oligodendroglioma, Oral cancer, Oral cavity cancer, Oropharyngeal cancer, Osteogenic sarcoma, Osteosarcoma, Ovarian cancer, Ovarian epithelial cancer, Ovarian germ cell tumor, Ovarian primary peritoneal carcinoma, Ovarian sex cord stromal tumor, Paget's disease, Pancreatic cancer, Papillary carcinoma, Paranasal sinus cancer, Parathyroid cancer, Pelvic cancer, Penile cancer, Peripheral nerve cancer, Peritoneal cancer, Pharyngeal cancer, Pheochromocytoma, Pilocytic astrocytoma, Pineal region tumor, Pineoblastoma, Pituitary gland cancer, Primary central nervous system lymphoma, Prostate cancer, Rectal cancer, Renal cell cancer, Renal pelvis cancer, Rhabdomyosarcoma, Salivary gland cancer, Sarcoma, Sarcoma, bone, Sarcoma, soft tissue, Sarcoma, uterine, Sinus cancer, Skin cancer, Small cell lung cancer, Small intestine cancer, Soft tissue sarcoma, Spinal cancer, Spinal column cancer, Spinal cord cancer, Spinal tumor, Squamous cell carcinoma, Stomach cancer, Synovial sarcoma, T-cell lymphoma), Testicular cancer, Throat cancer, Thymoma/thymic carcinoma, Thyroid cancer, Tongue cancer, Tonsil cancer, Transitional cell cancer, Transitional cell cancer, Transitional cell cancer, Triple-negative breast cancer, Tubal cancer, Tubular carcinoma, Ureteral cancer, Ureteral cancer, Urethral cancer, Uterine adenocarcinoma, Uterine cancer, Uterine sarcoma, Vaginal cancer, and Vulvar cancer.

In some embodiments, the method further comprises incubating the engineered platelet with the at least one therapeutic agent such as, but not limited to, a toxin, a protein, and a small molecule drug to produce the therapeutic delivery system. In some embodiments, the nucleic acid may be, but is not limited to, a mRNA, a miRNA, shRNA, and a clustered regularly interspaced short palindromic repeats (CRISPR) sequence. In some embodiments, the protein may be, but is not limited to, an antibody, an enzyme, and a CRISPR associated protein 9 (Cas9). In some embodiments, the enzyme is a nuclease. In some embodiments, the nuclease is a transcription activator-like effector nuclease (TALEN). In some embodiments, incubating occurs prior to administering. In some embodiments, the disease, disorder, or condition is an autoimmunity such as, but not limited to, Autoimmune disseminated encephalomyelitis, Autoimmune inner ear disease, Batten disease/Neuronal Ceroid Lipofuscinoses, Chronic inflammatory demyelinating polyneuropathy, Encephalitis lethargica, Anti-basal ganglia, Guillain-Barré syndrome, Hashimoto's Encephalopathy, Anti-TPO, Isaac's syndrome/acquired neuromyotonia, Miller Fisher syndrome Morvan's syndrome, Multiple sclerosis, Myasthenia gravis, Narcolepsy PANDAS, Rasmussen's encephalitis, Stiff-person syndrome, Vogt-Koyanagi-Harada syndrome, Addison's disease, Autoimmune hypoparathyroidism, Autoimmune hypophysitis, Autoimmune oophoritis, Autoimmune orchitis, Autoimmune polyglandular syndrome I (APECED), Autoimmune polyglandular syndrome II, Autoimmune polyglandular syndrome III, Diabetes mellitus, type 1, Graves' disease, Hashimoto's autoimmune thyroiditis, Immunodysregulation, polyendocrinopathy, enteropathy, X-linked, Autoimmune hepatitis type 1, Autoimmune hepatitis type 2, Autoimmune pancreatitis, Coeliac disease, Crohn's disease, Pernicious anemia/atrophic gastritis, Primary biliary cirrhosis, Primary sclerosing cholangitis, Ulcerative colitis, Acquired hemophilia A, Antiphospholipid syndrome, Autoimmune hemolytic anemia, Autoimmune lymphoproliferative syndrome, Autoimmune neutropenia, Evans syndrome, Felty's syndrome, Immune thrombocytopenic purpura, Polymyositis/dermatomyositis, Relapsing polychondritis, Rheumatoid arthritis, Still's disease, Alopecia areata, Bullous pemphigoid, Cicatricial pemphigoid, Dermatitis herpetiformis, Discoid lupus erythematosus, Epidermolysis bullosa acquisita, Linear morphea, Pemphigus foliaceus, Pemphigus vulgaris, Vitiligo, Behçet disease, Churg-Strauss syndrome, Cogan's syndrome, CREST syndrome, Anti-fibrillarin, Essential mixed cryoglobulinemia, Mixed connective tissue disease, POEMS syndrome, Scleroderma, Sjögren's syndrome, Systemic lupus erythematosus, Erythema elevatum diutinum, Kawasaki disease, Microscopic polyangiitis, Polyarteritis nodosa, Rheumatic fever, Takayasu arteritis Temporal arteritis, Wegener's granulomatosis, HLA-B27-associated acute anterior uveitis, Sympathetic ophthalmia, and Goodpasture's disease.

The invention also provides non-therapeutic methods of delivering a cargo to a subject in need or desirous thereof. For example the invention provides a non-therapeutic method of delivering cargo to a subject in need thereof. In such non-therapeutic methods, the cargo may be a cosmetic agent. In some embodiments the invention provides a non-therapeutic method of targeted delivery of a cargo to a subject in need thereof.

Various embodiments of the invention described herein provide an engineered platelet produced from a megakaryocyte comprising a mutation in the nucleic acid sequence resulting in disruption of a vesicle biogenesis pathway or a vesicle release pathway in the platelet, expression of a toxin, or expression of for example a cargo that is a protein or peptide or a RNA for example an mRNA, for example a therapeutic agent or imaging agent, or deletion of a platelet receptor, mediator, or signal transduction protein compared to a platelet produced from a megakaryocyte without the mutation.

In some embodiments, the megakaryocyte is differentiated from an iPSC progenitor or the megakaryocyte is immortalized. In some embodiments, the mutation occurs in a gene encoding a component of the vesicle biogenesis pathway or a vesicle release pathway of the engineered platelet such as, but not limited to, α-granules, dense granules, and large dense-core vesicle. In some embodiments, the mutation is an insertion of a gene encoding a major histocompatibility complex (MHC) molecule. In some embodiments, the deletion is of at least one gene such as, but not limited to, RAB27a (RAS oncogene), HPS (haptoglobin) genes, integrin AIIbB3, GP1b-IX-V (Glycoprotein Ib complexed with glycoprotein IX), Par1 (protease activated receptor 1), Par4 (protease activated receptor 4), P2Y1 (purinergic receptor P2Y1), P2Y12 (purinergic receptor P2Y12), IP (PGI2R or prostaglandin 12 receptor), TP (TxA2R or Thromboxane A2 Receptor), TLR (toll-like receptor), GPVI, a2B1 (type 1 collagen receptor), GPIIbIIIA (Glycoprotein IIb Platelet Subunit Alpha), CLEC-2 (C-type lectinlike receptor 2), MyD88 (Myeloid Differentiation Primary Response 88), Galphaq (G-protein alpha pathway q), LIMK1 (LIM Domain Kinase 1), vWF (von Willebrand), Fibrinogen, PDGF (platelet derived growth factor), VEGF (vascular endothelial growth factor), Factor V, Factor VIII, Factor XI, Factor XIII, PF4 (platelet factor 4), NAP2 (Nucleosome Assembly Protein 2), Prothrombin, High Molecular Weight Kininogens, Plasminogen activator inhibitor 1, a2-antiplasmin, plasminogen, P-Selectin, CXCL4 (C-X-C motif chemokine ligand 4), CXCL7 (C-X-C motif chemokine ligand 7), FGF (fibroblast growth factor), EGF (elongation growth factor), HGF (hepatocyte growth factor), IGF (insulin-like growth factor), Angipoetin, Thromboxane synthase, PAF (platelet activating factor), cPLA2a, Thromospondin, CD40L, SgIII (Secretogranin III), Endostatin, TGF-β (transforming growth factor beta), Talin1, Kindlins, and Anoctamin 6.

In some embodiments, the mutation is a deletion which is a knock-out of a gene encoding a pro-thrombotic factor. In some embodiments, the gene is a 02 microglobulin gene, wherein the deletion results in endogenous MHC class 1 disruption and the generation of a non-immunogenic platelet. In some embodiments, the mutation reduces the thrombogenic potential of the engineered platelet compared to a platelet produced from a megakaryocyte without the mutation.

Various embodiments of the invention described herein provide a method of reducing activity in the immune system of a subject, the method comprising: administering to the subject an engineered platelet presenting at least one receptor expressing a major histocompatibility complex (MHC) molecule bound to a peptide derived from a tumor antigen, a neoantigen, or an autoantigen.

In some embodiments, the receptor expresses a MHC class I molecule. In some embodiments, the receptor expresses a MHC class H molecule. In some embodiments, wherein the MHC molecule stimulates an immune response to an antigen. In some embodiments, the antigen is associated with at least one disease, disorder, or condition selected from the group consisting of: a cancer, an autoimmunity, and an infection.

Various embodiments of the invention described herein provide a method of in vitro production of platelets, the method comprising: transfecting a plurality of induced pluripotent stem cell (iPSC) progenitors with an expression system, wherein the expression system is induced by an agent not found in an iPSC; establishing a megakaryocyte progenitor cell line by contacting the expression system with the agent to expand megakaryocytes; engineering the megakaryocyte to have at least one mutation such as, but not limited to, insertion of a nucleic sequence encoding a chimeric platelet receptor previously described, insertion of a nucleic acid sequence encoding a toxin, or for example encoding a cargo that is a protein or peptide or a RNA for example an mRNA, for example a therapeutic agent or imaging agent, and deletion of a nucleic acid sequence encoding a platelet receptor; and removing the agent from the expression system to induce differentiation of the megakaryocytes into platelets.

In some embodiments, the mutation results in platelets with less immunogenicity compared to platelets from human donors. In some embodiments, the platelet does not function analogously to platelets derived from a human donor. In some embodiments, the deletion prevents toxin release or prevents cargo release in response to platelet activation signals. In some embodiments, the toxin or cargo is attached to an α-granule localization signal. In some embodiments, the α-granule localization signal. In some embodiments, the method of platelet production further comprising contacting the platelets with at least one of a cargo for example a cargo that is a protein or peptide or a RNA for example an mRNA, for example a therapeutic agent or imaging agent or a small molecule; a toxin; and a small molecule drug under conditions to facilitate absorption by the platelet. In some embodiments, the expression system further comprises a platelet-specific promoter.

Various embodiments of the invention described herein provide a method of in vivo gene editing or gene therapy in a subject, the method comprising: administering to the subject an engineered platelet comprising a chimeric platelet receptor described herein specific to a tissue to be edited, wherein the engineered platelet is cloaking an adenovirus loaded with genome engineering machinery; and releasing the genome machinery at the tissue. In some embodiments, the genome machinery is a CRISPR/Cas gene editing system.

Various embodiments of the invention described herein provide a use of the therapeutic delivery system previously described, wherein the chimeric receptor is specific to an antigen associated with the disease, disorder, or condition in treating a disease, disorder, or condition in a subject. In some embodiments of the use described herein, the disease, disorder, or condition is selected from the group consisting of: a cancer, an autoimmunity, and an infection.

In some embodiments of the use described herein, the cancer may be, but is not limited to, Acute granulocytic leukemia, Acute lymphocytic leukemia, Acute myelogenous leukemia, Adenocarcinoma, Adenosarcoma, Adrenal cancer, Adrenocortical carcinoma, Anal cancer, Anaplastic astrocytoma, Angiosarcoma, Appendix cancer, Astrocytoma, Basal cell carcinoma, B-Cell lymphoma), Bile duct cancer, Bladder cancer, Bone cancer, Bowel cancer, Brain cancer, Brain stem glioma, Brain tumor, Breast cancer, Carcinoid tumors, Cervical cancer, Cholangiocarcinoma, Chondrosarcoma, Chronic lymphocytic leukemia, Chronic myelogenous leukemia, Colon cancer, Colorectal cancer, Craniopharyngioma, Cutaneous lymphoma, Cutaneous melanoma, Diffuse astrocytoma, Ductal carcinoma in situ, Endometrial cancer, Ependymoma, Epithelioid sarcoma, Esophageal cancer, Ewing sarcoma, Extrahepatic bile duct cancer, Eye cancer, Fallopian tube cancer, Fibrosarcoma, Gallbladder cancer, Gastric cancer, Gastrointestinal cancer, Gastrointestinal carcinoid cancer, Gastrointestinal stromal tumors, General, Germ cell tumor, Glioblastoma multiforme, Glioma, Hairy cell leukemia, Head and neck cancer, Hemangioendothelioma, Hodgkin lymphoma, Hodgkin's disease, Hodgkin's lymphoma, Hypopharyngeal cancer, Infiltrating ductal carcinoma, Infiltrating lobular carcinoma, Inflammatory breast cancer, Intestinal Cancer, Intrahepatic bile duct cancer, Invasive/infiltrating breast cancer, Islet cell cancer, Jaw cancer, Kaposi sarcoma, Kidney cancer, Laryngeal cancer, Leiomyosarcoma, Leptomeningeal metastases, Leukemia, Lip cancer, Liposarcoma, Liver cancer, Lobular carcinoma in situ, Low-grade astrocytoma, Lung cancer, Lymph node cancer, Lymphoma. Male breast cancer, Medullary carcinoma, Medulloblastoma, Melanoma, Meningioma, Merkel cell carcinoma, Mesenchymal chondrosarcoma, Mesenchymous, Mesothelioma, Metastatic breast cancer, Metastatic melanoma, Metastatic squamous neck cancer, Mixed gliomas, Mouth cancer, Mucinous carcinoma, Mucosal melanoma, Multiple myeloma, Nasal cavity cancer, Nasopharyngeal cancer, Neck cancer, Neuroblastoma, Neuroendocrine tumors, Non-Hodgkin lymphoma, Non-Hodgkin's lymphoma, Non-small cell lung cancer, Oat cell cancer, Ocular cancer, Ocular melanoma, Oligodendroglioma, Oral cancer, Oral cavity cancer, Oropharyngeal cancer, Osteogenic sarcoma, Osteosarcoma, Ovarian cancer, Ovarian epithelial cancer, Ovarian germ cell tumor, Ovarian primary peritoneal carcinoma, Ovarian sex cord stromal tumor, Paget's disease, Pancreatic cancer, Papillary carcinoma, Paranasal sinus cancer, Parathyroid cancer, Pelvic cancer, Penile cancer, Peripheral nerve cancer, Peritoneal cancer, Pharyngeal cancer, Pheochromocytoma, Pilocytic astrocytoma, Pineal region tumor, Pineoblastoma, Pituitary gland cancer, Primary central nervous system lymphoma, Prostate cancer, Rectal cancer, Renal cell cancer, Renal pelvis cancer, Rhabdomyosarcoma, Salivary gland cancer, Sarcoma, Sarcoma, bone, Sarcoma, soft tissue, Sarcoma, uterine, Sinus cancer, Skin cancer, Small cell lung cancer, Small intestine cancer, Soft tissue sarcoma, Spinal cancer, Spinal column cancer, Spinal cord cancer, Spinal tumor, Squamous cell carcinoma, Stomach cancer, Synovial sarcoma, T-cell lymphoma), Testicular cancer, Throat cancer, Thymoma/thymic carcinoma, Thyroid cancer, Tongue cancer, Tonsil cancer, Transitional cell cancer, Transitional cell cancer, Transitional cell cancer, Triple-negative breast cancer, Tubal cancer, Tubular carcinoma, Ureteral cancer, Ureteral cancer, Urethral cancer, Uterine adenocarcinoma, Uterine cancer, Uterine sarcoma, Vaginal cancer, and Vulvar cancer.

In some embodiments of the use described herein, the disease, disorder, or condition is an autoimmunity such as, but not limited to, Autoimmune disseminated encephalomyelitis, Autoimmune inner ear disease, Batten disease/Neuronal Ceroid Lipofuscinoses, Chronic inflammatory demyelinating polyneuropathy, Encephalitis lethargica, Anti-basal ganglia, Guillain-Barré syndrome, Hashimoto's Encephalopathy, Anti-TPO, Isaac's syndrome/acquired neuromyotonia, Miller Fisher syndrome Morvan's syndrome, Multiple sclerosis, Myasthenia gravis, Narcolepsy PANDAS, Rasmussen's encephalitis, Stiff-person syndrome, Vogt-Koyanagi-Harada syndrome, Addison's disease, Autoimmune hypoparathyroidism, Autoimmune hypophysitis, Autoimmune oophoritis, Autoimmune orchitis, Autoimmune polyglandular syndrome I (APECED), Autoimmune polyglandular syndrome II, Autoimmune polyglandular syndrome III, Diabetes mellitus, type 1, Graves' disease, Hashimoto's autoimmune thyroiditis, Immunodysregulation, polyendocrinopathy, enteropathy, X-linked, Autoimmune hepatitis type 1, Autoimmune hepatitis type 2, Autoimmune pancreatitis, Coeliac disease, Crohn's disease, Pernicious anemia/atrophic gastritis, Primary biliary cirrhosis, Primary sclerosing cholangitis, Ulcerative colitis, Acquired hemophilia A, Antiphospholipid syndrome, Autoimmune hemolytic anemia, Autoimmune lymphoproliferative syndrome, Autoimmune neutropenia, Evans syndrome, Felty's syndrome, Immune thrombocytopenic purpura, Polymyositis/dermatomyositis, Relapsing polychondritis, Rheumatoid arthritis, Still's disease, Alopecia areata, Bullous pemphigoid, Cicatricial pemphigoid, Dermatitis herpetiformis, Discoid lupus erythematosus, Epidermolysis bullosa acquisita, Linear morphea, Pemphigus foliaceus, Pemphigus vulgaris, Vitiligo, Behçet disease, Churg-Strauss syndrome, Cogan's syndrome, CREST syndrome, Anti-fibrillarin, Essential mixed cryoglobulinemia, Mixed connective tissue disease, POEMS syndrome, Scleroderma, Sjögren's syndrome, Systemic lupus erythematosus, Erythema elevatum diutinum, Kawasaki disease, Microscopic polyangiitis, Polyarteritis nodosa, Rheumatic fever, Takayasu arteritis Temporal arteritis, Wegener's granulomatosis, HLA-B27-associated acute anterior uveitis, Sympathetic ophthalmia, and Goodpasture's disease.

Various embodiments of the invention herein provide a therapeutic delivery system comprising: (a) an engineered platelet presenting the chimeric platelet receptor, wherein the engineered platelet has been produced through genetic modification of a progenitor megakaryocyte to be non-thrombogenic and non-immunogenic; and (b) at least one therapeutic agent selected from the group consisting of: a cargo as defined herein, a toxin, a protein, a small molecule drug, and a nucleic acid packaged within a vesicle inside the platelet, i) wherein the therapeutic agent is the nucleic acid or the protein, loading occurs through expression in a progenitor megakaryocyte, or ii) wherein the therapeutic agent is loaded by incubation of the engineered platelet with the therapeutic agent.

DETAILED DESCRIPTION OF THE INVENTION

I. Introduction

Genetically engineered platelets generated outside of the body may be targeted to respond to specific proteins expressed on a target tissue or cell (e.g., on cancer) and release a therapeutic agent (e.g., a small molecule drug, antibody, or a nucleic acid encoding a protein). These engineered platelets would become targeted drug delivery devices. Unlike when transplanting other tissues, platelets require limited matching to a recipient's immune system and thus, the engineered platelets could function "off the shelf," without having to be matched to a specific patient (which is a major problem with current cell therapies).

The engineered platelets described herein may be generated outside the body from megakaryocytes. As the megakaryocyte is maintained in culture outside of the body, it can be extensively edited at the genome level (e.g. by CRISPR/Cas9) without fear of oncogenic transformation in the patient, which is not possible with other competing cell therapy products. The engineered platelets would have a lifespan in the body of 7-10 days, with little to no potential for continued reproduction, thus little to no chance of forming a tumour itself.

Platelets can be frozen and stored for extended period of time resulting in an extended shelf life, and with currently available technology, engineered platelets could be produced, stored, transported and administered to patients without issue due to their lack of immunogenicity.

Engineered platelets could be stripped of all thrombogenic potential by genome editing of megakaryocytes in vitro to alleviate potential thrombotic safety concerns. An engineered platelet, also called a SYNLET™ therapeutic delivery system, may act as a blank template, effectively functioning as a scaffold, having the capacity to store cargo internally in vesicles, and genetic alterations of megakaryocytes allow the engineered platelets to respond to specific antigens or signals. Platelets contain a variety of signaling pathways, therefore engineered inputs could be positive or negative, allowing the engineered platelets to integrate and compute a variety of stimuli before making the decision to activate. Interestingly, platelets also have the capacity to transfer RNA to nearby cells providing the potential to genetically manipulate target cells. For example, a CRISPR/Cas9 system may be delivered to a target cell by an engineered platelet. Additionally, signaling pathways within platelets can trigger the de novo translation of proteins, so these could be harnessed to deliver potentially toxic proteins locally to target locations.

In contrast to chimeric antigen receptor T (CAR-T) cells, the present invention provides an engineered platelet that is a universal product which does not require a match to a patient before administration. Further, platelet production in vitro from progenitors described herein, removes the need to continuously produce virus and edit cells. Due to the short life span of the engineered platelets described herein, safety concerns are limited as compared to current gene editing therapeutics. For example, gene editing and genome stability is less of a concern than with CAR-T cells because platelets are enucleate and therefore the complexity of the platelet therapy is not limited by the efficiency of editing or culture time limits. Additionally, due to their smaller size, the engineered platelets may provide better access to solid tumors than CAR-T cells.

Enucleated red blood cells, such as those commercially available from Rubius Therapeutics, Inc., have also been contemplated in the art for delivering therapeutic agents. In contrast to red blood cells, the engineered platelets described herein are highly metabolically active and include signaling systems that can be re-engineered. In fact, more targeted uses are possible with the engineered platelets compared to red blood cells. Vesicle degranulation of the platelets also allows for "hiding" of protein until the desired target is engaged, which is not possible with enucleated red blood cells because the biotherapeutic proteins are generally expressed on the surface of the cell. Accordingly, in one embodiment binding of the targeting domain of the chimeric platelet receptor to the target or antigen results in degranulation of a platelet that comprises the chimeric platelet receptor.

The engineered platelets described herein are smaller than red blood cells likely resulting in better biodistribution.

II. Gene Nomenclature

Gene symbols are used herein, along with ENSEMBL Gene IDs, to refer to genes from humans. Unless otherwise noted, the gene name and ENSEMBL Gene (ENSG) IDs corresponding to each gene symbol are shown in Table 1. The unique identifiers for each ENSEMBL entry has been modified to remove the first five leading zeros (0) of the identifier after the ENSG label.

TABLE 1

ENSEMBL identifiers for genes

| Given Symbol | Given Name | ENSG |
|---|---|---|
| RAB27A | RAS oncogene | 069974 |
| HP | haptoglobin | 257017 |
| integrin AIIbB3 or ITGB3 | glycoprotein beta III platelet subunit alpha 2 | 259207 |
| GP1b-IX-V | Glycoprotein Ib complexed with glycoprotein IX | N/A |
| Par1 or NR1I2 | protease activated receptor 1 | 144852 |
| Par4 or F2RL3 | protease activated receptor 4 | 127533 |
| P2Y1 or P2RY1 | purinergic receptor P2Y1 | 169860 |
| P2Y12 or P2RY12 | purinergic receptor P2Y12 | 169313 |
| IP or PTGIR | PGI2R or prostaglandin I2 receptor | 160013 |
| TP or TBXA2R | TxA2R or Thromboxane A2 Receptor | 006638 |
| TLR1 | toll-like receptor 1 | 174125 |
| TLR2 | toll-like receptor 2 | 137462 |
| TLR3 | toll-like receptor 3 | 164342 |
| TLR4 | toll-like receptor 4 | 136869 |
| TLR5 | toll-like receptor 5 | 187554 |
| TLR6 | toll-like receptor 6 | 174130 |
| TLR7 | toll-like receptor 7 | 196664 |
| TLR8 | toll-like receptor 8 | 101916 |
| TLR9 | toll-like receptor 9 | 239732 |
| TLR10 | toll-like receptor 10 | 174123 |

TABLE 1-continued

ENSEMBL identifiers for genes

| Given Symbol | Given Name | ENSG |
| --- | --- | --- |
| GPVI or GP6 | glycoprotein VI | 274050, 275931, 275633, 274566, 278316, 088053, 278670, 277439, 276211, 276065 |
| a2B1 or ITGB1 | type 1 collagen receptor | 150093 |
| GPIIbIIIA or ITGA2B | Glycoprotein IIb Platelet Subunit Alpha | 005961 |
| CLEC-2 or CLEC1B | C-type lectinlike receptor 2 | 165682 |
| MyD88 or MYD88 | Myeloid Differentiation Primary Response 88 | 172936 |
| Galphaq or GNAQ | G-protein alpha pathway q | 156052 |
| LIMK1 or LIMK1 | LIM Domain Kinase 1 | 106683 |
| vWF or VWF | von Willebrand | 110799 |
| FGA | Fibrinogen | 171560 |
| FGB | Fibrinogen | 171564 |
| FGG | Fibrinogen | 171557 |
| PDGFA | platelet derived growth factor A | 197461 |
| PDGFB | platelet derived growth factor B | 100311 |
| PDGFC | platelet derived growth factor C | 145431 |
| PDGFD | platelet derived growth factor D | 170962 |
| VEGF or VEGFA | vascular endothelial growth factor | 112715 |
| F5 | Factor V | 198734 |
| F8 | Factor VIII | 185010 |
| F11 | Factor XI | 088926 |
| F13A1 | Factor XIII A | 124491 |
| F13B | Factor XIII B | 143278 |
| CXCL4 or PF4 | C-X-C motif chemokine ligand 4 or platelet factor 4 | 163737, 163737 |
| NAP2 or PPBP | Nucleosome Assembly Protein 2 | 163736 |
| F2 | Prothrombin | 180210 |
| PAI-1 or SERPINE1 | Plasminogen activator inhibitor 1 | 106366 |
| SERPIN or SERPINF1 | a2-antiplasmin | 282307, 132386 |
| PLG | plasminogen | 122194 |
| SELP | P-Selectin | 174175 |
| CXCL7 or PPBP | C-X-C motif chemokine ligand 7 | 163736 |
| FGF1 | fibroblast growth factor 1 | 113578 |
| FGF2 | fibroblast growth factor 2 | 138685 |
| FGF3 | fibroblast growth factor 3 | 186895 |
| FGF4 | fibroblast growth factor 4 | 075388 |
| FGF5 | fibroblast growth factor 5 | 138675 |
| FGF6 | fibroblast growth factor 6 | 111241 |
| FGF7 | fibroblast growth factor 7 | 140285 |
| FGF8 | fibroblast growth factor 8 | 107831 |
| FGF9 | fibroblast growth factor 9 | 102678 |
| FGF10 | fibroblast growth factor 10 | 070193 |
| FGF11 | fibroblast growth factor 11 | 161958 |
| FGF12 | fibroblast growth factor 12 | 283903 |
| FGF13 | fibroblast growth factor 13 | 114279 |
| FGF14 | fibroblast growth factor 14 | 129682 |
| FGF15 | fibroblast growth factor 15 | 102466 |
| FGF16 | fibroblast growth factor 16 | 196468 |
| FGF17 | fibroblast growth factor 17 | 158815 |
| FGF18 | fibroblast growth factor 18 | 156427 |
| FGF19 | fibroblast growth factor 19 | 162344 |
| FGF20 | fibroblast growth factor 20 | 078579 |
| FGF21 | fibroblast growth factor 21 | 105550 |
| FGF22 | fibroblast growth factor 22 | 070388 |
| FGF23 | fibroblast growth factor 23 | 118972 |
| EGF | elongation growth factor | 138798 |
| HGF | hepatocyte growth factor | 019991 |
| IGF or IGF1 | insulin-like growth factor | 017427 |
| ANGPT or ANGPT1 | Angiopoetin | 154188 |
| TBXAS1 | Thromboxane synthase | 059377 |
| PAF or PCLAF | platelet activating factor | 166803 |
| cPLA2a or PLA2G1B | Phospholipase A2 | 170890 |
| THBS1 | Thrombospondin | 137801 |
| CD40L or CD40LG | CD40 ligand | 102245 |
| SgIII or SCG3 | Secretogranin III | 104112 |
| COL18A1 | Endostatin | 182871 |
| TGF-β or TGFB1 | transforming growth factor beta | 105329 |
| TLN1 | Talin1 | 137076 |
| MOG | myelin oligodendrocyte glycoprotein | 232641, 137345, 236561, 137345, 204655, 234623, 237834, 234096 |
| GAD2 | glutamic acid decarboxylase 2 | 136750, 136750 |
| MAG | myelin associated glycoprotein | 105695 |
| PMP22 | peripheral myelin protein 22 | 109099 |
| TPO | thyroid peroxidase | 277603, 115705 |
| VGKC | voltage-gated potassium channel genes | N/A |

TABLE 1-continued

ENSEMBL identifiers for genes

| Given Symbol | Given Name | ENSG |
|---|---|---|
| PLP or PLP1 | proteolipid protein | 123560 |
| AChR or CHRNA1 | acetylcholine receptor | 138435 |
| AChR or CHRNA10 | acetylcholinereceptor | 129749 |
| AChR or CHRNA2 | acetylcholinereceptor | 120903 |
| AChR or CHRNA3 | acetylcholinereceptor | 080644 |
| AChR or CHRNA4 | acetylcholinereceptor | 101204 |
| AChR or CHRNA5 | acetylcholinereceptor | 169684 |
| AChR or CHRNA6 | acetylcholinereceptor | 147434 |
| AChR or CHRNA7 | acetylcholinereceptor | 175344 |
| AChR or CHRNA9 | acetylcholinereceptor | 174343 |
| AChR or CHRNB1 | acetylcholinereceptor | 170175 |
| AChR or CHRNB1 | acetylcholinereceptor | 283946 |
| AChR or CHRNB2 | acetylcholinereceptor | 160716 |
| AChR or CHRNB3 | acetylcholinereceptor | 147432 |
| AChR or CHRNB4 | acetylcholinereceptor | 117971 |
| AChR or CHRND | acetylcholinereceptor | 135902 |
| AChR or CHRNE | acetylcholinereceptor | 108556 |
| AChR or CHRNG | acetylcholinereceptor | 196811 |
| TRIB2 | tribbles pseudokinase 2 | 071575 |
| GluR or GRIA1 | N-methyl-D-aspartate (NMDA)-type glutamate receptor | 155511 |
| GluR or GRIA2 | N-methyl-D-aspartate (NMDA)-type glutamate receptor | 120251 |
| GluR or GRIA3 | N-methyl-D-aspartate (NMDA)-type glutamate receptor | 125675 |
| GluR or GRIA4 | N-methyl-D-aspartate (NMDA)-type glutamate receptor | 152578 |
| GluR or GRIK3 | N-methyl-D-aspartate (NMDA)-type glutamate receptor | 163873 |
| GAD2 | glutamate decarboxylase 2 | 136750, 136750 |
| ARMC9 | Armadillo repeat containing 9 | 135931 |
| CYP21A2 | Cytochrome P450 Family 21 Subfamily A Member 2 | 231852, 235134, 198457, 232414, 233151, 206338 |
| CASR | calcium sensing receptor | 036828 |
| NASP | nuclear autoantigenic sperm protein | 132780 |
| INS | insulin | 254647 |
| TSHR | thyroid stimulating hormone receptor | 165409 |
| TPO | thyroperoxidase | 277603, 115705 |
| ASGR1 | asioglycoprotein receptor 1 | 141505 |
| ASGR2 | asioglycoprotein receptor 2 | 161944 |
| CYP2D6 | Cytochrome P450 Family 2 Subfamily D Member 6 | 272532, 275211, 100197, 280905, 282966, 283284 |
| LF or LTF | lactoferrin | 012223 |
| TTG or TGM1 | tissue trans-glutaminase 1 | 285348, 092295 |
| TTG or TGM2 | tissue trans-glutaminase 2 | 198959 |
| TTG or TGM3 | tissue trans-glutaminase 3 | 125780 |
| H/K ATP-ase | gastric hydrogen potassium ATPase | |
| F8 | Factor XIII | 185010 |
| Beta2-GPI or APOH | beta2-glycoprotein I | 091583 |
| ITGB2 | B2 integrin | 160255 |
| G-CSF or CSF3 | granulocyte-colony stimulating factor | 108342 |
| GP IIb/IIa | glycoprotein | N/A |
| COLII or COL2A1 | collagen II | 139219 |
| MPO | myeloperoxidase | 005381 |
| CYO or MYH7 | cardiac myosin | 092054 |
| PRTN3 | proteinase 3 | 277804, 196415 |
| TCHH | trichohyalin | 159450 |
| GP1 or GTPBP1 | glycoprotein 1 | 100226 |
| LM332 | laminin-332 | N/A |
| COLVII COL7A1 | type VII collagen | 114270 |
| COIL | P80 Coilin | 121058 |
| DSG1 | Desmoglein 1 | 134760 |
| DSG3 | Desmoglein III | 134757 |
| SOX10 | SRY-Box 10 | 100146 |
| 70SNRNP70 or RNU1-1 | small nuclear ribonucleoprotein U1 subunit | 206652 |
| SAG | S-antigen | 130561, 281857 |
| α3(IVNC1 collagen) or COL4A3 | Collagen alpha-3(IV chain) | 169031 |
| ANO6/TMEM16F | Anoctamin 6/Transmembrane Protein 16F | 177119 |

Symbols and names are used herein, along with ENSEMBL protein IDs, to refer to proteins from humans. Unless otherwise noted, the protein name (if used to refer to the protein herein) and symbol and ENSEMBL protein (ENSP) IDs corresponding to each symbol are shown in Table 2. The unique identifiers for each ENSEMBL entry has been modified to remove the first five leading zeros (0) of the identifier after the ENSP label.

TABLE 2

ENSEMBL identifiers for antibody targets

| Symbol | ENSP(s) |
|---|---|
| ACVR2B or ACVR2B | 340361 |
| ACVRL1 | 455848, 373574, 446724, 447884, 392492, 457394 |
| AFP | 379138, 226359 |
| ANGPT2 or Ang-2 | 314897, 486858, 343517, 428023 |
| ANGPTL3 | 360170 |
| AOC3 or AOC3 | 312326, 464787, 465913, 468632, 468043, 477686, 484312 |
| APCS | 255040 |
| APP or N/a | 284981, 346129, 345463, 350578, 387483, 398879, 351796, 396923, 406539, 352760 |
| AXL or AXL | 301178, 351995, 471497 |
| B4GALNT1 | n/a |
| BSG or CD147 | 473664, 344707, 333769, 458665, 343809, 495088, 484849, 478958, 484624, 473393, 473528 |
| C1S or C1s | 385035, 328173, 354057, 384171, 399892, 406643, 384464, 397921, 442298, 484657 |
| C5 or C5 | 223642 |
| CA9 | 367608, 482050 |
| CALCA | 417833, 420618, 331746, 379657, 354286 |
| CASP2 | 312664, 376656, 340030, 481929 |
| CCL11 or CCL11 (eotaxin-1) | 302234 |
| CCL2 or MCP-1 | 462156, 225831 |
| CCR2 or CCR2 | 399285, 396736, 383681, 292301 |
| CCR4 or CCR4 | 332659 |
| CCR5 or CCR5 | 292303, 404881 |
| CD19 or CD19 | 313419, 456201, 437940 |
| CD2 or CD2 | 358490, 358489 |
| CD200 or CD200 | 476114, 475860, 418576, 420298, 312766, 373179, 419816 |
| CD22 or CD22 | 469980, 470681, 469503, 472664, 472762, 471972, 471399, 469523, 470193, 442279, 085219, 441237, 403822, 469984, 470724, 482823, 473221, 339349 |
| CD27 or CD27 | 266557 |
| CD274 or PD-L1 | 370989, 370985 |
| CD276 or CD276 | 455366, 320084, 441087, 453907, 452649, 452736, 454258, 453330, 452905, 453336, 456657, 452669, 454940, 453014, 453842, 320058 |
| CD276 or B7-H3 | n/a |
| CD28 or CD28 | 393648, 324890, 363605 |
| CD3 or CD3 | n/a |
| CD33 or CD33 | 403331, 410126, 375673, 262262 |
| CD37 or CD37 | 375732, 470394, 413151, 471902, 325708, 441037, 471078, 470260, 470683 |
| CD38 or CD38 | 427277, 226279, 423047 |
| CD3E or CD3 epsilon | 354566, 433975 |
| CD4 or CD4 | 011653, 445167, 440720 |
| CD40 or CD40 | 361359, 361350, 434825, 484074 |
| CD40LG or CD154 (CD40L) | 359663, 359662 |
| CD44 or CD44 v6 | 263398, 398632, 435377, 389830, 432704, 395953, 392331, 432405, 278386, 404447, 309732, 398099, 434465, 279452, 434530, 432718, 433189, 436549, 436623, 436980, 278385, 435321, 436451, 434418, 431860, 434920, 492449 |
| CD52 or CD52 | 363330 |
| CD6 or CD6 | 323280, 443748, 340334, 440055, 410638, 390676, 340628, 443747 |
| CD70 or CD70 | 395294, 245903, 470805 |
| CD74 or CD74 | 367026, 230685, 430614, 429024, 009530, 430654, 429641, 429478 |
| CD79B or CD79B | 376544, 006750, 245862 |
| CD80 or CD80 | 264246, 418364, 373165 |
| CD97 or CD97B | n/a |
| CEACAM5 or CEA | 381600, 221992, 385072, 468997, 473252, 482303, 482157, 480800 |
| CFAP221 or PCDP1 | 295220, 470662, 391760, 409912, 470784, 393222, 472563, 470283, 472069, 471092, 413299, 471998, 399793 |
| CFD or CFD | 478745, 488580, 332139, 468253 |
| CLDN18 or CLDN18.2 | 340939, 183605, 419732 |
| CLEC6A | 371505 |
| CLTA4 or CD152 | n/a |
| CSF1 or CSF1 | 434527, 431547, 349854, 327513, 433837, 358817, 407317, 358816 |
| CSF1R or CSF1R | 422212, 286301, 427545, 421174, 445282 |
| CSF2 or CSF2 | 296871 |
| CSF2RA | 370940, 370935, 410667, 416437, 370920, 476684, 348058, 436825, 347606, 370911, 440491, 394227 |
| CTGF or CTGF | 356954 |
| CTLA4 or CTLA-4 | 497102, 303939, 295854, 497319, 417779 |
| CXCL10 | 305651 |
| CXCR4 or CXCR4 (CD184) | 386884, 241393 |
| DLL3 or DLL3 | 348810, 471688, 205143 |
| DLL4 or DLL4 | 497860, 249749 |
| DPP4 or DPP4 | 353731, 402259, 401359, 410264, 486421 |
| EGFL7 or EGFL7 | 360764, 385639, 473338, 360763, 307843 |
| EGFR or EGFR | 415559, 342376, 345973, 413843, 275493, 413354, 492462, 395243 |
| ENG | 362299, 341917, 479015 |
| EPCAM or EpCAM | 385476, 410675, 263735, 389028 |

TABLE 2-continued

ENSEMBL identifiers for antibody targets

| Symbol | ENSP(s) |
|---|---|
| EPHA3 | 337451, 399926, 419190 |
| ERBB2 or HER2 | 462438, 462808, 404047, 463714, 462024, 463427, 269571, 463719, 464420, 464252, 463002, 385185, 446466 |
| ERBB3 or ERBB3 (HER3) | 495453, 448636, 449138, 267101, 415753, 448671, 448483, 447510, 449713, 408340, 482073, 448946, 449129, 448729 |
| F3 | 334145, 359226 |
| F9, F10 | n/a |
| FAP or FAP | 441940, 417028, 188790, 411391, 400137, 407404, 485844 |
| FCER2 or CD23 | 264072, 471974, 472067, 353178 |
| FCGRT or FCGRT | 221466, 472350, 472794, 469968, 410798, 469933, 471300, 471118, 472604, 472256, 471232 |
| FGB or | 306099, 398719, 426757 |
| FGF23 or FGF 23 | 237837 |
| FGFR2 or FGFR2 | 351276, 474011, 491912, 348559, 358056, 474109, 358055, 404219, 263451, 410294, 353262, 358052, 358054, 337665, 352309, 481464, 484892, 490905, 350166, 484154, 358057, 309878 |
| FLT1 or VEGFR-1 | 282397, 437631, 484039, 491097, 442630, 484385, 443311, 484832, 437841 |
| FN1 | 394423, 323534, 338200, 350534, 346839, 410422, 415018, 399538, 348285, 416139, 392565, 398907, 352696 |
| FOLH1 | 256999, 349129, 434928, 344131, 431463, 436569, 431577, 431263 |
| FOLR1 | 308137, 377286, 377284, 377281 |
| FOLR2 | 405638, 298223, 414094, 443307, 441547, 438568, 444794, 321957, 440337, 480592 |
| FUT4 or CD15 | 351602 |
| FZD1 | 287934 |
| GCGR or GCGR | 383558, 460976, 458930 |
| GPC3 | 359854, 486325, 385307, 377836 |
| GPNMB or GPNMB | 258733, 371420, 386476, 497362 |
| GUCY2C or GUCY2C | 261170 |
| HGF or HGF | 494899, 222390, 391238, 389854, 408270, 413829, 494355, 346164, 496217, 396307, 388592 |
| HLA-DRA or HLA-DR | 372746, 372745, 404533, 392789, 410443, 411610, 479287, 405295, 398838, 378786, 364121, 372608, 403385, 402951, 412562 |
| HSP90AA1, HSP90AA2, HSP90AB1, HSOP90B1, TRAP1 or Hsp90 | 216281, 335153, 451400, 450712, 452241, 489370 |
| ICAM1 or 1CAM-1 | 264832, 413124, 465680 |
| ICOS or CD278, aka ICOS | 319476, 415951 |
| ICOSLG or ICOSL | 494882, 339477, 384432, 383230, 383228 |
| IFNA1 or IFN-α | 276927 |
| IFNAR1, IFNAR2 | 270139, 400161 |
| IFNG | 229135 |
| IGF1R or CD221 | 497069, 496919, 268035, 453007, 453630, 454115, 456950 |
| IGHE or IGHE | 492979, 374983, 481089 |
| IL12A or IL-12 | 303231, 420184, 419046 |
| IL13 or IL-13 | 304915, 479835 |
| IL17A or IL17A | n/a |
| IL17F or IL17F | 337432 |
| IL1A or IL1A | 263339 |
| IL1B or IL-1β | 263341, 407219, 409680, 400854 |
| IL2 or IL2 | 226730 |
| IL20 or IL 20 | 356065, 356063, 375796 |
| IL22 or IL-22 | 442424, 329384 |
| IL23A or IL23 | 228534 |
| IL2RA or CD25 | 369293, 369287, 256876, 402024 |
| IL31RA | 380048, 380046, 415900, 351935, 427533, 347047, 297015, 479432 |
| IL3RA or IL 3 receptor | 327890, 414867, 370878 |
| IL4 or IL4 | 231449, 325190, 480581 |
| IL5 or IL-5 | 231454, 409825 |
| IL5RA or CD125 | 412209, 390753, 256452, 373358, 309196, 400400, 392059, 398117, 391274, 388858 |
| IL6 or IL6 | 385675, 405150, 385718, 385043, 384928, 385227, 258743 |
| IL6R or IL-6R | 357470, 340589, 423184, 423668, 423036, 477739 |
| IL9 or IL9 | 274520 |
| ITGA2 or ITGA2 (CD49b) | 296585, 426489, 422095, 424397, 424642, 422145 |
| ITGA2B or CD41 | 498119, 467269, 262407 |
| ITGA5 | 293379, 450267, 405865, 447347 |
| ITGAL or LFA-1 (CD11a) | 349252, 456521, 350886, 457785, 454908, 454342, 456888, 409377, 461006, 458739 |
| ITGAV or CD51 | 261023, 364042, 404291, 389442 |
| ITGB2 or ITGB2 (CD18) | 380950, 380955, 380952, 347279, 380948, 427732, 317697, 428503, 428979, 428413, 428125, 428434, 430901, 428870, 380944, 429683, 303242 |
| ITGB3 | 452786, 461626, 465586 |
| ITGB7 | 267082, 456446, 408741, 455374, 437375, 450366, 456305, 446703 |

TABLE 2-continued

ENSEMBL identifiers for antibody targets

| Symbol | ENSP(s) |
|---|---|
| KDR or VEGFR2 | 495159, 263923 |
| KIR2DL1, KIR2DL2 or KIR2D | 480247, 484701, 477690, 479363, 484700, 482506, 478633, 484559, 481123, 478054, 478567, 480989, 479574, 482449, 336769, 291633, 478202, 484361, 479644, 483525, 478232, 481722, 478604, 484871, 478895, 482501, 478263, 482120, 479941, 484582, 482456, 481187, 492250, 492549, 492477, 491211, 491668, 492815, 491499, 492598, 492436, 492695, 491930, 491721, 491975, 492286, 491348, 492859 |
| KLRC1 or NKG2A | 441432, 352064, 385304, 256965, 442545, 438038 |
| LAG3 or LAG3 | 413825, 203629 |
| LINGO1 or LINGO-1 | 347451, 453853, 453780, 455605, 454465, 454687, 454051, 454245, 454577, 456516, 457101 |
| LOXL2 or LOXL2 | 373783, 473322, 427907, 427826, 427883, 429778, 430519, 428497, 428933 |
| LRRC15 or LRRC15 | 306276, 413707 |
| LTA or LTA | 403495, 413450, 372791, 372793, 383131, 372991, 395976, 416509, 395895, 407133, 416337, 387924, 412555, 402413 |
| LYPD3 or LYPD3 | 244333 |
| MADCAM1 | 475575, 304247, 215637, 372130, 480908, 484317, 480104, 483663, 484153 |
| MAG | 470772, 376048, 355234, 473125, 473245, 440695 |
| MAPT | 487613, 488245, 482244, 488081, 487819, 488373, 488046, 487837, 488101, 484491, 484321, 478602, 483396, 480217, 486039, 487570, 485913, 477703, 481769, 487403, 483784, 485831, 479142, 460048, 334886, 408975, 413056, 410838, 458742, 460965, 389250, 262410, 303214, 340820, 443028, 340438 |
| MASP2 or MASP-2 | 383690, 383691 |
| MCAM or MCAM | 264036 |
| MET | 413857, 380860, 317272, 398776, 398140, 410980 |
| MIF or MIF | 482779, 215754 |
| MMP9 | 361405 |
| MS4A1 or CD20 | 433179, 432219, 433519, 433277, 432270, 437002, 314620, 374589 |
| MSLN | 456008, 442965, 456702, 372313, 456132, 458003, 454295, 457847 |
| MST1R or MST1R (aka RON) | 296474, 407926, 341325, 393294, 414792, 482642, 481084, 482827 |
| MSTN or GDF-8 | 260950 |
| MUC1 | 481231, 479471, 478068, 357377, 389098, 482688, 357378, 357374, 357381, 339690, 342814, 483128, 484006, 484730, 357383, 357375, 338983, 483482, 343482, 483473, 484824, 483581, 388172, 482988, 480335, 480333 |
| MUC16 or CA-125 | 381008, 472883, 470885, 472781 |
| MUC5AC or 5AC | 485659, 490794 |
| MYH7 | 347507 |
| NCAM1 or CD56 | 480132, 384055, 481083, 479353, 318472, 482852, 484943, 482205, 480774, 484481, 479687, 475074, 486406, 480269, 478072, 486241, 477835, 480797, 477808, 479241 |
| NECTIN4 | 356991 |
| NGF or HNGF | 358525 |
| NOTCH1 or Notch 1 | 277541 |
| NRP1 or NRP1 | 364009, 265371, 390447, 416147, 476896, 393071, 363954, 363955, 363956, 408911, 390567, 379317, 364001, 363949 |
| NT5E | 358660, 257770, 414674, 387630, 358665 |
| PCDHAC1 or PCDC1 | 386356, 253807 |
| PCSK9 or PCSK9 | 303208 |
| PDCD1 or PD-1 | 480684, 486779, 487175, 335062, 390296, 340808 |
| PDGFRA or PDGF-Rα | 257290, 425648, 425626, 424218, 425902, 426472, 425232 |
| PDGFRB | 261799, 430026, 429218, 430715 |
| PTDSS1 | 430548, 337331, 430928 |
| PTK7 or PTK7 | 418386, 420186, 418462, 419096, 418545, 420765, 420165, 418754, 230418, 325992, 326029, 325462, 419037, 420322, 230419, 417607 |
| PTPRC or CD45 | 356349, 494132, 306782, 411355, 433536, 494327, 356337, 356334, 405494, 469141, 393360, 458846, 461347, 458322, 458662, 461074, 458191, 458418, 482203, 461712, 483380 |
| RGMA or RGMA | 330005, 440025, 451505, 452126, 452170, 456290, 451709, 452350, 404442, 442498 |
| RHD or RHD | 331871, 498055, 413849, 396420, 350150, 456966, 339577, 399640, 478087 |
| RHD, RHCE | 294413, 345084, 311185, 431741, 344485, 334570, 435401, 415417, 331871, 498055, 413849, 396420, 350150, 456966, 339577, 399640, 478087 |
| ROR1 or ROR1 | 360121, 360120, 441637 |
| RSPO3 | 349131, 357300 |
| RTN4 or RTN4 | 378107, 384471, 349944, 337838, 322147, 350365, 378109, 385650, 489133, 397808, 411628, 384825 |
| S1PR1 | 498194, 305416, 497175, 498038, 497478 |
| SAA1, SAA2 or | 348918, 436866, 497498, 384906 |
| SDC1 or SDC1 | 254351, 384613, 400773, 390201, 370542 |
| SELL or CD62L | 236147 |
| SELP | 356769, 356762, 399368, 356760, 263686, 391694 |
| SLAMF7 or CD319 | 357022, 357021, 352281, 473590, 403294, 416592, 409965, 405605, 483774 |
| SLC39A6 or LIV-1 | 269187, 465915, 401139, 467724 |
| SLITRK6 or SLITRK6 | 495507, 383143, 496428 |
| SNCA or NACP | 338345, 343683, 378437, 378442, 426955, 422238, 421485, 479604, 426034, 423445, 396241, 484044, 378440 |
| SOST or SOST | 301691 |
| ST8SIA1 | 379353, 261197, 441707, 444999, 440292, 384467, 370832 |

TABLE 2-continued

ENSEMBL identifiers for antibody targets

| Symbol | ENSP(s) |
|---|---|
| STEAP1 or STEAP1 | 297205, 394402 |
| TACSTD2 or TROP-2 | 360269 |
| TFPI or TFPI | 376172, 233156, 409177, 386344, 342306, 388159, 408170, 394185, 400179, 402954 |
| TGFB1 or TGF-β | 472767, 221930 |
| TGFB2 or TGF beta 2 | 355897, 355896 |
| TIGIT or TIGIT | 418917, 420552, 419085, 419706, 373167 |
| TNC | 265131, 339553, 411406, 443478, 442242, 445380, 489385, 443469, 438152 |
| TNF or TNF-α | 398698, 365290, 389492, 389490, 392858, 389265, 372988, 410668 |
| TNFRSF10A or TRAIL-R1 | 221132, 428884, 480778 |
| TNFRSF10B or TRAIL-R2 | 276431, 317859, 427999 |
| TNFRSF12A | 458898, 326737, 343894, 458305, 460610, 461756 |
| TNFRSF13C or BAFF-R | 291232 |
| TNFRSF17 or BCMA | 053243, 379753, 454314 |
| TNFRSF4 or OX-40 | 368538 |
| TNFRSF8 or CD30 (TNFRSF8) | 263932, 421938, 398337, 390650 |
| TNFRSF9 or 4-1BB (CD137) | 366729, 465272, 464978, 478699 |
| TNFSF11 or RANKL | 351347, 381775, 384042, 444913, 239849 |
| TNFSF13B or BAFF | 365048, 389540, 445334 |
| TPBG or 5T4 | 358765, 440049, 441219, 489447, 489143, 489140 |
| TRAP or TRAP | n/a |
| TSLP or TSLP | 399099, 339804, 427827 |
| TYRP1 or TYRP1 | 419006, 373570, 370528 |
| VEGFA or VEGF-A | 361137, 317598, 388663, 389864, 361125, 421561, 388465, 361134, 361148, 430594, 428321, 430479, 429643, 409911, 430829, 429008, 430002, 230480, 429592, 478570, 483241, 484284, 492199, 478034, 492413, 492800 |
| VIM | 446007, 489830, 490509, 224237, 435613, 431702 |
| VSIR or VSIR | 378409 |
| VWF or VWF | 261405, 461331, 459134 |
| TAG-72 | n/a |

CD3 or CD3 is also known as Cluster of differentiation 2 (multiple subunits). FCER2 or CD23 is also known as (IgE receptor. NT5E is also known as 5'-nucleotidase. F9, F10 is also known as activated F9, F10. ACVRL1 is also known as activin receptor-like kinase 1. AFP is also known as alpha-fetoprotein. ANGPTL3 is also known as angiopoietin 3. BSG or CD147 is also known as basigin. APP or N/a is also known as beta-amyloid. CALCA is also known as calcitonin gene-related peptide. CA9 is also known as carbonic anhydrase 9 (CA-IX). MYH7 is also known as cardiac myosin. MET is also known as c-Met. F3 is also known as coagulation factor III. CLEC6A is also known as dendritic cell-associated lectin 2. EGFR or EGFR is also known as elongating growth factor receptor. ENG is also known as endoglin. EPHA3 is also known as ephrin receptor A3. FGB or is also known as fibrin II, beta chain. FN1 is also known as fibronectin extra domain-B. FOLH1 is also known as folate hydrolase. FOLR2 is also known as folate receptor 2. FOLR1 is also known as folate receptor alpha. FZD1 is also known as Frizzled receptor. B4GALNT1 is also known as GD2 ganglioside. ST8SIA1 is also known as GD3 ganglioside. MMP9 is also known as gelatinase B. TYRP1 or TYRP1 is also known as glycoprotein 75. GPC3 is also known as glypican 3. CSF2RA is also known as GMCSF receptor α-chain. IGF1R or CD221 is also known as IGF-1 receptor. IL31RA is also known as IL31RA. ITGA2B or CD41 is also known as integrin alpha-IIb. ITGA5 is also known as integrin α5. ITGB3 is also known as integrin αIIbβ3. ITGB7 is also known as integrin β7. IFNG is also known as interferon gamma. IFNAR1, IFNAR2 is also known as interferon α/β receptor. CXCL10 is also known as interferon gamma-induced protein. IL12A or IL-12 is also known as interleukin 12. IL13 or IL-13 is also known as interleukin 13. IL17A or IL17A is also known as interleukin 17 alpha. IL17F or IL17F is also known as interleukin 17F. IL2 or IL2 is also known as interleukin 2. IL22 or IL-22 is also known as interleukin 22. IL23A or IL23 is also known as interleukin 23. IL6 or IL6 is also known as interleukin 6. SELL or CD62L is also known as L-selectin. MSLN is also known as mesothelin. MUC1 is also known as mucin CanAg. MADCAM1 is also known as mucosal addressin cell adhesion molecule. MAG is also known as myelin-associated glycoprotein. NECTIN4 is also known as nectin-4. CASP2 is also known as neural apoptosis-regulated proteinase 2. PTDSS1 is also known as phosphatidylserine. PDGFRB is also known as platelet-derived growth factor receptor beta. RHD, RHCE is also known as Rhesus factor. RSPO3 is also known as root plate-specific spondin 3. SELP is also known as selectin P. SAA1 or SAA2 is also known as serum amyloid A protein. APCS is also known as serum amyloid P component. SIPR1 is also known as sphingosine-1-phosphate. MAPT is also known as tau protein. TNC is also known as tenascin C. TNFRSF12A is also known as TWEAK receptor. VIM is also known as vimentin. VWF is also known as von Willebrand factor. IL2RA or CD25 is also known as α chain of IL-2receptor.

III. Compositions of the Invention

Various embodiments of the inventions described herein provide engineered megakaryocyte progenitors to encoding a chimeric platelet receptor (CPR). The receptor may bind a specific antigen or target present on a tumor or specific location in the body, for example the antigen to which the CPR binds may be an endogenous antigen. In some embodiments the target is not collagen. Alternatively, platelet receptors may be deleted to prevent cargo or toxin release in response to normal platelet activation signals. The multiple edits required to generate these progenitor cells are possible because the progenitor cells never enter the patient's body where there are concerns of continuous culture or genome instability. Only enucleated platelets are injected into the patient.

A. Engineering Megakaryocytes

In some embodiments, the engineered platelets described herein originate from genetically modified megakaryocytes. The genome of these megakaryocytes may include a knock-out of at least one, two, three, four, five, six, seven, eight, nine, or at least ten genes encoding an endogenous receptor, mediator protein, and/or signaling transduction protein. It will be clear that in some instances it may not be necessary to knock out or delete the entire gene. For example GP1b knockout results in abnormal platelets, however one can delete only the extracellular domain of the receptor (removing its ability to function) while retaining the intracellular domain, resulting in typical platelets that lack the ability to bind to von Willebrand factor the GP1b target). Accordingly in some embodiments, the disruptions, deletions or knockouts described herein are full disruptions, deletions or knockouts of the entire gene. In other embodiments, the disruptions, deletions and knockouts are disruptions deletions and functional knockouts i.e. disruption of the function of the protein, and in some embodiments the deletion is a deletion of the extracellular domain of the proteins.

Examples of genes that may be deleted from the megakaryocyte genome are shown in Table 3.

bus formation; recognition of secondary stimuli of thrombus formation; and release of secondary mediators of thrombus formation.

Recognition of primary stimuli of thrombus involves the platelets recognizing factors associated with exposed tissue that becomes exposed upon wounding, for example, recognizing the subendothelium. In typically circumstances, platelets are not exposed to subendothelium. Exposure of the subendothelium allows platelets to recognize ligands such as collagen, von Willebrand factor, fibronectin, thrombospondin via receptors on the platelet surface, such as GPIb/V/IX and GPVI (GP6), ITGA2B, integrins s $\alpha_{IIb}\beta_3$, $\alpha_2\beta_1$, $\alpha_5\beta_1$ and $\alpha_6\beta_1$. Accordingly, in some embodiments the genes encoding a protein involved in recognition of primary stimuli of thrombus formation include GPIb/V/IX and GPVI (GP6), ITGA2B, CLEC2, integrins s $\alpha_{IIb}\beta_3$, $\alpha_2\beta_1$, $\alpha_5\beta_1$ and $\alpha_6\beta_1$.

Once platelets have made contact with the exposed endothelium, for example via the interactions discussed above, the platelets release secondary messengers such as ADP, thrombin and $TxA_2$ which are detected by other platelets and which cause platelet aggregation at the wound site. In some embodiments, it is preferred if the ability of the platelets to recognize the secondary messengers is disrupted. It is not desirable if a platelet of the invention is targeted to wound site for example, rather than the intended target. Accordingly, in preferred embodiments the ability of the platelets to recognize the secondary messengers is disrupted. Receptors

TABLE 3

Potential genes for deletion

| Gene | Mediator or receptor? | Gene | Mediator or receptor? |
| --- | --- | --- | --- |
| Rab27a | Mediator | Factor XIII | mediator |
| HPS genes | Mediator | PF4 | mediator |
| integrin AIIbB3 | receptor | NAP2 (Nucleosome Assembly Protein 2) | mediator |
| GP1b-IX-V | receptor | Prothrombin | mediator |
| Par1 | receptor | High Molecular Weight Kininogens | mediator |
| Par4 | receptor | Plasminogen activator inhibitor 1 | mediator |
| P2Y1 | receptor | a2-antiplasmin | mediator |
| P2Y12 | receptor | plasminogen | mediator |
| IP | receptor | P-Selectin | mediator/receptor |
| TP | receptor | CXCL4 | mediator |
| TLR (many) | receptor | CXCL7 | mediator |
| GPV1 | receptor | FGF | mediator |
| a2B1 (type 1 collagen receptor) | receptor | EGF | mediator |
| GPIIbIIIA | | HGF | |
| CLEC-2 | receptor | IGF | |
| MyD88 (Myeloid Differentiation Primary Response 88) | signal transduction | Angipoetin | |
| Galphaq | signal transduction | Thromboxane synthase | mediator |
| LIMK1 | mediator | PAF | Mediator |
| vWF | mediator | cPLA2a | mediator |
| Fibrinogen | mediator | Thromospondin | |
| PDGF | mediator | CD40L | |
| VEGF | mediator | SgIII (Secretogranin III) | |
| Factor V | mediator | Endostatin | |
| Factor VIII | mediator | TGF-β (transforming growth factor beta) | |
| Factor XI | mediator | Talin1 | signal transduction |
| ANO6/TMEM16F | mediator | Kindlins | signal transduction |

The skilled person will appreciate that there are several pathways which should be disrupted to allow the production of a platelet with reduced thrombogenic potential. In some embodiments any one or more of the following three pathways are disrupted: recognition of primary stimuli of thrombus formation that are involved in this function include Par1, Par4, P2Y12, GPIb/V/IX, the Thromboxane receptor (TBXA2R), P2Y1, P2X1 and integrin $\alpha_{IIb}\beta_3$.

As mentioned above, once platelets have recognized the exposed tissue, they release secondary messengers to recruit other platelets to the site. Once a platelet of the invention has bound to a target, for example to a tumour antigen, it is not desirable for the platelet of the invention to then recruit other platelets to a target site and form a thrombus, for example a thrombus at a tumour site.

Accordingly, in preferred embodiments, the pathway by which the activated platelet releases the secondary messengers is disrupted. The pathway can include those proteins that are involved in the production and/or storage and/or release of the secondary mediators. Genes involved in this pathway include Cox1, HPS and thromboxane-A synthase (TBXAS1).

The skilled person will appreciate that a single gene can be involved in two or three of the above functions.

In some embodiments it is preferred if the megakaryocyte or progenitor thereof comprises a disruption or deletion of (e.g. a knockout of) at least one, two, three, four, five, six, seven, eight, nine, or at least ten genes encoding a protein involved in recognition of primary stimuli of thrombus formation; a protein involved in recognition of secondary mediators of thrombus formation; and/or a protein involved in the release of secondary mediators of thrombus formation.

It will be clear to the skilled person that by a protein involved in recognition of primary stimuli of thrombus we include the meaning of any protein that is involved in this process, for example includes the protein that is directly involved in contact with or recognition of primary stimuli of thrombus, and also genes that for example lead to the expression of those proteins that are directly involved in contact with or recognition of the primary stimuli of thrombus. The skilled person will understand which proteins are considered to be involved in recognition of primary stimuli. The key feature is that disruption of the proteins are that their disruption leads to a defect in the recognition of primary stimuli of thrombus. However, in some embodiments a protein involved in recognition of primary stimuli of thrombus includes only those proteins that directly make contact with the primary stimuli of thrombus.

By a protein involved in recognition of secondary mediators of thrombus formation we include those proteins that are directly involved in the contact with or recognition of secondar mediators of thrombus formation, as well as proteins that are indirectly involved in those processes, for example those proteins that are involved in the production of the proteins that are directly involved in the contact with or recognition of secondar mediators of thrombus formation. The skilled person will understand what is mean by proteins involved in recognition of secondary mediators of thrombus formation. The key feature of the proteins are that their disruption leads to a defect in the recognition of secondary mediators of thrombus formation. However, in some embodiments a protein involved in recognition of secondary mediators of thrombus formation includes only those proteins that make direct contact with the secondary mediators of thrombus formation.

By a protein involved in the release of secondary mediators of thrombus formation we include those proteins that are involved in the production and/or storage and/or release of the secondary mediators. The key feature of the proteins are that their disruption leads to a defect in the ultimate release of the secondary mediators. The defect may be in the production of the secondary mediators, the storage of the secondary mediators, and/or the actual release process.

In some embodiments the megakaryocyte or progenitor thereof comprises a disruption or deletion of at least:
  one gene that encodes a protein involved in recognition of primary stimuli of thrombus formation;
  one gene that encodes a protein involved in recognition of secondary mediators of thrombus formation; and
  one gene that encodes a protein involved in the release of secondary mediators of thrombus formation;

In some embodiments the megakaryocyte or progenitor thereof comprises a disruption or deletion of at least:
  two genes that encode a protein involved in recognition of primary stimuli of thrombus formation;
  two genes that encode a protein involved in recognition of secondary mediators of thrombus formation; and
  two genes that encode a protein involved in the release of secondary mediators of thrombus formation:

In some embodiments the megakaryocyte or progenitor thereof comprises a disruption or deletion of at least:
  three genes that encode a protein involved in recognition of primary stimuli of thrombus formation;
  three genes that encode a protein involved in recognition of secondary mediators of thrombus formation; and
  three genes that encode a protein involved in the release of secondary mediators of thrombus formation.

Genes that are considered to encode a protein involved in recognition of primary stimuli of thrombus formation include GPIb/V/IX and GPVI (GP6), ITGA2B, CLEC2, integrins s $\alpha_{IIb}\beta_3$, $\alpha_2\beta_1$, $\alpha_5\beta_1$ and $\alpha_6\beta_1$, or optionally include GPVI and ITGA2B.

Genes that are considered to encode a protein involved in recognition of secondary stimuli of thrombus formation include Par1, Par4, P2Y12, GPIb/V/IX, the Thromboxane receptor (TBXA2R), P2Y1, P2X1 and integrin $\alpha_{IIb}\beta_3$ or optionally include Par1, Par4 and P2Y12.

Genes that are considered to a protein involved in release of secondary mediators of thrombus formation include Cox1, HPS and thromboxane-A synthase (TBXAS1), or optionally include Cox1 and HPS.

In some embodiments
  the at least one, two or three genes that encode a protein involved in recognition of primary stimuli of thrombus formation are selected from the group consisting of: GPIb/V/IX and GPVI (GP6), ITGA2B, CLEC2, integrins s $\alpha_{IIb}\beta_3$, $\alpha_2\beta_1$, $\alpha_5\beta_1$ and $\alpha_6\beta_1$, or from the group consisting of GPVI and ITGA2B;
  the at least one, two or three that encode a protein involved in recognition of secondary mediators of thrombus formation are selected from the group consisting of Par1, Par4, P2Y12, GPIb/V/IX, the Thromboxane receptor (TBXA2R), P2Y1, P2X1 and integrin $\alpha_{IIb}\beta3$ or from the group consisting of Par1, Par4 and P2Y12; and/or
  the at least one, two or three genes that encode a protein involved in the release of secondary mediators of thrombus formation are selected from the group consisting of Cox1, HPS and thromboxane-A synthase (TBXAS1) or from the group consisting of Cox1 and HPS.

In a preferred embodiment, the genetically modified megakaryocyte or progenitor thereof has a disruption or deletion in each of the following genes:
  GPVI, ITGA2B, Par1, Par4, P2Y12, Cox1 and HPS.

For example the genetically modified megakaryocyte or progenitor thereof may comprise a knockout of each of GPVI, ITGA2B, Par1, Par4, P2Y12, Cox1 and HPS.

In some embodiments, expression of the genes in Table 3 may be altered or "knocked-out" using a CRISPR/Cas system, zinc finger nucleases, transcription activator-like effector nucleases (TALENs), a RNA interference construct (RNAi) (e.g., small interfering RNA (siRNA) or microRNA (miRNA)), or a short hairpin RNA (shRNA).

The effects of knock-out of a gene in a megakaryocyte on the resulting engineered platelet may be varied. For example, RAB27a (RAS oncogene) and HPS (haptoglobin) genes function in dense granule loading and formation, respectively. Knock-out or deletion of Rab27a may result in engineered platelets with no dense granule mediators but with otherwise normal platelet biology. Knock-out or deletion of HPS genes may result in engineered platelets containing no dense granules. Knock-out or deletion of AIIbB3 or GP1b-IX-V may result in failure of the platelets to aggregate with each other by decreasing interaction between the platelet and von Willebrand factors (vWF) after activation. Further, AIIbB3 is also involved in inside-out signaling to increase the affinity of the integrin for fibrinogen (See, Durrant, Blood. 2017 Oct. 5; 130(14): 1607-1619). Knock-out or deletion of IP (PGI2R or prostaglandin 12 receptor) may result in negative regulation of prostaglandin. Knock-out or deletion of TP (TxA2R or Thromboxane A2 Receptor) may result in reduction of recruitment of additional platelets on activation to stimulate clotting.

GPVI (ITAM receptor) has been observed to still be stimulated in G-protein alpha-q (Galphaq) knockout mice. Conversely, ITAM agonists, such as collagen, induce release of G-protein-coupled receptors (GPCR agonists), such as ADP and thromboxane A2 receptor (TXA2), thus indirectly activating phospholipase C (PLC) through the Gq pathway. Further, Galphaq is active for proper function for thrombin, ADP, 5-hydroxytryptamine (5HT), PAF, and thromboxane A (TXA).

Knock-out or deletion of P-selectin, thromboxane synthase, and platelet activating factor (PAF) may result in failure of platelet aggregation once activated. Knock-out or deletion of LIM Domain Kinase 1 (LIMK1) will likely reduce TxA2 synthesis. CXCL4 (C-X-C motif chemokine ligand 4) and CXCL7 (C-X-C motif chemokine ligand 7) are chemokines; therefore, knock-out or deletion of the gene would likely interfere in at least one signaling pathway. Talin1 and kindlins function in signal transduction to allow integrins to enter a sensitive state.

Knock-out or deletion of ANO6/TMEM16F disrupts the platelets ability to expose phosphatidylserine on platelet activation. Phosphatidlyserine is a membrane lipid which is usually kept on the cytoplasmic face of the platelet. On platelet activation, calcium influx triggers phosphatidylserine exposure on the outside of the platelet via ANO6/TMEM16F, where it acts to catalyse the production of active thrombin in combination with clotting factors. Thus, knock-out of TMEM16F prevents phosphatidylserine exposure and thus would decrease platelet thrombogenicity. This is exemplified by Scott's syndrome patients, who feature ANO6 mutations and clinically have increased risk of bleeding.

B. Chimeric Platelet Receptors (CPR)

In some embodiments, the engineered platelets described herein may include alterations to the endogenous platelet receptors. Alterations include, but are not limited to, deletions or additions or entire receptors or domains of these receptors, or combinations with domains from non-endogenous receptors to result in differences in the behavior of an engineered platelet compared to a platelet without the alteration. To stimulate activation of platelets, domains from an immunoreceptor tyrosine-based activation motif (ITAM) receptor may be used in a chimeric platelet receptor. To inhibit activation of platelets immunoreceptor tyrosine-based inhibition motif (ITIM). It will be clear to the skilled person that domains from an ITAM receptor that is not typically expressed in platelets will still function in the invention, since the ITAM domains are still capable of activating the same downstream signaling components as ITAM receptors are endogenously found in platelets.

1. Endogenous Platelet Receptors

In some embodiments, platelets may be redirected to degranulate by an antigen, rather than collagen. ITIM containing receptors inhibit platelet activation to directly counteract ITAM receptor activation. CEACAM-1, PECAM-1, and G6b-B are ITIM containing receptors. G6b-B clustering by antibody inhibits platelet activation through GPVI and CLEC-2 as shown in Mori et al. "G6b-B inhibits constitutive and agonist-induced signaling by glycoprotein VI and CLEC-2". JBC, 2008, which is hereby incorporated by reference in its entirety. Adding a chimeric "off" receptor may be used to improve specificity of the synthetic platelets described herein. An engineered chimeric immunoreceptor tyrosine-based inhibition motif (ITIM) receptor would allow logic gate construction.

Alternatively, ITAM receptors mediate platelet activation and stimulate an immune response. Glycoprotein VI (GPVI) binds to collagen and is a central mediator of platelet activation. It features extracellular IgG like domains, and the internal tyrosine kinase signaling pathway is triggered by receptor clustering through the Fc receptor (FcR) gamma chain. In certain embodiments, the intracellular domain is retained and the extracellular domain is swapped to target an antigen. For example, in some embodiments, the chimeric platelet receptor comprises an intracellular domain that stimulates platelets, but does not comprise the corresponding extracellular domain. For example in some embodiments the extracellular targeting domain of the receptor is heterologous to the intracellular domain of the receptor. By heterologous extracellular targeting domain we mean that the extracellular domain is not the usual extracellular domain associated with the intracellular domain. For instance, in embodiments where the intracellular domain comprises the intracellular domain of Glycoprotein VI (GPVI), the extra cellular domain is not the extracellular domain of Glycoprotein VI (GPVI), the domains are heterologous to one another.

Alternatively, C-type lectinlike receptor 2 (CLEC-2) or Fc Fragment of IgG Receptor IIa (FCgR2A) may be altered in a similar way. In other embodiments, where the intracellular domain comprises the intracellular domain of C-type lectin-like receptor 2 (CLEC-2), the extracellular targeting domain is not the extracellular domain of CLEC-2; and in some embodiments where the intracellular domain comprises Fc Fragment of IgG Receptor IIa (FCgR2A), the extracellular targeting domain does not comprise the extracellular domain of FCgR2A. It is clear that the extracellular targeting domain may be a domain that is native to the subject, but is not native to the intracellular domain.

It will be clear then that in some embodiments the CPR is not a naturally occurring protein.

CLEC-2 binds to podoplanin (associated with tumors) and triggers platelet activation in response to snake venom rhodocytin and elicits aggregation of platelets through activation of Src and Syk non-receptor tyrosine kinases in the internal tyrosine kinase signaling pathway triggered by receptor clustering through signaling proteins lymphocyte cytosolic protein 2 or SH2 domain containing leukocyte protein of 76 kDa (SLP-76) and 1-phosphatidylinositol-4, 5-bisphosphate phosphodiesterase gamma-2 (PLCγ2) (See, Fu et al. Blood, 127(13):1629-30, 2016, which is hereby incorporated by reference in its entirety).

FCgr2A binds to Fc region of antibodies and triggers platelet activation in response to opsonized bacteria through signaling protein Syk non-receptor tyrosine kinase. The internal tyrosine kinase signaling pathway is triggered by receptor clustering.

In some embodiments, additional ITAM receptors may be inserted into the genome of a megakaryocyte to enhance T cell signaling and stimulate an immune response. T cell receptors (TCRs) recognize antigens bound in the major histocompatibility complex (MHC) (See, James et al. Sci. Signal. 11, eaan1088 (2018), which is hereby incorporated by reference in its entirety). ITAMs on the TCRs convert the action of binding and recognition into an intracellular signal (Ibid). Inserting additional ITAMs into chimeric TCRs was observed to scale linearly with the number of ITAM receptors and decreasing or knocking-out the number of ITAM receptors was observed to inhibit T cell development by impairing thymocyte lineage commitment (Ibid).

In some embodiments, a CPR may include one or more domains or portions thereof from one or more immunoreceptor tyrosine-based activation motif (ITAM) receptors. Non-limiting examples of ITAM receptors include glycoprotein VI platelet (GPVIA), high affinity immunoglobulin epsilon receptor subunit gamma (FCERG), C-Type lectin domain family 1 (CLEC1), and Fc fragment of IgG receptor 11 (FCGR2).

In one embodiment, domains of ITAM receptors FCERG (SEQ ID NO: 1), CLEC1 (SEQ ID NO: 6), FCGR2 (SEQ ID NO: 10), and/or GPVIA (SEQ ID NO: 15) shown in Table 4 may be combined for expression in a megakaryocyte resulting in a CPR in the engineered platelet.

In one embodiment, domains of ITAM receptors may be combined with T cell receptor domains to form chimeric ITAM receptors which are also referred to as chimeric platelet receptors. These chimeric receptors may be combined for expression in a megakaryocyte resulting in a CPR in the engineered platelet. Non-limiting examples of chimeric ITAM receptors for FCERG (SEQ ID NO: 20), CLEC1 (SEQ ID NO: 21), FCGR2 (SEQ ID NO: 22) and GPVIA (SEQ ID NO: 23) are shown in Table 4.

SEQ ID NO: 1 is an embodiment of a complete FCERG receptor. SEQ ID NO: 2 is an embodiment of the signal peptide of FCERG. SEQ ID NO: 3 is an embodiment of the extracellular domain of FCERG. SEQ ID NO: 4 is an embodiment of the transmembrane domain of FCERG. SEQ ID NO: 5 is an embodiment of the cytoplasmic domain of FCERG. SEQ II) NO: 6 is an embodiment of the ITAM receptor of CLEC1. SEQ ID NO: 7 is an embodiment of the cytoplasmic domain of CLEC 1. SEQ ID NO: 8 is an embodiment of the transmembrane domain of CLEC 1. SEQ ID NO: 9 is an embodiment of the extracellular domain of CLEC1. SEQ ID NO: 10 is an embodiment of the ITAM receptor of FCGR2. SEQ ID NO: 11 is an embodiment of the signal peptide of FCGR2. SEQ ID NO: 12 is an embodiment of the extracellular domain of FCGR2. SEQ ID NO: 13 is an embodiment of the transmembrane domain of FCGR2. SEQ ID NO: 14 is an embodiment of the cytoplasmic domain of FCGR2. SEQ ID NO: 15 is an embodiment of the ITAM receptor of GPVIA. SEQ ID NO: 16 is an embodiment of the signal peptide of GPVIA. SEQ ID NO: 17 is an embodiment of the extracellular domain of GPVIA. SEQ ID NO: 18 is an embodiment of the transmembrane domain of GPVIA. SEQ ID NO: 19 is an embodiment of the cytoplasmic domain of GPVIA.

SEQ ID NO: 20 is an embodiment of a chimeric ITAM receptor based on FCERG. SEQ ID NO: 21 is an embodiment of a chimeric ITAM receptor based on CLEC1. SEQ ID NO: 22 is an embodiment of a chimeric ITAM receptor based on FCGR2. SEQ ID NO: 23 is an embodiment of a chimeric ITAM receptor based on GPVIA.

In some embodiments, a CPR may include one or more domains or portions thereof from one or more immunoreceptor tyrosine-based inhibition motif (ITIM) receptors. Non-limiting examples of ITIM receptors include platelet and endothelial cell adhesion molecule 1 (PECAM1), triggering receptor expressed on myeloid cells like 1 (TLT1), leukocyte immunoglobulin like receptor B2 (LILRB2), car-

TABLE 4

ITAM receptors and ITAM chimeric receptors

| Symbol | Regions | Sequence Identifier |
|---|---|---|
| FCERG | Signal Peptide (SEQ ID NO: 2); EC Domain (SEQ ID NO: 3); TM Domain (SEQ ID NO: 4); CytoDomain (SEQ ID NO: 5); stop | 1 |
| CLEC1 | CytoDomain (SEQ ID NO: 7); TM Domain (SEQ ID NO: 8); EC Domain (SEQ ID NO: 9); stop | 6 |
| FCGR2 | Signal Peptide (SEQ ID NO: 11); EC Domain (SEQ ID NO: 12); TM Domain (SEQ ID NO: 13); CytoDomain (SEQ ID NO: 14); stop | 10 |
| GPVIA | Signal Peptide (SEQ ID NO: 16); EC Domain (SEQ ID NO: 17); TM Domain (SEQ ID NO: 18); CytoDomain (SEQ ID NO: 19); stop | 15 |
| FCERG (chimeric) | Signal Peptide (SEQ ID NO: 2); Fv1HChain domain (SEQ ID NO: 50); Whitlow_Linker (SEQ ID NO: 49); Fv1_Lchain (SEQ ID NO: 48); Modified_Hinge_IGg4 (SEQ ID NO: 51); EC Domain (SEQ ID NO: 3); TM Domain (SEQ ID NO: 4); CytoDomain (SEQ ID NO: 5); stop | 20 |
| CLEC1 (chimeric) | CytoDomain (SEQ ID NO: 7); TM Domain (SEQ ID NO: 8); EC Domain (SEQ ID NO: 53); Modified_Hing_IGg4 (SEQ ID NO: 51); Fv1HChain (SEQ ID NO: 50); Whitlow_Linker (SEQ ID NO: 49); Fv1_Lchain (SEQ ID NO: 48); stop | 21 |
| FCGR2 (chimeric) | Signal Peptide (SEQ ID NO: 11); Fv1HChain (SEQ ID NO: 50); Whitlow_Linker (SEQ ID NO: 49); Fv1_Lchain (SEQ ID NO: 48); Modified_hinge_IGg4 (SEQ ID NO: 51); EC Domain (SEQ ID NO: 54); TM Domain (SEQ ID NO: 13); CytoDomain (SEQ ID NO: 14); stop | 22 |
| GPVIA (chimeric) | Signal Peptide (SEQ ID NO: 16); Fv1HChain (SEQ ID NO: 50); Whitlow_linker (SEQ ID NO: 49); Fv1_Lchain (SEQ ID NO: 48); Modified_hinge_IGg4 (SEQ ID NO: 51); EC Domain (SEQ ID NO: 55); TM Domain (SEQ ID NO: 18); CytoDomain (SEQ ID NO: 19); stop | 23 | cinoembryonic antigen related cell adhesion molecule 1 (CEACAM1), megakaryocyte and platelet inhibitory receptor G6b (G6b-B).

In one embodiment, domains of ITIM receptors LILRB2 (SEQ ID NO: 34), PECAM1 (SEQ ID NO: 38), TLT1 (SEQ ID NO: 43), and CEACAM1 (SEQ ID NO: 24) shown in Table 5 may be combined for expression in a megakaryocyte resulting in a CPR in the engineered platelet.

In one embodiment, domains of ITIM receptors may be combined with T cell receptor domains to form chimeric ITIM receptors which are also referred to as chimeric platelet receptors. These chimeric receptors may be combined for expression in a megakaryocyte resulting in a CPR in the engineered platelet.

TABLE 5

ITIM receptors

| Symbol | Regions | Sequence Identifier |
| --- | --- | --- |
| LILRB2 | Signal Peptide (SEQ ID NO: 35); EC Domain (SEQ ID NO: 36); TM Domain (SEQ ID NO: 37); CytoDomain (SEQ ID NO: 52); stop | 34 |
| PECAM1 | Signal Peptide (SEQ ID NO: 39); EC Domain (SEQ ID NO: 40); TM Domain (SEQ ID NO: 41); CytoDomain (SEQ ID NO: 42); stop | 38 |
| TLT1 | Signal Peptide (SEQ ID NO: 44); EC Domain (SEQ ID NO: 45); TM Domain (SEQ ID NO: 46); CytoDomain (SEQ ID NO: 47); stop | 43 |
| CEACAM1 | Signal Peptide (SEQ ID NO: 25); EC Domain (SEQ ID NO: 26); TM Domain (SEQ ID NO: 27); CytoDomain (SEQ ID NO: 28); stop | 24 |

SEQ ID NO: 24 is an embodiment of the ITIM receptor of CEACAM1. SEQ ID NO: 25 is an embodiment of the signal peptide of CEACAM1. SEQ ID NO: 26 is an embodiment of the extracellular domain of CEACAM1. SEQ ID NO: 27 is an embodiment of the transmembrane domain of CEACAM1. SEQ ID NO: 28 is an embodiment of the cytoplasmic domain of CEACAM1. SEQ ID NO: 29 is an embodiment of the ITIM receptor of G6b-B. SEQ ID NO: 30 is an embodiment of the signal peptide of G6b-B. SEQ ID NO: 31 is an embodiment of the extracellular domain of G6b-B. SEQ ID NO: 32 is an embodiment of the transmembrane domain of G6b-B. SEQ ID NO: 33 is an embodiment of the cytoplasmic domain of G6b-B. SEQ ID NO: 34 is an embodiment of the ITIM receptor of LILRB2. SEQ ID NO: 35 is an embodiment of the signal peptide of LILRB2. SEQ ID NO: 36 is an embodiment of the extra domain of LILRB2. SEQ ID NO: 37 is an embodiment of the transmembrane domain of LILRB2. SEQ ID NO: 38 is an embodiment of the ITIM receptor of PECAM1. SEQ ID NO: 39 is an embodiment of the signal peptide of PECAM1. SEQ ID NO: 40 is an embodiment of the extracellular domain of PECAM1. SEQ ID NO: 41 is an embodiment of the transmembrane domain of PECAM1. SEQ ID NO: 42 is an embodiment of the cytoplasmic domain of PECAM1. SEQ ID NO: 43 is an embodiment of the ITIM receptor of TLT1. SEQ ID NO: 44 is an embodiment of the signal peptide of TLT1. SEQ ID NO: 45 is an embodiment of the extracellular domain of TLT1. SEQ ID NO: 46 is an embodiment of the transmembrane domain of TLT1. SEQ ID NO: 47 is an embodiment of the cytoplasmic domain of TLT1.

a. Domains

A CPR may comprise any combination of a signal peptide, an extracellular domain, a transmembrane domain, a cytoplasmic domain, or linker or targeting domain.

In one embodiment, a CPR may comprise a signal peptide selected from Table 6.

TABLE 6

Signal peptides

| Sequence Identifier | Description |
| --- | --- |
| 2 | FCERG Signal Peptide |
| 11 | FCGR2 Signal Peptide |
| 16 | GPVIA Signal Peptide |
| 25 | CEACAM1 Signal Peptide |
| 30 | G6b-B Signal Peptide |
| 35 | LILRB2 Signal Peptide |
| 39 | PECAM1 Signal Peptide |
| 44 | TLT1 Signal Peptide |

In one embodiment, a CPR comprises at least one FCERG signal peptide. As a non-limiting example, the FCERG signal peptide is SEQ ID NO: 2.

In one embodiment, a CPR comprises at least one FCGR2 signal peptide. As a non-limiting example, the FCGR2 signal peptide is SEQ ID NO: 11.

In one embodiment, a CPR comprises at least one GPVIA signal peptide. As a non-limiting example, the GPVIA signal peptide is SEQ ID NO: 16.

In one embodiment, a CPR comprises at least one CEACAM1 signal peptide. As a non-limiting example, the CEACAM1 signal peptide is SEQ ID NO: 25.

In one embodiment, a CPR comprises at least one G6b-B signal peptide. As a non-limiting example, the G6b-B signal peptide is SEQ ID NO: 30.

In one embodiment, a CPR comprises at least one LILRB2 signal peptide. As a non-limiting example, the LILRB2 signal peptide is SEQ ID NO: 35.

In one embodiment, a CPR comprises at least one PECAM1 signal peptide. As a non-limiting example, the PECAM1 signal peptide is SEQ ID NO: 39.

In one embodiment, a CPR comprises at least one TLT1 signal peptide. As a non-limiting example, the TLT1 signal peptide is SEQ ID NO: 44.

The CPR may include a portion of the signal peptide in Table 6 or a signal peptide known in the art. The portion may be 10-30, 10-15, 10-20, 10-25, 15-20, 15-25, 15-30, 20-25, or 20-30, nucleotides of any of the sequences in Table 6 such as, but not limited to, SEQ ID NO: 2, 11, 16, 25, 30, 35, 39, and 44. The portion may be 10, 11, 12, 13, 14, 15, 16, 17, 18, 19, 20, 21, 22, 23, 24, 25, 26, 27, 28, 29, or 30 nucleotides of any of the sequences in Table 7 such as, but not limited to, SEQ ID NO: 2, 11, 16, 25, 30, 35, 39, and 44.

A CPR may comprise an extracellular (EC) domain or portion thereof selected from Table 7.

TABLE 7

Extracellular domain

| Sequence Identifier | Description |
| --- | --- |
| 3 | FCERG EC Domain |
| 9 | CLEC1 EC Domain |
| 53 | CLEC1 EC Domain |
| 12 | FCGR2 EC Domain |
| 54 | FCGR2 EC Domain |
| 17 | GPVIA EC Domain |
| 55 | GPVIA EC Domain |
| 26 | CEACAM1 EC Domain |
| 31 | G6b-B EC Domain |
| 36 | LILRB2 EC Domain |

TABLE 7-continued

| Extracellular domain | |
|---|---|
| Sequence Identifier | Description |
| 40 | PECAM1 EC Domain |
| 45 | TLT1 EC Domain |

In one embodiment, a CPR comprises at least one FCERG EC domain. As a non-limiting example, the FCERG EC domain is SEQ ID NO: 3.

In one embodiment, a CPR comprises at least one CLEC1 EC domain. As a non-limiting example, the CLEC1 EC domain is SEQ ID NO: 9.

In one embodiment, a CPR comprises at least one CLEC1 EC domain. As a non-limiting example, the CLEC1 EC domain is SEQ ID NO: 53.

In one embodiment, a CPR comprises at least one FCGR2 EC domain. As a non-limiting example, the FCGR2 EC domain is SEQ ID NO: 12.

In one embodiment, a CPR comprises at least one FCGR2 EC domain. As a non-limiting example, the FCGR2 EC domain is SEQ ID NO: 54.

In one embodiment, a CPR comprises at least one GPVIA EC domain. As a non-limiting example, the GPVIA EC domain is SEQ ID NO: 17.

In one embodiment, a CPR comprises at least one GPVIA EC domain. As a non-limiting example, the GPVIA EC domain is SEQ ID NO: 55.

In one embodiment, a CPR comprises at least one CEACAM1 EC domain. As a non-limiting example, the CEACAM1 EC domain is SEQ ID NO: 26.

In one embodiment, a CPR comprises at least one G6b-B EC domain. As a non-limiting example, the G6b-B EC domain is SEQ ID NO: 31.

In one embodiment, a CPR comprises at least one LILRB2 EC domain. As a non-limiting example, the LILRB2 EC domain is SEQ ID NO: 36.

In one embodiment, a CPR comprises at least one PECAM1 EC domain. As a non-limiting example, the PECAM1 EC domain is SEQ ID NO: 40.

In one embodiment, a CPR comprises at least one TLT1 EC domain. As a non-limiting example, the TLT1 EC domain is SEQ ID NO: 45.

The CPR may include a portion of the EC domain in Table 7 or a EC domain known in the art. The portion may be 10-30, 10-15, 10-20, 10-25, 15-20, 15-25, 15-30, 20-25, or 20-30, nucleotides of any of the sequences in Table 7 such as, but not limited to, SEQ ID NO: 3, 9, 12, 17, 26, 31, 36, 40, and 45. The portion may be 10, 11, 12, 13, 14, 15, 16, 17, 18, 19, 20, 21, 22, 23, 24, 25, 26, 27, 28, 29, or 30 nucleotides of any of the sequences in Table 7 such as, but not limited to, SEQ ID NO: 3, 9, 12, 17, 26, 31, 36, 40, and 45.

In one embodiment, CPR may include a portion of the FCERG EC domain in Table 7. The portion may be 10-30, 10-15, 10-20, 10-25, 15-20, 15-25, 15-30, 20-25, or 20-30, nucleotides of SEQ ID NO: 3. The portion may be 10, 11, 12, 13, 14, 15, 16, 17, 18, 19, 20, 21, 22, 23, 24, 25, 26, 27, 28, 29, or 30 nucleotides of SEQ ID NO: 3.

In one embodiment, CPR may include a portion of the CLEC1 EC domain in Table 7. The portion may be 10-30, 10-15, 10-20, 10-25, 15-20, 15-25, 15-30, 20-25, or 20-30, nucleotides of SEQ ID NO: 9. The portion may be 10, 11, 12, 13, 14, 15, 16, 17, 18, 19, 20, 21, 22, 23, 24, 25, 26, 27, 28, 29, or 30 nucleotides of SEQ ID NO: 9.

In one embodiment, CPR may include a portion of the FCERG EC domain in Table 7 that is 10-15 nucleotides in length. The portion may be 10, 11, 12, 13, 14, or 15 nucleotides of SEQ ID NO: 3.

In one embodiment, CPR may include a portion of the CLEC1 EC domain in Table 7 that is 10-15 nucleotides in length. The portion may be 10, 11, 12, 13, 14, or 15 nucleotides of SEQ ID NO: 9 or 53. As a non-limiting example, a portion of SEQ ID NO: 9 may be SEQ ID NO: 53.

In one embodiment, CPR may include a portion of the CLEC1 EC Domain in Table 7. The portion may be 10-30, 10-15, 10-20, 10-25, 15-20, 15-25, 15-30, 20-25, or 20-30, nucleotides of SEQ ID NO: 53. The portion may be 10, 11, 12, 13, 14, 15, 16, 17, 18, 19, 20, 21, 22, 23, 24, 25, 26, 27, 28, 29, or 30 nucleotides of SEQ ID NO: 53.

In one embodiment, CPR may include a portion of the FCGR2 EC Domain in Table 7. The portion may be 10-30, 10-15, 10-20, 10-25, 15-20, 15-25, 15-30, 20-25, or 20-30, nucleotides of SEQ ID NO: 12. The portion may be 10, 11, 12, 13, 14, 15, 16, 17, 18, 19, 20, 21, 22, 23, 24, 25, 26, 27, 28, 29, or 30 nucleotides of SEQ ID NO: 12.

In one embodiment, CPR may include a portion of the FCGR2 EC Domain in Table 7. The portion may be 10-30, 10-15, 10-20, 10-25, 15-20, 15-25, 15-30, 20-25, or 20-30, nucleotides of SEQ ID NO: 54. The portion may be 10, 11, 12, 13, 14, 15, 16, 17, 18, 19, 20, 21, 22, 23, 24, 25, 26, 27, 28, 29, or 30 nucleotides of SEQ ID NO: 54.

In one embodiment, CPR may include a portion of the GPVIA EC Domain in Table 7. The portion may be 10-30, 10-15, 10-20, 10-25, 15-20, 15-25, 15-30, 20-25, or 20-30, nucleotides of SEQ ID NO: 17. The portion may be 10, 11, 12, 13, 14, 15, 16, 17, 18, 19, 20, 21, 22, 23, 24, 25, 26, 27, 28, 29, or 30 nucleotides of SEQ ID NO: 17.

In one embodiment, CPR may include a portion of the GPVIA EC Domain in Table 7. The portion may be 10-30, 10-15, 10-20, 10-25, 15-20, 15-25, 15-30, 20-25, or 20-30, nucleotides of SEQ ID NO: 55. The portion may be 10, 11, 12, 13, 14, 15, 16, 17, 18, 19, 20, 21, 22, 23, 24, 25, 26, 27, 28, 29, or 30 nucleotides of SEQ ID NO: 55.

In one embodiment, CPR may include a portion of the CEACAM1 EC Domain in Table 7. The portion may be 10-30, 10-15, 10-20, 10-25, 15-20, 15-25, 15-30, 20-25, or 20-30, nucleotides of SEQ ID NO: 26. The portion may be 10, 11, 12, 13, 14, 15, 16, 17, 18, 19, 20, 21, 22, 23, 24, 25, 26, 27, 28, 29, or 30 nucleotides of SEQ ID NO: 26.

In one embodiment, CPR may include a portion of the G6b-B EC Domain in Table 7. The portion may be 10-30, 10-15, 10-20, 10-25, 15-20, 15-25, 15-30, 20-25, or 20-30, nucleotides of SEQ ID NO: 31. The portion may be 10, 11, 12, 13, 14, 15, 16, 17, 18, 19, 20, 21, 22, 23, 24, 25, 26, 27, 28, 29, or 30 nucleotides of SEQ ID NO: 31.

In one embodiment, CPR may include a portion of the LILRB2 EC Domain in Table 7. The portion may be 10-30, 10-15, 10-20, 10-25, 15-20, 15-25, 15-30, 20-25, or 20-30, nucleotides of SEQ ID NO: 36. The portion may be 10, 11, 12, 13, 14, 15, 16, 17, 18, 19, 20, 21, 22, 23, 24, 25, 26, 27, 28, 29, or 30 nucleotides of SEQ ID NO: 36.

In one embodiment, CPR may include a portion of the PECAM1 EC Domain in Table 7 The portion may be 10-30, 10-15, 10-20, 10-25, 15-20, 15-25, 15-30, 20-25, or 20-30, nucleotides of SEQ ID NO: 40. The portion may be 10, 11, 12, 13, 14, 15, 16, 17, 18, 19, 20, 21, 22, 23, 24, 25, 26, 27, 28, 29, or 30 nucleotides of SEQ ID NO: 40.

In one embodiment, CPR may include a portion of the TLT1 EC Domain in Table 7. The portion may be 10-30, 10-15, 10-20, 10-25, 15-20, 15-25, 15-30, 20-25, or 20-30, nucleotides of SEQ ID NO: 45. The portion may be 10, 11, 12, 13, 14, 15, 16, 17, 18, 19, 20, 21, 22, 23, 24, 25, 26, 27, 28, 29, or 30 nucleotides of SEQ ID NO: 45.

A CPR may comprise a transmembrane (TM) domain selected from Table 8.

TABLE 8

| Transmembrane domain | |
|---|---|
| Sequence Identifier | Description |
| 4 | FCERG TM Domain |
| 8 | CLEC1 TM Domain |
| 13 | FCGR2 TM Domain |
| 18 | GPVIA TM Domain |
| 27 | CEACAM1 TM Domain |
| 32 | G6b-B TM Domain |
| 37 | LILRB2 TM Domain |
| 41 | PECAM1 TM Domain |
| 46 | TLT1 TM Domain |

In one embodiment, a CPR comprises at least one FCERG TM Domain. As a non-limiting example, the FCERG TM Domain is SEQ ID NO: 4.

In one embodiment, a CPR comprises at least one CLEC1 TM Domain. As a non-limiting example, the CLEC1 TM Domain is SEQ ID NO: 8.

In one embodiment, a CPR comprises at least one FCGR2 TM Domain. As a non-limiting example, the FCGR2 TM Domain is SEQ ID NO: 13.

In one embodiment, a CPR comprises at least one GPVIA TM Domain. As a non-limiting example, the GPVIA TM Domain is SEQ ID NO: 18.

In one embodiment, a CPR comprises at least one CEACAM1 TM Domain. As a non-limiting example, the CEACAM1 TM Domain is SEQ ID NO: 27.

In one embodiment, a CPR comprises at least one G6b-B TM Domain. As a non-limiting example, the G6b-B TM Domain is SEQ ID NO: 32.

In one embodiment, a CPR comprises at least one LILRB2 TM Domain. As a non-limiting example, the LILRB2 TM Domain is SEQ ID NO: 37.

In one embodiment, a CPR comprises at least one PECAM1 TM Domain. As a non-limiting example, the PECAM1 TM Domain is SEQ ID NO: 41.

In one embodiment, a CPR comprises at least one TLT1 TM Domain. As a non-limiting example, the TLT1 TM Domain is SEQ ID NO: 46.

A CPR may comprise a cytoplasm (cyto) domain selected from Table 9.

TABLE 9

| Cytoplasm domain | |
|---|---|
| Sequence Identifier | Description |
| 5 | FCERG CytoDomain |
| 7 | CLEC1 CytoDomain |
| 14 | FCGR2 CytoDomain |
| 19 | GPVIA CytoDomain |
| 28 | CEACAM1 CytoDomain |
| 33 | G6b-B CytoDomain |
| 52 | LILRB2 CytoDomain |
| 42 | PECAM1 CytoDomain |
| 47 | TLT1 CytoDomain |

In one embodiment, a CPR comprises at least one FCERG CytoDomain. As a non-limiting example, the FCERG CytoDomain is SEQ ID NO: 5.

In one embodiment, a CPR comprises at least one CLEC1 CytoDomain. As a non-limiting example, the CLEC1 CytoDomain is SEQ ID NO: 7.

In one embodiment, a CPR comprises at least one FCGR2 CytoDomain. As a non-limiting example, the FCGR2 CytoDomain is SEQ ID NO: 14.

In one embodiment, a CPR comprises at least one GPVIA CytoDomain. As a non-limiting example, the GPVIA CytoDomain is SEQ ID NO: 19.

In one embodiment, a CPR comprises at least one CEACAM1 CytoDomain. As a non-limiting example, the CEACAM1 CytoDomain is SEQ ID NO: 28.

In one embodiment, a CPR comprises at least one G6b-B CytoDomain. As a non-limiting example, the G6b-B CytoDomain is SEQ ID NO: 33.

In one embodiment, a CPR comprises at least one LILRB2 CytoDomain. As a non-limiting example, the LILRB2 CytoDomain is SEQ ID NO: 52.

In one embodiment, a CPR comprises at least one PECAM1 CytoDomain. As a non-limiting example, the PECAM1 CytoDomain is SEQ ID NO: 42.

In one embodiment, a CPR comprises at least one TLT1 CytoDomain. As a non-limiting example, the TLT1 CytoDomain is SEQ ID NO: 47.

Genes encoding fusion peptides, targeting domain, or linking protein may be added to the genome of the megakaryocyte as shown in Table 10, such as the L chain of variable fragment 1 (Fv1_Lchain) with a nucleic acid sequence of SEQ ID NO: 48 or an improved linker from a single-chain variable fragment with reduced aggregation and enhanced proteolytic stability (Whitlow_linker) with a nucleic acid sequence of SEQ ID NO: 49. Alternatively, at least a portion of an antibody may be added to the genome of the megakaryocyte for expression in a resulting platelet, such as a kappa light chain of an anti-human B cell CD19 antibody (F1HChain_CD19FMC63) with a nucleic acid sequence of SEQ ID NO: 50 and a modified IGg4 hinge region with a nucleic acid sequence of SEQ ID NO: 51 also shown in Table 10.

In some embodiments, a CPR comprises at least one domain selected from Tables 4-9 and a linker and/or targeting domains selected from Table 10.

TABLE 10

| Linkers and Targeting Domains | |
|---|---|
| Sequence Identifier | Description |
| 48 | Fv1_Lchain (Light Chain) |
| 49 | Whitlow_linker (Linker) |
| 50 | Fv1HChain_CD19FMC63 (Heavy Chain) |
| 51 | Modified_hinge_IGg4 (Hinge) |

In one embodiment, the CPR has a domain, having at least 95% identity to any of the sequences of Tables 4-10, including, SEQ ID NO: 1-55. In one embodiment, the CPR has a domain having 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to one or more of the sequences of Tables 4-10, including, SEQ ID NO: 1-55.

In one embodiment, the CPR has at least one signal peptide, having at least 95% identity to any of the sequences of Table 6, including, SEQ ID NO: 2, 11, 16, 25, 30, 35, 39, and 44. In one embodiment, the CPR has at least one signal peptide domain having 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to one or more of the sequences of Table 6, including, SEQ ID NO: 2, 11, 16, 25, 30, 35, 39, and 44.

In one embodiment, the CPR has at least one extracellular domain, having at least 95% identity to any of the sequences of Table 7, including, SEQ ID NO: 3, 9, 53, 12, 54, 17, 55, 26, 31, 36, 40, or 45. In one embodiment, the CPR has at least one extracellular domain having 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to one or more of the sequences of Table 7, including, SEQ ID NO: 3, 9, 53, 12, 54, 17, 55, 26, 31, 36, 40, or 45.

In one embodiment, the CPR has at least one transmembrane domain, having at least 95% identity to any of the sequences of Table 8, including, SEQ ID NO: 4, 8, 13, 18, 27, 32, 37, 41, or 46. In one embodiment, the CPR has at least one transmembrane domain having 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90° %, 91%, 92%, 93%, 94%, 95%, 96%, 97%, 98%, 99%, or 100% identity to one or more of the sequences of Table 8, including, SEQ ID NO: 4, 8, 13, 18, 27, 32, 37, 41, or 46.

In one embodiment, the CPR has at least one cytoplasmic domain, having at least 95% identity to any of the sequences of Table 9, including, SEQ ID NO: 5, 7, 14, 19, 28, 33, 52, 42, or 47. In one embodiment, the CPR has at least one cytoplasmic domain having 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to one or more of the sequences of Table 9, including, SEQ ID NO: 5, 7, 14, 19, 28, 33, 52, 42, or 47.

In one embodiment, the CPR has at least one linker or targeting domain, having at least 95% identity to any of the sequences of Table 10, including, SEQ ID NO: 48, 49, 50, or 51. In one embodiment, the CPR has at least one linker or targeting domain having 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to one or more of the sequences of Table 10, including, SEQ ID NO: 48, 49, 50, or 51.

In one embodiment, the CPR comprises a signal peptide, extracellular domain, a transmembrane domain and a cytoplasm domain.

In one embodiment, the CPR comprises an extracellular domain, a transmembrane domain and a cytoplasm domain.

b. Domain Swapping

In one embodiment, any of the domains in the ITAM and/or ITIM receptors in Tables 4 and 5, respectfully, may be replaced with domains from other ITAM and/or ITIM receptors.

In one embodiment, the EC domain in the ITAM receptors in Table 4 may be replaced with domains from other ITAM and/or ITIM receptors. For example, the EC domain in the FCERG ITAM receptor may be replaced by a CLEC1 EC domain or a portion thereof in order to create a CPR. For example, the EC domain in the FCERG ITAM receptor may be replaced by a FCGR2 EC domain or a portion thereof in order to create a CPR For example, the EC domain in the FCERG ITAM receptor may be replaced by a GPVIA EC domain or a portion thereof in order to create a CPR. For example, the EC domain in the FCERG ITAM receptor may be replaced by a LILRB2 EC domain or a portion thereof in order to create a CPR. For example, the EC domain in the FCERG ITAM receptor may be replaced by a PECAM1 EC domain or a portion thereof in order to create a CPR. For example, the EC domain in the FCERG ITAM receptor may be replaced by a TLT1 EC domain or a portion thereof in order to create a CPR. For example, the EC domain in the FCERG ITAM receptor may be replaced by a CEACAM1 EC domain or a portion thereof in order to create a CPR.

For example, the TM domain in the FCERG ITAM receptor may be replaced by a CLEC1 TM domain or a portion thereof in order to create a CPR. For example, the TM domain in the FCERG ITAM receptor may be replaced by a FCGR2 TM domain or a portion thereof in order to create a CPR. For example, the TM domain in the FCERG ITAM receptor may be replaced by a GPVIA TM domain or a portion thereof in order to create a CPR For example, the TM domain in the FCERG ITAM receptor may be replaced by a LILRB2 TM domain or a portion thereof in order to create a CPR For example, the TM domain in the FCERG ITAM receptor may be replaced by a PECAM1 TM domain or a portion thereof in order to create a CPR For example, the TM domain in the FCERG ITAM receptor may be replaced by a TLT1 TM domain or a portion thereof in order to create a CPR. For example, the TM domain in the FCERG ITAM receptor may be replaced by a CEACAM1 TM domain or a portion thereof in order to create a CPR.

For example, the signal peptide in the FCERG ITAM receptor may be replaced by a CLEC1 signal peptide or a portion thereof in order to create a CPR For example, the signal peptide in the FCERG ITAM receptor may be replaced by a FCGR2 signal peptide or a portion thereof in order to create a CPR For example, the signal peptide in the FCERG ITAM receptor may be replaced by a GPVIA signal peptide or a portion thereof in order to create a CPR. For example, the signal peptide in the FCERG ITAM receptor may be replaced by a LILRB2 signal peptide or a portion thereof in order to create a CPR For example, the signal peptide in the FCERG ITAM receptor may be replaced by a PECAM1 signal peptide or a portion thereof in order to create a CPR. For example, the signal peptide in the FCERG ITAM receptor may be replaced by a TLT1 signal peptide or a portion thereof in order to create a CPR. For example, the signal peptide in the FCERG ITAM receptor may be replaced by a CEACAM1 signal peptide or a portion thereof in order to create a CPR.

For example, the cytodomain in the FCERG ITAM receptor may be replaced by a CLEC1 cytodomain or a portion thereof in order to create a CPR For example, the cytodomain in the FCERG ITAM receptor may be replaced by a FCGR2 cytodomain or a portion thereof in order to create a CPR. For example, the cytodomain in the FCERG ITAM receptor may be replaced by a GPVIA cytodomain or a portion thereof in order to create a CPR. For example, the cytodomain in the FCERG ITAM receptor may be replaced by a LILRB2 cytodomain or a portion thereof in order to create a CPR. For example, the cytodomain in the FCERG ITAM receptor may be replaced by a PECAM1 cytodomain or a portion thereof in order to create a CPR. For example, the cytodomain in the FCERG ITAM receptor may be replaced by a TLT1 cytodomain or a portion thereof in order to create a CPR. For example, the cytodomain in the FCERG ITAM receptor may be replaced by a CEACAM1 cytodomain or a portion thereof in order to create a CPR.

For example, the EC domain in the CLEC1 ITAM receptor may be replaced by a FCGR2 EC domain or a portion thereof in order to create a CPR. For example, the EC domain in the CLEC1 ITAM receptor may be replaced by a GPVIA EC domain or a portion thereof in order to create a CPR For example, the EC domain in the CLEC1 ITAM receptor may be replaced by a LILRB2 EC domain or a portion thereof in order to create a CPR For example, the EC domain in the CLEC1 ITAM receptor may be replaced by a PECAM1 EC domain or a portion thereof in order to create a CPR. For example, the EC domain in the CLEC1 ITAM receptor may be replaced by a TLT1 EC domain or a portion thereof in order to create a CPR For example, the EC domain in the CLEC1 ITAM receptor may be replaced by a CEACAM1 EC domain or a portion thereof in order to create a CPR For example, the TM domain in the CLEC1 ITAM receptor may be replaced by a FCERG TM domain or a portion thereof in order to create a CPR For example, the TM domain in the CLEC1 ITAM receptor may be replaced by a FCGR2 TM domain or a portion thereof in order to create a CPR. For example, the TM domain in the CLEC1 ITAM receptor may be replaced by a GPVIA TM domain or a portion thereof in order to create a CPR For example, the TM domain in the CLEC1 ITAM receptor may be replaced by a LILRB2 TM domain or a portion thereof in order to create a CPR. For example, the TM domain in the CLEC1 ITAM receptor may be replaced by a PECAM1 TM domain or a portion thereof in order to create a CPR For example, the TM domain in the CLEC1 ITAM receptor may be replaced by a TLT1 TM domain or a portion thereof in order to create a CPR. For example, the TM domain in the CLEC1 ITAM receptor may be replaced by a CEACAM1 TM domain or a portion thereof in order to create a CPR.

For example, the signal peptide in the CLEC1 ITAM receptor may be replaced by a FCERG signal peptide or a portion thereof in order to create a CPR For example, the signal peptide in the CLEC1 ITAM receptor may be replaced by a FCGR2 signal peptide or a portion thereof in order to create a CPR. For example, the signal peptide in the CLEC1 ITAM receptor may be replaced by a GPVIA signal peptide or a portion thereof in order to create a CPR. For example, the signal peptide in the CLEC1 ITAM receptor may be replaced by a LILRB2 signal peptide or a portion thereof in order to create a CPR. For example, the signal peptide in the CLEC1 ITAM receptor may be replaced by a PECAM1 signal peptide or a portion thereof in order to create a CPR. For example, the signal peptide in the CLEC1 ITAM receptor may be replaced by a TLT1 signal peptide or a portion thereof in order to create a CPR. For example, the signal peptide in the CLEC1 ITAM receptor may be replaced by a CEACAM1 signal peptide or a portion thereof in order to create a CPR.

For example, the cytodomain in the CLEC1 ITAM receptor may be replaced by a FCERG cytodomain or a portion thereof in order to create a CPR For example, the cytodomain in the CLEC1 ITAM receptor may be replaced by a FCGR2 cytodomain or a portion thereof in order to create a CPR. For example, the cytodomain in the CLEC1 ITAM receptor may be replaced by a GPVIA cytodomain or a portion thereof in order to create a CPR. For example, the cytodomain in the CLEC1 ITAM receptor may be replaced by a LILRB2 cytodomain or a portion thereof in order to create a CPR For example, the cytodomain in the CLEC1 ITAM receptor may be replaced by a PECAM1 cytodomain or a portion thereof in order to create a CPR. For example, the cytodomain in the CLEC1 ITAM receptor may be replaced by a TLT1 cytodomain or a portion thereof in order to create a CPR. For example, the cytodomain in the CLEC1 ITAM receptor may be replaced by a CEACAM1 cytodomain or a portion thereof in order to create a CPR For example, the EC domain in the FCGR2 ITAM receptor may be replaced by a CLEC1 EC domain or a portion thereof in order to create a CPR For example, the EC domain in the FCGR2 ITAM receptor may be replaced by a GPVIA EC domain or a portion thereof in order to create a CPR. For example, the EC domain in the FCGR2 ITAM receptor may be replaced by a LILRB2 EC domain or a portion thereof in order to create a CPR For example, the EC domain in the FCGR2 ITAM receptor may be replaced by a PECAM1 EC domain or a portion thereof in order to create a CPR. For example, the EC domain in the FCGR2 ITAM receptor may be replaced by a TLT1 EC domain or a portion thereof in order to create a CPR For example, the EC domain in the FCGR2 ITAM receptor may be replaced by a CEACAM1 EC domain or a portion thereof in order to create a CPR.

For example, the TM domain in the FCGR2 ITAM receptor may be replaced by a FCERG TM domain or a portion thereof in order to create a CPR. For example, the TM domain in the FCGR2 ITAM receptor may be replaced by a CLEC1 TM domain or a portion thereof in order to create a CPR. For example, the TM domain in the FCGR2 ITAM receptor may be replaced by a GPVIA TM domain or a portion thereof in order to create a CPR. For example, the TM domain in the FCGR2 ITAM receptor may be replaced by a LILRB2 TM domain or a portion thereof in order to create a CPR For example, the TM domain in the FCGR2 ITAM receptor may be replaced by a PECAM1 TM domain or a portion thereof in order to create a CPR. For example, the TM domain in the FCGR2 ITAM receptor may be replaced by a TLT1 TM domain or a portion thereof in order to create a CPR. For example, the TM domain in the FCGR2 ITAM receptor may be replaced by a CEACAM1 TM domain or a portion thereof in order to create a CPR For example, the signal peptide in the FCGR2 ITAM receptor may be replaced by a FCERG signal peptide or a portion thereof in order to create a CPR For example, the signal peptide in the FCGR2 ITAM receptor may be replaced by a CLEC1 signal peptide or a portion thereof in order to create a CPR For example, the signal peptide in the FCGR2 ITAM receptor may be replaced by a GPVIA signal peptide or a portion thereof in order to create a CPR For example, the signal peptide in the FCGR2 ITAM receptor may be replaced by a LILRB2 signal peptide or a portion thereof in order to create a CPR For example, the signal peptide in the FCGR2 ITAM receptor may be replaced by a PECAM1 signal peptide or a portion thereof in order to create a CPR For example, the signal peptide in the FCGR2 ITAM receptor may be replaced by a TLT1 signal peptide or a portion thereof in order to create a CPR For example, the signal peptide in the FCGR2 ITAM receptor may be replaced by a CEACAM1 signal peptide or a portion thereof in order to create a CPR For example, the cytodomain in the FCGR2 ITAM receptor may be replaced by a FCERG cytodomain or a portion thereof in order to create a CPR For example, the cytodomain in the FCGR2 ITAM receptor may be replaced by a CLEC1 cytodomain or a portion thereof in order to create a CPR. For example, the cytodomain in the FCGR2 ITAM receptor may be replaced by a GPVIA cytodomain or a portion thereof in order to create a CPR. For example, the cytodomain in the FCGR2 ITAM receptor may be replaced by a LILRB2 cytodomain or a portion thereof in order to create a CPR For example, the cytodomain in the FCGR2 ITAM receptor may be replaced by a PECAM1 cytodomain or a portion thereof in order to create a CPR. For example, the cytodomain in the FCGR2 ITAM receptor may be replaced by a TLT1 cytodomain or a portion thereof in order to create a CPR. For example, the cytodomain in the FCGR2 ITAM receptor may be replaced by a CEACAM1 cytodomain or a portion thereof in order to create a CPR.

For example, the EC domain in the GPVIA ITAM receptor may be replaced by a CLEC1 EC domain or a portion thereof in order to create a CPR. For example, the EC domain in the GPVIA ITAM receptor may be replaced by a FCGR2 EC domain or a portion thereof in order to create a CPR. For example, the EC domain in the GPVIA ITAM receptor may be replaced by a LILRB2 EC domain or a portion thereof in order to create a CPR For example, the EC domain in the GPVIA ITAM receptor may be replaced by a PECAM1 EC domain or a portion thereof in order to create a CPR For example, the EC domain in the GPVIA ITAM receptor may be replaced by a TLT1 EC domain or a portion thereof in order to create a CPR For example, the EC domain in the GPVIA ITAM receptor may be replaced by a CEACAM1 EC domain or a portion thereof in order to create a CPR.

For example, the TM domain in the GPVIA ITAM receptor may be replaced by a FCERG TM domain or a portion thereof in order to create a CPR For example, the TM domain in the GPVIA ITAM receptor may be replaced by a CLEC1 TM domain or a portion thereof in order to create a CPR. For example, the TM domain in the GPVIA ITAM receptor may be replaced by a FCGR2 TM domain or a portion thereof in order to create a CPR For example, the TM domain in the GPVIA ITAM receptor may be replaced by a LILRB2 TM domain or a portion thereof in order to create a CPR For example, the TM domain in the GPVIA ITAM receptor may be replaced by a PECAM1 TM domain or a portion thereof in order to create a CPR For example, the TM domain in the GPVIA ITAM receptor may be replaced by a TLT1 TM domain or a portion thereof in order to create a CPR. For example, the TM domain in the GPVIA ITAM receptor may be replaced by a CEACAM1 TM domain or a portion thereof in order to create a CPR.

For example, the signal peptide in the GPVIA ITAM receptor may be replaced by a FCERG signal peptide or a portion thereof in order to create a CPR For example, the signal peptide in the GPVIA ITAM receptor may be replaced by a CLEC1 signal peptide or a portion thereof in order to create a CPR For example, the signal peptide in the GPVIA ITAM receptor may be replaced by a FCGR2 signal peptide or a portion thereof in order to create a CPR. For example, the signal peptide in the GPVIA ITAM receptor may be replaced by a LILRB2 signal peptide or a portion thereof in order to create a CPR For example, the signal peptide in the GPVIA ITAM receptor may be replaced by a PECAM1 signal peptide or a portion thereof in order to create a CPR. For example, the signal peptide in the GPVIA ITAM receptor may be replaced by a TLT1 signal peptide or a portion thereof in order to create a CPR. For example, the signal peptide in the GPVIA ITAM receptor may be replaced by a CEACAM1 signal peptide or a portion thereof in order to create a CPR.

For example, the cytodomain in the GPVIA ITAM receptor may be replaced by a FCERG cytodomain or a portion thereof in order to create a CPR For example, the cytodomain in the GPVIA ITAM receptor may be replaced by a CLEC1 cytodomain or a portion thereof in order to create a CPR. For example, the cytodomain in the GPVIA ITAM receptor may be replaced by a FCGR2 cytodomain or a portion thereof in order to create a CPR. For example, the cytodomain in the GPVIA ITAM receptor may be replaced by a LILRB2 cytodomain or a portion thereof in order to create a CPR For example, the cytodomain in the GPVIA ITAM receptor may be replaced by a PECAM1 cytodomain or a portion thereof in order to create a CPR. For example, the cytodomain in the GPVIA ITAM receptor may be replaced by a TLT1 cytodomain or a portion thereof in order to create a CPR. For example, the cytodomain in the GPVIA ITAM receptor may be replaced by a CEACAM1 cytodomain or a portion thereof in order to create a CPR.

In one embodiment, the EC domain in the ITIM receptors in Table 5 may be replaced with domains from other ITAM and/or ITIM receptors.

For example, the EC domain in the LILRB2 ITIM receptor may be replaced by a CLEC1 EC domain or a portion thereof in order to create a CPR For example, the EC domain in the LILRB2 ITIM receptor may be replaced by a GPVIA EC domain or a portion thereof in order to create a CPR For example, the EC domain in the LILRB2 ITIM receptor may be replaced by a FCGR2 EC domain or a portion thereof in order to create a CPR. For example, the EC domain in the LILRB2 ITIM receptor may be replaced by a PECAM1 EC domain or a portion thereof in order to create a CPR. For example, the EC domain in the LILRB2 ITIM receptor may be replaced by a TLT1 EC domain or a portion thereof in order to create a CPR. For example, the EC domain in the LILRB2 ITIM receptor may be replaced by a CEACAM1 EC domain or a portion thereof in order to create a CPR.

For example, the TM domain in the LILRB2 ITIM receptor may be replaced by a FCERG TM domain or a portion thereof in order to create a CPR. For example, the TM domain in the LILRB2 ITIM receptor may be replaced by a CLEC1 TM domain or a portion thereof in order to create a CPR. For example, the TM domain in the LILRB2 ITIM receptor may be replaced by a GPVIA TM domain or a portion thereof in order to create a CPR. For example, the TM domain in the LILRB2 ITIM receptor may be replaced by a FCGR2 TM domain or a portion thereof in order to create a CPR. For example, the TM domain in the LILRB2 ITIM receptor may be replaced by a PECAM1 TM domain or a portion thereof in order to create a CPR. For example, the TM domain in the LILRB2 ITIM receptor may be replaced by a TLT1 TM domain or a portion thereof in order to create a CPR. For example, the TM domain in the LILRB2 ITIM receptor may be replaced by a CEACAM1 TM domain or a portion thereof in order to create a CPR For example, the signal peptide in the LILRB2 ITIM receptor may be replaced by a FCERG signal peptide or a portion thereof in order to create a CPR For example, the signal peptide in the LILRB2 ITIM receptor may be replaced by a CLEC1 signal peptide or a portion thereof in order to create a CPR For example, the signal peptide in the LILRB2 ITIM receptor may be replaced by a GPVIA signal peptide or a portion thereof in order to create a CPR. For example, the signal peptide in the LILRB2 ITIM receptor may be replaced by a FCGR2 signal peptide or a portion thereof in order to create a CPR For example, the signal peptide in the LILRB2 ITIM receptor may be replaced by a PECAM1 signal peptide or a portion thereof in order to create a CPR. For example, the signal peptide in the LILRB2 ITIM receptor may be replaced by a TLT1 signal peptide or a portion thereof in order to create a CPR For example, the signal peptide in the LILRB2 ITIM receptor may be replaced by a CEACAM1 signal peptide or a portion thereof in order to create a CPR For example, the cytodomain in the LILRB2 ITIM receptor may be replaced by a FCERG cytodomain or a portion thereof in order to create a CPR For example, the cytodomain in the LILRB2 ITIM receptor may be replaced by a CLEC1 cytodomain or a portion thereof in order to create a CPR. For example, the cytodomain in the LILRB2 ITIM receptor may be replaced by a GPVIA cytodomain or a portion thereof in order to create a CPR. For example, the cytodomain in the LILRB2 ITIM receptor may be replaced by a FCGR2 cytodomain or a portion thereof in order to create a CPR For example, the cytodomain in the LILRB2 ITIM receptor may be replaced by a PECAM1 cytodomain or a portion thereof in order to create a CPR. For example, the cytodomain in the LILRB2 ITIM receptor may be replaced by a TLT1 cytodomain or a portion thereof in order to create a CPR. For example, the cytodomain in the LILRB2 ITIM receptor may be replaced by a CEACAM1 cytodomain or a portion thereof in order to create a CPR. For example, the EC domain in the PECAM1 ITIM receptor may be replaced by a CLEC1 EC domain or a portion thereof in order to create a CPR For example, the EC domain in the PECAM1 ITIM receptor may be replaced by a GPVIA EC domain or a portion thereof in order to create a CPR For example, the EC domain in the PECAM1 ITIM receptor may be replaced by a FCGR2 EC domain or a portion thereof in order to create a CPR. For example, the EC domain in the PECAM1 ITIM receptor may be replaced by a LILRB2 EC domain or a portion thereof in order to create a CPR For example, the EC domain in the PECAM1 ITIM receptor may be replaced by a TLT1 EC domain or a portion thereof in order to create a CPR. For example, the EC domain in the PECAM1 ITIM receptor may be replaced by a CEACAM1 EC domain or a portion thereof in order to create a CPR For example, the TM domain in the PECAM1 ITIM receptor may be replaced by a FCERG TM domain or a portion thereof in order to create a CPR For example, the TM domain in the PECAM1 ITIM receptor may be replaced by a CLEC1 TM domain or a portion thereof in order to create a CPR For example, the TM domain in the PECAM1 ITIM receptor may be replaced by a GPVIA TM domain or a portion thereof in order to create a CPR. For example, the TM domain in the PECAM1 ITIM receptor may be replaced by a FCGR2 TM domain or a portion thereof in order to create a CPR For example, the TM domain in the PECAM1 ITIM receptor may be replaced by a LILRB2 TM domain or a portion thereof in order to create a CPR For example, the TM domain in the PECAM1 ITIM receptor may be replaced by a TLT1 TM domain or a portion thereof in order to create a CPR. For example, the TM domain in the PECAM1 ITIM receptor may be replaced by a CEACAM1 TM domain or a portion thereof in order to create a CPR.

For example, the signal peptide in the PECAM1 ITIM receptor may be replaced by a FCERG signal peptide or a portion thereof in order to create a CPR For example, the signal peptide in the PECAM1 ITIM receptor may be replaced by a CLEC1 signal peptide or a portion thereof in order to create a CPR For example, the signal peptide in the PECAM1 ITIM receptor may be replaced by a GPVIA signal peptide or a portion thereof in order to create a CPR. For example, the signal peptide in the PECAM1 ITIM receptor may be replaced by a FCGR2 signal peptide or a portion thereof in order to create a CPR For example, the signal peptide in the PECAM1 ITIM receptor may be replaced by a LILRB2 signal peptide or a portion thereof in order to create a CPR For example, the signal peptide in the PECAM1 ITIM receptor may be replaced by a TLT1 signal peptide or a portion thereof in order to create a CPR For example, the signal peptide in the PECAM1 ITIM receptor may be replaced by a CEACAM1 signal peptide or a portion thereof in order to create a CPR.

For example, the cytodomain in the PECAM1 ITIM receptor may be replaced by a FCERG cytodomain or a portion thereof in order to create a CPR For example, the cytodomain in the PECAM1 ITIM receptor may be replaced by a CLEC1 cytodomain or a portion thereof in order to create a CPR. For example, the cytodomain in the PECAM1 ITIM receptor may be replaced by a GPVIA cytodomain or a portion thereof in order to create a CPR. For example, the cytodomain in the PECAM1 ITIM receptor may be replaced by a FCGR2 cytodomain or a portion thereof in order to create a CPR For example, the cytodomain in the PECAM1 ITIM receptor may be replaced by a LILRB2 cytodomain or a portion thereof in order to create a CPR For example, the cytodomain in the PECAM1 ITIM receptor may be replaced by a TLT1 cytodomain or a portion thereof in order to create a CPR. For example, the cytodomain in the CEACAM1 ITIM receptor may be replaced by a CEACAM1 cytodomain or a portion thereof in order to create a CPR.

For example, the EC domain in the CEACAM1 ITIM receptor may be replaced by a CLEC1 EC domain or a portion thereof in order to create a CPR For example, the EC domain in the CEACAM1 ITIM receptor may be replaced by a GPVIA EC domain or a portion thereof in order to create a CPR. For example, the EC domain in the CEACAM1 ITIM receptor may be replaced by a FCGR2 EC domain or a portion thereof in order to create a CPR For example, the EC domain in the CEACAM1 ITIM receptor may be replaced by a LILRB2 EC domain or a portion thereof in order to create a CPR For example, the EC domain in the CEACAM1 ITIM receptor may be replaced by a PECAM1 EC domain or a portion thereof in order to create a CPR For example, the EC domain in the CEACAM1 ITIM receptor may be replaced by a TLT1 EC domain or a portion thereof in order to create a CPR For example, the TM domain in the CEACAM1 ITIM receptor may be replaced by a FCERG TM domain or a portion thereof in order to create a CPR. For example, the TM domain in the CEACAM1 ITIM receptor may be replaced by a CLEC1 TM domain or a portion thereof in order to create a CPR For example, the TM domain in the CEACAM1 ITIM receptor may be replaced by a GPVIA TM domain or a portion thereof in order to create a CPR. For example, the TM domain in the CEACAM1 ITIM receptor may be replaced by a FCGR2 TM domain or a portion thereof in order to create a CPR. For example, the TM domain in the CEACAM1 ITIM receptor may be replaced by a LILRB2 TM domain or a portion thereof in order to create a CPR. For example, the TM domain in the CEACAM1 ITIM receptor may be replaced by a PECAM1 TM domain or a portion thereof in order to create a CPR. For example, the TM domain in the CEACAM1 ITIM receptor may be replaced by a TLT1 TM domain or a portion thereof in order to create a CPR.

For example, the signal peptide in the CEACAM1 ITIM receptor may be replaced by a FCERG signal peptide or a portion thereof in order to create a CPR. For example, the signal peptide in the CEACAM1 ITIM receptor may be replaced by a CLEC1 signal peptide or a portion thereof in order to create a CPR For example, the signal peptide in the CEACAM1 ITIM receptor may be replaced by a GPVIA signal peptide or a portion thereof in order to create a CPR For example, the signal peptide in the CEACAM1 ITIM receptor may be replaced by a FCGR2 signal peptide or a portion thereof in order to create a CPR For example, the signal peptide in the CEACAM1 ITIM receptor may be replaced by a LILRB2 signal peptide or a portion thereof in order to create a CPR For example, the signal peptide in the CEACAM1 ITIM receptor may be replaced by a PECAM1 signal peptide or a portion thereof in order to create a CPR For example, the signal peptide in the CEACAM1 ITIM receptor may be replaced by a TLT1 signal peptide or a portion thereof in order to create a CPR.

For example, the cytodomain in the CEACAM1 ITIM receptor may be replaced by a FCERG cytodomain or a portion thereof in order to create a CPR For example, the cytodomain in the CEACAM1 ITIM receptor may be replaced by a CLEC1 cytodomain or a portion thereof in order to create a CPR For example, the cytodomain in the CEACAM1 ITIM receptor may be replaced by a GPVIA cytodomain or a portion thereof in order to create a CPR For example, the cytodomain in the CEACAM1 ITIM receptor may be replaced by a FCGR2 cytodomain or a portion thereof in order to create a CPR. For example, the cytodomain in the CEACAM1 ITIM receptor may be replaced by a LILRB2 cytodomain or a portion thereof in order to create a CPR. For example, the cytodomain in the CEACAM1 ITIM receptor may be replaced by a PECAM1 cytodomain or a portion thereof in order to create a CPR For example, the cytodomain in the CEACAM1 ITIM receptor may be replaced by a TLT1 cytodomain or a portion thereof in order to create a CPR In some embodiments, the signal peptide, EC domain, TM domain, or cytodomain of an ITIM or ITAM reception may be replaced by a portion of a domain from a different receptor. The portion may have a length within the range of 10-30, 10-15, 10-20, 10-25, 15-20, 15-25, 15-30, 20-25, or 20-30 nucleotides. The portion may be 10, 11, 12, 13, 14, 15, 16, 17, 18, 19, 20, 21, 22, 23, 24, 25, 26, 27, 28, 29, or 30 nucleotides of any of the sequences in Tables 6-10 herein, for example, but not limited to, SEQ ID NO: 1-55. In certain embodiments, an EC domain from a CLEC1 ITAM receptor is SEQ ID NO: 53. In certain embodiments, an EC domain from a FCGR2 ITAM receptor is SEQ ID NO: 54. In certain embodiments, an EC domain from a GPVIA ITAM receptor is SEQ ID NO: 55.

2. Antibodies or Fragments Thereof

The CPR may include a region comprising any ligand or fragment thereof or epitope that recognizes and binds to a target, for example, a neoantigen on tumor cells, with high specificity and affinity. The region of the CPR may be an antibody or variants thereof or a variant or fragment thereof that can bind to the target on tumor cells such as a tumor specific antigen (TSA), or recognition components such as a linked cytokine that leads to recognition of target cells bearing the cytokine receptor, or a natural ligand of a receptor or fragment thereof. In some embodiments, the CPR of the engineered platelets described herein may be a scFv. An antibody, variant, or fragment thereof can be generated using routine recombinant DNA technology techniques known in the art.

In some embodiments, the engineered platelets comprise a CPR with a region including an antibody or an antibody fragment to bind a target of interest. For example, the CPR may include a variable heavy chain domain of an antibody. For example, the CPR may include a variable light chain domain of an antibody. Alternatively, the CPR of the engineered platelets may include a kappa light chain or a fragment thereof targeting CD19.

In some embodiments, the antibody or the antibody fragment thereof is chosen from Table 11. The antibodies are listed with their DrugBank identifier (DB ID).

TABLE 11

| Antibodies for use in chimeric receptors | | | |
|---|---|---|---|
| Antibody (Given Name) | IGMT/ mAb-DB ID | INN (International Nonproprietary Name) | INN Number |
| Abagovomab | 111 | abagovomab | 8659 |
| Abciximab | 146 | abciximab | 7200 |
| Abituzumab | 489 | abituzumab | 9509 |
| Abrezekimab | 804 | abrezekimab | 10745 |
| Abrilumab | 495 | abrilumab | 9921 |
| Actoxumab | 410 | actoxumab | 9568 |
| Adalimumab | 165 | adalimumab | 7860 |
| Adecatumumab | 164 | adecatumumab | 8449 |
| Atidortoxumab | 763 | atidortoxumab | 10638 |
| Aducanumab | 479 | aducanumab | 9838 |
| Afasevikumab | 576 | afasevikumab | 10178 |
| Afelimomab | 128 | afelimomab | 7340 |
| Alemtuzumab | 11 | alemtuzumab | 8005 |
| Alirocumab | 412 | alirocumab | 9620 |
| Amatuximab | 64 | amatuximab | 9343 |
| Anatumomab mafenatox | 287 | anatumomab mafenatox | 7655 |
| Andecaliximab | 533 | andecaliximab | 10035 |
| Anetumab ravtansine | 471 | anetumab ravtansine | 9788 |
| Anifrolumab | 474 | anifrolumab | 9800 |
| Anrukinzumab | 231 | anrukinzumab | 8942 |
| Apolizumab | 18 | apolizumab | 8210 |
| Aprutumab ixadotin | 656 | aprutumab ixadotin | 10383 |
| Arcitumomab | 113 | arcitumomab | 7417 |
| Ascrinvacumab | 561 | ascrinvacumab | 10106 |
| Aselizumab | 272 | aselizumab | 8291 |

TABLE 11-continued

Antibodies for use in chimeric receptors

| Antibody (Given Name) | IGMT/ mAb-DB ID | INN (International Nonproprietary Name) | INN Number |
|---|---|---|---|
| Atezolizumab | 526 | atezolizumab | 9814 |
| Atinumab | 358 | atinumab | 9336 |
| Atorelimumab | 308 | atorolimumab | 7647 |
| Avelumab | 512 | avelumab | 10062 |
| Azintuxizumab vedotin | 721 | azintuxizumab vedotin | 10499 |
| Bapineuzumab | 252 | bapineuzumab | 8624 |
| Basiliximab | 148 | basiliximab | 7578 |
| Bavituximab | 149 | bavituximab | 8734 |
| Bectumomab | 306 | bectumomab | 7514 |
| Begelomab | 503 | begelomab | 9959 |
| Belantamab mafodotin | 784 | belantamab mafodotin | 10754 |
| Belimumab | 266 | belimumab | 8381 |
| Bemarituzumab | 770 | bemarituzumab | 10681 |
| Benralizumab | 334 | benralizumab | 9233 |
| Berlimatoxumab | 764 | berlimatoxumab | 10639 |
| Bersanlimab | 800 | bersanlimab | 10709 |
| Bertilimumab | 170 | bertilimumab | 8332 |
| Besilesomab | 258 | besilesomab | 8451 |
| Bevacizumab | 24 | bevacizumab | 8017 |
| Bezlotoxumab | 411 | bezlotoxumab | 9608 |
| Biciromab | 131 | biciromab | 6867 |
| Bimagrumab | 456 | bimagrumab | 9711 |
| Bimekizumab | 486 | bimekizumab | 9878 |
| Birtamimab | 619 | birtamimab | 10198 |
| Bleselumab | 563 | bleselumab | 10114 |
| Blinatumomab | 101 | blinatumomab | 9028 |
| Blontuvetmab | 593 | blontuvetmab | 10194 |
| Blosozumab | 375 | blosozumab | 9440 |
| Bococizumab | 485 | bococizumab | 9840 |
| Brazikumab | 664 | brazikumab | 10425 |
| Brentuximab vedotin | 324 | brentuximab vedotin | 9144 |
| Briakinumab | 162 | briakinumab | 9153 |
| Brodalumab | 376 | brodalumab | 9475 |
| Brolucizumab | 536 | brolucizumab | 10053 |
| Brontictuzumab | 492 | brontictuzumab | 9982 |
| Burosumab | 647 | burosumab | 10301 |
| Cabiralizumab | 587 | cabiralizumab | 10121 |
| Camidanlumab tesirine | 775 | camidanlumab tesirine | 10592 |
| Camrelizumab | 659 | camrelizumab | 10400 |
| Canakinumab | 244 | canakinumab | 8836 |
| Cantuzumab mertansine | 52 | cantuzumab mertansine | 8223 |
| Cantuzumab ravtansine | 387 | cantuzumab ravtansine | 9441 |
| Caplacizumab | 401 | caplacizumab | 9511 |
| Carlumab | 359 | carlumab | 9372 |
| Carotuximab | 605 | carotuximab | 10244 |
| Catumaxomab | 218 | Catumaxomab | 8406 |
| Cedelizumab | 78 | cedelizumab | 7567 |
| Cemiplimab | 846 | cemiplimab | 10691 |
| Cergutuzumab amunaleukin | 555 | cergutuzumab amunaleukin | 10080 |
| Certolizumab pegol | 242 | certolizumab pegol | 8448 |
| Cetrelimab | 809 | cetrelimab | 10757 |
| Cetuximab | 151 | cetuximab | 7906 |
| Cibisatamab | 795 | cibisatamab | 10636 |
| Citatuzumab bogatox | 236 | citatuzumab bogatox | 9046 |
| Cixutumumab | 290 | cixutumumab | 9099 |
| Clazakizumab | 414 | clazakizumab | 9599 |
| Clenoliximab | 152 | clenoliximab | 7615 |
| Clivatuzumab tetraxetan | 560 | clivatuzumab tetraxetan | 10103 |
| Codrituzumab | 466 | codrituzumab | 9759 |
| Cofetuzumab pelidotin | 777 | cofetuzumab pelidotin | 10674 |
| Coltuximab ravtansine | 490 | coltuximab ravtansine | 9558 |
| Conatumumab | 224 | conatumumab | 9029 |
| Concizumab | 447 | concizumab | 9636 |
| Cosfroviximab | 726 | cosfroviximab | 10535 |
| Crenezumab | 378 | crenezumab | 9482 |
| Crizanlizumab | 667 | crizanlizumab | 10316 |
| Crotedumab | 595 | crotedumab | 10196 |
| Cusatuzumab | 792 | cusatuzumab | 10558 |
| Dacetuzumab | 232 | dacetuzumab | 8959 |
| Daclizumab | 36 | daclizumab | 7164 |
| Dalotuzumab | 333 | dalotuzumab | 9200 |
| Dapirolizumab pegol | 481 | dapirolizumab pegol | 9869 |
| Daratumumab | 301 | daratumumab | 9128 |
| Dectrekumab | 537 | dectrekumab | 10059 |
| Demcizumab | 415 | demcizumab | 9572 |

TABLE 11-continued

Antibodies for use in chimeric receptors

| Antibody (Given Name) | IGMT/ mAb-DB ID | INN (International Nonproprietary Name) | INN Number |
|---|---|---|---|
| Denintuzumab mafodotin | 493 | denintuzumab mafedotin | 9886 |
| Denosumab | 249 | denosumab | 8653 |
| Depatuxizumab mafodotin | 645 | depatuxizumab mafedotin | 10263 |
| Detumomab | 313 | detumomab | 7156 |
| Dezamizumab | 652 | dezamizumab | 10364 |
| Dinutuximab | 464 | dinutuximab | 9754 |
| Diridavumab | 494 | diridavumab | 9922 |
| Domagrozumab | 610 | domagrozumab | 10286 |
| Dorlimomab aritox | 207 | dorlimomab aritox | 6516 |
| Dostarlimab | 849 | dostarlimab | 10787 |
| Drozitumab | 348 | drozitumab | 9255 |
| Duligotuzumab | 416 | duligotuzumab | 9646 |
| Dupilumab | 449 | dupilumab | 9669 |
| Durvalumab | 528 | durvalumab | 10010 |
| Dusigitumab | 451 | dusigitumab | 9679 |
| Duvortuxizumab | 640 | duvortuxizumab | 10506 |
| Ecromeximab | 274 | ecromeximab | 8239 |
| Eculizumab | 37 | eculizumab | 8231 |
| Edobacomab | 118 | edobacomab | 7056 |
| Edrecolomab | 119 | edrecolomab | 7471 |
| Efalizumab | 38 | efalizumab | 8122 |
| Efungumab | 173 | efungumab | 8658 |
| Eldelumab | 463 | eldelumab | 9746 |
| Elezanumab | 650 | elezanumab | 10344 |
| Elgemtumab | 534 | elgemtumab | 10041 |
| Elotuzumab | 291 | elotuzumab | 9074 |
| Elsilimomab | 268 | elsilimomab | 8371 |
| Emactuzumab | 501 | emactuzumab | 9951 |
| Emapalumab | 666 | emapalumab | 10319 |
| Emibetuzumab | 496 | emibetuzumab | 9932 |
| Emicizumab | 564 | emicizumab | 10115 |
| Enapotamab vedotin | 814 | enapotamab vedotin | 10769 |
| Enavatuzumab | 360 | enavatuzumab | 9354 |
| Enfortumab vedotin | 476 | enfortumab vedotin | 9821 |
| Enlimomab pegol | 317 | enlimomab pegol | 7525 |
| Enoblituzumab | 590 | enoblituzumab | 10165 |
| Enokizumab | 361 | enokizumab | 9262 |
| Enoticumab | 417 | enoticumab | 9575 |
| Ensituximab | 349 | ensituximab | 9300 |
| Epitumomab cituxetan | 269 | epitumomab cituxetan | 8372 |
| Epratuzumab | 40 | epratuzumab | 7920 |
| Eptinezumab | 648 | eptinezumab | 10308 |
| Erenumab | 618 | erenumab | 10296 |
| Erlizumab | 280 | erlizumab | 8076 |
| Ertumaxomab | 219 | ertumaxomab | 8407 |
| Etaricizumab | 240 | etaracizumab | 8862 |
| Etigilimab | 803 | etigilimab | 10742 |
| Etrolizumab | 362 | etrolizumab | 9290 |
| Evinacumab | 529 | evinacumab | 10013 |
| Evolocumab | 448 | evolocumab | 9643 |
| Exbivirumab | 262 | exbivirumab | 8536 |
| Faralimomab | 305 | faralimomab | 7496 |
| Faricimab | 793 | faricimab | 10563 |
| Farletuzumab | 292 | farletuzumab | 9067 |
| Fasinumab | 418 | fasinumab | 9589 |
| Felvizumab | 86 | felvizumab | 7623 |
| Fezakinumab | 323 | fezakinumab | 9137 |
| Ficlatuzumab | 379 | ficlatuzumab | 9465 |
| Figitumumab | 293 | figitumumab | 9085 |
| Firivumab | 506 | firivumab | 9975 |
| Flanvotumab | 403 | flanvotumab | 9520 |
| Fletikumab | 480 | fletikumab | 9876 |
| Flotetuzumab | 679 | flotetuzumab | 10569 |
| Fontolizumab | 43 | fontolizumab | 8264 |
| Foralumab | 350 | foralumab | 9309 |
| Foravirumab | 90 | foravirumab | 9053 |
| Fremanezumab | 646 | fremanezumab | 10299 |
| Fresolimumab | 174 | fresolimumab | 9158 |
| Frovocimab | 850 | frovocimab | 10859 |
| Frunevetmab | 717 | frunevetmab | 10440 |
| Fulranumab | 363 | fulranumab | 9373 |
| Futuximab | 419 | futuximab | 9612 |
| Galcanezumab | 609 | galcanezumab | 10277 |
| Galiximab | 154 | galiximab | 8339 |
| Gancotamab | 865 | gancotamab | 10562 |

TABLE 11-continued

Antibodies for use in chimeric receptors

| Antibody (Given Name) | IGMT/ mAb-DB ID | INN (International Nonproprietary Name) | INN Number |
|---|---|---|---|
| Ganitumab | 168 | ganitumab | 9323 |
| Gantenerumab | 223 | gantenerumab | 8894 |
| Gatipotuzumab | 740 | gatipotuzumab | 10336 |
| Gavilimomab | 112 | gavilimomab | 8060 |
| Gedivumab | 719 | gedivumab | 10459 |
| Gemtuzumab ozogamicin | 649 | gemtuzumab ozogamicin | 10315 |
| Gevokizumab | 102 | gevokizumab | 9310 |
| Gilvetmab | 725 | gilvetmab | 10528 |
| Gimsilumab | 756 | gimsilumab | 10534 |
| Girentuximab | 328 | girentuximab | 9116 |
| Glembatumumab vedotin | 565 | glembatumumab vedotin | 10123 |
| Golimumab | 175 | golimumab | 8497 |
| Gosuranemab | 851 | gosuranemab | 10663 |
| Guselkumab | 468 | guselkumab | 9774 |
| Ianalumab | 758 | ianalumab | 10580 |
| Ibalizumab | 241 | ibalizumab | 8818 |
| Ibritumomab tiuxetan | 122 | ibritumomab tiuxetan | 7873 |
| Icrumcumab | 365 | icrucumab | 9370 |
| Idarucizumab | 462 | idarucizumab | 9698 |
| Ifabotuzumab | 572 | ifabotuzumab | 10149 |
| Igovomab | 123 | igovomab | 7433 |
| Iladatuzumab vedotin | 774 | iladatuzumab vedotin | 10647 |
| Imalumab | 504 | imalumab | 9961 |
| Imaprelimab | 808 | imaprelimab | 10753 |
| Imciromab | 124 | imciromab | 6605 |
| Imgatuzumab | 420 | imgatuzumab | 9598 |
| Inclacumab | 402. | inclacumab | 9512 |
| Indatuximab ravtansine | 389 | indatuximab ravtansine | 9486 |
| Indusatumab vedotin | 532 | indusatumab vedotin | 10033 |
| Inebilizumab | 553 | inebilizumab | 9985 |
| Infliximab | 156 | infliximab | 7602 |
| intetumumab | 321 | intetumumab | 9134 |
| inolimomab | 126 | inolimomab | 7253 |
| inotuzumab ozogamicin | 259 | inotuzumab ozogamicin | 8574 |
| Ipilimumab | 180 | ipilimumab | 8568 |
| Iratumumab | 250 | iratumumab | 8713 |
| Isatuximab | 539 | isatuximab | 10068 |
| Iscalimab | 799 | iscalimab | 10707 |
| Istiratumab | 545 | istiratumab | 10431 |
| Itolizumab | 351 | itolizumab | 9321 |
| Ixekizumab | 380 | ixekizumab | 9467 |
| Keliximab | 157 | keliximab | 7560 |
| Labetuzumab | 62 | labetuzumab | 8127 |
| Lacnotuzumab | 724 | lacnotuzumab | 10524 |
| Ladiratuzumab vedotin | 773 | ladiratuzumab vedotin | 10625 |
| Lampalizumab | 421 | lampalizumab | 9578 |
| Lanadelumab | 607 | lanadelumab | 10265 |
| Landogrozumab | 578 | landogrozumab | 10188 |
| Laprituximab emtansine | 600 | laprituximab emtansine | 10236 |
| Larcaviximab | 728 | larcaviximab | 10537 |
| Lebrikizumab | 325 | lebrikizumab | 9165 |
| Lemalesomab | 281 | lemalesomab | 8046 |
| Lenvervimab | 805 | lenvervimab | 10746 |
| Lenzilumab | 505 | lenzilumab | 9965 |
| Lerdelimumab | 182 | lerdelimumab | 7882 |
| Leronlimab | 807 | leronlimab | 10751 |
| Lesofavumab | 718 | lesofavumab | 10458 |
| Letolizumab | 715 | letolizumab | 10436 |
| Lexatumumab | 183 | lexatumumab | 8753 |
| Libivirumab | 263 | libivirumab | 8481 |
| Lifastuzumab vedotin | 478 | lifastuzumab vedotin | 9835 |
| Ligelizumab | 422 | ligelizumab | 9653 |
| Loncastuximab tesirine | 749 | loncastuximab tesirine | 10586 |
| Losatuxizumab vedotin | 712 | losatuxizumab vedotin | 10342 |
| Lintuzumab | 53 | lintuzumab | 7580 |
| Lirilumab | 423 | lirilumab | 9415 |
| Lodelcizumab | 461 | lodelcizumab | 9733 |
| Lokivetmab | 527 | lokivetmab | 10002 |
| Lorvotuzumab mertansine | 58 | lorvotuzumab mertansine | 9299 |
| Lucatumumab | 176 | lucatumumab | 8887 |
| Lulizumab pegol | 499 | lulizumab pegol | 9940 |
| Lumiliximab | 158 | lumiliximab | 8443 |
| Lumretuzumab | 502 | lumretuzumab | 9952 |
| Lupartumab amadotin | 665 | lupartumab amadotin | 10257 |
| Lutikizumab | 651 | lutikizumab | 10347 |

TABLE 11-continued

Antibodies for use in chimeric receptors

| Antibody (Given Name) | IGMT/ mAb-DB ID | INN (International Nonproprietary Name) | INN Number |
|---|---|---|---|
| Mapatumumab | 184 | mapatumumab | 8635 |
| Margetuximab | 473 | margetuximab | 9799 |
| Marstacimab | 852 | marstacimab | 10789 |
| Maslimomab | 318 | maslimomab | 6614 |
| Mavrilimumab | 335 | mavrilimumab | 9234 |
| Matuzumab | 39 | matuzumab | 8103 |
| Mepolizumab | 87 | mepolizumab | 7876 |
| Metelimumab | 186 | metelimumab | 8087 |
| Milatuzumab | 135 | milatuzumab | 8922 |
| Minretumomab | 309 | minretumomab | 7821 |
| Mirikizumab | 767 | mirikizumab | 10657 |
| Mirvetuximab soravtansine | 575 | mirvetuximab soravtansine | 10176 |
| Mitumomab | 130 | mitumomab | 7934 |
| Modotuximab | 433 | modotuximab | 9613 |
| Mogamulizumab | 366 | mogamulizumab | 9374 |
| Monalizumab | 562 | monalizumab | 10113 |
| Morolimumab | 311 | morolimumab | 7646 |
| Mosunetuzumab | 760 | mosunetuzumab | 10621 |
| Motavizumab | 73 | motavizumab | 8693 |
| Moxetumomab pasudotox | 198 | moxetumomab pasudotox | 9236 |
| Muromonab-CD3 | 132 | muromonab-CD3 | 6281 |
| Nacolomab tafenatox | 316 | nacolomab tafenatox | 7227 |
| Namilumab | 367 | namilumab | 9382 |
| Naptumomab estafenatox | 65 | naptumomab estafenatox | 8598 |
| Naratuximab emtansine | 602 | naratuximab emtansine | 10238 |
| Narnatumab | 381 | narnatumab | 9447 |
| Natalizumab | 75 | natalizumab | 7716 |
| Navicixizumab | 597 | navicixizumab | 10220 |
| Navivumab | 551 | navivumab | 9976 |
| Nebacumab | 193 | nebacumab | 6658 |
| Necitumumab | 294 | necitumumab | 9083 |
| Nemolizumab | 538 | nemolizumab | 10064 |
| Nerelimomab | 307 | nerelimomab | 7546 |
| Nesvacumab | 452 | nesvacumab | 9688 |
| Netakimab | 790 | netakimab | 10387 |
| Nimotuzumab | 76 | nimotuzumab | 8545 |
| Nirsevimab | 853 | nirsevimab | 10780 |
| Nivolumab | 424 | nivolumab | 9623 |
| Obiltoxaximab | 549 | obiltoxaximab | 9825 |
| Obinutuzumab | 238 | obinutuzumab | 9043 |
| Ocaratuzumab | 425 | ocaratuzumab | 9590 |
| Ocrelizumab | 227 | ocrelizumab | 8636 |
| Odulimomab | 134 | odulimomab | 7364 |
| Ofatumumab | 194 | ofatumumab | 8606 |
| Olaratumab | 352 | olaratumab | 9308 |
| Oleclumab | 729 | oleclumab | 10545 |
| Olendalizumab | 585 | olendalizumab | 10037 |
| Olokizumab | 353 | olokizumab | 9333 |
| Omalizumab | 77 | omalizumab | 8039 |
| Omburtamab | 855 | omburtamab | 10803 |
| Onartuzumab | 368 | onartuzumab | 9368 |
| Ontuxizumab | 491 | ontuxizumab | 9519 |
| Onvatilimab | 810 | onvatilimab | 10758 |
| Opicinumab | 557 | opicinumab | 10090 |
| Oportuzumab monatox | 237 | oportuzumab monatox | 9045 |
| Oregovomab | 136 | oregovomab | 8183 |
| Orticumab | 426 | orticumab | 9635 |
| Otelixizumab | 235 | otelixizumab | 8864 |
| Otilimab | 189 | otilimab | 10783 |
| Otlertuzumab | 488 | otlertuzumab | 9832 |
| Oxelumab | 354 | oxelumab | 9320 |
| Ozanezumab | 454 | ozanezumab | 9703 |
| Ozoralizumab | 382 | ozoralizumab | 9369 |
| Pagibaximab | 253 | pagibaximab | 8643 |
| Palivizumab | 79 | palivizumab | 7753 |
| Pamrevlumab | 554 | pamrevlumab | 10060 |
| Panitumumab | 196 | panitumumab | 8499 |
| Panobacumab | 243 | panobacumab | 8888 |
| Parsatuzumab | 427 | parsatuzumab | 9647 |
| Pascolizumab | 88 | pascolizumab | 8227 |
| Pasotuxizumab | 498 | pasotuxizumab | 9937 |
| Pateclizumab | 383 | pateclizumab | 9428 |
| Patritumab | 407 | patritumab | 9549 |
| Pembrolizumab | 472 | pembrolizumab | 9798 |
| Perakizumab | 428 | perakizumab | 9648 |

TABLE 11-continued

Antibodies for use in chimeric receptors

| Antibody (Given Name) | IGMT/ mAb-DB ID | INN (International Nonproprietary Name) | INN Number |
|---|---|---|---|
| Pertuzumab | 80 | pertuzumab | 8380 |
| Pexelizumab | 81 | pexelizumab | 8153 |
| Pidilizumab | 453 | pidilizumab | 9689 |
| Pinatuzumab vedotin | 457 | pinatuzumab vedotin | 9713 |
| Placulumab | 429 | placulumab | 9567 |
| Plozalizumab | 566 | plozalizumab | 10124 |
| Polatuzumab vedotin | 458 | polatuzumab vedotin | 9714 |
| Ponezumab | 369 | ponezumab | 9322 |
| Porgaviximab | 777 | porgaviximab | 10536 |
| Prasinezumab | 769 | prasinezumab | 10680 |
| Priliximab | 160 | priliximab | 7263 |
| Pritoxaximab | 459 | pritoxaximab | 9723 |
| Pritumumab | 270 | pritumumab | 8132 |
| Quilizumab | 406 | quilizumab | 9541 |
| Racotumomab | 225 | racotumomab | 8998 |
| Radretumab | 370 | radretumab | 9340 |
| Rafivirumab | 94 | rafivirumab | 9052 |
| Ralpancizumab | 484 | ralpancizumab | 9841 |
| Ramucirumab | 295 | ramucirumab | 9098 |
| Ranevetmab | 663 | ranevetmab | 10422 |
| Ranibizumab | 84 | ranibizumab | 8313 |
| Raxibacumab | 260 | raxibacumab | 8580 |
| Ravagalimab | 806 | ravagalimab | 10750 |
| Ravulizumab | 674 | ravulizumab | 10659 |
| Refanezumab | 591 | refanezumab | 10174 |
| Regavirumab | 197 | regavirumab | 7250 |
| Relatlimab | 781 | relatlimab | 10735 |
| Remtolumab | 517 | remtolumab | 10345 |
| Reslizumab | 279 | reslizumab | 8106 |
| Rilotumumab | 302 | rilotumumab | 9123 |
| Rinucumab | 574 | rinucumab | 10175 |
| Risankizumab | 567 | risankizumab | 10128 |
| Rituximab | 161 | rituximab | 7609 |
| Rivabazumab pegol | 106 | rivabazumab pegol | 10144 |
| Robatumumab | 296 | robatumumab | 9092 |
| Roledumab | 355 | roledumab | 9335 |
| Romilkimab | 794 | romilkimab | 10622 |
| Romosozumab | 404 | romosozumab | 9533 |
| Rontalizumab | 327 | rontalizumab | 9114 |
| Rosmantuzumab | 660 | rosmantuzumab | 10415 |
| Rovalpituzumab tesirine | 569 | rovalpituzumab tesirine | 10141 |
| Rovelizumab | 304 | rovelizumab | 7869 |
| Rozanolixizumab | 642 | rozanolixizumab | 10213 |
| Ruplizumab | 17 | ruplizumab | 8014 |
| Sacituzumab govitecan | 559 | sacituzumab govitecan | 10097 |
| Samalizumab | 356 | samalizumab | 9307 |
| Samrotamab vedotin | 815 | samrotamab vedotin | 10791 |
| Sarilumab | 400 | sarilumab | 9476 |
| Satralizumab | 586 | satralizumab | 10065 |
| Secukinumab | 326 | secukinumab | 9182 |
| Selicrelumab | 723 | selicrelumab | 10523 |
| Seribantumab | 455 | seribantumab | 9710 |
| Setoxaximab | 460 | setoxaximab | 9724 |
| Setrusumab | 632 | setrusumab | 10539 |
| Sevirumab | 83 | sevirumab | 6560 |
| Sibrotuzumab | 285 | sibrotuzumab | 7866 |
| Sifalimumab | 322 | sifalimumab | 9135 |
| Siltuximab | 297 | siltuximab | 9051 |
| Simtuzumab | 430 | simtuzumab | 9626 |
| Siplizumab | 71 | siplizumab | 8251 |
| Sirtratumab vedotin | 772 | sirtratumab vedotin | 10467 |
| Sirukumab | 384 | sirukumab | 9431 |
| Sofituzumab vedotin | 482 | sofituzumab vedotin | 9861 |
| Solanezumab | 298 | solanezumab | 9097 |
| Solitomab | 405 | solitomab | 9537 |
| Sontuzumab | 251 | sontuzumab | 8438 |
| Spartalizumab | 761 | spartalizumab | 10624 |
| Stamulumab | 192 | stamulumab | 8683 |
| Sulesomab | 139 | sulesomab | 7519 |
| Suptavumab | 621 | suptavumab | 10303 |
| Sutimlimab | 802 | sutimlimab | 10737 |
| Suvizumab | 330 | suvizumab | 9185 |
| Suvratoxumab | 716 | suvratoxumab | 10441 |
| Tabalumab | 385 | tabalumab | 9430 |
| Tadocizumab | 103 | tadocizumab | 8651 |

TABLE 11-continued

Antibodies for use in chimeric receptors

| Antibody (Given Name) | IGMT/ mAb-DB ID | INN (International Nonproprietary Name) | INN Number |
|---|---|---|---|
| Talacotuzumab | 754 | talacotuzumab | 10508 |
| Talizumab | 271 | talizumab | 8370 |
| Tamtuvetmab | 594 | tamtuvetmab | 10195 |
| Tanezumab | 230 | tanezumab | 8941 |
| Taplitumomab paptox | 282 | taplitumomab paptox | 8047 |
| Tarextumab | 467 | tarextumab | 9762 |
| Tavolimab | 662 | tavolimab | 10420 |
| Tefibazumab | 261 | tefibazumab | 8500 |
| Telimomab aritox | 320 | telimomab aritox | 6345 |
| Telisotuzumab vedotin | 653 | telisotuzumab vedotin | 10365 |
| Tenatumomab | 226 | tenatumomab | 8832 |
| Teneliximab | 276 | teneliximab | 8211 |
| Teplizumab | 92 | teplizumab | 8869 |
| Tepoditamab | 812 | tepoditamab | 10766 |
| Teprotumumab | 336 | teprotumumab | 9107 |
| Tesidolumab | 535 | tesidolumab | 10051 |
| Tezepelumab | 573 | tezepelumab | 10172 |
| Tibulizumab | 776 | tibulizumab | 10656 |
| Tildrakizumab | 450 | tildrakizumab | 9672 |
| Tigatuzumab | 234 | tigatuzumab | 8979 |
| Timigutuzumab | 739 | timigutuzumab | 10335 |
| Timolumab | 606 | timolumab | 10248 |
| Tislelizumab | 757 | tislelizumab | 10553 |
| Tisotumab vedotin | 571 | tisotumab vedotin | 10148 |
| Tocilizumab | 96 | tocilizumab | 8394 |
| Tomuzotuximab | 738 | tomuzotuximab | 10334 |
| Toralizumab | 60 | toralizumab | 8232 |
| Tosatoxumab | 465 | tosatoxumab | 9757 |
| Tositumomab | 142 | tositumomab | 7827 |
| Tovetumab | 469 | tovetumab | 9778 |
| Tralokinumab | 171 | tralokinumab | 9235 |
| Trastuzumab | 97 | trastuzumab | 7637 |
| Trastuzumab emtansine | 357 | trastuzumab emtansine | 9295 |
| Tregalizumab | 371 | tregalizumab | 9413 |
| Tremelimumab | 248 | tremelimumab | 8716 |
| Trevogrumab | 556 | trevogrumab | 10087 |
| Tucotuzumab celmoleukin | 254 | tucotuzumab celmoleukin | 8652 |
| Tuvirumab | 169 | tuvirumab | 6559 |
| Ublituximab | 372 | ublituximab | 9334 |
| Ulocuplumab | 483 | ulocuplumab | 9854 |
| Urelumab | 373 | urelumab | 9365 |
| Urtoxazumab | 265 | urtoxazumab | 8276 |
| Ustekinumab | 172 | ustekinumab | 8954 |
| Utomilumab | 657 | utomilumab | 10385 |
| Vadastuximab talirine | 552 | vadastuximab talirine | 9983 |
| Vandortuzumab vedotin | 531 | vandortuzumab vedotin | 10018 |
| Vantictumab | 470 | vantictumab | 9779 |
| Vanucizumab | 500 | vanucizumab | 9950 |
| Vapaliximab | 277 | vapaliximab | 8207 |
| Varisacumab | 714 | varisacumab | 10427 |
| Varlilumab | 497 | varlilumab | 9933 |
| Vatelizumab | 386 | vatelizumab | 9439 |
| Vedolizumab | 300 | vedolizumab | 9093 |
| Veltuzumab | 21 | veltuzumab | 8932 |
| Vepalimomab | 310 | vepalimomab | 7757 |
| Vesencumab | 374 | vesencumab | 9380 |
| Visilizumab | 100 | visilizumab | 8054 |
| Vobarilizumab | 523 | vobarilizumab | 10210 |
| Volociximab | 256 | volociximab | 8600 |
| Vonlerolizumab | 608 | vonlerolizumab | 10272 |
| Vopratelimab | 801 | vopratelimab | 10730 |
| Vorsetuzumab mafodotin | 432 | vorsetuzumab mafodotin | 9610 |
| Votumumab | 199 | votumumab | 7165 |
| Vunakizumab | 658 | vunakizumab | 10399 |
| Xentuzumab | 588 | xentuzumab | 10129 |
| Zalutumumab | 200 | zalutumumab | 8605 |
| Zanolimumab | 201 | zanolimumab | 8298 |
| Zenocutuzumab | 771 | zenocutuzumab | 10687 |
| Ziralimumab | 8 | ziralimumab | 8061 |
| Zolbetuximab | 753 | zolbetuximab | 10473 |
| Zolimomab aritox | 314 | zolimomab aritox | 7055 |

In some embodiments, the antibody may target or bind an antigen associated with a disease, disorder, or condition. Further, the antibody or antibody fragment may be effective in the treatment of the disease, disorder, or condition by binding the target antigen. In some embodiments, the target of the antibody may be used to identify or describe said antibody. For example, 3F8 targets GD2 ganglioside for treatment of neuroblastoma. For example, 8H19 targets B7-H13 for treatment of neuroblastoma, sarcoma, metastatic brain cancers. For example, Abagovomab targets CA-125 (imitation) for treatment of ovarian cancer. For example, Abciximab targets CD41 (integrin alpha-IIb) for treatment of platelet aggregation inhibitor. For example, Abituzunmab targets CD51 for treatment of cancer. For example, Abrezekinmab targets interleukin 13. For example, Abrilumab targets integrin α4β7 for treatment of inflammatory bowel disease, ulcerative colitis, Crohn's disease. For example, Actoxumiab targets *Clostridium difficile* for treatment of *Clostridium difficile* colitis. For example, Adalimumab targets TNF-α for treatment of Rheumatoid arthritis, Crohn's disease, Plaque Psoriasis, Psoriatic Arthritis, Ankylosing Spondylitis, Juvenile Idiopathic Arthritis, Hemolytic disease of the newborn. For example, Adecatumumab targets EpCAM for treatment of prostate and breast cancer. For example, Atidortoxumab targets *Staphylococcus* aureusalpha toxin. For example, Aducanumab targets beta-amyloid for treatment of Alzheimer's disease. For example. Afasevikumab targets IL17A and IL17F for treatment of multiple sclerosis. For example, Afelimomab targets TNF-α for treatment of sepsis. For example, Alacizumab pego targets VEGFR2 for treatment of cancer. For example, Alemtuzumab targets CD52 for treatment of Multiple sclerosis. For example, Alirocumab targets PCSK9 for treatment of hypercholesterolemia. For example, Altumomab pentetate targets CEA for treatment of colorectal cancer (diagnosis). For example, Amatuximab targets mesothelin for treatment of cancer. For example, Anatumomab mafenatox targets TAG-72 for treatment of non-small cell lung carcinoma. For example, Andecaliximab targets gelatinase B for treatment of gastric cancer or gastroesophageal junction adenocarcinoma. For example, Anetumab ravtansine targets MSLN for treatment of cancer. For example, Anifrolumab targets interferon α/β receptor for treatment of systemic lupus erythematosus. For example, Anrukinzumab targets IL-13 for treatment of asthma. For example, Apolizumab targets HLA-DR for treatment of hematological cancers. For example, Aprutumab ixadotin targets FGFR2. For example, Arcitumomab targets CEA for treatment of gastrointestinal cancers (diagnosis). For example, Ascrinvacumab targets activin receptor-like kinase 1 for treatment of cancer. For example, Aselizumab targets L-selectin (CD62L) for treatment of severely injured patients. For example, Atezolizumab targets PD-L1 for treatment of cancer. For example, Atinumab targets RTN4. For example, Atorolimumab targets Rhesus factor for treatment of hemolytic disease of the newborn[citation needed]. For example, Avelumab targets PD-L1 for treatment of cancer. For example, Azintuxizumab vedotin targets CD319 for treatment of cancer. For example, Bapineuzumab targets beta amyloid for treatment of Alzheimer's disease. For example, Basiliximab targets CD25 (α chain of IL-2receptor) for treatment of prevention of organ transplant rejections. For example, Bavituximab targets phosphatidylserine for treatment of cancer, viral infections. For example, BCD-100 targets PD-1 for treatment of melanoma. For example, Bectumomab targets CD22 for treatment of non-Hodgkin's lymphoma (detection). For example, Begelomab targets DPP4. For example, Belantamab mafodotin targets BCMA for treatment of cancer. For example, Belimumab targets BAFF for treatment of non-Hodgkin lymphoma. For example, Bemarituzumab targets FGFR2 for treatment of gastric cancer or gastroesophageal junction adenocarcinoma. For example, Benralizumab targets CD125 for treatment of asthma. For example, Berlimatoxumab targets *Staphylococcus aureus* bi-component leukocidin. For example, Bermekimab targets IL1A for treatment of colorectal cancer. For example, Bersanlimab targets ICAM-1. For example, Bertilimumab targets CCL11 (eotaxin-1) for treatment of severe allergic disorders. For example, Besilesomab targets CEA-related antigen for treatment of inflammatory lesions and metastases (detection). For example, Bevacizumab targets VEGF-A for treatment of metastatic cancer, retinopathy of prematurity. For example, Bezlotoxumab targets *Clostridium difficile* for treatment of *Clostridium difficile* colitis. For example, Biciromab targets fibrin II, beta chain for treatment of thromboembolism (diagnosis). For example, Bimagrumab targets ACVR2B for treatment of myostatin inhibitor. For example, Bimekizumab targets IL 17A and IL 17F for treatment of ankylosing spondylitis, psoriasis. For example, Birtamimab targets serum amyloid A protein for treatment of amyloidosis. For example, Bivatuzumab mertansine targets CD44 v6 for treatment of squamous cell carcinoma. For example, Bleselumab targets CD40 for treatment of organ transplant rejection. For example, Blinatumomab targets CD19 for treatment of pre-B ALL (CD19+). For example, Blontuvetmab targets CD20. For example, Blosozumab targets SOST for treatment of osteoporosis. For example, Bococizumab targets neural apoptosis-regulated proteinase 1 for treatment of dyslipidemia. For example, Brazikumab targets IL23 for treatment of Crohn's disease. For example, Brentuximab vedotin targets CD30 (TNFRSF8) for treatment of Hodgkin lymphoma, Anaplastic large-cell lymphoma. For example, Briakinumab targets IL-12, IL-23 for treatment of psoriasis, rheumatoid arthritis, inflammatory bowel diseases, multiple sclerosis. For example, Brodalumab targets IL-17 for treatment of Plaque psoriasis. For example, Brolucizumab targets VEGFA for treatment of wet age-related macular degeneration. For example, Brontictuzumab targets Notch 1 for treatment of cancer. For example, Burosumab targets FGF 23 for treatment of X-linked hypophosphatemia. For example, Cabiralizumab targets CSF1R for treatment of metastatic pancreatic cancer. For example, Camidanlumab tesirine targets CD25 for treatment of B-cell Hodgkin's lymphoma, non-Hodgkin lymphoma, acute lymphoblastic leukemia, acute myeloid leukemia. For example, Camrelizumab targets PD-1 for treatment of hepatocellular carcinoma. For example, Canakinumab targets IL-1 for treatment of Cryopyrin-associated periodic syndrome. For example, Cantuzumab mertansine targets mucin CanAg for treatment of colorectal cancer. For example, Cantuzumab ravtansine targets MUC1 for treatment of cancers. For example, Caplacizumab targets VWF for treatment of thrombotic thrombocytopenic purpura, thrombosis. For example, Capromab pendetide targets prostatic carcinoma cells for treatment of prostate cancer (detection). For example, Carlumab targets MCP-1 for treatment of oncology/immune indications. For example, Carotuximab targets endoglin for treatment of angiosarcoma. For example, Catumaxomab targets EpCAM, CD3 for treatment of ovarian cancer, malignant ascites, gastric cancer. For example, cBR96-doxorubicin immunoconjugate targets Lewis-Y antigen for treatment of cancer. For example, Cedelizumab targets CD4 for treatment of prevention of organ transplant rejections, treatment of autoimmune diseases. For example, Cemiplimab targets PCDC1 for treatment of cutaneous squamous cell carcinoma. For example, Cerguzumab amunaleukin targets IL2 for treatment of cancer. For example, Certolizumab pegol targets TNF-α for treatment of Crohn's disease, Rheumatoid arthritis, axial spondyloarthritis, psoriasis arthritis. For example, Cetrelimab targets PD-1 for treatment of cancer. For example, Cetuximab targets EGFR for treatment of metastatic colorectal cancer and head and neck cancer. For example, Cibisatamab targets CEACAM5 for treatment of cancer. For example, Cirmtuzumab targets ROR1 for treatment of chronic lymphocytic leukemia. For example, Citatuzumab bogatox targets EpCAM for treatment of ovarian cancer and other solid tumors. For example, Cixutumumab targets IGF-1 receptor (CD221) for treatment of solid tumors. For example, Clazakizumab targets IL6 for treatment of rheumatoid arthritis. For example, Clenoliximab targets CD4 for treatment of rheumatoid arthritis. For example, Clivatuzumab tetraxetan targets MUC1 for treatment of pancreatic cancer. For example, Codrituzumab targets glypican 3 for treatment of cancer. For example, Cofetuzumab pelidotin targets PTK7 for treatment of cancer. For example, Coltuximab ravtansine targets CD19 for treatment of cancer. For example, Conatumumab targets TRAIL-R2 for treatment of cancer. For example, Concizumab targets TFPI for treatment of bleeding. For example, Cosfroviximab targets ebolavirus glycoprotein for treatment of Ebola virus. For example, Crenezumab targets 1-40-β-amyloid for treatment of Alzheimer's disease. For example, Crizanlizumab targets selectin P for treatment of sickle-cell disease. For example, Crotedumab targets GCGR for treatment of diabetes. For example, CR6261 targets Influenza A hemagglutinin for treatment of infectious disease/influenza A. For example, Cusatuzumab targets CD70 for treatment of cancer. For example, Dacetuzumab targets CD40 for treatment of hematologic cancers. For example, Daclizumab targets CD25 (α chain of IL-2receptor) for treatment of prevention of organ transplant rejections, multiple sclerosis. For example, Dalotuzumab targets IGF-1 receptor (CD221) for treatment of cancer. For example, Dapirolizumab pegol targets CD154 (CD40L). For example, Daratumumab targets CD38 for treatment of Multiple myeloma. For example, Dectrekumab targets IL-13. For example, Demcizumab targets DLL4 for treatment of cancer. For example, Denintuzumab mafodotin targets CD19 for treatment of cancer. For example, Denosumab targets RANKL for treatment of osteoporosis and bone metastases. For example, Depatuxizumab mafodotin targets EGFR for treatment of glioblastoma. For example, Derlotuximab biotin targets histone complex for treatment of recurrent glioblastoma multiforme. For example, Detumomab targets B-lymphoma cell for treatment of lymphoma. For example, Dezamizumab targets serum amyloid P component. For example, Dinutuximab targets GD2 ganglioside for treatment of neuroblastoma. For example, Diridavumab targets hemagglutinin for treatment of influenza A. For example, Domagrozumab targets GDF-8 for treatment of Duchenne muscular dystrophy. For example, Dostarlimab targets PCDP1 for treatment of cancer. For example, Drozitumab targets DR5 for treatment of cancer. For example, DS-8201 targets HER2 for treatment of gastric or gastroesophageal junction adenocarcinoma. For example, Duligotuzumab targets ERBB3 (HER3) for treatment of testicular cancer. For example, Dupilumab targets IL4 for treatment of atopic diseases. For example, Durvalumab targets PD-L1 for treatment of cancer. For example, Dusigitumab targets ILGF2 for treatment of B-cell malignancies. For example, Duvortuxizumab targets CD19, CD3E for treatment of cancer. For example, Ecromeximab targets GD3 ganglioside for treatment of malignant melanoma. For example, Eculizumab targets C5 for treatment of paroxysmal nocturnal hemoglobinuria, atypical HUS. For example, Edobacomab targets endotoxin for treatment of sepsis caused by Gram-negative bacteria. For example, Edrecolomab targets EpCAM for treatment of colorectal carcinoma. For example, Efalizumab targets LFA-1 (CD11a) for treatment of psoriasis (blocks T-cell migration). For example, Efungumab targets Hsp90 for treatment of invasive Candida infection. For example, Eldelumab targets interferon gamma-induced protein for treatment of Crohn's disease, ulcerative colitis. For example, Elezanumab targets RGMA for treatment of spinal cord injury and multiple sclerosis. For example, Elgemtumab targets ERBB3 (HER3) for treatment of cancer. For example, Elotuzumab targets SLAMF7 for treatment of multiple myeloma. For example, Elsilimomab targets IL-6. For example, Emactuzumab targets CSF1R for treatment of cancer. For example, Emapalumab targets interferon gamma for treatment of hemophagocytic lymphohistiocytosis. For example, Emibetuzumab targets HHGFR for treatment of cancer. For example, Emicizumab targets activated F9, F10 for treatment of haemophilia A. For example, Enapotamab vedotin targets AXL for treatment of cancer. For example, Enavatuzumab targets TWEAK receptor for treatment of cancer etc. For example, Enfortumab vedotin targets nectin-4 for treatment of urothelial cancer. For example, Enlimomab pegol targets ICAM-1 (CD54). For example, Enoblituzumab targets CD276 for treatment of cancer. For example, Enokizumab targets IL9 for treatment of asthma. For example, Enoticumab targets DLL4. For example, Ensituximab targets 5AC for treatment of cancer. For example, Epitumomab cituxetan targets episialin. For example, Epratuzumab targets CD22 for treatment of cancer, SLE. For example, Eptinezumab targets calcitonin gene-related peptide for treatment of migraine. For example, Erenumab targets CGRP for treatment of migraine. For example, Erlizumab targets ITGB2 (CD18) for treatment of heart attack, stroke, traumatic shock. For example, Ertumaxomab targets HER2/neu, CD3 for treatment of breast cancer etc. For example, Etaracizumab targets integrin αvβ3 for treatment of melanoma, prostate cancer, ovarian cancer etc. For example, Etigilimab targets TIGIT. For example, Etrolizumab targets integrin β7 for treatment of inflammatory bowel disease. For example, Evinacumab targets angiopoietin 3 for treatment of dyslipidemia. For example, Evolocumab targets PCSK9 for treatment of hypercholesterolemia. For example, Exbivirumab targets hepatitis B surface antigen for treatment of hepatitis B. For example, Fanolesomab targets CD15 for treatment of appendicitis (diagnosis). For example, Faralimomab targets interferon receptor. For example, Faricimab targets VEGF-A and Ang-2 for treatment of angiogenesis, ocular vascular diseases. For example, Farletuzumab targets folate receptor 1 for treatment of ovarian cancer. For example, Fasinumab targets HNGF for treatment of acute sciatic pain. For example, FBTA05 targets CD20 for treatment of chronic lymphocytic leukaemia. For example, Felvizumab targets respiratory syncytial virus for treatment of respiratory syncytial virus infection. For example, Fezakinumab targets IL-22 for treatment of rheumatoid arthritis, psoriasis. For example, Fibatuzumab targets ephrin receptor A3. For example, Ficlatuzumab targets HGF for treatment of cancer. For example, Figitumumab targets IGF-1 receptor (CD221) for treatment of adrenocortical carcinoma and non-small cell lung carcinoma. For example, Firivumab targets influenza A virus hemagglutinin. For example, Flanvotumab targets TYRP1 (glycoprotein 75) for treatment of melanoma. For example, Fletikumab targets IL 20 for treatment of rheumatoid arthritis. For example, Flotetuzumab targets IL 3 receptor for treatment of hematological malignancies. For example, Fontolizumab targets IFN-γ for treatment of Crohn's disease. For example, Foralumab targets CD3 epsilon. For example, Foravirumab targets rabies virus glycoprotein for treatment of rabies (prophylaxis). For example, Fremanezumab targets calcitonin gene-related peptide alpha for treatment of migraine and cluster headache. For example, Fresolimumab targets TGF-β for treatment of idiopathic pulmonary fibrosis, focal segmental glomerulosclerosis, cancer. For example, Frovocimab targets PCSK9 for treatment of hypercholesterolemia. For example, Frunevetmab targets NGF. For example, Fulranumab targets NGF for treatment of pain. For example, Futuximab targets EGFR for treatment of cancer. For example, Galcanezumab targets calcitonin for treatment of migraine. For example, Galiximab targets CD80 for treatment of B-cell lymphoma. For example, Gancotamab targets HER2/neu for treatment of cancer. For example, Ganitumab targets IGF-1 receptor (CD221) for treatment of cancer. For example, Gantenerumab targets beta amyloid for treatment of Alzheimer's disease. For example, Gatipotuzumab targets MUC1 for treatment of cancer. For example, Gavilimomab targets CD147 (basigin) for treatment of graft versus host disease. For example, Gedivumab targets hemagglutinin HA. For example, Gemtuzumab ozogamicin targets CD33 for treatment of acute myelogenous leukemia. For example, Gevokizumab targets IL-1β for treatment of diabetes. For example, Gilvetmab targets PCDC1. For example, Gimsilumab targets CSF2 for treatment of rheumatoid arthritis. For example, Girentuximab targets carbonic anhydrase 9 (CA-IX) for treatment of clear cell renal cell carcinoma. For example, Glembatumumab vedotin targets GPNMB for treatment of melanoma, breast cancer. For example, Golimumab targets TNF-α for treatment of rheumatoid arthritis, psoriatic arthritis, ankylosing spondylitis. For example, Gomiliximab targets CD23 (IgE receptor) for treatment of allergic asthma. For example, Gosuranemab targets tau protein for treatment of progressive supranuclear palsy. For example, Guselkumab targets IL23 for treatment of psoriasis. For example, Ianalumab targets BAFF-R for treatment of autoimmune hepatitis. For example, Ibalizumab targets CD4 for treatment of HIV infection. For example, IBI308 targets PD-1 for treatment of squamous cell non-small cell lung cancer. For example, Ibritumomab tiuxetan targets CD20 for treatment of non-Hodgkin's lymphoma. For example, Icrucumab targets VEGFR-1 for treatment of cancer. For example, Idarucizumab targets dabigatran for treatment of reversal of anticoagulant effects of dabigatran. For example, Ifabotuzumab targets EPHA3. For example, Igovomab targets CA-125 for treatment of ovarian cancer (diagnosis). For example, Iladatuzumab vedotin targets CD97B for treatment of cancer. For example, IMAB362 targets CLDN18.2 for treatment of gastrointestinal adenocarcinomas and pancreatic tumor. For example, Imalumab targets MIF for treatment of cancer. For example, Imaprelimab targets MCAM. For example, Imciromab targets cardiac myosin for treatment of cardiac imaging. For example, Imgatuzumab targets EGFR for treatment of cancer. For example, Inclacumab targets selectin P for treatment of cardiovascular disease. For example, Indatuximab ravtansine targets SDC1 for treatment of cancer. For example, Indusatumab vedotin targets GUCY2C for treatment of cancer. For example, Inebilizumab targets CD19 for treatment of cancer, systemic sclerosis, multiple sclerosis. For example, Infliximab targets TNF-α for treatment of rheumatoid arthritis, ankylosing spondylitis, psoriatic arthritis, psoriasis, Crohn's disease, ulcerative colitis. For example, Intetumumab targets CD51 for treatment of solid tumors (prostate cancer, melanoma). For example, Inolimomab targets CD25 (α chain of IL-2receptor) for treatment of graft versus host disease. For example, inotuzumab ozogamicin targets CD22 for treatment of ALL. For example, Ipilimumab targets CD152 for treatment of melanoma. For example, Iomab-B targets CD45 for treatment of ablation of bone marrow. For example, Iratumumab targets CD30 (TNFRSF8) for treatment of Hodgkin's lymphoma. For example, Isatuximab targets CD38 for treatment of multiple myeloma. For example, Iscalimab targets CD40. For example, Istiratumab targets IGF1R, CD221 for treatment of advanced solid tumors. For example, Itolizumab targets CD6 for treatment of psoriasis. For example, Ixekizumab targets IL 17A for treatment of autoimmune diseases. For example, Keliximab targets CD4 for treatment of chronic asthma. For example, Labetuzumab targets CEA for treatment of colorectal cancer. For example, Lacnotuzumab targets CSF1, MCSF for treatment of cancer. For example, Ladiratuzumab vedotin targets LIV-1 for treatment of cancer. For example, Lampalizumab targets CFD for treatment of geographic atrophy secondary to age-related macular degeneration. For example, Lanadelumab targets kallikrein for treatment of angioedema. For example, Landogrozumab targets GDF-8 for treatment of muscle wasting disorders. For example, Laprituximab emtansine targets EGFR For example, Larcaviximab targets ebolavirus glycoprotein for treatment of Ebola virus. For example, Lebrikizumab targets IL-13 for treatment of asthma. For example, Lemalesomab targets NCA-90 (granulocyte antigen) for treatment of diagnostic agent. For example, Lendalizumab targets C5. For example, Lenvervimab targets hepatitis B surface antigen for treatment of hepatitis B. For example, Lenzilumab targets CSF2 for treatment of chronic myelomonocytic leukemia and juvenile myelomonocytic leukemia. For example, Lerdelimumab targets TGF beta 2 for treatment of reduction of scarring after glaucoma surgery. For example, Leronlimab targets CCR5. For example, Lesofavumab targets hemagglutinin HA. For example, Letolizumab targets TRAP for treatment of inflammatory diseases. For example, Lexatumumab targets TRAIL-R2 for treatment of cancer. For example, Libivirumab targets hepatitis B surface antigen for treatment of hepatitis B. For example, Lifastuzumab vedotin targets phosphate-sodium co-transporter for treatment of cancer. For example, Ligelizumab targets IGHE for treatment of severe asthma and chronic spontaneous urticaria. For example, Loncastuximab tesirine targets CD19 for treatment of cancer. For example, Losatuxizumab vedotin targets EGRF, ERBB1 HER1 for treatment of cancer. For example, Lilotomab satetraxetan targets CD37 for treatment of cancer. For example, Lintuzumab targets CD33 for treatment of cancer. For example, Lirilumab targets KIR2D for treatment of solid and hematological cancers. For example, Lodelcizumab targets PCSK9 for treatment of hypercholesterolemia. For example, Lokivetmab targets *Canis lupus familiaris* IL31 for treatment of clinical signs of atopic dermatitis in dogs[50]. For example, Lorvotuzumab mertansine targets CD56 for treatment of cancer. For example, Lucatumumab targets CD40 for treatment of multiple myeloma, non-Hodgkin's lymphoma, Hodgkin's lymphoma. For example, Lulizumab pegol targets CD28 for treatment of autoimmune diseases. For example, Lumiliximab targets CD23 (IgE receptor) for treatment of chronic lymphocytic leukemia. For example, Lumretuzumab targets ERBB3 (HER3) for treatment of cancer. For example, Lupartumab amadotin targets LYPD3. For example, Lutikizumab targets interleukin 1 alpha. For example, Mapatumumab targets TRAIL-R1 for treatment of cancer. For example, Margetuximab targets HER2 for treatment of breast cancer. For example, Marstacimab targets TFPI for treatment of bleeding with hemophilia. For example, Maslimomab targets T-cell receptor. For example, Mavrilimumab targets GMCSF receptor α-chain for treatment of rheumatoid arthritis. For example, Matuzumab targets EGFR for treatment of colorectal, lung and stomach cancer. For example, Mepolizumab targets IL-5 for treatment of asthma and white blood cell diseases. For example, Metelimumab targets TGF beta 1 for treatment of systemic scleroderma. For example, Milatuzumab targets CD74 for treatment of multiple myeloma and other hematological malignancies. For example, Minretumomab targets TAG-72 for tumor detection and therapy. For example, Mirikizumab targets IL23A for treatment of psoriasis. For example, Mirvetuximab soravtansine targets folate receptor alpha for treatment of ovarian cancer. For example, Mitumomab targets GD3 ganglioside for treatment of small cell lung carcinoma. For example, Modotuximab targets EGFR extracellular domain III for treatment of cancer. For example, Mogamulizumab targets CCR4 for treatment of adult T-cell leukemia/lymphoma. For example, Monalizumab targets NKG2A for treatment of rheumatoid arthritis, gynecologic malignancies, and other cancers. For example, Morolimumab targets Rhesus factor. For example, Mosunetuzumab targets CD3E, MS4A1, CD20 for treatment of cancer. For example, Motavizumab targets respiratory syncytial virus for treatment of respiratory syncytial virus (prevention). For example, Moxetumomab pasudotox targets CD22 for treatment of hairy cell leukemia. For example, Muromonab-CD3 targets CD3 for treatment of prevention of organ transplant rejections. For example, Nacolomab tafenatox targets C242 antigen for treatment of colorectal cancer. For example, Namilumab targets CSF2. For example, Naptumomab estafenatox targets 5T4 for treatment of non-small cell lung carcinoma, renal cell carcinoma. For example, Naratuximab emtansine targets CD37 for treatment of. For example, Narnatumab targets MST1R (aka RON) for treatment of cancer. For example, Natalizumab targets integrin α4 for treatment of multiple sclerosis, Crohn's disease. For example, Navicixizumab targets DLL4 and VEGFA for treatment of cancer. For example, Navivumab targets influenza A virushemagglutinin HA. For example, Naxitamab targets c-Met for treatment of high-risk neuroblastoma and refractory osteomedullary disease. For example, Nebacumab targets endotoxin for treatment of sepsis. For example, Necitumumab targets EGFR for treatment of non-small cell lung carcinoma. For example, Nemolizumab targets IL31RA for treatment of eczema[53]. For example, NEOD001 targets amyloid for treatment of primary systemic amyloidosis. For example, Nerelimomab targets TNF-α. For example, Nesvacumab targets angiopoietin 2 for treatment of cancer. For example, Netakimab targets interleukin 17A. For example, Nimotuzumab targets EGFR for treatment of squamous cell carcinoma, head and neck cancer, nasopharyngeal cancer, glioma. For example, Nirsevimab targets RSVFR for treatment of respiratory syncytial virus. For example, Nivolumab targets PD-1 for treatment of cancer. For example, Nofetumomab merpentan treats cancer (diagnosis). For example, Obiltoxaximab targets *Bacillus anthracis* anthrax for treatment of *Bacillus anthracis* spores. For example, Obinutuzumab targets CD20 for treatment of Chronic lymphatic leukemia. For example, Ocaratuzumab targets CD20 for treatment of cancer. For example, Ocrelizumab targets CD20 for treatment of rheumatoid arthritis, lupus erythematosus. For example, Odulimomab targets LFA-1 (CD11a) for treatment of prevention of organ transplant rejections, immunological diseases. For example, Ofatumumab targets CD20 for treatment of chronic lymphocytic leukemia. For example, Olaratumab targets PDGF-R α for treatment of cancer. For example, Oleclumab targets 5'-nucleotidase for treatment of pancreatic and colorectal cancer. For example, Olendalizumab targets complement C5a for treatment of systemic lupus erythematosus, lupus nephritis, acute graft-versus-host disease. For example, Olokizumab targets IL6 for treatment of rheumatoid arthritis. For example, Omalizumab targets IgE Fc region for treatment of allergic asthma. For example, Omburtamab targets CD276 for treatment of cancer. For example, OMS721 targets MASP-2 for treatment of atypical hemolytic uremic syndrome. For example, Onartuzumab targets human scatter factor receptor kinase for treatment of cancer. For example, Ontuxizumab targets TEM1 for treatment of cancer. For example, Onvatilimab targets VSIR For example, Opicinumab targets LINGO-1 for treatment of multiple sclerosis. For example, Oportuzumab monatox targets EpCAM for treatment of bladder cancer. For example, Oregovomab targets CA-125 for treatment of ovarian cancer. For example, Orticumab targets oxLDL. For example, Otelixizumab targets CD3 for treatment of diabetes mellitus type 1. For example, Otilimab targets GMCSF for treatment of osteoarthritis, rheumatoid arthritis. For example, Otlertuzumab targets CD37 for treatment of cancer. For example, Oxelumab targets OX-40 for treatment of asthma. For example, Ozanezumab targets NOGO-A for treatment of ALS and multiple sclerosis. For example, Ozoralizumab targets TNF-α for treatment of inflammation. For example, Pagibaximab targets lipoteichoic acid for treatment of sepsis (*Staphylococcus*). For example, Palivizumab targets F protein of respiratory syncytial virus for treatment of respiratory syncytial virus (prevention). For example, Pamrevlumab targets CTGF for treatment of idiopathic pulmonary fibrosis (IPF), pancreatic cancer. For example, Panitumumab targets EGFR for treatment of colorectal cancer. For example, Pankomab targets tumor specific glycosylation of MUC1 for treatment of ovarian cancer. For example, Panobacumab targets *Pseudomonas aeruginosa* for treatment of *Pseudomonas aeruginosa* infection. For example, Parsatuzumab targets EGFL7 for treatment of cancer. For example, Pascolizumab targets IL-4 for treatment of asthma. For example, Pasotuxizumab targets folate hydrolase for treatment of cancer. For example, Pateclizumab targets LTA for treatment of TNF. For example, Patritumab targets ERBB3 (HER3) for treatment of cancer. For example, PDR001 targets PD-1 for treatment of melanoma. For example, Pembrolizumab targets PD-1 for treatment of melanoma and other cancers. For example, Pemtumomab targets MUC1 for treatment of cancer. For example, Perakizumab targets IL 17A for treatment of arthritis. For example, Pertuzumab targets HER2/neu for treatment of cancer. For example, Pexelizumab targets C5 for treatment of reduction of side effects of cardiac surgery. For example, Pidilizumab targets PD-1 for treatment of cancer and infectious diseases. For example, Pinatuzumab vedotin targets CD22 for treatment of cancer. For example, Pintumomab targets adenocarcinoma antigen for treatment of adenocarcinoma (imaging). For example, Placulumab targets human TNF for treatment of pain and inflammatory diseases. For example, Plozalizumab targets CCR2 for treatment of diabetic nephropathy and arteriovenous graft patency. For example, Pogalizumab targets TNFR superfamily member 4. For example, Polatuzumab vedotin targets CD79B for treatment of diffuse large B-cell lymphoma. For example, Ponezumab targets human beta-amyloid for treatment of Alzheimer's disease. For example, Porgaviximab targets Zaire ebolavirus glycoprotein for treatment of Ebola virus disease. For example, Prasinezumab targets NACP for treatment of Parkinson's disease. For example, Prezalizumab targets ICOSL. For example, Priliximab targets CD4 for treatment of Crohn's disease, multiple sclerosis. For example, Pritoxaximab targets *E. coli* shiga toxin type-1. For example, Pritumumab targets vimentin for treatment of brain cancer. For example, PRO 140 targets CCR5 for treatment of HIV infection. For example, Quilizumab targets IGHE for treatment of asthma. For example, Racotumomab targets NGNA ganglioside for treatment of non-small cell lung cancer. For example, Radretumab targets fibronectin extra domain-B for treatment of cancer. For example, Rafivirumab targets rabies virus glycoprotein for treatment of rabies (prophylaxis). For example, Ralpancizumab targets neural apoptosis-regulated proteinase 1 for treatment of dyslipidemia. For example, Ramucirumab targets VEGFR2 for treatment of solid tumors. For example, Ranevetmab targets NGF for treatment of osteoarthritis in dogs. For example, Ranibizumab targets VEGF-A for treatment of macular degeneration (wet form). For example, Raxibacumab targets anthrax toxin, protective antigen for treatment of anthrax (prophylaxis and treatment). For example, Ravagalimab targets CD40 for treatment of Crohn's disease. For example, Ravulizumab targets C5 for treatment of paroxysmal nocturnal hemoglobinuria, atypical hemolytic uremic syndrome. For example, Refanezumab targets myelin-associated glycoprotein for treatment of recovery of motor function after stroke. For example, Regavirumab targets cytomegalovirus glycoprotein B for treatment of cytomegalovirus infection. For example, Relatlimab targets LAG3 for treatment of melanoma. For example, Remtolumab targets interleukin 17 alpha (TNF-α). For example, Reslizumab targets IL-5 for treatment of inflammations of the airways, skin and gastrointestinal tract. For example, Rilotumumab targets HGF for treatment of solid tumors. For example, Rinucumab targets platelet-derived growth factor receptor beta for treatment of neovascular age-related macular degeneration. For example, Risankizumab targets IL23A for treatment of Crohn's disease, psoriasis, psoriatic arthritis, and asthma. For example, Rituximab targets CD20 for treatment of lymphomas, leukemias, some autoimmune disorders. For example, Rivabazumab pegol targets *Pseudomonas aeruginosa* type III secretion system. For example, Robatumumab targets IGF-1 receptor (CD221) for treatment of cancer. For example, Rmab targets rabies virus G glycoprotein for treatment of post-exposure prophylaxis of rabies. For example, Roledumab targets RHD for treatment of Rh disease. For example, Romilkimab targets interleukin 13. For example, Romosozumab targets sclerostin for treatment of osteoporosis. For example, Rontalizumab targets IFN-α for treatment of systemic lupus erythematosus. For example, Rosmantuzumab targets root plate-specific spondin 3 for treatment of cancer. For example, Rovalpituzumab tesirine targets DLL3 for treatment of small cell lung cancer. For example, Rovelizumab targets CD11, CD18 for treatment of hemorrhagic shock. For example, Rozanolixizumab targets FCGRT. For example, Ruplizumab targets CD154 (CD40L) for treatment of rheumatic diseases. For example, SA237 targets IL-6R for treatment of neuromyelitis optica and neuromyelitis optica spectrum disorders. For example, Sacituzumab govitecan targets TROP-2 for treatment of triple-negative breast cancer. For example, Samalizumab targets CD200 for treatment of cancer. For example, Samrotamab vedotin targets LRRC15 for treatment of cancer. For example, Sarilumab targets IL6 for treatment of rheumatoid arthritis, ankylosing spondylitis. For example, Satralizumab targets IL6 receptor for treatment of neuromyelitis optica.

For example, Satumomab pendetide targets TAG-72 for treatment of cancer (diagnosis). For example, Secukinumab targets IL 17A for treatment of uveitis, rheumatoid arthritis psoriasis. For example, Selicrelumab targets CD40. For example, Seribantumab targets ERBB3 (HER3) for treatment of cancer. For example, Setoxaximab targets *E. coli* shiga toxin type-2. For example, Setrusumab targets SOST. For example, Sevirumab targets cytomegalovirus for treatment of cytomegalovirus infection. For example, Sibrotuzumab targets FAP for treatment of cancer. For example, SGN-CD19A targets CD19 for treatment of acute lymphoblastic leukemia and B-cell non-Hodgkin lymphoma. For example, SHP647 targets mucosal addressin cell adhesion molecule for treatment of Crohn's disease. For example, Sifalimumab targets IFN-α for treatment of SLE, dermatomyositis, polymyositis. For example, Siltuximab targets IL-6 for treatment of cancer. For example, Simtuzumab targets LOXL2 for treatment of fibrosis. For example, Siplizumab targets CD2 for treatment of psoriasis, graft-versus-host disease (prevention). For example, Sirtratumab vedotin targets SLITRK6 for treatment of cancer. For example, Sirukumab targets IL-6 for treatment of rheumatoid arthritis. For example, Sofituzumab vedotin targets CA-125 for treatment of ovarian cancer. For example, Solanezumab targets beta amyloid for treatment of Alzheimer's disease. For example, Solitomab targets EpCAM for treatment of gastrointestinal, lung, and other cancers. For example, Sonepcizumab targets sphingosine-1-phosphate for treatment of choroidal and retinal neovascularization. For example, Sontuzumab targets episialin. For example, Spartalizumab targets PDCD1, CD279 for treatment of melanoma. For example, Stamulumab targets myostatin for treatment of muscular dystrophy. For example, Sulesomab targets NCA-90 (granulocyte antigen) for treatment of osteomyelitis. For example, Suptavumab targets RSVFR for treatment of medically attended lower respiratory disease. For example, Sutimlimab targets C1s for treatment of cold agglutinin disease. For example, Suvizumab targets HIV-1 for treatment of viral infections. For example, Suvratoxumab targets *Staphylococcus* aureusalpha toxin for treatment of nosocomial pneumonia. For example, Tabalumab targets BAFF for treatment of B-cell cancers. For example, Tacatuzumab tetraxetan targets alpha-fetoprotein for treatment of cancer. For example, Tadocizumab targets integrin αIIbβ3 for treatment of percutaneous coronary intervention. For example, Talacotuzumab targets CD123. For example, Talizumab targets IgE for treatment of allergic reaction. For example, Tamtuvetmab targets CD52 for treatment of. For example, Tanezumab targets NGF for treatment of pain. For example, Taplitumomab paptox targets CD19 for treatment of cancer. For example, Tarextumab targets Notch receptor for treatment of cancer. For example, Tavolimab targets CD134 for treatment of cancer. For example, Tefibazumab targets clumping factor A for treatment of *Staphylococcus aureus* infection. For example, Telisotuzumab vedotin targets HGFR for treatment of cancer. For example, Tenatumomab targets tenascin C for treatment of cancer. For example, Teneliximab targets CD40 for treatment of autoimmune diseases and prevention of organ transplant rejection. For example, Teplizumab targets CD3 for treatment of diabetes mellitus type 1. For example, Tepoditamab targets dendritic cell-associated lectin 2 for treatment of cancer. For example, Teprotumumab targets IGF-1 receptor (CD221) for treatment of thyroid eye disease. For example, Tesidolumab targets C5. For example, Tetulomab targets CD37 for treatment of cancer. For example, Tezepelumab targets TSLP for treatment of asthma, atopic dermatitis. For example, TGN1412 targets CD28 for treatment of chronic lymphocytic leukemia, rheumatoid arthritis. For example, Tibulizumab targets BAFF for treatment of autoimmune disorders. For example, Tildrakizumab targets IL23 for treatment of immunologically mediated inflammatory disorders. For example, Tigatuzumab targets TRAIL-R2 for treatment of cancer. For example, Timigutuzumab targets HER2 for treatment of cancer. For example, Timolumab targets AOC3. For example, Tiragotumab targets TIGIT for treatment of cancer. For example, Tislelizumab targets PCDC1, CD279 for treatment of non-small cell lung cancer. For example, Tisotumab vedotin targets coagulation factor III for treatment of relapsed or refractory cervical cancer for example, TNX-650 targets IL-13 for treatment of Hodgkin's lymphoma. For example, Tocilizumab targets IL-6 receptor for treatment of rheumatoid arthritis. For example, Tomuzotuximab targets EGFR, HER1 for treatment of cancer. For example, Toralizumab targets CD154 (CD40L) for treatment of rheumatoid arthritis, lupus nephritis. For example, Tosatoxumab targets *Staphylococcus aureus*. For example, Tositumomab targets CD20 for treatment of follicular lymphoma. For example, Tovetumab targets PDGFRA for treatment of cancer. For example, Tralokinumab targets IL-13 for treatment of asthma, atopic dermatitis. For example, Trastuzumab targets HER2/neu for treatment of breast cancer. For example, Trastuzumab emtansine targets HER2/neu for treatment of breast cancer. For example, TRBS07 targets GD2 ganglioside for treatment of melanoma. For example, Tregalizumab targets CD4 for treatment of. For example, Tremelimumab targets CTLA-4 for treatment of non-small cell lung, head & neck, urothelial cancer. For example, Trevogrumab targets growth differentiation factor8 for treatment of muscle atrophy due to orthopedic disuse and sarcopenia. For example, Tucotuzumab celmoleukin targets EpCAM for treatment of cancer. For example, Tuvirumab targets hepatitis B virus for treatment of chronic hepatitis B. For example, Ublituximab targets MS4A1 for treatment of multiple sclerosis, chronic lymphocytic leukemia. For example, Ulocuplumab targets CXCR4 (CD184) for treatment of hematologic malignancies. For example, Urelumab targets 4-1BB (CD137) for treatment of cancer. For example, Urtoxazumab targets *Escherichia coli* for treatment of diarrhea caused by *E. coli*. For example, Ustekinumab targets IL-12, IL-23 for treatment of multiple sclerosis, psoriasis, psoriatic arthritis. For example, Utomilumab targets 4-1BB (CD137) for treatment of diffuse large B-cell lymphoma. For example, Vadastuximab talirine targets CD33 for treatment of Acute myeloid leukemia. For example, Vanalimab targets CD40. For example, Vandortuzumab vedotin targets STEAP1 for treatment of cancer. For example, Vantictumab targets Frizzled receptor for treatment of cancer. For example, Vanucizumab targets angiopoietin 2 for treatment of cancer. For example, Vapaliximab targets AOC3 (VAP-1). For example, Varisacumab targets VEGF-A for treatment of angiogenesis. For example, Varlilumab targets CD27 for treatment of solid tumors and hematologic malignancies. For example, Vatelizumab targets ITGA2 (CD49b). For example, Vedolizumab targets integrin α4β7 for treatment of Crohn's disease, ulcerative colitis. For example, Veltuzumab targets CD20 for treatment of non-Hodgkin's lymphoma. For example, Vepalimomab targets AOC3 (VAP-1) for treatment of inflammation. For example, Vesencumab targets NRP1 for treatment of solid malignancies. For example, Visilizumab targets CD3 for treatment of Crohn's disease, ulcerative colitis. For example, Vobarilizumab targets IL6R for treatment of inflammatory autoimmune diseases. For example, Volociximab targets integrin α5β1 for treatment of solid tumors. For example, Vonlerolizumab targets CD134 for treatment of cancer. For example, Vopratelimab targets CD278, aka ICOS. For example, Vorsetuzumab mafodotin targets CD70 for treatment of cancer. For example, Votumumab targets tumor antigen CTAA16.88 for treatment of colorectal tumors. For example, Vunakizumab targets interleukin 17 alpha. For example, Xentuzumab targets IGF1, IGF2. For example, XMAB-5574 targets CD19 for treatment of diffuse large B-cell lymphoma. For example, Zalutumumab targets EGFR for treatment of squamous cell carcinoma of the head and neck. For example, Zanolimumab targets CD4 for treatment of rheumatoid arthritis, psoriasis, T-cell lymphoma. For example, Zatuximab targets HER1 for treatment of cancer. For example, Zenocutuzumab targets ERBB3, HER3 for treatment of cancer. For example, Ziralimumab targets CD147 (basigin). For example, Zolbetuximab targets CLDN18 for treatment of cancer. For example, Zolimomab aritox targets CD5 for treatment of systemic lupus erythematosus, graft-versus-host disease.

In some embodiments, the antibody or antibody fragment may be human. Alternatively, the antibody or the antibody fragment may be from a mouse. In some embodiments, the antibody or the antibody fragment may be humanized.

In some embodiments, the antibody or antibody fragment may bind a protein selected from Table 2. In some embodiments, the antibody or the antibody fragment may bind a protein encoded by IL2 (interleukin 2; ENSG00000109471). In some embodiments, the antibody or antibody fragment may bind a histone complex. In some embodiments, the antibody or antibody fragment may bind a protein encoded by kallikrein (KLK; ENSG00000167759). In some embodiments, the antibody or antibody fragment may bind amyloid. In some embodiments, the antibody or antibody fragment may bind a Notch receptor. In some embodiments, the antibody or antibody fragment may bind a protein encoded by oxidized low density receptor 1 (OLR1; ENSG00000173391).

3. Signaling Pathways

Engineered platelets described herein may contain genetic modifications within the gene components of pathways for platelet adhesion, migration, and extravasation, or the engineered platelets may be loaded with proteins, nucleic acids, or small molecule drugs. The engineered platelets may not respond to endogenous stimuli usually resulting in clot formation, may not be recruited by other activated platelets, and on activation, may not be able to recruit and activate endogenous platelets in the patient.

Alternatively, the deletion or modification is introduced to genes that mediate platelet signal transduction, such as HPS (biogenesis of lysosomal organelles complex 3 subunit) genes, which are vital to ADP, serotonin, and ATP release from dense granules; and mitochondrially encoded cytochrome C oxidase II (COX2), which generates inflammatory and prothrombogenic mediators and is a target of aspirin. Alternatively, the deletion or modification is introduced to genes expressing thrombotic mediators, such as prothrombin (major protein thrombotic inducer); PDGF which is a pro-angiogenic factor; EGF (elongation growth factor); and von Willebrand Factor (collagen adaptor protein).

The combinatorial loss of thrombin and ADP signaling has been observed to abrogate vessel occlusion, but ITAM receptors can still be activated (See, Boulaftali et al. "Platelet ITAM signaling is critical for vascular integrity in inflammation". JCI, 2013 and Cornelissen et al. "Roles and interactions among protease-activated receptors and P2ry12 in hemostasis and thrombosis", PNAS. 2010, each of which is hereby incorporated by reference in its entirety). This work demonstrates that disruption of crucial endogenous platelet signaling pathways does not abrogate a platelet's ability to signal through ITAM receptors, indicating that the engineered CPRs described herein are likely to function on a non-thrombogenic platelet background.

For example, thrombin activates platelets through cleavage of PARs (protease activated receptors). Platelet signaling is also driven by protease activated GPCRs, namely PAR1 and PAR4 which are cleaved by thrombin. Signaling is potent and acts to recruit platelets and facilitate positive feedback between platelets after platelet activation. The thrombin cleavage sequence on PAR1 and PAR4 is well defined.

In some embodiments, the engineered platelets described herein may comprise at least one deletion or modification introduced into or replacing domains of endogenous platelet receptors, such as, but not limited to, PAR4 (protease activated receptor 4), which is a primary thrombin receptor; GPIb-1X-V (Glycoprotein Ib complexed with glycoprotein IX), which is a primary anchor receptor; P2Y12 (purinergic receptor P2Y12), which is an ADP (adenosine diphosphate) receptor and target of clopidogrel inhibition; GPVI (glycoprotein deletiontein VI platelet), which is a collagen receptor; or a thromboxan receptor to prevent activation of the engineered platelet.

In some embodiments, the engineered platelets can synthesize protein in response to an activation signal. For example, in Weyrich et al., BCL-3 was specifically upregulated in activated platelets through a mechanistic target of rapamycin (mTOR) dependent signaling mechanism (See, Weyrich et al. "Signal-dependent translation of a regulatory protein, Bcl-3, in activated human platelets". PNAS, 1998, which is hereby incorporated by reference in its entirety). Therefore, knock-in of a gene into the BCL-3 locus or identification of the minimal 5' UTR region that mediates activation dependent translation would allow synthetic gene expression regulation in platelets. Therefore, platelets described herein may have an altered signaling pathway resulting in signaling induced protein translation. For example, expressing a toxic protein once activated or triggering downstream events following target cell recognition.

4. Proteins Associated with Autoimmunity

In some embodiments, a CPR of the engineered platelets described herein may comprise at least a portion of a protein associated with autoimmunity. For example, the CPR may comprise at least a portion of a protein selected from the group consisting of: myelin oligodendrocyte glycoprotein (MOG), glutamic acid decarboxylase 2 (GAD65), myelin associated glycoprotein (MAG), peripheral myelin protein 22 (PMP22), thyroid peroxidase (TPO), voltage-gated potassium channel (VGKC), proteolipid protein (PLP), acetylcholine receptor (AChR), tribbles pseudokinase 2 (TRIB2), N-methyl-D-aspartate (NMDA)-type glutamate receptor (GluR), glutamate decarboxylase 2 (GAD2), Armadillo repeat containing 9 (ARMC9), Cytochrome P450 Family 21 Subfamily A Member 2 (CYP21A2), calcium sensing receptor (CASR), nuclear autoantigenic sperm protein (NASP), insulin, thyroid stimulating hormone receptor (TSHR), thyroperoxidase, asioglycoprotein receptor, Cytochrome P450 Family 2 Subfamily D Member 6 (CYP2D6), lactoferrin (LF), tissue trans-glutaminase (TTG), H/K ATP-ase, Factor XIII (F8), beta2-glycoprotein I (Beta2-GPI), erythrocyte I/I, B2 integrin (ITGB2), granulocyte-colony stimulating factor (G-CSF), glycoprotein (GP) IIb/IIa, collagen II (COLII), fibrinogen (FBG) βα, myeloperoxidase (MPO), cardiac myosin (CYO), proteinase 3 (PRTN3), trichohyalin (TCHH), bullous pemphigoid associated (BP), glycoprotein 1 (GP1), laminin-332 (LM332), transglutaminase (TGM), type VII collagen (COLVII), P80 Coilin (COIL), Desmoglein I (DSG1), Desmoglein III (DSG3), SRY-Box 10 (SOX10), small nuclear ribonucleoprotein U1 subunit (70SNRNP70), S-antigen (SAG), and Collagen alpha-3(IV) chain (α3(IV)NC1 collagen). For example, desmoglein3-ITAM CPR may be used to target pemphigus vulgaris B cells. Alternatively, the engineered platelets described herein express an MHC class 1-ITAM chimeric platelet receptor or MHC class 2-ITAM chimeric platelet receptor, such that the MHC class 1 or the MHC class 2 may be loaded with a peptide from the list above on the surface of the platelet to target autoimmune mediating T cells for destruction or for suppression through the release of anti-inflammatory cytokines, such as TGF-β. Additionally, RNA encoding transcription factors may be released, such as FOXP3 to transdifferentiate bound T cells into TRegs C. Universal Platelets In some embodiments, the engineered platelets described herein are less immunogenic than platelets produced in vivo, (e.g., platelets from a human donor). In vitro generated platelets may be made universal through deletion of the 32 microglobulin gene (See, Feng et al. "Scalable Generation of Universal Platelets from Human Induced Pluripotent Stem Cells". Stem Cell Reports, 2014, which is hereby incorporated by reference in its entirety). Even without this deletion, platelets with ABO matching are generally used in clinical practice without adverse effects. O-type platelets from humans are not universal donors as they are contaminated with anti-A/B antibodies, but contamination would not be an issue with in vitro platelets. Therefore, in certain embodiments, the inventions described herein may use these technologies to mass produce gene-edited platelets, which are also easily stored, transported, and do not require patient matching.

D. Cargo

Platelets naturally absorb drugs and antibodies in their environment through endocytosis and the open canalicular system (See, Xu et al. "Doxorubicin-loaded platelets as a smart drug delivery system: An improved therapy for lymphoma". Scientific reports, 2017 and Verheul et al. "Platelets Take Up the Monoclonal Antibody Bevacizumab". Human Cancer Biology, 2007, which of which is hereby incorporated by reference in its entirety). Platelets may be used to deliver passively loaded and genetically encoded therapeutic agents. For example, the engineered platelets may be passively loaded with therapeutic agents through endocytosis and absorption. In fact, platelet α-granules contain protein effectors and loading of soluble proteins is performed through a simple signal peptide. A minimal targeting sequence for directing proteins into platelet secretory α-granules has been previously defined (See, Golli et al. "Evidence for a Granule Targeting Sequence within Platelet Factor 4.", JBC, 2004, which is hereby incorporated by reference in its entirety). In some embodiments, activation trigger drug release in the engineered platelets. Cargo may be soluble or membrane-bound.

The cargo may also be an imaging agent.

In some preferred embodiments the cargo is not an agent that is naturally found within the platelet, i.e. the cargo is an exogenous cargo rather than an endogenous cargo with respect to the platelet. The skilled person will appreciate that a cargo can be exogenous to the platelet but endogenous to the subject.

In some preferred embodiments the cargo is not an agent that is naturally found within the platelet α-granule. For example the cargo may be an agent that is naturally found within the platelet, but not naturally found within the α-granule.

In some embodiments the cargo may be an agent that is endogenously found within the platelet but is found at a higher concentration or amount within the platelet, or within the α-granule of the platelet than in a platelet not of the invention.

In some embodiments the cargo comprises an α-granule localization signal wherein the α-granule localization signal directs the cargo to uptake into α-granule vesicles of the engineered platelet. For example in some embodiments a therapeutic agent or an imaging agent comprises or is conjugated to an α-granule localization signal.

1. Toxins

In some embodiments, engineered platelets may be loaded with toxin, which would be cloaked from the immune system. The engineered platelets may also be loaded with chemokines and/or selectins to mediate transfer of an agent across the blood brain barrier (BBB). Other embodiments of the engineered platelets may have platelet secretory granules loaded with membrane and/or soluble proteins. In certain embodiments, a toxin may be encoded with an α-granule localization signal attached to direct its uptake into secretory granules, which would be released on platelet receptor activation.

Platelet expression of programmed cell death protein (PD-1) and loading of an engineered platelet with cyclophosphamide has been observed to function as a potent anti-melanoma agent (See, Zhang et al. "Engineering PD-1-Presenting Platelets for Cancer Immunotherapy." Nano Letters, 2018, which is hereby incorporated by reference in its entirety). Specifically, megakaryocytes were engineered to express PD-1, then the resulting engineered platelets were passively loaded with cyclophosphamide. Platelet targeting to the melanoma was driven by surgical wounding of the tumor in vivo, not a synthetic receptor, resulting in $T_{reg}$ depletion in the tumor and increased CD8$^+$ T cell mediated killing. Tumor volume was observed to be significantly less 20 days after the beginning treatment for animals in the group with both PD-1 and cyclophosphamide compared to animals treated with platelets either expressing PD-1 or loaded with cyclophosphamide.

2. Nucleic Acid and Amino Acid Sequences

In some embodiments, the cargo of the engineered platelets of the invention may be a messenger RNA (mRNA). As used herein, the term "messenger RNA" (mRNA) refers to any polynucleotide which encodes a polypeptide of interest and which is capable of being translated to produce the encoded polypeptide of interest in vitro, in vivo, in situ or ex vivo. Such mRNA molecules may have the structural components or features of any of those taught in International Publication No. WO 2013/151666, which is incorporated herein by reference in its entirety.

c. CRISPR/Cas Systems

In some embodiments, a CRISPR/Cas gene editing system may be used to alter the genome of a megakaryocyte to produce the engineered platelets described herein. Alternatively, a CRISPR/Cas system may be packaged in a vesicle to be released on activation of the platelet by an antigen recognized by the CPR CRISPR/Cas systems are bacterial adaptive immune systems that utilize RNA-guided endonucleases to target specific sequences and degrade target nucleic acids. They have been adapted for use in various applications in the field of genome editing and/or transcription modulation. Any of the enzymes or orthologs known in the art or disclosed herein may be utilized in the methods herein for genome editing.

In certain embodiments, the CRISPR/Cas system may be a Type II CRISPR/Cas9 system. Cas9 is an endonuclease that functions together with a trans-activating CRISPR RNA (tracrRNA) and a CRISPR RNA (crRNA) to cleave double stranded DNAs. The two RNAs can be engineered to form a single-molecule guide RNA by connecting the 3' end of the crRNA to the 5' end of tracrRNA with a linker loop. Jinek et al., Science, 337(6096):816-821 (2012), which is hereby incorporated by reference in its entirety, showed that the CRISPR/Cas9 system is useful for RNA-programmable genome editing, and international patent application WO 2013/176772 provides numerous examples and applications of the CRISPR/Cas endonuclease system for site-specific gene editing, which are incorporated herein by reference in their entirety. Exemplary CRISPR/Cas9 systems include those derived from *Streptococcus pyogenes, Streptococcus thermophilus, Neisseria meningitidis, Treponema denticola, Streptococcus aureas*, and *Francisella tularensis*.

In certain embodiments, the CRISPR/Cas system may be a Type V CRISPR/Cpf1 system. Cpf1 is a single RNA-guided endonuclease that, in contrast to Type II systems, lacks tracrRNA. Cpf1 produces staggered DNA double-stranded break with a 4 or 5 nucleotide 5' overhang. Zetsche et al. Cell. 2015 Oct. 22; 163(3):759-71, which is hereby incorporated by reference in its entirety, provides examples of Cpf1 endonuclease that can be used in genome editing applications, which is incorporated herein by reference in its entirety. Exemplary CRISPR/Cpf1 systems include those derived from *Francisella tularensis*, Acidaminococcus sp., and Lachnospiraceae bacterium.

In certain embodiments, nickase variants of the CRISPR/Cas endonucleases that have one or the other nuclease domain inactivated may be used to increase the specificity of CRISPR-mediated genome editing. Nickases have been shown to promote HDR versus NHEJ. HDR can be directed from individual Cas nickases or using pairs of nickases that flank the target area.

In certain embodiments, catalytically inactive CRISPR/Cas systems may be used to bind to target regions (e.g., gene encoding an antigen, such as a receptor) and interfere with their function. Cas nucleases such as Cas9 and Cpf1 encompass two nuclease domains. Mutating critical residues at the catalytic sites creates variants that only bind to target sites but do not result in cleavage.

In certain embodiments, a CRISPR/Cas system may include additional functional domain(s) fused to the CRISPR/Cas endonuclease or enzyme. The functional domains may be involved in processes including but not limited to transcription activation, transcription repression, DNA methylation, histone modification, and/or chromatin remodeling. Such functional domains include but are not limited to a transcriptional activation domain (e.g., VP64 or KRAB, SID or SID4X), a transcriptional repressor, a recombinase, a transposase, a histone remodeler, a DNA methyltransferase, a cryptochrome, a light inducible/controllable domain or a chemically inducible/controllable domain.

In certain embodiments, a CRISPR/Cas endonuclease or enzyme may be administered to a cell or a patient as one or a combination of the following: one or more polypeptides, one or more mRNAs encoding the polypeptide, or one or more DNAs encoding the polypeptide.

d. Guide Nucleic Acids

In embodiments, guide nucleic acids may be used to direct the activities of an associated CRISPR/Cas enzymes to a specific target sequence within a target nucleic acid. Guide nucleic acids provide target specificity to the guide nucleic acid and CRISPR/Cas complexes by virtue of their association with the CRISPR/Cas enzymes, and the guide nucleic acids thus can direct the activity of the CRISPR/Cas enzymes.

In one aspect, guide nucleic acids may be RNA molecules. In one aspect, guide RNAs may be single-molecule guide RNAs. In one aspect, guide RNAs may be chemically modified. In certain embodiments, more than one guide RNAs may be provided to mediate multiple CRISPR/Cas-mediated activities at different sites within the genome.

3. Small Molecules Drugs

In some embodiments, the cargo in the vesicles of an engineered platelets described herein is a small molecule drug such as, but not limited to, (−)-Epigallocatechin 3-gallate, (−)-phenserine, (+)-calanolide A, (R)-folitixorin, (R)-mequitazine, (S)-pantoprazole sodium, [11C]DASB, [11C]-raclopride, [18F]FDG, [18F] HX4, 1-(2-chloroethyl)-3-cyclohexyl-1-nitrosourea, 1,2-decanediol, 11,11-di-deutero-ethyl linoleate, 11C-PBR-28, 123I-iometopane, 124I-CLR-1404, 131I-MIBG, 131-Iodine, 13-cis-retinoic acid, 13C-labeled methacetin, 13N-ammonia, 1400W94, 17 beta-estradiol, 17-alpha hydroxyprogesterone caproate, 17-beta-estradiol, 17-beta-estradiol valerate, 17-hydroxysteroid dehydrogenase inhibitors, 18F-EF5, 18F-FDG, 2 L polyethylene glycol, 25-dihydroxy-vitamin D3, 25-OH vitamin D, 2-chloroprocaine, 2-deoxyglucose, 2-Hydroxypropyl-Beta-Cyclodextrin, 2MD, 2-methoxyestradiol, 4-aminopyridine, 4-aminosalicylic acid, 4-FEC, 4-hydroxytamoxifen, 5-aminolevulinic acid, 5-aminosalicylic acid, 5-aracytine, 5-fluorouracil (5-FU), 5-hydroxytryptophan, 5-methoxypsoralen, 6-mercaptopurine, 6-thioguanine, 9-aminocamptothecin, 9-aminofusin, 9-nitrocamptothecin, abacavir, abafungin, abametapir, abediterol, abexinostat, abiraterone, ABT-072, ABT-751, acadesine, acalabrutinib, acamprosate, acamprosate calcium, acarbose, acebilustat, acebutolol, aceclidine, aceclofenac, aceneuramic acid, acenocoumarol, Acetadote, acetaminophen, acetate-free bicarbonate, acetazolamide, acetic acid, acetylcholine, acetylcysteine, acetyl-L-carnitine, acetyl-L-carnitine hydrochloride, acetyl-L-leucine, acetylsalicylic acid, acetyl-salicylic acid, Acetylsalicylic acid (ASA), acetylsalicylic acid lysinate, aciclovir, acipimox, acitretin, aclarubicin, aclidinium, aclidinium bromide, acolbifene, acorafloxacin, acotiamide hydrochloride, ACP-104, acrivastine, ACT-01, ACT-280778, actinomycin D, acumapimod, acyline, adapalene, ADC-3680, Adderall XR, adefovir dipivoxil, ademetionine, adenosine, adinazolam, adipiplon, adomeglivant, adozelesin, adramycin, adrenalin, adrenaline, adriamycin, Advair, Advil, AE-941, afacifenacin fumarate, afatinib, afegostat, afeletecan, afimoxifene, aflibercept, aftobetin, afuresertib, aganepag isopropyl, agatolimod, agave inulin, agomelatine, Aiphagan, ajmaline, aladorian, alagebrium chloride, alanyl-glutamine dipeptide, albaconazole, albendazole, albiglutide, albitiazolium bromide, albumin, albuterol, albuterol sulphate, albuterpenoids, alcaftadine, alcipotriol/betamethasone, aldesleukin, aldoxorubicin, alectinib, aleglitazar, alemtuzumab, alendronate, alendronate sodium, alendronic acid, Alequel, Aleve, alpha-calcidol, alfentanil, alfuzosin, algeldrate/magnesium oxide, Alimta, alisertib, aliskiren, alisporivir, alitretinoin, alizapride, allantoin, allisartan isoproxil, allopregnanolone, allopurinol, all-trans retinoic acid, almorexant, almotriptan, Alodan, alogliptin benzoate, alosetron, alovudine, alpelisib, alpha lipoic acid, alpha tocopherol, alpha-1 antitrypsin, alpha-cyclodextrin, alpha-glucosidase inhibitor, alpha-interferon, alpha-lipoic acid, alpha-tocopherol, alpha-tocopherol acetate, alpha-trichosanthin, alprazolam, alprostadil, alprostadil alphadex, ALS-08, altinicline, Altropane, aluminium MgS, aluminum hydroxide, alvespimycin hydrochloride, alvimopan, alvocidib, amantadine, amantadine hydrochloride, ambrisentan, ambroxol, ambroxol hydrochloride, AMD-070, amdoxovir, amelubant, amenamevir, Ametop, amfetamine, amibegron, amifampridine phosphate, amifostine, amikacin, amiloride, amiloride hydrochloride, amino acid, Aminocaproic Acid, aminoglutethimide, aminoguanidine, aminolevulinic acid, aminolevulinic acid hydrochloride, aminophylline, aminopterin, amiodarone, amiprilose, amiselimod, amisulpride, amitifadine hydrochloride, amitriptyline, Amitriptyline hydrochloride, amlexanox, amlodipine, amlodipine besilate, amlodipine besylate, amlodipine camsylate, amlodipine maleate, ammonium lactate, amnion, amodiaquine, amonafide dihydrochloride, amonafide L-malate, amorolfine, amoxapine, amoxicillin, amoxicillin clavulanate, amoxicillin MR, amoxicillin/clavulanate, amoxicillin-clavulanic acid, amoxycillin, amphetamine, amphetamine aspartate, amphetamine sulphate, amphotericin, amphotericin B, ampicillin, ampicillin sodium, ampicillin/flucloxacillin, amprenavir, amrubicin, amsacrine, amsilarotene, AN-2898, AN-9, anacetrapib, anagliptin, anagrelide, anamorelin, anastrozole, anatibant, ancriviroc, ancrod, androgen, Androxy, anecortave, angiotensin converting enzyme inhibitor, angiotensin I, angiotensin II, Angiozyme, anidulafungin, aniracetam, annamycin, antazoline, anthocyanin, anthracycline, anti-emetic, antihistamine, antilymphocyte globulin, antineoplaston A-10, antineoplaston A10-I, antineoplaston AS2-1, Antioxidant Vitamins, antipsychotic, antiretroviral drugs, antithymocyte globulin, anti-thymocyte globulin, apabet, apadenoson, apaziquone, apelin, apheresis, apilimod, apimostinel, apitolisib, apixaban, aplaviroc, aplindore, apomorphine, Apovir, apratastat, apremilast, aprepitant, apricitabine, apricoxib, aprotinin, AR-623, Ara-C, arachidonic acid, aracytine, Aralast, aramchol, arasertaconazole, arbaclofen, arbaclofen placarbil, arbekacin sulphate, arbutin, ARC-100, arformoterol, argatoroban, argatroban, arginine, arginine vasopressin, ARH-1, arhalofenate, arimoclomol, aripiprazole, armodafinil, arogliptin, arsenic trioxide, artefenomel mesylate, artemether, artemether-lumefantrine combination, artemisinin, artemisone, artemotil, artenimol, arterolane, arterolane maleate, artesunate, artesunate+mefloquine, artesunate-amodiaquine, articaine, articaine hydrochloride, arundic acid, arzoxifene, asapiprant, ASCJ-9, ascorbate, ascorbic acid, asenapine, asimadoline, ASM-024, asoprisnil, aspirin, astaxanthin, astodrimer, asunaprevir, AT-101, ataciguat, atagabalin, ataluren, atamestane, atazanavir, atazanavir sulphate, atazanavir/ritonavir, atecegatran fexenetil, Atelvia, Atenativ, atenolol, atevirdine, ATHX-105, atiprimod, atiratecan, Ativan, atomoxetine, atopaxar, atorvastatin, atovaquone, atracurium, atracurium besylate, atrasentan, atreleuton, Atripla, atropine, auranofin, auriclosene, AVAC, avacopan, avagacestat, avanafil, avasimibe, avatrombopag, AVE-0657, AVE-2268, avibactam sodium, Avil, avobenzone, avoralstat, avosentan, AWD-12-281, axelopran, Axiron, axitinib, axomadol, azacitidine, azathioprine, AZD-1775, AZD-4547, AZD-9668, Azedra, azelaic acid, azelastine, azelastine hydrochloride, azeliragon, azelnidipine, azidothimidine, azilsartan, azilsartan medoxomil potassium, azimilide, azithromycin, azithromycin dihydrate, azosemide, aztreonam, aztreonam lysine, bacitracin, baclofen, bafetinib, baicalin, balaglitazone, balicatib, balsalazide, bambuterol, banoxantrone, barasertib, bardoxolone methyl, baricitinib, barnidipine, basiliximab, basimglurant, basmisanil, batabulin, batefenterol succinate, bavisant, bazedoxifene, BCG vaccine, BCNU, becatecarin, beclabuvir, beclometasone, beclometasone dipropionate, beclomethasone, beclomethasone dipropionate, becocalcidiol, Beconase, bedaquiline, bedoradrine, bedrocon, belinostat, belladonna, belnacasan, beloranib, belotecan, bempedoic acid, benazepril, bendamustine, bendroflumethiazide, beneh, benfotiamine, benidipine, benserazide, bentamapimod, benzalkonium, benzalkonium chloride, benzathine penicillin, benzbromarone, benznidazole, benzocaine, benzodiazepine, benzophenone-3, benzoyl peroxide, benztropine, benzydamine hydrochloride, benzylic alcohol, benzylpenicillin, benzylpiperazine, Bepantol, bepotastine, beractant, beraprost sodium, berberine, berubicin, besifloxacin, besifovir, beta erythropoietin, beta-1,3/1,6-glucan, beta-blocker, beta-blockers, beta-carotene, beta-cryptoxanthin, betadine, Betafectin, betahistine, betaine, Betaine anhydrous, beta-lactamase inhibitor, Betamarc, betamethasone, betamethasone dipropionate, betamethasone mousse, betamethasone valerate, betamethasone dipropionate, beta-tricalcium phosphate bone substitute, betaxolol, betaxolol hydrochloride, bethanechol, bethanechol chloride, betrixaban, betulinic acid, bevacizumab, bevenopran, bevirimat, bexagliflozin, bexarotene, bezafibrate, BF-derm1, BGP-15, BI-54903, biapenem, bicalutamide, bicifadine, bifeprunox, bifidobacterium, Bifidobacterium bifidum, Bifidobacterium infantis 35624, bifonazole, biguanide, BIB-021, bilastine, BILR-355-BS, bimatoprost, bimoclomol, bimosiamose, bindarit, binimetinib, binodenoson. Bio-25, biotin, biperiden, biphentin, birabresib dihydrate, biricodar, birinapant, bisacodyl, biskalcitrate potassium, bismuth, bismuth citrate, bismuth potassium citrate, bismuth sodium tartrate, bismuth subcitrate, bismuth subsalicylate, bisoprolol, bisoprolol fumarate, bisphosphate, bitopertin, bixalomer, bleomycin, bleomycin sulphate, blonanserin, BMP-7, BNC-105P, boceprevir, boric acid, boron-anticancers, bortezomib, bosentan, bosutinib, bradanicline, bradykinin, Bramitob, branched chain amino acid, brecanavir, brexpiprazole, Bricanyl, Bricasol, brimonidine, brimonidine tartrate, Brinavess, brinzolamide, brivanib alaninate, brivaracetam, brivudine, brolucizumab, bromfenac, bromfenac sodium, bromhexine, bromocriptine, brompheniramine, bronopol, brostallicin, brotizolam, bryostatin-1, BTI-320, BTL-TML-HSV, BTS-67582, bucindolol, budesonide, budesonide/formoterol, budesonine, budiodarone, bumetanide, bunazosin, buparlisib, bupivacaine, bupivacaine hydrochloride, bupivacaine with fentanyl, bupivacaine-clonidine, buprenorphine, buprenorphine hemiadipate hydrochloride, buprenorphine hydrochloride, buprenorphine/naloxone, bupropion, bupropion hydrochloride, bupropion SR, burapitant, burixafor, buserelin, buserelin acetate, buspirone, buspirone hydrochloride, busulfan, Busulfex, butalbital, butenafine, butoconazole, butoconazole nitrate, butorphanol, butorphanol tartrate, C5a, Cabaseril, cabazitaxel, cabergoline, cabotegravir, cabozantinib S-malate, Cacit D3, cadazolid, CAF regimen, caffeic acid, caffeine, caffeine citrate, caffeinol, Calcichew D3 Forte, calcipotriol, calcipotriol/betamethasone, calcitriol, calcium, calcium acetate, calcium ascorbate, calcium carbonate, Calcium chloride, calcium chloride dihydrate, calcium citrate, calcium dobesilate, calcium fluoride, calcium folinate, calcium glucarate, calcium gluconate, calcium hydrogenphosphate, calcium L-aspartate, calcium levofolinate, calcium phosphate, calcium polycarbophil, Calcium sodium phosphosilicate, Calcium supplements, calcium and vitamin D, calcium leucovorin, caldaret, calphactant, camicinal, camobucol, camptothecin, canagliflozin, candesartan, candesartan cilexetil, canertinib, canfosfamide, cangrelor, cannabidiol, Cannabidiol (CBD), cannabidivarin, cantharidin, capadenoson, capecitabine, capmatinib, Capolac, capravirine, Capros, capsaicin, captopril, carbamazepine, carbenoxolone, carbetimer, carbetocin, carbidopa, carbocisteine, carbocysteine, Carbogen, carbon [14C] oxaliplatin, carbon dioxide, carbon monoxide, carbondioxide, carboplatin, Carboxymethylcellulose sodium, cardidopa, cardonutrient, carfilzomib, carglumic acid, cariporide, cariprazine, carisbamate, carisoprodol, carmegliptin, carmoterol, carmustine, camitine, carotegrast methyl, carteolol, carteolol hydrochloride, carvedilol, carvedilol phosphate, CASAD, casein, casopitant, caspofungin, catechin, CBT-1, CCPI, cebranopadol, cediranib, cefaclor, cefadroxil, cefalexin, cefazolin, cefazolin sodium, cefdinir, cefditoren pivoxil, cefepime, cefilavancin, cefixime, cefmetazole, cefoperazone, cefotaxime, cefotetan, cefoxitin, cefozopran, cefpirome, cefpodoxime, cefprozil, ceftaroline, ceftaroline fosamil, ceftazidime, ceftibuten, ceftobiprole medocaril, ceftolozane sulphate, ceftriaxone, cefuroxime, celecoxib, Celestone, celgosivir, celiprolol, celivarone, Cenestin, ceniviroc, cenobamate, censavudine, centanafadine, Centrum forte, Centrum Silver, cephalexin, cephalosporin, ceralifimod, ceramide, ceritinib, cerium nitrate, cerivastatin, cerlapirdine, certoparin, cetaphil, cethromycin, cetilistat, cetirizine, cetylpyridinium chloride, cevimeline, chenodeoxycholic acid, CHF-1535, CHF-5992, chitosan, chitosan-thiomer, chlorambucil, chloramphenicol, chlordiazepoxide, chlorhexidin, chlorhexidine, chlorhexidine digluconate, chlorhexidine gluconate, chlorhexidine-alcohol, chlorhydrate, chlormadinone acetate, chloroprocaine, chloroquine, chloroquine diphosphate, chloroquine phosphate, chlorpheniramine, chlorpheniramine maleate, chlorproguanil, chlorpromazine, chlortalidone, chlorthalidone, chlorzoxazone, cholecalciferol, cholecystokinin-8, cholesterol absorption inhibitors, cholestyramine, cholic acid, choline, choline alfoscerate, choline diepalrestat, choline fenofibrate, choline magnesium trisalicylate, chondroitin, chondroitin sulphate, CHP-HER2, Chromium cobalt, Chromium Picolinate, CHS-131, CHVP-interferon, ciclesonide, cicletanine, ciclopirox, ciclopirox olamine, ciclosporin, ciclosporine A, cidofovir, cilansetron, cilastatin, cilazapril, cilnidipine, cilomilast, cilostazol, ciluprevir, cimetidine, cimicoxib, cinacalcet, cinaciguat, cindunistat hydrochloride maleate, cinhyaluronate sodium, cinitapride, cinitapride tartrate, cinnamaldehyde, cinnarizine, cipargamin, ciprofibrate, ciprofloxacin, ciprofloxacin hydrochloride, ciraparantag, Cisapride, cisatracurium, cisatracurium besilate, cisplatin, cisplatin liposomal, cisplatinum, citalopram, citalopram hydrobromide, Citanest, citicoline, citrate, citrate fentanyl, citric acid, citric acid monohydrate, citrulline, CK-2017357, cladribine, Clarinex, clarithromycin, clavulanate, clavulanate potassium, clavulanic acid, clazosentan, clebopride, clemastine, clemastine fumarate, clenbuterol, clevidipine, clevudine, clindamicin, clindamycin, clindamycin phosphate, clindamycin/benzoyl peroxide, Clinisol, clioquinol, clobazam, clobetasol, clobetasol propionate, Clobex, clodronic acid, clofarabine, clofazimine, clomethiazole edisylate, clomifen, clomifene, clomifene citrate, clomiphene, clomiphene citrate, clomipramine, clonazepam, clonidine, clonidine hydrochloride, clopidogrel, clopidogrel hydrogen sulphate, clopidogrel napadisilate, Cloratadd-D, clorazepate, *Clostridium butyricum* MIYAIRI 588, clotrimazole, cloxacillin, clozapine, coamoxiclav, cobalamin, cobamamide, cobicistat, cobimetinib, cobiprostone, cocaine, codeine, codeine phosphate, coenzyme Q10, Coeruleus, cogentin, Cogentus, colchicine, colcine, colecalciferol, colecalciferol D3, coleneuramide, colesevelam, colestilan, colestipol, colfosceril palmitate, colistimethate, colistimethate sodium, colistin, colistin sulphate, colistineb, colloidal bismuth, colloidal bismuth tartrate, coloxyl, coluracetam, combretastatin, Comp-01, Comp-02, Comp-03, Comp-04, conivaptan, conivaptan hydrochloride, conjugated estrogen, conjugated estrogens, controlled-release carvedilol, copanlisib, copper, copper histidine, coQ10, cortexolone 17alpha-propionate, corticosteroid, cortisol, cortivazol, cositecan, CosmoFer, cotrifazid, cotrimoxazol, cotrimoxazole, co-trimoxazole, COX-inhibitor, CPI-613, CRAd 3/5-delta, creatine, creatine ethyl ester, creatine monohydrate, crenolanib, crisaborole, crizotinib, CRM-197, crobenetine, crofelemer, cromoglicate, cromoglicic acid, cromolyn sodium, Crsytalloids, C-Tb, CTO, CUDC-305, *Curcuma aeruginosa*, curcumin, curcuminoids, curdlan sulphate, cutamesine dihydrochloride, CX-516, cyanocobalamin, cyclizine, cyclizine lactate, cyclobenzaprine, cyclobenzaprine hydrochloride, cyclodextrin, cyclodextrin-combined diclofenac. Cyclogest, cyclopentolate, cyclophophamide, cyclophosphamide, cyclophosphamide monohydrate, cyclophosphan, cycloserine, cyclosporin, cyclosporine, cyclosporine A, cyclosporine microemulsion, cyclphosphamide, cyproheptadine, cyproterane acetate, cyproteron, cyproterone, cyproterone acetate, cysteamine, Cysteamine hydrochloride, cysteine, cysteine hydrochloride monohydrate, cytarabine, cytarabine arabinoside, cytarabine-asparagine conjugate, cytophosphan, Cytosin-Arabinosid, cytosine arabinoside, cytoxan, Cytozar, D3 vitamine, DA-9601, dabigatran etexilate, dabrafenib, dacarbazine, daclatasvir, daclizumab, dacomitinib, dactinomycin, dactolisib, daglutril, daidzein, dalbavancin, dalcetrapib, dalfopristin, dalteparin sodium, D-amphetamine, danazol, danirixin, danoprevir, dantrolene, dantrolene sodium, danusertib, dapaconazole, dapagliflozin, dapagliflozin propanediol, dapansutrile, dapivirine, daporinad, dapoxetine, dapsone, dapsone gel, darapladib, darifenacin, darinaparsin, darolutamide, darotropium bromide, darunavir, darunavir/ritonavir, darusentan, dasabuvir, dasatinib, dasotraline, daunorubicin, daunorubicin hydrochloride, daunorubicine, D-cycloserine, dDAVP, DDP, DE-104, DE-110, DE-112, Deanxit, Debio-1450, Debio-1452, decadron, decarbazine, decernotinib, decitabine, decoglurant, Decuprate, defactinib, deferasirox, deferiprone, deferitazole, deferoxamine, deferoxamine mesylate, deflazacort, dehydroepiandrosterone, delafloxacin, delamanid, delanzomib, delapril, delapril hydrochloride, delavirdine, Delazine, deleobuvir, deligoparin sodium, delorazepam, delta-8-THC, delta-9-tetrahydrocannabinol, denagliptin, denufosol tetrasodium, Depacon, Depade, depo-medroxyprogesterone, depomedroxyprogesterone acetate, depomethylprednisolone, depotestosterone, DER-45-EV, derenofylline, dersalazine sodium, desferrioxamine, desflurane, desipramine, desloratadine, desmopressin, desmopressin acetate, desogestrel, desonide, desote fumarate, desoximetasone, desvenlafaxine, Detox-B adjuvant, deutetrabenazine, dexamethasone, dexamethasone acetate, dexamethasone cipecilate, dexamethasone diphosphate, dexamethasone phosphate, dexamethasone sodium phosphate, dexamfetamine, dexanabinol, dexchlorpheniramine, dexedrine, dexelvucitabine, dexfenfluramine, dexibuprofen. Dexid, dexisometheptene mucate, dexketoprofen, dexketoprofen trometamol, dexlansoprazole, dexlipotam, dexioxiglumide, dexmecamylamine, dexmedetomidine, dexmethylphenidate, dexniguldipine, dexpanthenol, dexpramipexole, dexrazoxane, dexrazoxane hydrochloride, dextofisopam, dextran, dextroamphetamine, dextroamphetamine saccharate, dextroamphetamine sulphate, dextromethorphan, dextromethorphan hydrobromide, dextropropoxyphene, dextropropoxyphene hydrochloride, dextrose, dexverapamil, dezocine, DHEA, diacerein, diacetylmorphine, Dialysate calcium, Diamel, diammindichloridoplatin, diamorphine, diamorphine hydrochloride, dianhydrogalactitol, dianicline, Diao Xin Xue Kang, diazemuls, diazepam, diazepam autoinjector, diazoxide, diazoxide choline, dibasic dihydrate sodium phosphate, dibasic sodium phosphate, dibekacin, dichlorphenamide, Diclazuril, diclofenac, diclofenac diethylamine, diclofenac potassium, diclofenac sodium, dicloxacillin, didanosine, dienogest, diethylcarbamazine, diethylnorspermine, diethylpropion, diethylstilbestrol, diflomotecan, diflunisal, difluprednate, digitoxin, digoxin, dihematoporphyrin, dihomo gamma-linolenic acid, dihydralazine, dihydroartemisinin, dihydroartemisinin-piperaquine, dihydrocodeine, dihydroergotamine, dihydroergotamine mesylate, dihydroxy vitamin D3, diiodothyropropionic acid and its analogs, diiphenhydramine, dilaudid, dilmapimod, diltiazem, diltiazem hydrochloride, dimenhidrinate, dimenhydrinate, dimesna, dimethindene, dimethindene maleate, dimethyl fumarate, dimethylfumarate, dimiracetam, dinoprostone, diosmin, diphencyprone, diphenhydramine, diphenylcyclopropenone, dipirone, dipraglurant-IR, dipyradimole, dipyridamole, dipyrone, diquafosol sodium, diquafosol tetrasodium, disopyramide, Dispase H, disufenton sodium, disulfiram, dithranol, ditiocarb sodium, DLBS-1033, DLBS-1425, D-methadone, DNE3, dobutamine, docetaxel, dociparstat, doconexent, doconexent ethyl ester, docosahexaenoic acid [DHA], docosahexaenoic acid monoglycerides, docosanol, docusate, docusate sodium, dofetilide, dolasetron, dolastatin-10, dologesic, dolutegravir, domperidone, donepezil, donepezil hydrochloride, donu, dopamine, dopexamine, doramapimod, doravirine, doripenem, dorzolamide, dorzolamide hydrochloride, dorzolamide hydrochloride+timolol maleate, dothiepin, dovitinib, doxapram, doxazosin, doxazosin mesylate, doxepin, doxepin hydrochloride, doxercalciferol, doxifluridine, Doxil, doxophylline, doxorubicin, doxorubicin etarfolatide, doxorubicin HCl liposome, doxorubicin hydrochloride, doxorubicin hydrochloride liposome, doxycycline, doxycycline hyclate, doxylamine, doxylamine succinate, D-penicillamine, DPP-IV inhibitors, DPS-102, draflazine, drinabant, dronabinol, dronedarone, droperidol, dropropizine, drospirenone, drotaverine, droxidopa, D-tagatose, D-TRANS fentanyl, Duac, dual-release hydrocortisone, dulaglutide, Dulcolax, duloxetine, Duracain, duramorph, Durolane, dutasteride, dutogliptin, duvelisib, duvoglustat, D-xylose, dydrogesterone, dyhydroprogesterone, DZ-1, *E. coli* Nissle, E-7016, E-7820, ebastine, ebselen, EC-17, ecabet, ecabet sodium, *Echinacea*, econazole nitrate, ecopipam, ecosprin, ecraprost, Ecural, edaglitazone, edaravone, edetate calcium disodium, edivoxetine, edonerpic maleate, edotecarin, edoxaban, EES0000645/A, efaproxiral, efatutazone, efavirenz, efinaconazole, eflornithine, efonidipine hydrochloride, EGb-761, EGCG, eicosapentaenoic acid, eicosapentanoeic acid, elacestrant, elacridar, elacytarabine, elafibranor, elagolix, elamipretide, elbasvir, elbion, eldecalcitol, eleclazine, elesclomol sodium, eletriptan, eliglustat tartrate, elinogrel, eliprodil, ELND-005, elobixibat, elocalcitol, Elomet, Elosalic, elsamitrucin, eltoprazine, eltrombopag, elubrixin, eluxadoline dihydrochloride, elvitegravir, elvorin, elvucitabine, elzasonan, Emdogain, emedastine, emepepimut-S, emicerfont, emivirine, emixustat, empagliflozin, emricasan, emtricitabine, enalapril, enalapril maleate, enalaprilat, enasidenib, encaleret sulphate, enclomifene citrate, enclomiphene, encorafenib, endocannabinoid palmitoylethanolamide, endonase, endotoxin, endoxan, enecadin, enflurane, enfuvirtide, eniluracil, ENMD-2076, enobosarm, enocitabine, enoxaparin sodium, enoximone, entacapone, entecavir, entecavir maleate, enteric-coated mycophenolate sodium, enteric-coated tegafur-uracil, Enteroaggregative *E. coli*, entinostat, entonox, enzalutamide, enzastaurin, epacadostat, Epadel, epairestat, eperisone, eperisone hydrochloride, epetirimod, epetraborole, ephedrine, Epiceram, epidoxirubicin, epidoxorubicin, epidural/paravertebral analgesia, epigallocatechin gallate, epigallocatechin-3-gallate, epigallocatechin-gallate, Epiggallocatechin, epinastine, epinastine hydrochloride, epinephrine, epirubicin, epirubicin hydrochloride, Episalvan, eplerenone, eplivanserin, epoprostenol, Eppikajutsutou, eprodisate, eprosartan, eprotirome, epsilon-aminocaproic acid, eptastigmine, eptifibatide, Equine antithymocyte immunoglobulin, Equisetum arvense, eravacycline, erdosteine, Eremostachys laciniata, ergocalciferol, ergotamine, eribaxaban, eribulin mesylate, Eritex, eritoran, erlotinib, ertapenem, erteberel, ertugliflozin, erythromycin, erythromycin lactobionate, erythropoetin, erythropoietin beta, ESAT-6CFP10, esaxerenone, *Escherichia coli* endotoxin, escitalopram, esflurbiprofen, Eskalith, esketamine, esketamine hydrochloride, eslicarbazepine acetate, Esmeron, esmirtazapine, esmolol, esmolol hydrochloride, esomeprazole, esoxybutynin, esreboxetine, estazolam, estetrol, estradiol, estradiol acetate, estradiol cypionate, estradiol valerate, estradiol/norethindrone acetate, estramustine, estramustine phosphate, estramustine phosphate sodium, Estratest, estriol, estriol E3, estrodiol, estrogen, estrogens, eszopiclone, etacrynic acid, etalocib, Etalpha, etanercept biosimilar, etazolate, Ethacrynic acid, ethambutol, ethambutol hydrochloride, ethanol, ethinyl estradiol, ethinyl estradiol/levonorgestrel, ethinylestradiol, ethiodized oil, ethosuximide, ethyl chloride, ethyl eicosapentaenoate, ethyl hydrogen fumarate calcium, ethyl hydrogen fumarate magnesium, ethyl hydrogen fumarate zinc, ethylenediaminetetraacetate, ethylhexyl triazone, ethynylcytidine, etidronic acid, etilefrine, etodolac, etomidate, etomidate Lipuro, etomoxir, etonogestrel, etonox, etoposide, etoposide phosphate, etoricoxib, etravirine, EV-06, evacetrapib, evatanepag, everolimus, eviprostat, evofosfamide, evogliptin, exatecan, exemestane, exenatide, exeporfinium chloride, exisulind, ezatiostat, ezetimibe, ezetimibe/atorvastatin, F-0434, F0-MO, F0-M1700, F160-M0, F160-M1000, F160-M1700, F80-M1000, F80-M1700, FA, facinicline hydrochloride, faldaprevir, famciclovir, famitinib L-malate, famotidine, fampridine, Fangji, farampator, farglitazar, faropenem, faropenem medoxomil, fasiglifam hemihydrate, fasitibant chloride, fasudil, favipiravir, FBG-18, FBP peptides, FE[50]C, FE[75]C, Fe-58, febuxostat, fedovapagon, fedratinib, felbamate, felbinac, felodipine, fenatnyl, fenobam, fenofibrate, fenoldopam, fenoterol, fenoterol prednisone, fenretinide, fentanyl, fentanyl citrate, fermagate, ferric carboxymaltose, ferric citrate, ferric maltol, ferric pyrophosphate, Ferripel-3, ferroquine, ferrous fumarate, ferrous sulphate, ferumoxtran-10, ferumoxytol, FeSO4, fesoterodine fumarate, fevipiprant, fexinidazole, fexofenadine, fiboflapon, fibrinogen, fidaxomicin, filanesib, filgotinib, filgrastim, filibuvir, filorexant, fimaporfin, fimasartan, finafloxacin, finafloxacin hydrochloride, finasteride, finerenone, fingolimod, Fioricet, fipamezole, fish oil (eicosapentaenoic acid [EPA] plus docosahexaenoic acid [DHA]), Fisiogel, fispemifene, Flagyl, Flavan-3-ol, flavanone, flavoxate, flecainide, flibanserin, flomoxef, flomoxef sodium, flopristin, florbenazine, florbetapir, flortaucipir F 18, flourinic acid, flovagatran, floxuridine, fluciclatide F 18, flucloxacillin, fluconazole, flucytosine, fludarabine, fludeoxyglucose, fludeoxyglucose F 18, fludrocortisone, flumazenil, flunarizine, flunisolide, fluocinolone acetonide, fluocinonide, fluorescein, fluorometholone, fluorometholone acetate, fluoropyrimidine, fluoroquinolones, fluorouracil, fluoxetine, fluoxetine hydrochloride, flupenthixol, flupentixol, fluphenazine, flupirtine, flurbiprofen, flurbiprofen axetil, flurbiprofen sodium, flutamide, fluticasone, fluticasone furoate, fluticasone propionate, flutrimazole, fluvastatin, fluvoxamine, FM-VP4, folacin, folate, folate/iron, FOLFIRI, FOLFOX4, FOLFOXIRI, folic acid, folinate, folinic acid, folitixorin calcium, follitropin beta, fonadelpar, fondaparinux sodium, Foradil, foretinib, formoterol, formoterol fumarate, forodesine, foropafant, fosalvudine tidoxil, fosamprenavir, fosamprenavir calcium, fosaprepitant, fosbretabulin, fosbretabulin disodium, foscarnet, foscarnet sodium, fosdagrocorat, fosdevirine, fosfluridine tidoxil, fosfomycin, fosfomycin trometamol, fosfructose, fosinopril, fosmidomycin, fosphenytoin, fospropofol, fostamatinib, fostemsavir tromethamine, Fostimone, Fostrap, fotemustine, fozivudine tidoxil, freselestat, Fresubin, frovatriptan, fructose, fructose-1,6-diphosphate, fruquintinib, frusemide, fucoidan, fulvestrant, fumarate, funapide, furaprevir, furazolidone, furosemide, fusidate sodium, fusidic acid, Fuzheng Huayu, gabapentin, gabapentin enacarbil, gaboxadol, gadobenic acid, gadobutrol, gadofosveset, gadolinium, gadopentetate dimeglumine, gadoterate meglumine, gadoversetamide, gadoxetate disodium, Galactooligosaccharide, Galacto-oligosaccharides, galantamine, galantamine CR, galeterone, gallium maltolate, gallium nitrate, gallopamil, gambogic acid, Gamma-Linolenic Acid, gamma-tocopherol, ganaxolone, ganciclovir, ganciclovir phosphonate, ganetespib, ganirelix acetate, ganstigmine, garenoxacin, garlic, gatifloxacin, GCS-100, G-CSF, gedatolisib, gefitinib, gelatin, Gelofusine, Gelpart, gemcabene, gemcitabine, gemcitabine elaidate, gemcitabine prodrug, gemfibrozil, gemifloxacin, gemigliptin, gemigliptin tartaric acid, Gemzar, Genaera, genistein, genistein+decitabine, gentamicin, gentamicin sulphate, gentamycin, gepirone, gepotidacin, gestodene, gestodone, gestrinone, gilteritinib, gimatecan, gimeracil, *Ginkgo biloba*, ginkgolides meglumine, ginsenoside Rg3, ginsenoside-Rd, giripladib, gisadenafil, givinostat, GKT-831, glatiramer acetate, glecaprevir, glesatinib glycolate, glibenclamide, gliclazide, glimepiride, glinide, glipizide, glitazone, GLP-1 analog, glucagon-like peptide-1, glucocorticoids, glucocorticosteroid, glucosamine, glucosamine hydrochloride, glucose, glufosfamide, glutamic acid, glutamine, glutathione, glycerin, glycerol, glycerol phenylbutyrate, glycoprotein IIb/IIIa inhibitor, glycopyrolate, glycopyrrolate, glycopyrronium bromide, glycopyrronium tosylate, glycopyrronium-bromide, glycyrrhizin, glyminox, GM1, GM-CT-01, GnRH antagonist, gold sodium thiosulphate, golotimod, golvatinib tartrate, gonadotopin, gonadotropin, gonadotropins, GoodBelly probiotic, goserelin acetate, goshajinkigan, gosogliptin, gp100, GPO-Vir Z30, granisetron, granotapide, grazoprevir, grepafloxacin, griseofulvin, GR-MD-02, GSK-2269557, GSK-2330672, GSK-2339345, guaifenesin, guanethidine, guanfacine, Guizhi fulings, gusperimus trihydrochloride, GWP-42004, gycerol, Gynostemma pentapyllum, H2 blockers, haldol, halofuginone, haloperidol, haloperidol decanoate, halothane, Hangeshashin-to, HBW, HE-3286, Healon, Helico DR, heliox, heme arginate, hemin, hemoximer, heparin, heparin sodium, Her-2/neu, heroin, hexachlorophene, hexaminolevulinate hydrochloride, Hextend, HF-0220, *Hibiscus sabdariffa*, hidrotalcid, himantane, histamine dihydrochloride, homatropine, honey, hpFSH, HPP-404, HQK-1004, huachansu, Huai Qi Huang, human chorionic gonadotrophin, huperzine A, Hyabest J, hyaluronan, hyaluronate sodium, hyaluronic acid, hyaluronic acid hydrogel, hydralazine, hydrochloric acid, hydrochlorothiazide, hydrochlorothiazide tablet, hydrochlorthiazide, hydrocodone, hydrocodone bitartrate, hydrocodone/acetaminophen, hydrocortisone, hydrocortisone sodium succinate, hydrocortisone-17-butyrate, hydrocortone, hydrogel, hydrogen peroxide, hydromorphine, hydromorphone, hydromorphone hydrochloride, hydroquinidine, hydroquinone, hydroxocobalamin, hydroxycarbamide, hydroxychloroquine, hydroxydaunorubicin, hydroxyethyl starch, hydroxyethylstarch solution, Hydroxyl-propyl-methyl cellulose powder, hydroxymethylbutyrate, hydroxynortriptyline, hydroxyprogesterone caproate, hydroxypropyl cellulose, hydroxytryptophan, hydroxyurea, hydroxyzine, hylastan, Hylenex recombinant, hyoscine butylbromide, hyoscine hydrobromide, hyoscine N-butylbromide, hyoscyamine sulphate, hyperbaric bupivacaine, hypericin, *Hypericum perforatum*, hyperosmolar dextrose, hypertonic saline, hypromellose, ibandronate, ibandronic acid, iberogast, iberogast N, IBH-B, ibipinabant, ibodutant, ibopamine, ibrutinib, ibudilast, ibuprofen, ibutamoren mesylate, ibuterol, ibutilide, icaritin, icodextrin, icofungipen, icosabutate, icosapent, icosapent ethyl, icosapent ethyl ester, icotinib hydrochloride, idalopirdine, idarubicin, idazoxan, IdB-1016, idebenone, idelalisib, idoxuridine, idrabiotaparinux sodium, idraparinux sodium, idronoxil, iferanserin, ifetroban, ifetroban sodium, IFN-alpha2b, ifosfamide, iguratimod, IHBG-10, IL-2, ilaprazole, ilepatril, iloperidone, iloprost, iloprost betadex clathrate, imagabalin, imatinib, ImCOOH, imeglimin, imexon, imidafenacin, imidapril, imiglitazar, imipenem, imipramine, imiquimod, imisopasem manganese, IMO-2125, implitapide, incyclinide, indacaterol, indacaterol acetate, indacaterol maleate, indacaterol xinafoate, indantadol, indapamide, indapamide SR, indeglitazar, indinavir, Indinol Forto, indiplon, indisetron, indisulam, Indium In 111 anti-CD66 monoclonal antibody BW250/183, indocyanine green, indomethacin, indomethacin, indoramin, industrial nitric oxide, inecalcitol, INF-alpha, infigratinib, infliximab, Ingaviril, ingenol mebutate, inhaled sodium nitrite, iniparib, injectable progestin, inosine, inosine pranobex, inositol, INS-1, insulin, insulin glargine, insulin NPH, intepirdine, interferon, interferon alpha, interferon alpha-2a, interferon alpha-2b, interferon beta-1a, interferon beta1b, interleukin, interleukin-2, interleukin-6, intetumumab, Intracel, intranasal ketamine, intravenous immunoglobulin, intravenous minocycline, iobenguane I-131, iodine, iodine I 131 ethiodized oil, iodine I 131 monoclonal antibody BC8, iodine tincture, iodixanol, iohexol, iopamidol, iopromide, ipragliflozin, ipratropium, ipratropium bromide, IPX-159, IPX-231, irbesartan, irinotecan, irinotecan hydrochloride, irinotecan sucrosofate, irofulven, iron, iron folic acid, iron hydroxide polymaltose, iron oxide, iron proteinsuccinylate, iron solution, iron sucrose, iron supplements, irosustat, irsogladine maleate, IRX-5183, ISA-51, isavuconazonium chloride/sulphate, Iscar, iseganan, Isobide, isocaloric diet, isocarboxazid, isoflavone, isoflavones, isoflurane, Isolyte-S, isoniazid, isoniazide, isoprinosine, isopropyl alcohol, isopropyl unoprostone, isoproterenol, isoquercetin, isosorbide dinitrate, isosorbide mononitrate, isosorbide-5-mononitrate, isosulfan blue, isotretinoin, isovaleramide, ispinesib, ispronicline, isradipine, israpafant, istaroxime, itacitinib, itasetron, itopride hydrochloride, itraconazole, itriglumide, ivabradine, ivabradine hydrochloride, ivacaftor, ivermectin, ixabepilone, ixazomib citrate, Jin Fu Kang, JNJ-56914845, Jobelyn, josamycin, *Juglans regia* extract, Juvidex, Kamikihi-to, kanamycin, kava, KD-018, Keflin, Kenalog, Kenalog-10, ketamine, ketamine hydrochloride, ketanserin, ketoconazole, ketoprofen, ketorolac, ketorolac tromethamine, ketotifen, KLH, Krestin, KRX-0402, KT6-971, KW-2450, KW-2478, KWA-0711, KX2-391, L9NC, labetalol, labradimil, lacidipine, Lacidofil Strong, lacosamide, lactated ringer's solution, lactic acid, LACTIN-V, lactitol, *lactobacillus, Lactobacillus acidophilus, Lactobacillus acidophilus* KS400, *Lactobacillus casei rhamnosus, Lactobacillus delbrueckii, Lactobacillus paracasei* F19, *Lactobacillus paracasei* LP-33, *Lactobacillus plantarum* 299v, *Lactobacillus reuteri, Lactobacillus rhamnosus, Lactobacillus* Sporogens, lactose, lactose monohydrate, lactulose, ladarixin, ladostigil, lafutidine, L-alanosine, lamivudine, lamotrigine, landiolol, lanicemine, laninamivir octanoate, laniquidar, lanoconazole, lanopepden, lanperisone, lansoprazole, lanthanum carbonate, lapaquistat, lapatinib, laquinimod, L-arginine, laromustine, laropiprant, larotaxel, L-ascorbic acid, lasmiditan, lasofoxifene, L-asparaginase, latanoprost, latanoprost, latanoprostene bunod, latrepirdine, lauric acid, lazabemide, LC-150444, L-carnitine, L-citrulline, LCL-161, Lcr-35, L-dopa, lecovorin, lecozotan, lecozotan SR, lederfolin, ledipasvir, lefamulin, leflunomide, lemborexant, lemuteporfin, lenalidomide, lenograstim, lentinan, lentinan viral, lenvatinib mesylate, LEO-80122, L-epinephrine, lercanidipine, lersivirine, lesinurad, lesogaberan, lestaurtinib, letaxaban, leteprinim, letermovir, letrozole, leucine, leucoverin, leucovorin, leucovorin calcium, leukapheresis, leukotriene B4 (LTB4), leuprorelide, leuprorelin acetate, levalbuterol, levalbuterol hydrochloride, levamfetamine, levamisole, levamlodipine, levamlodipine besylate, levetiracetam, levobetaxolol, levobupivacaine, levocabastine hydrochloride, levocarnitine, levocetirizine, levocetirizine dihydrochloride, levodopa, levofloxacin, levofolinate, levogestrel, levoketoconazole, levoleucovorin, levo-leucovorin, levomequitazine, levomilnacipran, levonorgestrel, levo-phencynonate hydrochloride, levorphanol, levosalbutamol, levosimendan, levosulpiride, levothyroxine, levothyroxine sodium, levotofisopam, lexibulin, lexipafant, L-folinic acid, L-glutamine, LH-RH agonist, liafensine, liarozole, Libifem, licarbazepine, licochalcone A, licofelone, lidocaine, lidocaine chlorhydrate, lidocaine-prilocaine, lifibrol, lifitegrast, lignocaine, LIK-066, limaprost, Limtop, linagliptin, linaprazan, lincomycin, linezolid, linifanib, linoleic acid, linopristin, linsitinib, liothyronine, liothyronine sodium, lipid, lipiodol, Lipiodol-ethanol mixture, Lipocine, LipoCol, lipoic acid, lipopolysaccharide, liposomal amphotericin B, liposomal cisplatin, liposomal doxorubicin, liposomal paclitaxel, liposomal prostaglandin E-1, liposomal vincristine, Liproca Depot, lisavanbulin hydrochloride, lisdexamfetamine, lisinopril, lisofylline, lisuride, lithium, lithium carbonate, Lithium citrate, lithium salt, litronesib, lixivaptan, L-leucovorin, L-leucyl-L-leucine methyl ester, L-NMMA, lobaplatin, lobeglitazone, lobeline, lobeline sulphate, lobucavir, lodenafil carbonate, lodenosine, lofepramine, lofexidine, lomibuvir, lomitapide, lomustine, Lomustine (CCNU), lonafarnib, lonaprisan, Long chain fatty acids, long-chain polyunsaturated fatty acids, lonidamine, loperamide, loperamide hydrochloride, loperamide oxide, lopinavir, lopinavir/ritonavir, loratadine, lorazepam, lorcaserin, lorediplon, lormetazepam, L-ornithine L-aspartate, lornoxicam, losartan, losartan potassium, losigamone, losmapimod, loteprednol etabonate, lovastatin, loxapine, loxoprofen, lubiprostone, lucanthone, lucitanib hydrochloride, luliconazole, lumacaftor, lumateperone toluenesulfonate, lumefantrine, lumicitabine, luminespib, lumiracoxib, lunacalcipol, lurasidone, lurbinectedin, Lurotin, lurtotecan, luseogliflozin hydrate, lusutrombopag, lutein, LY-2090314, LY-2623091, Lybrido, lycopene, lymecycline, lynestrenol, Lysomucil, macimorelin, macitentan, Macrolids, mafenide, mafosfamide, MAGE-A1, MAG-EPA oil, magnesium, magnesium aluminum hydroxide, magnesium carbonate, magnesium chloride, magnesium chloride hexahydrate, magnesium citrate, magnesium gluconate, magnesium hydroxide, magnesium isoglycyrrhizinate, magnesium oxide, magnesium sulphate, magnesium valproate, malathion, managlinat dialanetil, mangafodipir, manganese, manidipine, manidipine dihydrochloride, manitimus, mannitol, mapracorat, maprotiline, maralixibat chloride, maraviroc, maribavir, Marijuana, marimastat, marvelone, masilukast, masitinib, masoprocol, mavoglurant, maxacalcitol, mazindol, MCC-135, MDR1, MDT-10013, mebendazole, mebeverine, mebeverine hydrochloride, mecamylamine, mechlorethamine, meclinertant, meclizine, mecobalamin, mecobalamin monohydrate, Medium chain fatty acids, medroxyprogesterone, medroxyprogesterone acetate, mefenamic acid, mefloquine, megestrol, megestrol acetate, meglumine antimoniate, melagatran, Melan-A, melarsoprol, melatonin, meldonium, melfalan, meloxicam, melperone, melphalan, melphalan hydrochloride, memantine hydrochloride, menaquinone, menaquinone-7, menatetrenone, Meniace, menotropin, menotropins, menstrogol, mepacrine, meperidine, mephalan, mepivacaine, mepivacaine chlorhydrate, mepivacaine hydrochloride, mepridine, MER-104, merbarone, mercaptamine, mercaptamine bitartrate, mercaptopurine, mericitabine, merimepodib, meropenem, mesalamine, mesalazine, mesna, metadoxine, Metafolin, Metaglip, metamizole, metamizole sodium, metaraminol, Meteospasmyl, metformin, metformin glycinate, metformin HCl, metformin hydrochloride, metformin SR, methacholine, methadone, methadone hydrochloride, methamphetamine, methazolamide, methimazole, methionine, methocarbamol, methohexital, methotrexate, methotrimeprazine, methoxsalen, methoxyflurane, methoxypsoralen, methyl aminolevulinate hydrochloride, methyl prednisolone, methyl prednisolone acetate, methylcobalamin, methyldibromoglutaronitrile, methyldopa, methylene blue, methylnaltrexone bromide, methylphenidate, methylphenidate hydrochloride, methylprednisolone, methylprednisolone aceponate, methylprednisolone acetate, methylprednisolone sodium succinate, methylprednisone, methylsamidorphan, methylsulfonylmethane, methyltetrahydrofolate, methylthioninium chloride, metirosine, Metobes-compound, metocloperamide, metoclopramide, metolazone, metoprolol, metoprolol succinate, metoprolol tartrate, metoprolol XL, metranidazole, MetroGel, metronidazole, metronomic cyclophosphamide, metyrapone, mexiletine, mexiletine hydrochloride, Mexoryl SX, Mexoryl X1+titanium dioxide, mianserin, mibampator, MIBG, miconazole, miconazole nitrate, microalgal oil, micronized progesterone, micronutrient mixture, midazolam, midazolam hydrochloride, middle-chain and polyunsaturated fatty acids, midodrine, midostaurin, mifepristone, miflonide, migalastat, miglitol, miglustat, milataxel, milnacipran, milrinone, miltefosine, milveterol, mimopezil, minocycline, minocycline hydrochloride, minodronic acid, minoxidil, mirabegron, miriplatin hydrate, mirodenafil, mirtazapine, misoprostol, mitemcinal, mitiglinide, mitoguazone, mitolactol, mitomycin, Mitomycin C, mitoquinone/mitoquinol redox mixture, mitotane, mitoxantrone, mivacurium, mivacurium chloride, mivobulin, mixed salt amphetamine, mizolastine, mizoribine, MK-0782, MK-0893, MK-2206, MK-7622, MK-8457, MMF, mocetinostat dihydrobromide, moclobemide, modafinil, moexipril, molidustat, molindone, molsidomine, molybdenum, momelotinib, mometasone, mometasone furoate, monolaurin, monosodium glutamate, montanide ISA-51, montelukast, montelukast sodium, moracizine, morphine, morphine chloride, morphine glucuronide, morphine hydrochloride, morphine sulphate, mosapride, motesanib diphosphate, motexafin gadolinium, motexafin lutetium, motolimod, moxidectin, moxifloxacin, moxifloxacin hydrochloride, moxonidine, MP-435, MSC-apceth-111, MT-102, Mucaine, Mucopolysaccharide, *Mucuna pruriens*, multivitamins, muparfostat sodium, mupirocin, muraglitazar, mustine, *Mycobacterium* w, mycophenolate acid, mycophenolate mofetil, mycophenolate sodium, mycophenolic acid, mycostatin, Mydriasert, Myfenax, Myrtus *Communis* L, mytomycin, N2O-O2, nabilone, nabiximols, nabumetone, N-acetyl cysteine, N-acetylcisteine, N-acetylcysteine, N-acetyl-L-cysteine, N-acetyl-p-aminophenol, NaCl, nadifloxacin, nadolol, nadroparin calcium, nafamostat, nafamostat mesilate, nafarelin, NaFeEDTA, naftifine, naftifine hydrochloride, naftopidil, nalbuphine, nalbuphine sebacate, naldemedine, nalfurafine, nalmefene, naloxegol, naloxone, naltrexone, naltrexone hydrochloride, naltrexone-poly(DL-lactide), naluzotan, Namodenoson, nandrolone, Naoxintong, napabucasin, naphthoquine, naproxcinod, naproxen, naproxen etemesil, naproxen sodium, naratriptan, naronapride, narrowband UVB, nasapaque, nastorazepide calcium, natamycin, nateglinide, navamepent, navarixin, naveglitazar, navitoclax, N-chlorotaurine, nebentan, nebicapone, nebivolol, nebulized amikacin, nebulized budesonide, Nebusal, nedaplatin, nefazodone, nefiracetam, neflamapimod, nefopam, neladenoson bialanate, nelarabine, nelfinavir, nelivaptan, nelociguat, nelonicline, nelotanserin, nemonoxacin, nemorubicin, neomycin, neomycin sulphate, neostigmine, nepadutant, nepafenac, nepicastat, neramexane, neratinib, neridronic acid, nerispirdine, netarsudil, netilmicin, netivudine, netupitant, Neu-120, neurotropin, nevirapine, niacin, niacinamide, Niacor, NIC5-15, nicardipine, nicergoline, Niclosamide, niconinamide, nicorandil, nicotinamide, nicotine, nicotine polacrilex, nicotinic acid, nifedipine, nifurtimox, *Nigella sativa*, nikkomycin Z, nilotinib, nilutamide, nilvadipine, nimesulide, nimodipine, nimorazole, nimotuzumab, nimustine hydrochloride, nintedanib, nipradilol, niraparib, nirogacestat, nitazoxanide, nitisinone, nitrazepam, nitrendipine, nitric oxide, nitroflurbiprofen, nitrofurantoin, nitrogen gas, nitroglycerin, nitroglycerine, nitroprusside, nitrous oxide, Nitrousoxide, nivocasan, nizatidine, N-Lite, N-monomethyl-L-arginine, Nobactine, nolatrexed, nolpitantium besilate, nomegestrol acetate, non-amlodipine calcium channel blockers, nonoxynol-9, non-preserved latanoprost, norelgestromin, norepinephrine, norethandrolone, norethindrone, norethindrone acetate, norethisterone, norethisterone acetate, norethisterone enantate, norethrindone acetate, norfloxacin, norgestimate, nortriptylatine, nortriptyline, norursodeoxycholic acid, noscapine, novabupivacaine, Novasoy, Novotaks, NPC-18, NRTI, NS-2, NS-8, NTC-510A, NucleomaxX, nucleoside antiretroviral drugs, NVB, nystatin, Nystatin LF, Nyxol, O2, obatoclax, obeticholic acid, obicetrapib, obinepitide, OBT, ocaperidone, ocinaplon, octinoxate, octocrylene, octocrylene+tinosorb, octreotide acetate, odalasvir, odanacatib, odiparcil, Odyliresin, oestrogen, ofloxacin, oglemilast, oglufanide disodium, olanzapine, olanzapine/fluoxetine, olaparib, olcegepant, oleic acid, olepra, olesoxime, oliceridine, OligoG CF-5/20, olmesartan, olmesartan cilexetil, olmesartan medoxomil, olodaterol, olodaterol hydrochloride, olopatadine, olopatadine hydrochloride, olprinone, olsalazine, oltipraz, omacetaxine mepesuccinate, omadacycline, omapatrilat, omarigliptin, omaveloxolone, ombitasvir, ombrabulin, omecamtiv mecarbil, omega, omega-3, omega-3 carboxylic acids, omega-3 fatty acids, Omega-3 polyunsaturated fatty acids, omega-3-acid ethyl esters, omega-3-carboxylic acids, omega-6, OmegaMAX, Omegaven, omeprazole, omeprazole and bicarbonate, omeprazole sodium, o-methylphenidate, omidenepag isopropyl, omigapil, Ommaya reservoir, Omri-Hep-B, onalespib, oncovin, ondansetron, ondelopran, opicapone, opipramol, opium, fumagillin, orantinib, orbofiban, Org-9426, orilotimod, oritavancin, orlistat, ornithine phenylacetate, orphenadrine citrate, ortataxel, orteronel, Orthokine, orthosilicic acid, Orthostat, Orthostat-L, Orthovisc, orvepitant, oseltamivir, osemozotan, OSI-632, osilodrostat, ospemifene, OsteoDex, Osteonil, otenabant, oracil potassium, oteseconazole, otilonium bromide, oxacillin, oxaliplatin, oxandrolone, oxantel pamoate, oxazepam, oxcarbazepine, oxidized glutathione sodium, Oximax, oxitriptan, oxitropium bromide, OX-NLA, oxybuprocaine, oxybutinin, oxybutynin, oxybutynin chloride, oxybutynin hydrochloride, oxycodone, oxycodone CR, oxycodone extended-release, oxycodone hydrochloride, oxycodone IR, Oxycyte, oxygen, oxymetazoline, oxymetazoline hydrochloride, oxymetholone, oxymorphone ER, oxymorphone IR, oxypurinol, oxytocin, ozagrel, ozagrel hydrochloride, ozanimod, ozenoxacin, P-276-00, P-53, PAC-14028, paclitaxel, paclitaxel poliglumex, paclitaxel-PM, pacritinib, pactimibe, pafuramidine, pagoclone, palanosetron hydrochloride, palbociclib, palifosfamide, paliperidone, paliperidone ER, paliperidone palmitate, paliroden, palivizumab, palonosetron, palovarotene, pamapimod, pamidronate disodium, PAN-90806, Panavir 1, panobinostat, pantoprazole, pantothenic acid, pantovigar, papaverine, paquinimod, paracetamol, pardoprunox, parecoxib, paricalcitol, paritaprevir, parnaparin sodium, parogrelil, paromomycin, paroxetine, paroxetine hydrochloride, paroxetine hydrochloride hemihydrate, paroxetine mesylate, parthenolide, *Passiflora incarnata*, patidegib, patiromer calcium, patupilone, pazopanib, pazufloxacin, pazufloxacin mesylate, PCI-24781, PCI-27483, PD-110843, PD-115934, pectin, pefcalcitol, peficitinib, pegamotecan, pegcantratinib, pegylated liposomal doxorubicin, PEITC, pelitinib, pelitrexol, pelubiprofen, pemafibrate, pemetrexate, pemetrexed, pemetrexed disodium, pemirolast, pemirolast sodium, pemoline, penciclovir, penclomedine, penehyclidine hydrochloride, penicillamine, penicillin, penicillin G, penicillin V, pentaerythritol tetranitrate, PentaLyte, pentamidine, pentamidine isethionate, pentazocine, pentobarbital, pentosan polysulphate sodium, pentostatin, pentothal, pentoxifylline, pentoxyphilline, peramivir, perchlozone, peretinoin, perflubron emulsion, perflutren lipid microsphere, pergolide, perhexiline, perifosine, perillyl alcohol, perindopril, perindopril arginine, permethrin, perospirone, perphenazine, perzinfotel, pethidine, pethidine hydrochloride, petrolatum, pexacerfont, pexidartinib, PF-04447943, PF-05089771, PF-05175157, PF-3654746, PF-3654764, PF-4191834, PF-4531083, PF-4691502, PF-489791, PF-610355, PG-2, PGL-2001, PGP/BCRP inhibitor, PH-797804, phenelzine, phenindione, pheniramine maleate, phenobarbital, phenobarbital sodium, phenoxybenzamine, phenprocoumon, phenserine, phentermine, phentolamine mesylate, phenylbutyrate, phenylephrine, phenylephrine hydrochloride, phenytoin, phloroglucinol, PHN-031, PHN-033, phosphate, phosphatidyl serine, phosphatidylcholine, phosphatidylcholine-associated naproxen, phosphatidylcholine-encapsulated ibuprofen, Phospho-Lax, phosphorus, photopheresis, physostigmine, phytate, phytonadione, phytosterols, piboserod, pibrentasvir, picibanil, piclidenoson, piclozotan, picoplatin, picotamide, picroliv, picropodophyllin, picrorhiza, pictilisib, pilaralisib, pilocarpine, pilocarpine hydrochloride, pilsicainide, PIM-447, pimagedine, pimasertib hydrochloride, pimavanserin, pimecrolimus, pimodivir, pimozide, pindolol, pinocembrin, pioglitazone, pioglitazone hydrochloride, pipamperone, piperacillin, piperacillin sodium, piperacillin-tazobactam, piperaquine, piperaquine phosphate, piperine, piracetam, piragliatin, pirarubicin, pirenzepine, pirfenidone, piribedil, piridoxine, piritramide, piritrexim, piromelatine, piroxicam, pitavastatin, pitavastatin calcium, pitolisant, pivmeciellinam, pivmecillinam, pixantrone, PL-3994, plant sterols, platinum, plazomicin, pleconaril, plerixafor, plevitrexed, plinabulin, PLX-8394, PM-00104/50, PMI-001, PMK-N02RS1, pocapavir, polaprezinc, policosanol, polidocanol, polifeprosan 20 with carmustine, polmacoxib, polyethylene glycol, polyethylene glycolated IL-2, polyethylene glycol-citrate-simethicone, polymeric nanoparticle docetaxel, polymyxin B sulphate, polyphenon E, polysaccharide-K, polysorbate 80, polysporin, polytetrafluoroethylene, pomaglumetad methionil, pomalidomide, ponatinib, ponesimod, poractant alpha, porfimer sodium, porfiromycin, posaconazole, posizolid, Posterisan akut, potassium, potassium canrenoate, potassium chloride, Potassium iodide, potassium nitrate, Potassium perchlorate, povidone, povidone iodine, pozanicline, poziotinib, PPA Lux 680, PPA-904, PPD-10558, PPI, PR-104, pracinostat, pradefovir, pradigastat, pralatrexate, pralidoxime, pralnacasan, pramiconazole, pramipexole, pranlukast, pranlukast hydrate, prasterone, prasugrel, pravastatin, praziquantel, prazosin, prednicarbate, prednisolone, prednisolone acetate, prednisolone phosphate, prednisolone sodium metazoate, prednisolone sodium succinate, prednisone, pregabalin, pregnenolone, preladenant, Premarin, Prempro, Prenatal vitamin, presatovir, pretomanid, prilocaine, primaquine, prinaberel, prinomastat, pritelivir, probenecid, Probiotics, probucol, procainamide, procaine, procaine hydrochloride, procarbazine, procarbazine hydrochloride, procaterol, procaterol hydrochloride, prochlorperazine, Procysteine, prodocosapentaenoic acid, pro-eicosapentaenoic acid, progesterone, progestin, progestogen, progestogen dienogest, proglumide, proguanil, proguanil hydrochloride, Prolarix, promethazine, Prometra, Prometrium, Promisan, propacaine hydrochloride, propacetamol, propafenone, propafenone-SR, propanolol, proparacaine, propionyl-L-carnitine, propiverine, propiverine hydrochloride, propofol, Propofol Lipuro, propofol-lipuro, propranolol, propranolol hydrochloride, propranolol LA, propranolol XL, propylthiouracil, propyphenazone, Prosorba, prostaglandin, prostaglandin-E2, Prostin, Protelos, protriptyline, ProvideXtra, proxymetacaine, proxymetacaine hydrochloride, PRS-211375, prucalopride, prulifloxacin, Prurisol, pruvanserin, PRX-3140, PRX-8066, PSD-508, pseudoephedrine, pseudoephedrine hydrochloride, *Pseudomonas aeruginosa* mannose-sensitive hemagglutinin (PA-MSHA), PSI-5004, PSI-938, psyllium powder, PTH, p-toluene sulfonamide, puerarin, puerarin sodium phosphate, pumosetrag, PVAC, PVP-ILH liposomes, PX-12, PYN-17, pyrantel-oxantel, pyrazinamide, pyridostigmine bromide, pyridoxal, pyridoxamine dihydrochloride, pyridoxine, pyridoxine hydrochloride, pyrimethamine, pyrimethamine % sulfadoxine, pyrimethamine/sulphadoxine, pyronaridine, Q-301, QAV-680, Qinbudan, Qizhitongluo, quercetin, quetiapine, quetiapine fumarate, quetiapine IR, quinacrine, quinagolide hydrochloride, quinapril hydrochloride, quinfamide, quinidine, quinine, quinolone, quinolones, quinupristin, quisinostat, quizartinib dihydrochloride, R-112, rabacfosadine, rabeprazole, rabeximod, rabusertib, racecadotril, raclopride, radafaxine, radalbuvir, radequinil, radezolid, Radha-108, radioactive iodine, Radioiodine, radiolabeled iodobenzamide, radiprodil, radium Ra 223 dichloride, radotinib, ragaglitazar, ralfinamide, raloxifene, raltegravir, raltitrexed, ramatroban, rameltedon, ramipril, ramosetron, ranibizumab, ranimustine, ranirestat, ranitidine, ranolazine, rapamycin, rasagiline, raseglurant, ravidasvir hydrochloride, ravuconazole, raxatrigine, razupenem, RBP-8000, RBx-10017609, RDEA-806, RDP-58, rebamipide, rebaudioside A, rebimastat, reboxetine, refametinib, reformulated diclofenac, reformulated mebendazole, regadenoson, regorafenib, regrelor, relebactam, relenopride, relugolix, remifentanil, remimazolam, remimazolam tosylate, remogliflozin etabonate, REN-1654, renzapride, repaglinide, reparixin, repinotan, repurposed ajulemic acid, repurposed ondansetron, resatorvid, reserpine, resiniferatoxin, resminostat, Resoferon, Respifor, Respimat, Restylane, Restylane SubQ, resveratrol, retagliptin, retapamulin, retaspimycin, retigabine, retinoic acid, retinoid, retinol, retosiban, retrovir, revamilast, revefenacin, revexepride, reviparin sodium, rezatomidine, RF-07026, rFSH, RG-4929, RG-7234, RG-7795, RGH-478, RGH-507, Rhenium-188-HEDP, Rhinox, RhuDex, ribavirin, ribociclib, riboflavin, ridaforolimus, ridinilazole, rifabutin, rifalazil, rifampicin, rifampin, rifamycin, rifapentine, rifaximin, rigosertib sodium, rikkunshito, rilapladib, rilmenidine, rilpivirine hydrochloride, riluzole, rimacalib, rimegepant, rimexolone, rimonabant, Ringer's acetate, Ringer's lactate solution, riociguat, ripasudil hydrochloride hydrate, risedronate sodium, risperidone, ritanserin, ritobegron ethyl ester hydrochloride, ritodrine, ritonavir, rituximab, rivaroxaban, rivastigmine, rivenprost, rivipansel sodium, rivoglitazone, rizatriptan, RLP-068, RNF43, RNS-60, RO-4929097, RO-5036505, robalzotan, rociletinib, rocuronium, rocuronium bromide, rofecoxib, Roferon-A, roflumilast, rolapitant, rolipram, rolofylline, ronacaleret, roniciclib, ronopterin, ropinirole, ropinirole hydrochloride, ropivacaine, roquinimex, rose bengal sodium, rosiglitazone, rosiglitazone maleate, rosiglitazone XR, rosiptor acetate, rostafuroxin, rostaporfin, rosuvastatin, rosuvastatin calcium, rotigotine, rovatirelin, roxadustat, roxithromycin, RP-323, RPh-201, RPL-554, RPM-02/08, RQ-00000004, R-salbutamol sulphate, rubitecan, ruboxistaurin, rucaparib, rucaparib camsylate, rucaparib phosphate, rufinamide, rupatadine, ruxolitinib, S Ketamine, S(+)-Ketamine, S-1, S-111, S-38093, S-707106, SAB-378, sabarubicin, *Saccharomyces boulardii*, sacubitril, S-adenosyl methionine, SAF-312, saffron, safinamide, safotibant, sagopilone, salbutamol, salbutamol HFA, salbutamol sulphate, salicylic acid, salicylic acid+benzoic acid, salidroside, saline, salirasib, salmon calcitonin, salsalate, Salubrin, samarium (153Sm) lexidronam, samatasvir, samidorphan, S-amlodipine gentisate, sapacitabine, sapanisertib, sapitinib, sapropterin, sapropterin dihydrochloride, saquinavir, SAR-110894, saracatinib, sarecycline, saredutant, sargramostim, sarizotan hydrochloride, saroglitazar, sarpogrelate hydrochloride, satavaptan, satraplatin, saxagliptin, SB-773812, SBP-002, SC-49483, SCH-002063, SCH-497079, SCH-900776, schisandra sphenanthera extract, scopolamine, SCY-078, SDX-101, secnidazole, Sedlitzia rosmarinus, segesterone acetate, seladelpar L-lysine dihydrate, selegiline, selegiline hydrochloride, selenium, selenium sulfide, selenomethionine, selepressin, seletracetam, selexipag, seliciclib, selinexor, selisistat, selodenoson, selonsertib, Selozok, selumetinib, selurampanel, semagacestat, semapimod, semaxanib, sembragiline, senicapoc, senna, Sensorcaine, Sentra PM, seocalcitol, sepantronium bromide, sepetaprost, sepranolone, septin, SER-150-DN, Serenoa repens, sergliflozin etabonate, serlopitant, serotonin reuptake inhibitors, serotonin/norepinephrine reuptake inhibitors, sertaconazole, sertindole, sertraline, S-ethylisothiourea diethylphosphate, setileuton, setipiprant, S-etodolac, setrobuvir, sevelamer carbonate, sevelamer hydrochloride, sevoflurane, Sevofran, sevuparin sodium, SG-2000, Shanhuang Wuji decoction, SHP-465, sibrafiban, sibutramine, sildenafil, sildenafil citrate, Silexan, silibin, silibinin dihydrogensuccinate, silimarine, silodosin, silver nanoparticle, silver nitrate, silver sulfadiazine, silybin, silymarin, simenepag isopropyl, simeprevir, simethicone, simeticone, simvastatin, Sinbaro, siponimod, sirolimus, sitafloxacin, sitagliptin, sitamaquine, sitaxentan, sitosterol, sivelestat, sivifene, s-ketamine, SKP-1052, SK-PC-B70M, SLx-4090, SMANCS, S-methionyl-L-citrulline, smilagenin, SMP-028, SN-38, SNX-5422, sodelglitazar, sodium, sodium 4-phenylbutyrate, sodium ascorbate, sodium benzoate, sodium bicarbonate, sodium butyrate, sodium carboxymethylcellulose, sodium chloride, sodium chromoglycate, sodium citrate, sodium dichloroacetate, sodium ferric gluconate complex, sodium fluoride, sodium folinate, sodium fusidate, sodium hyaluronate, sodium hydroxide, sodium hypochlorite, sodium ketorolac, sodium lactate, sodium nitrate, sodium nitrite, sodium nitroprusside, sodium oxybate, sodium phenylacetate, sodium phenylbutyrate, sodium phosphate, sodium picosulphate hydrate, sodium polystyrene sulfonate, sodium prasterone sulphate, sodium pyruvate, sodium stibogluconate, sodium sulfide, sodium tetradecyl sulphate, sodium thiopental, sodium thiosulphate, sodium valproate, sodium-fluoride, sofinicline, sofosbuvir, sofosbuvir+daclatasvir, sofpironium bromide, solabegron, solcitinib, Soldesam, solifenacin, solithromycin, soluble ferric pyrophosphate citrate, Solvazinc, somatostatin, sonedenoson, sonidegib, sonolisib, sorafenib, soraprazan, sorbitol, sorivudine, sotagliflozin, sotalol, sotrastaurin, sovaprevir, soy isoflavones, sparsentan, spebrutinib, spiramycin, spironolactone, sPLA2 inhibitors, SQ-109, squalamine, SR-T100, SSS, ST-101, STA-4783, standard bicarbonate, standard pneumoperitoneum, stannous compounds, stannsoporfin, statin, stavudine, stearidonic acid, S-tenatoprazole, Sterofundin, steroid, steroids, stiripentol, Stopain, *Streptococcus faecium, Streptococcus thermophillus*, streptomycin, streptozocin, strontium chloride Sr 89, strontium malonate, strontium ranelate, strontium-89, STW-5, STX-107, SU, SU-101, SU-14813, succimer, succinic acid, succinylcholine, sucralphate, sucralose, sucroferric oxyhydroxide, sucrose, Sufenta, sufentanil, sufentanil citrate, sufentanyl, sugammadex, sulbactam, sulbactam sodium, sulfadiazine, sulfadoxine, sulfadoxine+pyrimethamine, sulfalene-pyrimethamine, sulfamethoxazole, sulfasalazine, sulphate salt solution, sulfonyl urea, sulfonylurea, sulfonylureas, sulforaphane, sulindac, sulodexide, sulopenem, sulopenem etzadroxil, sulphacetamide sodium, sulphadoxine, sulphadoxine-pyrimethamine, sulphamethoxazole, sulphonylurea, sulpiride, sultamicillin, sumanirole, sumatriptan, sumatriptan succinate, SUN-0597, SUN-1334H, sunitinib, suplatast tosilate, suramin, suramin sodium, surinabant, sutezolid, suxamethonium, SYI-2074, symbiotic, synbiotics, SYNSORB-Pk, synthetic hypericin, T/S, T-1225, T-2000, T3, tacalcitol, tacedinaline, tacrine, tacrolimus, Tacrolimus Hexal, tadalafil, tadekinig alpha, tafamidis, tafenoquine, tafluprost, tafoxiparin sodium, TAK-715, TAK-783, talabostat, taladegib, talampanel, talaporfin, talarozole, talazoparib, talc, TALL-104, talmapimod, talnetant, talniflumate, talotrexin, talsaclidine fumarate, taltirelin, tamibarotene, tamoxifen, tamsulosin, tamsulosin hydrochloride, tandospirone, tandutinib, tanespimycin, tanomastat, tanzisertib, tapentadol, taprenepag, Taradyal, tarafenacin, taranabant, tarenflurbil, taribavirin hydrochloride, tariquidar, tarloxotinib bromide, tasidotin HCl, tasimelteon, tasisulam, taspoglutide, tasquinimod, taurolidine, tauroursodeoxycholic acid, tavaborole, tavilermide, Taxol, Taxus, tazarotene, tazobactam, TC-2403, TC-3, TCM-606F, tebipenem pivoxil, tecadenoson, tecalcet, tecarfarin, tecastemizole, technetium bicisate, technetium etarfolatide, technetium Tc 99m tilmanocept, technetium Tc 99m trofolastat, technetium-99, tecovirimat, tedatioxetine, tedisamil, tedizolid phosphate, tegafur, tegaserod, teglarinad chloride, tegobuvir, teicoplanin, telaprevir, telapristone acetate, telatinib, telbivudine, telcagepant, telithromycin, telmisartan, telotristat etiprate, temazepam, temocapril, temocillin, temoporfin, temozolomide, temsirolimus, tenapanor, teneligliptin, teniposide, tenofovir, tenofovir alafenamide, tenofovir alafenamide fumarate, tenofovir disoproxil fumarate, tenofovir exalidex, tenofovir/emtricitabine, tenoxicam, teprenone, teramepro-col, terazosin, terbinafine, terbinafine gel, terbinafine hydrochloride, terbogrel, terbutaline, terbutaline sulphate, terconazole, terguride, teriparatide, terlipressin acetate, terutroban, tesaglitazar, tesetaxel, tesevatinib, tesmilifene, tesofensine, Testagen, testosterone, testosterone cypionate, testosterone enanthate, testosterone undecanoate, Tetanus toxoid, tetomilast, tetrabenazine, tetracaine, tetracaine hydrochloride, tetracycline, tetracycline HCl, tetrahydrobiopterin, tetrahydrocannabinol, tetrathiomolybdate, Tetrodin, tezacaftor, tezacitabine, tezampanel, tezosentan, TG-100-115, TG-100801, thalidomide, THC, theophyllamine, theophylline, theophylline SR, theracurmin, thiamine, thiamine hydrochloride, thiazide, thiazide diuretics, thiazolidinedione, thiazolidinediones, thiocolchicoside, thioctic acid, thioguanine, thiopental, thiopental sodium, thiopentone, thioridazine, thiotepa, thiothixene, THR-0921, THR-4109, thrombin, thrombin microcapsules, thymoctonan, Thymoglobulin, thyroxine, tiagabine, tianeptine, tiapride, tibolone, ticagrelor, ticlopidine, tideglusib, tigecycline, tilapertin, tilarginine acetate, tiludronate disodium, timapiprant, timcodar, timnodonic acid, timolol, timolol, timolol maleate, tinidazole, tinzaparin sodium, tiopronin, tiotropium, tiotropium bromide, tipelukast, tipifarnib, tipiracil hydrochloride, tipranavir, tirapazamine, tirasemtiv, tirilazad, tirofiban, tirofiban hydrochloride, titanium dioxide, TIVA, tivantinib, tivozanib, tizanidine, TMC-114/RTV, TMC-310911, TMC-647055, TNF-alpha, TNP-470, tobramycin, tocladesine, tocofersolan, tocopherol, tocopherols, tocopheryl phosphate mixture (TPM), tofacitinib, tofimilast, tofogliflozin, tolcapone, tolevamer, tolnaftato, tolperisone, tolterodine, tolterodine tartrate, tolvaptan, TOMM34, tonabersat, Tonalin SG1000T FFA, tonapofylline, Tongxinluo, topiramate, topiroxostat, topotecan, topotecan hydrochloride, torasemide, torcetrapib, toreforant, toremifene, tosedostat, tosufloxacin, tozadenant, tozasertib, trabectedin, trabectome, trabodenoson, tradipitant, tramadol, tramadol hydrochloride, tramazoline, trametinib, tramiprosate, trandolapril, tranexamic acid, tranilast, transcrocetinate-sodium, tranylcypromine, trastuzumab, travoprost, traxoprodil, trazadone, trazodone, trazodone hydrochloride, TRC-101, trehalose, trelagliptin succinate, trelanserin, treosulfan, treprostinil, treprostinil diolamine, tretinoin, triamcinolone, triamcinolone acetonide, triamcinolone hexacetonide, Triapine, Triatec HCT, Triaz, triazavirin, triazolam, tribendimidine, trichlormethiazide, trichlorothiazide, triciribine, tridolgosir, trientine, trientine hydrochloride, trifarotene, trifluoperazine, trifluridine, triflusal, triheptanoin, trihexyphenidyl, triiodothyronine, trilostane, trimebutine, trimebutine 3-thiocarbamoyl-benzenesulfonate, trimegestone, trimetazidine, trimethaphan, trimethobenzamide, trimethoprim, trimethoprim-sulfa, trimetrexate, trimipramine, trimipramine maleate, trinitrate, Triomune, Triplixam, tripotassium dicitrate bismuthate, tripterygium wilfordii, triptorelin acetate, triptorelin pamoate, trisodium citrate dihydrate, Trivax-AD, trofinetide, trofosfamide, troglitazone, tropicamide, tropisetron, trospium chloride, troxacitabine, troxipide, Trunature, trypsin-EDTA, TS-022, TTK, TTP-054, TTP-399, TTP-435, TTP-889, TTX-9401, tucaresol, tucidinostat, tulobuterol, TV-46763, TV-5010, TY-51924, tylenol, TZD, TZP-102, ubidecarenone, ubiquinol, ubrogepant, UCA-001, UCA-002, UCN-01, udenafil, UFT, UFT/LV, UFUR, UISH-001, UK-390957, UK-432097, UK-447841, ulimorelin, ulinastatin, ulipristal, ulobetasol, ulodesine, umeclidinium, umeclidinium bromide, umirolimus, unfractionated heparin, uniphyllin, upadacitinib, upamostat, uprifosbuvir, uprosertib, UR-906, uracil, urapidil, urea, uridine, uridine triacetate, URLC10, ursodeoxycholic acid, Ursolic acid, Urtica dioicea, usistapide, UTD-1, utrogestan, V-116517, V-158866, V-404, VA-111913, vabicaserin, vaborbactam, vadadustat, vadimezan, Vagiprost, VAK-694, valaciclovir, valacyclovir, valbenazine, valdecoxib, valerian extract, valganciclovir, valium, valnivudine hydrochloride, valnoctamide stereoisomers, valomaciclovir stearate, valopicitabine dihydrochloride, valproate, valproic acid, valrocemide, valrubicin, valsartan, valsartan trisodium hemipentahydrate, valspodar, valtorcitabine, vancomycin, vancomycin hydrochloride, vandetanib, vaniprevir, vanoxerine, vapendavir, vapitadine, vardenafil hydrochloride, varenicline, varespladib, varespladib methyl, varlitinib, vasopressin, vatalanib, vatiquinone, VDC-2008, vecuronium, vecuronium bromide, vedroprevir, VEGFR1, VEGFR1 peptide, VEGFR1-A02-770, VEGFR2 peptide, VEGFR2-derived HLA-A0201, veliflapon, veliparib, velneperit, velpatasvir, velusetrag, vemurafenib, venetoclax, venlafaxine, venlafaxine hydrochloride, venlafaxine XR, vepoloxamer, verapamil, verapamil hydrochloride, vercirnon, verdiperstat, vericiguat, verinurad, vernakalant, vernakalant hydrochloride, verteporfin, verubulin, verucerfont, Verutex, vesatolimod, vesnarinone, vestipitant, vibegron, vicriviroc, Vidoca, vidofludimus, vidupiprant, vigabatrin, viitamin D, vilanterol, vilanterol trifenatate, vilaprisan, vilazodone, vildagliptin, vinblastin, vinblastine, vinblastine sulphate, vincristin, vincristine, vincristine sulphate, vindesine, vinflunine, vinorelbine, vinorelbine ditartrate, vinpocetine, vintafolide, vipadenant, vismodegib, vistusertib, Vit B12, Vitamac, vitamin A, vitamin B, vitamin B1, vitamin B12, vitamin B-12, vitamin B2, vitamin B6, vitamin B-6, vitamin C, vitamin D, vitamin D2, vitamin D3, vitamin E, vitamin E succinate derivatives, vitamin K, vitamin K1, vitamins B1, vitamins B12, vitamins B2, vitamins B6, Vitreosolve, Viusid, Vizomitin, vofopitant, voglibose, volasertib, volinanserin, vonoprazan fumarate, vorapaxar, voriconazole, vorinostat, vortioxetine hydrobromide, vosaroxin, voxilaprevir, voxtalisib, VP-101, VRx-3996, VSL-3, VVZ-149, VX-105, VX-135, VX-702, VX-710, Wafermine, warfarin, warfarin sodium, Water, WF-10, WH-1, Wobenzym, WX-554, xaliproden, xemilofiban, xenon, Xiang-sha-liu-jun decoction, xiaoqinglong, Xibrom, Xilei-San, ximelagatran, Xiyanping, XL-139, XP-21279, Xylitol, xylometazoline, Y-39983, Yallaferon, yonkenafil, yttrium clivatuzumab tetraxetan, yttrium Y 90 anti-CD66 monoclonal antibody BW 250/183, zabofloxacin, zafirlukast, zalcitabine, zaleplon, zaltoprofen, zanamivir, ZD-6126, zeaxanthin, zibotentan, zicronapine, zidovudine, zileuton, zinc, zinc acetate, zinc oxide, zinc picolinate, zinc sulphate, zinc supplement, Zincas Forte, Zinthionein, ziprasidone, zofenopril, zoledronate, zoledronic acid, zoliflodacin, zolmitriptan, zolpidem, zolpidem tartrate, Zometa, zonampanel, zonisamide, zonisamide SR, zopiclone, zosuquidar, zotarolimus, zotepine, zucapsaicin, zuclopenthixol, and zuretinol acetate.

In some embodiments, the cargo of the engineered platelets descried herein is a small molecule such as, but not limited to, those from the CeMM Library of Unique Drugs (CLOUD), as shown in Licciardello et al., Nat Chem Biol; Vol. 13, pages 781-780 (2017)), which is hereby incorporated by reference in its entirety. For example, the small molecule may be, but it not limited to, Pinacidil, Altretamine, Pipobroman, Uracil Mustard, Trioxsalen, Plicamycin, Ambenonium, Edrophonium, Hexafluorenium, Oxtriphylline, Arbutamine, Guanabenz, Mephentermine, Methoxamine, Phenylpropanolamine, Protokylol, Tetrahydrozoline, Tolazoline, Bethanidine, Ergoloid, Oxprenolol, Penbutolol, Phentolamine, Propiomazine, Thiethylperazine, Fomepizole, Triamterene, Stanozolol, Dromostanolone, Ethylestrenol, Fluoxymesterone, Methyltestosterone, Deserpidine, Quinapril, Rescinnamine, Spirapril, Testolactone, Ethionamide, Sulfameter, Sulfacytine, Sulfamerazine, Sulfamethazine, Sulfamethizole, Sulfaphenazole, Sulfapyridine, Sulfathiazole, Sulfisoxazole, Sulfoxone, Cefmenoxime, Amdinocillin, Azlocillin, Bacampicillin, Carbenicillin, Cefalotin, Cefamandole, Cefditoren, Cefonicid, Ceforanide, Cefotiam, Cefpiramide, Cefradine, Ceftizoxime, Cephaloglycin, Cephapirin, Cyclacillin, Hetacillin, Loracarbef, Methicillin, Mezlocillin, Moxalactam, Nafcillin, Ticarcillin, Capreomycin, Demeclocycline, Dirithromycin, Methacycline, Oxytetracycline, Spectinomycin, Troleandomycin, Viomycin, Enoxacin, Novobiocin, Alatrofloxacin, Cinoxacin, Lomefloxacin, Nalidixic Acid, Sparfloxacin, Trovafloxacin, Acetohydroxamic Acid, Marinol, Ethoxzolamide, Acetohexamide, Fenoprofen, Oxyphenbutazone, Carprofen, Oxaprozin, Phenylbutazone, Tolmetin, Meclofenamic Acid, Methylergonovine, Acetophenazine, Carphenazine, Chlorprothixene, Mesoridazine, Triflupromazine, Promazine, Benzphetamine, Phenmetrazine, Chlorotrianisene, Estrone, Mestranol, Polyestradiol, Quinestrol, Cortisone, Fluprednisolone, Meprednisone, Paramethasone, Oxamniquine, Azatadine, Bromodiphenhydramine, Buclizine, Carbinoxamine, Chlophedianol, Dexbrompheniramine, Diphenylpyraline, Mepyramine, Methdilazine, Trimeprazine, Tripelennamine, Triprolidine, Romidepsin, Primidone, Butabarbital, Chlormezanone, Flurazepam, Glutethimide, Halazepam, Meprobamate, Metharbital, Methyprylon, Prazepam, Quazepam, Secobarbital, Talbutal, Thiamylal, Gamma Hydroxybutyric Acid, Memantine, Triclofos, Piperazine Hexahydrate, Desoxycorticosterone Pivalate, Pargyline, Carbachol, Oxyphenonium Bromide, Anisotropine, Clidinium, Cycrimine, Dicyclomine, Diphemanil, Ethopropazine, Fesoterodine, Hexocyclium, Isopropamide, Mepenzolate, Methantheline, Methylscopolamine, Metixene, Orphenadrine, Oxyphencyclimine, Procyclidine, Propantheline, Tridihexethyl, Trospium, Decamethonium, Pentolinium Tartrate, Cisatracurium Besylate, Succinylcholine Chloride, Doxacurium, Gallamine, Metocurine, Pancuronium, Pipecuronium, Rapacuronium, Tubocurarine, Guanadrel, Phendimetrazine, Anileridine, Difenoxin, Diphenoxylate, Levomethadyl, Oxymorphone, Propoxyphene, Levallorphan, Methylnaltrexone, (+/−)-Sulfinpyrazone, Pamidronic Acid, Risedronate, Tiludronate, Clofibrate, Dyphylline, Inamrinone, Vardenafil, Ethynodiol, Hydroxyprogesterone, Norethynodrel, Ulipristal Acetate, Carboprost, Etretinate, Methysergide, Chlorphentermine, Acetyldigitoxin, Deslanoside, Chlorpropamide, Tolazamide, Tolbutamide, Methyclothiazide, Benzthiazide, Chlorothiazide, Cyclothiazide, Hydroflumethiazide, Polythiazide, Quinethazone, 5-Fluorouracil, Dextrothyroxine, Metyrosine, Rimantadine, Adefovir, Anisindione, Dicumarol, Nisoldipine, Trimethadione, Bepridil, Paramethadione, Bretylium Tosylate, Mephenytoin, Benzonatate, Ethotoin, Indecainide, Moricizine, Phenacemide, Tocainide, Pyrvinium Chloride Dihydrate, Halofantrine, Metaxalone, Diphenidol, Mebutamate, Chlorphenesin, Phensuximide, Thiabendazole, Benzquinamide, Piperacetazine, Ethchlorvynol, and Ethinamate.

IV. Production

In some embodiments, the engineered platelets described herein may be produced using the technique described in Ito et al. (Cell, 174(3): 636-648.e18, 2018, which is hereby incorporated by reference in its entirety). Ito provides a method of clinical scale production of platelets from iPSC progenitors. Turbulence was observed to activate platelet biogenesis for clinical scale ex vivo production of platelets from human-induced pluripotent stem cells (iPSCs) (Ibid.). iPSCs derived from immortalized megakaryocyte progenitor cell lines (imMKCLs) were combined with soluble factors insulin Like Growth Factor Binding Protein 2 (IGFBP2), macrophage migration inhibitory factor (MIF), and nardilysin convertase (NRDC) in a bioreactor with control over the physical parameters of turbulent energy and shear stress (Ibid.). Production of greater than $10^{11}$ platelets were observed (Ibid.). Platelets were observed to function analogously to those derived from donors (Ibid.).

In certain embodiments of the invention herein, the imMKCL may be established by introducing cancer-derived MYC (c-MYC)/polycomb ring finger proto-oncogene (BMI-1) and BCL2 1 like 1 (BCL-XL) genes into the iPSC using a lentivirus. Additional genes may be introduced or deleted resulting in an edited megakaryocyte, in fact even platelet specific promoters have been previously characterized. These genes provide inducible gene expression in the presence of an agent, such as doxorubicin (DOX). The imMKCL may be cyropreserved until cultivation is desired. Megakaryocyte expansion is stimulated by contacting the cell line with the agent resulting expression of the inserted genes. The agent is removed to halt gene expression and allow platelet production.

Current Federal Drug Administration (FDA)-approved rules for storage of platelets for transfusion require storage at 22° C. and must be used within 6 days. Slichter et al. "Treatment of Bleeding in Severely Thrombocytopenic Patients with Transfusion of Dimethyl Sulfoxide (DMSO) Cryopreserved Platelets (CPP) Is Safe—Report of a Phase 1 Dose Escalation Safety Trial". Blood, 2016, which is hereby incorporated by reference in its entirety, hypothesizes cryopreservation is possible for two years when frozen with DMSO. After a positive phase 1 trial, phase 2 and 3 trials are underway. Infusion of up to three sequential units of cryopreserved platelets (CPP) in patients with severe thrombocytopenia and active bleeding appeared to be "safe and without any evidence of thrombotic complications despite CPP having a procoagulant phenotype resulting from the cryopreservation process." Therefore, cryopreserved platelets likely have efficacy for stabilizing, reducing, or stopping bleeding in thrombocytopenic patients as measured using the World Health Organization (WHO) bleeding grades. No evidence was found to undermine the hypothesis that cryopreserved platelets used for non-clotting purposes would be as effective as platelets stored according to the present FDA rules.

V. Pharmaceutical Compositions

The present teachings further comprise pharmaceutical compositions comprising one or more of the engineered platelets of the present invention, and optionally at least one pharmaceutically acceptable excipient or inert ingredient.

Further, a pharmaceutical may comprise the therapeutic delivery system described herein.

As used herein the term "pharmaceutical composition" refers to a preparation of one or more of the engineered platelets described herein, or pharmaceutically acceptable salts thereof, optionally with other chemical components such as physiologically suitable carriers and excipients.

The term "excipient" or "inactive ingredient" refers to an inert or inactive substance added to a pharmaceutical composition to further facilitate administration of a compound. Non-limiting examples of such inert ingredients are disclosed herein under Formulations.

In some embodiments, compositions are administered to humans, human patients or subjects. For the purposes of the present disclosure, the phrase "active ingredient" generally refers to any one or more of the engineered platelets to be delivered as described herein.

Although the descriptions of pharmaceutical compositions provided herein are principally directed to pharmaceutical compositions which are suitable for administration to humans, it will be understood by the skilled artisan that such compositions are generally suitable for administration to any other animal, e.g., to non-human animals, e.g. non-human mammals. Subjects to which administration of the pharmaceutical compositions is contemplated include, but are not limited to, non-human mammals, including agricultural animals such as cattle, horses, chickens and pigs, domestic animals such as cats, dogs, or research animals such as mice, rats, rabbits, dogs and non-human primates.

A pharmaceutical composition in accordance with the invention may be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient or inert ingredient, and/or any additional ingredients in a pharmaceutical composition in accordance with the invention will vary, depending upon the identity, size, and/or condition of the subject treated and further depending upon the route by which the composition is to be administered. By way of example, the composition may comprise between 0.1% and 100%, e.g., between 0.5 and 50%, between 1-30%, between 5-80%, at least 80% (w/w) active ingredient.

Efficacy of treatment or amelioration of disease can be assessed, for example by measuring disease progression, disease remission, symptom severity, reduction in pain, quality of life, dose of a medication required to sustain a treatment effect, level of a disease marker or any other measurable parameter appropriate for a given disease being treated or targeted for prevention. It is well within the ability of one skilled in the art to monitor efficacy of treatment or prevention by measuring any one of such parameters, or any combination of parameters. In connection with the administration of compositions of the present invention, "effective against" for example a cancer, indicates that administration in a clinically appropriate manner results in a beneficial effect for at least a statistically significant fraction of patients, such as an improvement of symptoms, a cure, a reduction in disease load, reduction in tumor mass or cell numbers, extension of life, improvement in quality of life, or other effect generally recognized as positive by medical doctors familiar with treating the particular type of cancer.

A treatment or preventive effect is evident when there is a statistically significant improvement in one or more parameters of disease status, or by a failure to worsen or to develop symptoms where they would otherwise be anticipated. As an example, a favorable change of at least 10% in a measurable parameter of disease, and preferably at least 20%, 30%, 40%, 50% or more can be indicative of effective treatment. Efficacy for a given composition or formulation of the present invention can also be judged using an experimental animal model for the given disease as known in the art. When using an experimental animal model, efficacy of treatment is evidenced when a statistically significant change is observed.

A. Therapeutic Delivery System

Various embodiments of the invention herein provide a non-thrombogenic therapeutic delivery system comprising at least one engineered platelet, also referred to as a SYNLET™ therapeutic delivery system.

SYNLET™ therapeutic delivery system may be produced using the megakaryocyte/platelet production strategies described herein. Progenitor cell can be sequentially edited with no consequences for safety creating the possibility of designing entirely synthetic networks. Immunogenic cargo may be cloaked within the platelet followed by release at target site. Control antigen sensitivity through differential loading of CPR-ITAMs and inhibitor CPR-ITIMs.

1. Treatment of Cancer

In some embodiments, the engineered platelets herein increased specificity may be used to treat solid tumors. In the field of immuno-oncology, the engineered platelets may be altered to be activated by antigen specific T Cells to upregulate their function to clear tumors expressing defined neoantigens. Conversely, antigen specific T Cells that mediate autoimmune diseases could be targeted for destruction, with defined antigens known in a variety of common diseases including Hashimoto's thyroiditis, type 1 diabetes and multiple sclerosis.

In one embodiment, the targeting moiety of the CPR may recognize CD19 to deliver chemotherapeutics locally. CD19 is a well-known B cell surface molecule, which upon B cell receptor activation enhances B-cell antigen receptor induced signaling and expansion of B cell populations. CD19 is broadly expressed in both normal and neoplastic B cells. Malignancies derived from B cells such as chronic lymphocytic leukemia, acute lymphocytic leukemia and many non-Hodgkin lymphomas frequently retain CD19 expression. This near universal expression and specificity for a single cell lineage has made CD19 an attractive target for immunotherapies.

In some embodiments, the targeting moiety of a CPR may recognize a tumor specific antigen (TSA), for example a cancer neoantigen that is only expressed by tumor cells because of genetic mutations or alterations in transcription which alter protein coding sequences, therefore creating novel, foreign antigens. The genetic changes result from genetic substitution, insertion, deletion or any other genetic changes of a native cognate protein (i.e. a molecule that is expressed in normal cells).

For example, the tumor may be starved by the platelet causing clot formation to stop blood supply. Alternatively, CPR may target a tumor by expression of an α-granule directed cargo or toxin mediating local delivery of a therapeutic. In additional embodiments, the CPR may target a tumor by expression of an α-granule directed antibody, such as a checkpoint inhibitor, to increase anti-tumor immunity.

The engineered platelets described herein may be engineered to kill cancerous cells. For example, CD19 targeted TRAIL expressing platelets that treat cancerous B cell leukemias (BCL). CD19 targeted CAR-T cells have shown great promise in the clinic versus BCL. TNF Superfamily Member (TRAIL) and Fas ligand (FASL) have been shown to induce BCL death via apoptosis upon CD40 stimulation (See, Dicker et al. "Fas-ligand (CD178) and TRAIL synergistically induce apoptosis of CD40-activated chronic lymphocytic leukemia B cells". Blood, 2005, which is hereby incorporated by reference in its entirety). CD40L is naturally exposed on activated platelets (see, Henn et al. "CD40 ligand on activated platelets triggers an inflammatory reaction of endothelial cells". Nature, 1998, which is hereby incorporated by reference in its entirety) and could thus activate FASL/TRAIL dependent cell death pathways when bound to BCL. FASL is naturally exposed on activated platelets (See, Schleicher et al. "Platelets induce apoptosis via membrane-bound FasL". Blood, 2015, which is hereby incorporated by reference in its entirety). TRAIL expressing platelets have been used to decrease prostate cancer metastasis in mice (See, Li et al. "Genetic engineering of platelets to neutralize circulating tumor cells". Journal of Controlled Release, 2016, which is hereby incorporated by reference in its entirety). In one embodiment, a resting platelet presenting a CD19-single-chain variable fragment (scFv)-ITAM and containing TRAIL, CD40L, and FASL ligands is activated by binding of the CD19-scFv-ITAM with CD19 on a B cell. Activation results in the presentation of TRAIL, CD40L, and FASL on the platelet surface. Platelet-induced death of leukemia cells is mediated by binding of CD40L to the CD40 receptor of the B cell to activate the FASL/TRAIL-dependent cell death pathways.

In certain embodiments, platelets may be engineered to direct expansion of neoantigen specific T cells in vivo. Neoantigens are presented in many human tumors and can be computationally identified. Expansion of T cells ex vivo and reinfusion results in targeted tumor killing. Immune checkpoint inhibition allows for T cells to kill tumors expressing neoantigens (however non-specificity results in severe side effects). Megakaryocytes can be loaded with MHC class 1 molecules with exogenous peptides and transfer these to platelets. Neoantigens may be expressed in megakaryocytes, and an MHC class 1-ITAM fusion protein is able to stimulate checkpoint inhibitors. This would allow in vivo expansion of neoantigen specific T cells. For example, a platelet may be engineered to express MHC1-Neoantigen-ITAM. Both the engineered platelets and the T cell are activated by interaction of the MHC1-Neoantigen-ITAM with a neoantigen specific T cell receptor (TCR). Activation results in presentation of cytotoxic T-lymphocyte associated protein 4 (CTLA4) and programmed cell death 1 (PD-1) on the surface of the platelet and interaction with CTLA4 inhibitor (CTLA4i) and PD-1 inhibitor (PD-li), respectively, on the T cell. Maximum T cell activation and expansion is reached by checkpoint blockade.

2. Treatment of Autoimmunity

In some embodiments, the engineered platelets described herein may be used to treat autoimmunity conditions. At least eighty-one autoimmune diseases have been identified in humans, and forty-five of the eighty-one disease have been associated with autoantigens with thirty-six of the autoantigens being tissue-specific. (See, Hayter, et al., Autoimmunity Reviews 11(2012) 754-765, which is hereby incorporated by reference in its entirety). Autoimmune diseases were defined as disorders where "1) the specific adaptive immune response is directed to the affected organ or tissue; 2) autoreactive T cells and/or autoantibodies are present in the affected organ or tissue; 3) autoreactive T cells and/or autoantibodies can transfer the disease to healthy individuals or animals; 4) immunization with the autoantigen induces the disease in animal models: 5) elimination or suppression of the autoimmune response prevents disease progression or even ameliorates the clinical manifestation." (Ibid.) Additional criterion considered for the definition was that antibody binding would disrupt functioning of the autoantigen (Ibid.). Self-tolerance check-points at each stage of lymphocyte development and activation have also been identified (Ibid.).

In some embodiments, the engineered platelets described herein may be used to suppress autoantigen specific T cells to treat autoimmune disease. In some embodiments, CPRs in the engineered platelets may include a region specific to a tissue associate with the autoantigen. For example, the tissue is selected from the group consisting of: adipose tissue, adrenal gland, ascites, bladder, blood, bone, bone marrow, brain, cervix, connective tissue, ear, embryonic tissue, esophagus, eye, heart, intestine, kidney, larynx, liver, lung, lymph, lymph node, mammary gland, mouth, muscle, nerve, ovary, pancreas, parathyroid, pharynx, pituitary gland, placenta, prostate, salivary gland, skin, stomach, testis, thymus, thyroid, tonsil, trachea, umbilical cord, uterus, vascular, and spleen.

Table 12 shows the molecular target and/or tissue target for a non-exhaustive list of neurological system autoimmunity disorders from Hayter, et al.

TABLE 12

Neurological System Autoimmunity Disorders

| Disorder | Tissue autoantibody | Molecular target |
| --- | --- | --- |
| Autoimmune disseminated encephalomyelitis | Anti-myelin | MOG |
| Autoimmune inner ear disease | Anti-cochlear | |
| Batten disease/Neuronal Ceroid Lipofuscinoses | Anti-GAD | GAD65, GAD2 |
| Chronic inflammatory demyelinating polyneuropathy | Anti-myelin | Myelin associated glycoprotein, MPZ |
| Encephalitis lethargica | Anti-sleptolysin-O | |
| Anti-basal ganglia | | |
| Guillain-Barr syndrome | Anti-ganglioside GM1, Anti-PMP22 | PMP22 |
| Hashimoto's Encephalopathy | Anti-thyroid microsomal antibodies; anti-TPO | TPO/TG |
| Anti-TPO | | |
| Isaac's syndrome/acquired neuromyotonia | Anti-VGKC, Anti-AChR | VGKC, KCNA6 |
| Miller Fisher syndrome | Anti-GQ1b; Anti-GM1; Anti-GD1a | |
| Morvan's syndrome | Anti-VGKC; Anti-neuronal AChR | KCNA1, VGKC |

TABLE 12-continued

Neurological System Autoimmunity Disorders

| Disorder | Tissue autoantibody | Molecular target |
| --- | --- | --- |
| Multiple sclerosis | Anti-MOG; Anti-proteolipid protein | MOG, MBP, NEFL Proteolipid protein, myelin oligodendrocyte glycoprotein, myelin basic protein, neurofilament light polypeptide. |
| Myasthenia gravis | Anti-AChR; MuSK | CHRNA1; AChR |
| Narcolepsy PANDAS | Anti-TRIB2; Anti-neuronal; Anti-GlcNAc; Anti-Dnase B | TRIB2 |
| Rasmussen's encephalitis | Anti-NMDA-type GluR | NMDA-type GluR, GRIA3 |
| Stiff-person syndrome | Anti-GAD; Anti-amphiphysin | GAD2 |
| Vogt-Koyanagi-Harada syndrome | Anti-Ku-Mel-1 | KUMEL1, ARMC9 |

Table 13 shows the molecular target and/or tissue target for a non-exhaustive list of endocrine system autoimmunity disorders from Hayter, et al.

TABLE 13

Endocrine System Autoimmunity Disorders

| Disorder (system) | Tissue autoantibody | Molecular target |
| --- | --- | --- |
| Addison's disease | Anti-21-hydroxylase; Anti-17 alpha-hydroxylase; Anti-P450scc | CYP21A2, 21OH |
| Autoimmune hypoparathyroidism | Anti-CaSR | Calcium sensing receptor |
| Autoimmune hypophysitis | Anti-pituitary cytosolic protein | |
| Autoimmune oophoritis | Anti-OA; Anti-21OH | |
| Autoimmune orchitis | Anti-NASP | Nuclear autoantigenic sperm protein |
| Autoimmune polyglandular syndrome I (APECED) | Anti-candidal enolase, anti-pituitary, anti-calcium sensing receptor protein, anti-aromatic L-amino acid decarboxylase, anti-tyrosine hydroxylase | |
| Autoimmune polyglandular syndrome II | Anti-21-hydroxylase; Anti-17 alpha-hydroxylase | |
| Autoimmune polyglandular syndrome III | Anti-21-hydroxylase, anti-17 alpha-hydroxylase, and-thyroperoxidase. | |
| Diabetes mellitus, type 1 | Anti-GAD; Anti-insulin; Anti-ICA512; Anti-IA-2β | Insulin, GAD65, PTPRN, |
| Graves' disease | TSIg; Anti-TBII | TSHR, LMOD1 |
| Hashimoto's autoimmune thyroiditis | Anti-TPO; Anti-TG | Thyroperoxidase |
| Immunodysregulation, polyendocrinopathy, enteropathy, X-linked | | |

Table 14 shows the molecular target and/or tissue target for a non-exhaustive list of gastrointestinal system autoimmunity disorders from Hayter, et at.

TABLE 14

Gastrointestinal System Autoimmunity Disorders

| Disorder | Tissue autoantibody | Molecular target |
| --- | --- | --- |
| Autoimmune hepatitis type 1 | Anti-smooth muscle antibody; Anti-nuclear antibody (ANA); Anti-actin | SIMA, ASGPR (Asioglycoprotein receptor) |
| Autoimmune hepatitis type 2 | Anti-LKM-1; Anti-P-450 IID6 | LKM1, CYP2D6 |
| Autoimmune pancreatitis | Anti-lactoferrin; Anti-amylase alpha 2A; Anti-ACA-II | Lactoferrin |
| Coeliac disease | Anti-TG2; Anti-gliadin | Tissue trans-glutaminase 2 |
| Crohn's disease | ASCA | |
| Pernicious anemia/ atrophic gastritis | Anti-H/K | HK ATPase; ATP4A |
| Primary biliary cirrhosis | Anti-mitochondrial antibodies | 74-kDa E2, KRT7, SP100, 74-kDa E2, keratin, sp100, actin. |
| Primary sclerosing cholangitis | pANCA | |
| Ulcerative colitis | pANCA | |

Table 15 shows the molecular target and/or tissue target for a non-exhaustive list of hematopoietic autoimmunity disorders from Hayter, et al.

TABLE 15

Hematopoietic Autoimmunity Disorders

| Disorder | Tissue autoantibody | Molecular target |
|---|---|---|
| Acquired hemophilia A | Anti-FVIII | Factor VIII |
| Antiphospholipid syndrome | Anti-cardiolipin; Lupus anticoagulant; Anti-b2GPI | Beta2-GPI, APOH |
| Autoinuatme hemolytic anemia | Anti-erythrocyte I/i | Erythrocyte I/i, RHCE/D |
| Autoimmune lymphoproliferative syndrome | Anti-erythrocyte; Anti-neutrophil | |
| Autoimmune neutropenia | Anti-NA1; Anti-NA2 | ITGB2; β2 integrin |
| Evans syndrome | Anti-platelet; Anti-erythrocyte | |
| Felty's syndrome | Anti-G-CSF | G-CSF |
| Immune thrombocytopenic purpura | Anti-GpIIb/IIIa; Anti-ADAMTS13; Anti-glycoprotein Ib-IX | ITGA2B, ITGP3 |

Table 16 shows the molecular target and/or tissue target for a non-exhaustive list of musculoskeletal system autoimmunity disorders from Hayter, et al.

TABLE 16

Museuloskeletal System Autoimmunity Disorders

| Disorder | Tissue autoantibody | Molecular target |
|---|---|---|
| Polymyositis/dermatomyositis | Anti-Jo1; Anti-Mi-2; Anti-CADM140 | Mi-2, EXOSC10, HARS, Histidyl tRNA, aminoacyl tRNA synthetase, DNA-dependent nucleosome-stimulated ATPase, EXOSC10 protein, chromodomain-helicase-DNA-binding protein 4 |
| Relapsing polychondritis | Anti-collagen II; Anti-collagen IV; Anti-collagen IX | COL2A1 |
| Rheumatoid arthritis | Rheumatoid factor; Anti-CCP; Anti-collagen II | Fibrinogen, βα, PADI4, FGA |
| Still's disease | ANA; Anti-endothelial cell antibodies; | |

Table 17 shows the molecular target and/or tissue target for a non-exhaustive list of cutaneous and mucous autoimmunity disorders from Hayter, et al.

TABLE 17

Cutaneous and Mucous Autoimmunity Disorders

| Disorder | Tissue autoantibody | Molecular target |
|---|---|---|
| Alopecia areata | Anti-hair follicle antibodies | Trichohyalin |
| Bullous pemphigoid | Anti-BP 180 | BPAG1 (bullous pemphigoid associate glycoprotein 1) |
| Cicatricial pemphigoid | Anti-BP230 | Laminin-332, BPAG1 |
| Dermatitis herpetiformis | Anti-TGase3 | TGM1 (transglutaminase) |
| Discoid lupus erythematosus | | |
| Epidermolysis bullosa acquisita | Anti-type VII collagen; Anti-plectin | COL7A |
| Linear morphea | Anti-P80 Coilin | P80 Coilin |
| Pemphigus foliaceus | Anti-Desmoglein I | Desmoglein I |
| Pemphigus vulgaris | Anti-Desmoglein III | Desmoglein III |
| Vitiligo | Anti-MCHR1; Anti-SOX-10 | SOX10 |

Table 18 shows the molecular target and/or tissue target for a non-exhaustive list of cutaneous autoimmunity disorders from Hayter, et al.

TABLE 18

Systemic Autoimmunity Disorders

| Disorder | Tissue autoantibody | Molecular target |
|---|---|---|
| Behçet disease | Anti-oral mucous membrane | |
| Churg-Strauss syndrome | cANCA | |
| Cogan's syndrome | | |
| CREST syndrome | Anti-centromere | |
| Anti-fibrillarin | | |
| Essential mixed cryoglobulinemia | Anti-IgG; AECA | |
| Mixed connective tissue disease | Anti-U1-ribonucleoprotein | SNRNP70 |
| POEMS syndrome | Anti-MAG; Anti-GM1 | |
| Scleroderma | Anti-Scl70, anti-PM/Scl, anti-RNA polymerase III, anti-centromere | TOP1, EXOSC10, TRIM21, SSB, Topoisomerase I, Ro, La, Ku, fibrillarin. |
| Sjögren's syndrome | ANA; SSB; SSA | SSA/SSB, Ro, La, golgin |
| Systemic lupus erythematosus | Anti-dsDNA, Anti-U1A, Anti-U2B, Anti-PCNA, Anti-Smith, Anti-SSA, Anti-SSB. | SNRPB2, SNRPD1, PCNA, SNRPN, VIM, TRIM21, SSB, U2 snRNP B, cardiolipin, fibronectin, Ro, La, histone H2A H2B, vimentin. |

Table 19 shows the molecular target and/or tissue target for a non-exhaustive list of cardiovascular autoimmunity disorders from Hayter, et al.

TABLE 19

Cardiovascular Autoimmunity Disorders

| Disorder | Tissue autoantibody | Molecular target |
|---|---|---|
| Erythema elevatum diutinum | IgA ANCA | |
| Kawasaki disease | | |
| Microscopic polyangiitis | pANCA | Myeloperoxidase |
| Polyarteritis nodosa | Anti-endothelial cell antibodies | |
| Rheumatic fever | Anti-streptolysin O; Anti-DNase B | MYH6/7; cardiac myosin |
| Takayasu arteritis | | |
| Temporal arteritis | | |
| Wegener's granulomatosis | cANCA | proteinase 3, F2RL2 |

Table 20 shows the molecular target and/or tissue target for a non-exhaustive list of other autoimmunity disorders from Hayter, et al.

TABLE 20

Other Autoimmunity Disorders

| Disorder | Tissue autoantibody | Molecular target |
|---|---|---|
| HLA-B27-associated acute anterior uveitis | Anti-S-antigen | SAG |
| Sympathetic ophthalmia | | |
| Goodpasture's disease | Anti-basement membrane | α3(IV)NC1 collagen, GBM |

In some embodiments, the engineered platelets comprise CPR with a region recognized by the autoreactive T cells that mediate the disease. For example, the CPR comprises an epitope from the molecular target in Tables 12-20 loaded on to an MHC-ITAM fusion to directly target the autoreactive T cells. The engineered platelets may be loaded with cytotoxic or immunosuppressive protein or antibodies, which are released on activation of the platelet.

For instance, some cases of diabetes mellitus type 1 (T1DM) features T cells specific to a particular insulin peptide. Therefore, using the MHC1-ITAM receptor fusion protein with an autoimmune driving peptide, in a platelet designed to release immunosuppressive factors would result in T cell specific immunosuppression. Exposure of an TL-2 receptor (IL-2R) to compete for IL-2, release of TGF-β1 or IL-10, and many other potential options on MHC1-ITAM activation mediates immunosuppression similar to regulatory T ($T_{reg}$) cells.

In some embodiments, the engineered platelets comprising a CPR with a major histocompatibility complex (MHC) class I or class H is used in the treatment of an autoimmune disease. T cells expressing chimeric antigen receptors (CAR) comprising the MHC ligand of a pathogenic T cell receptor as an antigen binding domain of the CAR have been previously shown to be effective in the treatment of type 1 diabetes (T1D) (See, Perez et al., Immunology, 143, 609-617, which is hereby incorporated by reference in its entirety). In T1D, autoreactive CD8 and CD4 T cells selectively destroy insulin-producing B cells in the pancreas (Ibid.). Some of the MHC-II-restricted epitopes recognized by the autoreactive cells have been observed to be derived from insulin/pre-proinsulin, islet-specific glucose-6-phosphatase catalytic subunit-related protein, glutamic acid decarboxylases 65 and 67, heat-shock proteins 60 and 70, insulinoma-associated protein 2, zinc transporter ZnT8, islet amyloid polypeptide, chromogranin A, and other self antigens (Ibid.). Therefore, in some embodiments, the engineered platelets described herein include a CPR with a ligand or fragment thereof that will interact with the autoreactive cells to destroy the cells.

Some autoimmune conditions (e.g. autoimmune thyroiditis, pemphigus vulgaris) are driven by antibody dependent processes. CAR-T cells have been previously created to target the B cells that mediate autoimmunity (See, Ellebrecht et al. Science 2016). Engineered platelets described herein expressing autoantigen-ITAM CPRs could kill B cells responsible for producing the autoantibodies driving autoimmunity. Activation of the engineered platelets on B cell binding could allow specific B cell killing. An "AND" gate could be engineered to only permit activation of the engineered platelets in response to autoantigen B cell receptor (BCR) and CD19 binding, which would increase specificity of delivery of cargo or toxin loaded into the platelet.

3. Treatment of Infection

Platelets have also been implicated in the clearance of bacterial infections and constitute an important component of the innate immune response, and thus SYNLET™ therapeutic delivery system could be used for the treatment of drug resistant infections.

VI. Dosing and Administration

The present invention provides methods comprising administering any one or more compositions for immunotherapy to a subject in need thereof. These may be administered to a subject using any amount and any route of administration effective for preventing or treating a clinical condition such as cancer, infection diseases and other immunodeficient diseases.

Pharmaceutical compositions in accordance with the invention are typically formulated in dosage unit form for ease of administration and uniformity of dosage. It will be understood, however, that the total daily usage of the compositions of the present invention may be decided by the attending physician within the scope of sound medical judgment. The specific therapeutically effective, or prophylactically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, previous or concurrent therapeutic interventions and rate of excretion of the specific compound employed; the duration of the treatment; drugs used in combination or coincidental with the specific compound employed; and like factors well known in the medical arts.

The term "effective amount" refers to the amount of the active ingredient needed to prevent or alleviate at least one or more signs or symptoms of a specific disease and/or condition, and relates to a sufficient amount of a composition to provide the desired effect. The term "therapeutically effective amount" therefore refers to an amount of active ingredient or a composition comprising the active ingredient that is sufficient to promote a particular effect when administered to a typical subject. An effective amount would also include an amount sufficient to prevent or delay the development of a symptom of the disease, alter the course of a symptom of the disease (for example but not limited to, slow the progression of a symptom of the disease), or reverse a symptom of the disease. It is understood that for any given case, an appropriate "effective amount" can be determined by one of ordinary skill in the art using routine experimentation.

The pharmaceutical, diagnostic, or prophylactic compositions of the present invention may be administered to a subject using any amount and any route of administration effective for preventing, treating, managing, or diagnosing diseases, disorders and/or conditions. The exact amount required will vary from subject to subject, depending on the species, age, and general condition of the subject, the severity of the disease, the particular composition, its mode of administration, its mode of activity, and the like. The subject may be a human, a mammal, or an animal. Compositions in accordance with the invention are typically formulated in unit dosage form for ease of administration and uniformity of dosage. It will be understood, however, that the total daily usage of the compositions of the present invention may be decided by the attending physician within the scope of sound medical judgment. The specific therapeutically effective, prophylactically effective, or appropriate diagnostic dose level for any particular individual will depend upon a variety of factors including the disorder being treated and the severity of the disorder; the activity of the specific payload employed; the specific composition employed; the age, body weight, general health, sex and diet of the patient; the time of administration, and route of administration; the duration of the treatment; drugs used in combination or coincidental with the active ingredient; and like factors well known in the medical arts.

In certain embodiments, pharmaceutical compositions in accordance with the present invention may be administered at dosage levels sufficient to deliver from about 0.01 mg/kg to about 100 mg/kg, from about 0.01 mg/kg to about 0.05 mg/kg, from about 0.05 mg/kg to about 0.5 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg, of subject body weight per day, one or more times a day, to obtain the desired therapeutic, diagnostic, or prophylactic, effect.

The desired dosage of the pharmaceutical composition described herein may be delivered only once, three times a day, two times a day, once a day, every other day, every third day, every week, every two weeks, every three weeks, or every four weeks. In certain embodiments, the desired dosage may be delivered using multiple administrations (e.g., two, three, four, five, six, seven, eight, nine, ten, eleven, twelve, thirteen, fourteen, or more administrations). When multiple administrations are employed, split dosing regimens such as those described herein may be used. As used herein, a "split dose" is the division of "single unit dose" or total daily dose into two or more doses, e.g., two or more administrations of the "single unit dose". As used herein, a "single unit dose" is a dose of any therapeutic administered in one dose/at one time/single route/single point of contact, i.e., single administration event.

In some embodiments, depending upon the nature of the engineered platelets, the engineered platelets may be introduced into a host organism, e.g., a mammal, in a wide variety of ways including by injection, transfusion, infusion, local instillation or implantation. In some aspects, the engineered platelets of the invention may be introduced at the site of the tumor. The number of engineered platelets that are employed will depend upon a number of circumstances, the purpose for the introduction, the lifetime of the engineered platelets, the protocol to be used, for example, the number of administrations, the ability of the engineered platelets to multiply, or the like. The engineered platelets may be in a physiologically-acceptable medium.

In some embodiments, the engineered platelets of the invention may be administrated in multiple doses to subjects having a disease or condition. The administrations generally effect an improvement in one or more symptoms of cancer or a clinical condition and/or treat or prevent cancer or clinical condition or symptom thereof.

The pharmaceutical compositions comprising the engineered platelets of the present invention may be administered by any route to achieve a therapeutically effective outcome.

These routes include, but are not limited to enteral (into the intestine), gastroenteral, epidural (into the dura matter), oral (by way of the mouth), transdermal, peridural, intracerebral (into the cerebrum), intracerebroventricular (into the cerebral ventricles), epicutaneous (application onto the skin), intradermal, (into the skin itself), subcutaneous (under the skin), nasal administration (through the nose), intravenous (into a vein), intravenous bolus, intravenous drip, intra-arterial (into an artery), intramuscular (into a muscle), intracranial (into the heart), intraosseous infusion (into the bone marrow), intrathecal (into the spinal canal), intraperitoneal, (infusion or injection into the peritoneum), intrasinal infusion, intravitreal, (through the eye), intravenous injection (into a pathologic cavity) intracavitary (into the base of the penis), intravaginal administration, intrauterine, extra-amniotic administration, transdermal (diffusion through the intact skin for systemic distribution), transmucosal (diffusion through a mucous membrane), transvaginal, insufflation (snorting), sublingual, sublabial, enema, eye drops (onto the conjunctiva), in ear drops, auricular (in or by way of the ear), buccal (directed toward the cheek), conjunctival, cutaneous, dental (to a tooth or teeth), electro-osmosis, endocervical, endosinusial, endotracheal, extracorporeal, hemodialysis, infiltration, interstitial, intra-abdominal, intra-amniotic, intra-articular, intrabiliary, intrabronchial, intrabursal, intra-cartilaginous (within a cartilage), intracaudal (within the cauda equine), intracisternal (within the cisterna magna cerebellomedularis), intracorneal (within the cornea), dental intracornal, intracoronary (within the coronary arteries), intracorporus cavernosum (within the dilatable spaces of the corpora cavernosa of the penis), intradiscal (within a disc), intraductal (within a duct of a gland), intraduodenal (within the duodenum), intradural (within or beneath the dura), intraepidermal (to the epidermis), intraesophageal (to the esophagus), intragastric (within the stomach), intragingival (within the gingivae), intraileal (within the distal portion of the small intestine), intralesional (within or introduced directly to a localized lesion), intraluminal (within a lumen of a tube), intralymphatic (within the lymph), intramedullary (within the marrow cavity of a bone), intrameningeal (within the meninges), intramyocardial (within the myocardium), intraocular (within the eye), intraovarian (within the ovary), intrapericardial (within the pericardium), intrapleural (within the pleura), intraprostatic (within the prostate gland), intrapulmonary (within the lungs or its bronchi), intrasinal (within the nasal or periorbital sinuses), intraspinal (within the vertebral column), intrasynovial (within the synovial cavity of a joint), intratendinous (within a tendon), intratesticular (within the testicle), intrathecal (within the cerebrospinal fluid at any level of the cerebrospinal axis), intrathoracic (within the thorax), intratubular (within the tubules of an organ), intratumor (within a tumor), intratympanic (within the aurus media), intravascular (within a vessel or vessels), intraventricular (within a ventricle), iontophoresis (by means of electric current where ions of soluble salts migrate into the tissues of the body), irrigation (to bathe or flush open wounds or body cavities), laryngeal (directly upon the larynx), nasogastric (through the nose and into the stomach), occlusive dressing technique (topical route administration which is then covered by a dressing which occludes the area), ophthalmic (to the external eye), oropharyngeal (directly to the mouth and pharynx), parenteral, percutaneous, periarticular, peridural, perineural, periodontal, rectal, respiratory (within the respiratory tract by inhaling orally or nasally for local or systemic effect), retrobulbar (behind the pons or behind the eyeball), intramyocardial (entering the myocardium), soft tissue, subarachnoid, subconjunctival, submucosal, topical, transplacental (through or across the placenta), transtracheal (through the wall of the trachea), transtympanic (across or through the tympanic cavity), ureteral (to the ureter), urethral (to the urethra), vaginal, caudal block, diagnostic, nerve block, biliary perfusion, cardiac perfusion, photopheresis or spinal.

VII. Definitions

At various places in the present specification, features or functions of the compositions of the present disclosure are disclosed in groups or in ranges. It is specifically intended that the present disclosure include each and every individual sub combination of the members of such groups and ranges. The following is a non-limiting list of term definitions.

As used herein, the term "antigen" is defined as a molecule that provokes an immune response when it is introduced into a subject or produced by a subject such as tumor antigens which arise by the cancer development itself. This immune response may involve either antibody production, or the activation of specific immunologically-competent cells such as cytotoxic T lymphocytes and T helper cells, or both.

As used herein, the term "approximately" or "about," as applied to one or more values of interest, refers to a value that is similar to a stated reference value. In certain embodiments, the term "approximately" or "about" refers to a range of values that fall within 25, 20, 19, 18, 17, 16, 15, 14, 13, 12, 11, 10, 9, 8, 7, 6, 5, 4, 3, 2, 1, or less in either direction (greater than or less than) of the stated reference value unless otherwise stated or otherwise evident from the context (except where such number would exceed 100 of a possible value).

As used herein, the terms "associated with," "conjugated," "linked," "attached," and "tethered," when used with respect to two or more moieties, mean that the moieties are physically associated or connected with one another, either directly or via one or more additional moieties that serve as linking agents, to form a structure that is sufficiently stable so that the moieties remain physically associated under the conditions in which the structure is used, e.g., physiological conditions. An "association" need not be strictly through direct covalent chemical bonding. It may also suggest ionic or hydrogen bonding or a hybridization-based connectivity sufficiently stable such that the "associated" entities remain physically associated.

As used herein, the term "cancer" refers a broad group of various diseases characterized by the uncontrolled growth of abnormal cells in the body. Unregulated cell division and growth results in the formation of malignant tumors that invade neighboring tissues ultimately metastasize to distant parts of the body through the lymphatic system or bloodstream.

As used herein, the term "cytokines" refers to a family of small soluble factors with pleiotropic functions that are produced by many cell types that can influence and regulate the function of the immune system.

As used herein, the term "delivery" refers to the act or manner of delivering a compound, substance, entity, moiety, cargo or payload. A "delivery agent" refers to any agent which facilitates, at least in part, the in vivo delivery of one or more substances (including, but not limited to a compound and/or compositions of the present invention) to a cell, subject or other biological system cells.

As used herein, embodiments of the invention described herein are "engineered" when they are designed to have a feature or property, whether structural or chemical, that varies from a starting point, wild type or native molecule.

As used herein, "expression" of a nucleic acid sequence refers to one or more of the following events: (1) production of an RNA template from a DNA sequence (e.g., by transcription); (2) processing of an RNA transcript (e.g., by splicing, editing, 5' cap formation, and/or 3' end processing); (3) translation of an RNA into a polypeptide or protein; (4) folding of a polypeptide or protein; and (5) post-translational modification of a polypeptide or protein.

As used herein, a "formulation" includes at least a compound and/or composition of the present invention and a delivery agent.

As used herein, a "fragment," as used herein, refers to a portion. For example, fragments of proteins may comprise polypeptides obtained by digesting full-length protein. In some embodiments, a fragment of a protein includes at least 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 150, 200, 250 or more amino acids. In some embodiments, fragments of an antibody include portions of an antibody.

As used herein, the term "an immune cell" refers to any cell of the immune system that originates from a hematopoietic stem cell in the bone marrow, which gives rise to two major lineages, a myeloid progenitor cell (which give rise to myeloid cells such as monocytes, macrophages, dendritic cells, megakaryocytes and granulocytes) and a lymphoid progenitor cell (which give rise to lymphoid cells such as T cells, B cells and natural killer (NK) cells). Exemplary immune system cells include a CD4+ T cell, a CD8+ T cell, a CD4– CD8– double negative T cell, a T γδ cell, a Tap cell, a regulatory T cell, a natural killer cell, and a dendritic cell. Macrophages and dendritic cells may be referred to as "antigen presenting cells" or "APCs," which are specialized cells that can activate T cells when a major histocompatibility complex (MHC) receptor on the surface of the APC complexed with a peptide interacts with a TCR on the surface of a T cell.

As used herein, the term "in vitro" refers to events that occur in an artificial environment, e.g., in a test tube or reaction vessel, in cell culture, in a Petri dish, etc., rather than within an organism (e.g., animal, plant, or microbe).

As used herein, the term "in vivo" refers to events that occur within an organism (e.g., animal, plant, or microbe or cell or tissue thereof).

As used herein, a "linker" or "targeting domain" refers to a portion of a chimeric platelet receptor that recognizes and binds a desired antigen.

As used herein, a "checkpoint factor" is any moiety or molecule whose function acts at the junction of a process. For example, a checkpoint protein, ligand or receptor may function to stall or accelerate the cell cycle.

As used herein, the term "messenger RNA" (mRNA) refers to any polynucleotide which encodes a polypeptide of interest and which is capable of being translated to produce the encoded polypeptide of interest in vitro, in vivo, in situ, or ex vivo.

As used herein, the term "mutation" refers to a change and/or alteration. In some embodiments, mutations may be changes and/or alterations to proteins (including peptides and polypeptides) and/or nucleic acids (including polynucleic acids). In some embodiments, mutations comprise changes and/or alterations to a protein and/or nucleic acid sequence. Such changes and/or alterations may comprise the addition, substitution and or deletion of one or more amino acids (in the case of proteins and/or peptides) and/or nucleotides (in the case of nucleic acids and or polynucleic acids e.g., polynucleotides). In some embodiments, wherein mutations comprise the addition and/or substitution of amino acids and/or nucleotides, such additions and/or substitutions may comprise 1 or more amino acid and/or nucleotide residues and may include modified amino acids and/or nucleotides. The resulting construct, molecule or sequence of a mutation, change or alteration may be referred to herein as a mutant.

As used herein, the term "neoantigen", as used herein, refers to a tumor antigen that is present in tumor cells but not normal cells and do not induce deletion of their cognate antigen specific T cells in thymus (i.e., central tolerance). These tumor neoantigens may provide a "foreign" signal, similar to pathogens, to induce an effective immune response needed for cancer immunotherapy. A neoantigen may be restricted to a specific tumor. A neoantigen be a peptide/protein with a missense mutation (missense neoantigen), or a new peptide with long, completely novel stretches of amino acids from novel open reading frames (neoORFs). The neoORFs can be generated in some tumors by out-of-frame insertions or deletions (due to defects in DNA mismatch repair causing microsatellite instability), gene-fusion, read-through mutations in stop codons, or translation of improperly spliced RNA (e.g., Saeterdal et al., Proc Natl Acad Sci USA, 2001, 98: 13255-13260, which is hereby incorporated by reference in its entirety).

As used herein, the term "pharmaceutically acceptable excipient," as used herein, refers to any ingredient other than active agents (e.g., as described herein) present in pharmaceutical compositions and having the properties of being substantially nontoxic and non-inflammatory in subjects. In some embodiments, pharmaceutically acceptable excipients are vehicles capable of suspending and/or dissolving active agents. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, and waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E, vitamin C, and xylitol.

Pharmaceutically acceptable salts of the compounds described herein are forms of the disclosed compounds wherein the acid or base moiety is in its salt form (e.g., as generated by reacting a free base group with a suitable organic acid). Examples of pharmaceutically acceptable salts include, but are not limited to, mineral or organic acid salts of basic residues such as amines; alkali or organic salts of acidic residues such as carboxylic acids; and the like. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. Pharmaceutically acceptable salts include the conventional non-toxic salts, for example, from non-toxic inorganic or organic acids. In some embodiments, a pharmaceutically acceptable salt is prepared from a parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418, Pharmaceutical Salts: Properties, Selection, and Use, P. H. Stahl and C. G. Wermuth (eds.), Wiley-VCH, 2008, and Berge et al., Journal of Pharmaceutical Science, 66, 1-19 (1977), each of which is incorporated herein by reference in its entirety.

As used herein, the term "subject" or "patient" refers to any organism to which a composition in accordance with the invention may be administered, e.g., for experimental, diagnostic, prophylactic, and/or therapeutic purposes. Typical subjects include animals (e.g., mammals such as mice, rats, rabbits, non-human primates, and humans) and/or plants.

As used herein, the term "T cell" refers to an immune cell that produces T cell receptors (TCRs).

As used herein, the term "T cell receptor" (TCR) refers to an immunoglobulin superfamily member having a variable antigen binding domain, a constant domain, a transmembrane region, and a short cytoplasmic tail, which is capable of specifically binding to an antigen peptide bound to a MHC receptor. A TCR can be found on the surface of a cell or in soluble form and generally is comprised of a heterodimer having $\alpha$ and $\beta$ chains (also known as TCR$\alpha$ and TCR$\beta$, respectively), or $\gamma$ and $\delta$ chains (also known as TCR$\gamma$ and TCR$\delta$, respectively). The extracellular portion of TCR chains (e.g., $\alpha$-chain, $\beta$-chain) contains two immunoglobulin domains, a variable domain (e.g., $\alpha$-chain variable domain or V$\alpha$, $\beta$-chain variable domain or V$\beta$) at the N-terminus, and one constant domain (e.g., $\alpha$-chain constant domain or C$\alpha$ and $\beta$-chain constant domain or C$\beta$) adjacent to the cell membrane. Similar to immunoglobulin, the variable domains contain complementary determining regions (CDRs) separated by framework regions (FRs).

As used herein, the term "therapeutically effective amount" means an amount of an agent to be delivered (e.g., nucleic acid, drug, therapeutic agent, diagnostic agent, prophylactic agent, etc.) that is sufficient, when administered to a subject suffering from or susceptible to an infection, disease, disorder, and/or condition, to treat, improve symptoms of, diagnose, prevent, and/or delay the onset of the infection, disease, disorder, and/or condition. In some embodiments, a therapeutically effective amount is provided in a single dose. In some embodiments, a therapeutically effective amount is administered in a dosage regimen comprising a plurality of doses. Those skilled in the art will appreciate that in some embodiments, a unit dosage form may be considered to comprise a therapeutically effective amount of a particular agent or entity if it comprises an amount that is effective when administered as part of such a dosage regimen.

As used herein, the terms "treatment" or "treating" denote an approach for obtaining a beneficial or desired result including and preferably a beneficial or desired clinical result. Such beneficial or desired clinical results include, but are not limited to, one or more of the following: reducing the proliferation of (or destroying) cancerous cells or other diseased, reducing metastasis of cancerous cells found in cancers, shrinking the size of the tumor, decreasing symptoms resulting from the disease, increasing the quality of life of those suffering from the disease, decreasing the dose of other medications required to treat the disease, delaying the progression of the disease, and/or prolonging survival of individuals.

As used herein, the term "therapeutic agent" refers to a biological, pharmaceutical, or chemical compound. Non-limiting examples include simple or complex organic or inorganic molecule, a peptide, a protein, an oligonucleotide, an antibody, an antibody derivative, antibody fragment, a receptor, and a soluble factor.

EQUIVALENTS AND SCOPE

Those skilled in the art will recognize, or be able to ascertain using no more than routine experimentation, many equivalents to the specific embodiments in accordance with the invention described herein. The scope of the present invention is not intended to be limited to the above Description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or the entire group members are present in, employed in or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any antibiotic, therapeutic or active ingredient; any method of production; any method of use; etc.) can be excluded from any one or more claims, for any reason, whether or not related to the existence of prior art.

It is to be understood that the words which have been used are words of description rather than limitation, and that changes may be made within the purview of the appended claims without departing from the true scope and spirit of the invention in its broader aspects.

Described herein are compositions and methods for the design, production, administration, and/or formulation of engineered platelets described herein. In some embodiments, the engineered platelets may carry cargo in the vesicles for delivery on activation by a target, which does not activate wild-type platelets. In some embodiments then the engineered platelets of the invention carny cargo in the vesicles for delivery on activation by a target, wherein the target does not activate wild-type platelets. For example the target to which the CPR binds is not a target that would typically activate wild-type platelets, but which does activate the engineered platelet through the interaction with the target-binding CPR The present invention is further illustrated by the following non-limiting examples. Although any materials and methods similar or equivalent to those described herein can be used in the practice or testing of the present invention, the preferred materials and methods are now described. Other features, objects and advantages of the invention will be apparent from the description. In the description, the singular forms also include the plural unless the context clearly dictates otherwise. Unless defined otherwise, all technical and scientific terms used herein have the same meaning as commonly understood by one of ordinary skill in the art to which this invention belongs. In the case of conflict, the present description will control.

FIGURE LEGENDS

FIG. 1—genome editing optimization/guide ID. A) Schematic of CRISPR guide selection and screening procedure. B) Guide KO generation efficiency (as predicted by Synthego ICE algorithm) within a pools of iPSCs. C) Summary and repetition of highest efficiency guide nucleofection. N=2 per result, error bars indicate standard deviation.

Figure 2:
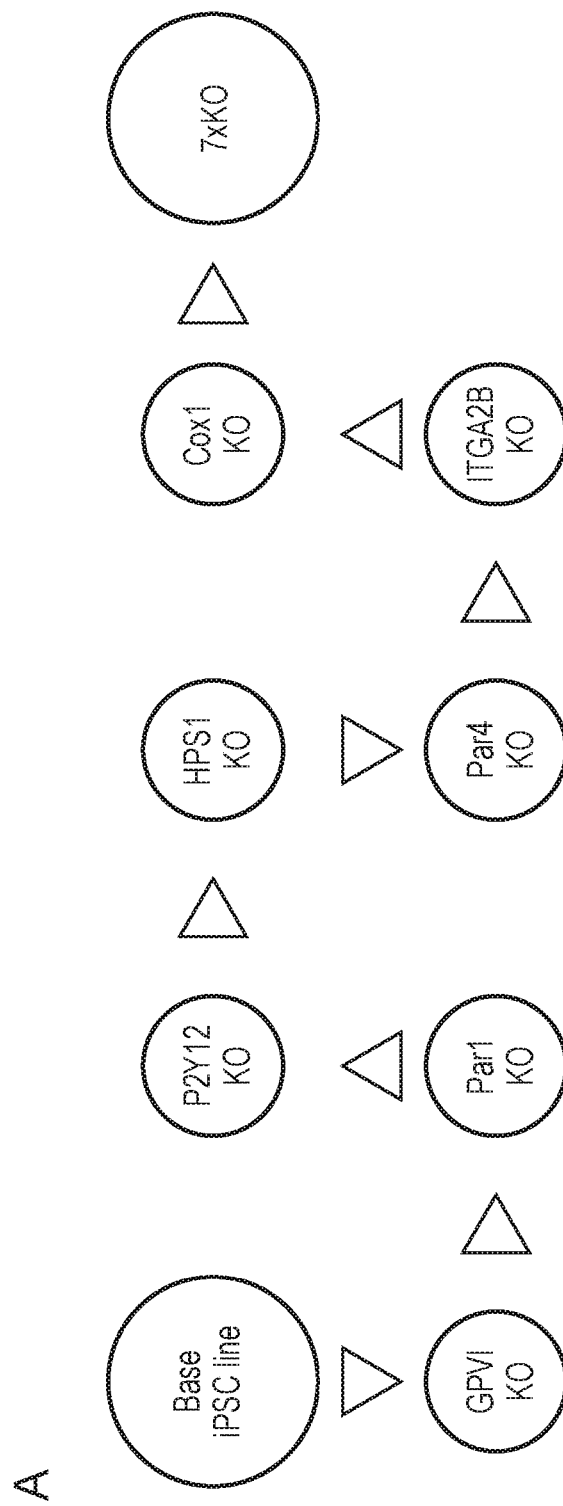
Figure 2:
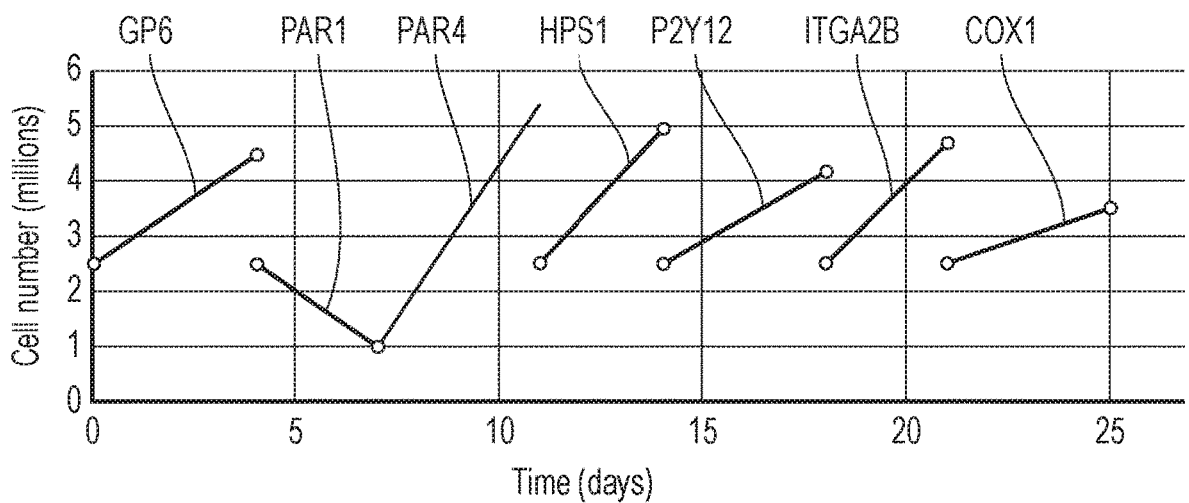
Figure 4:
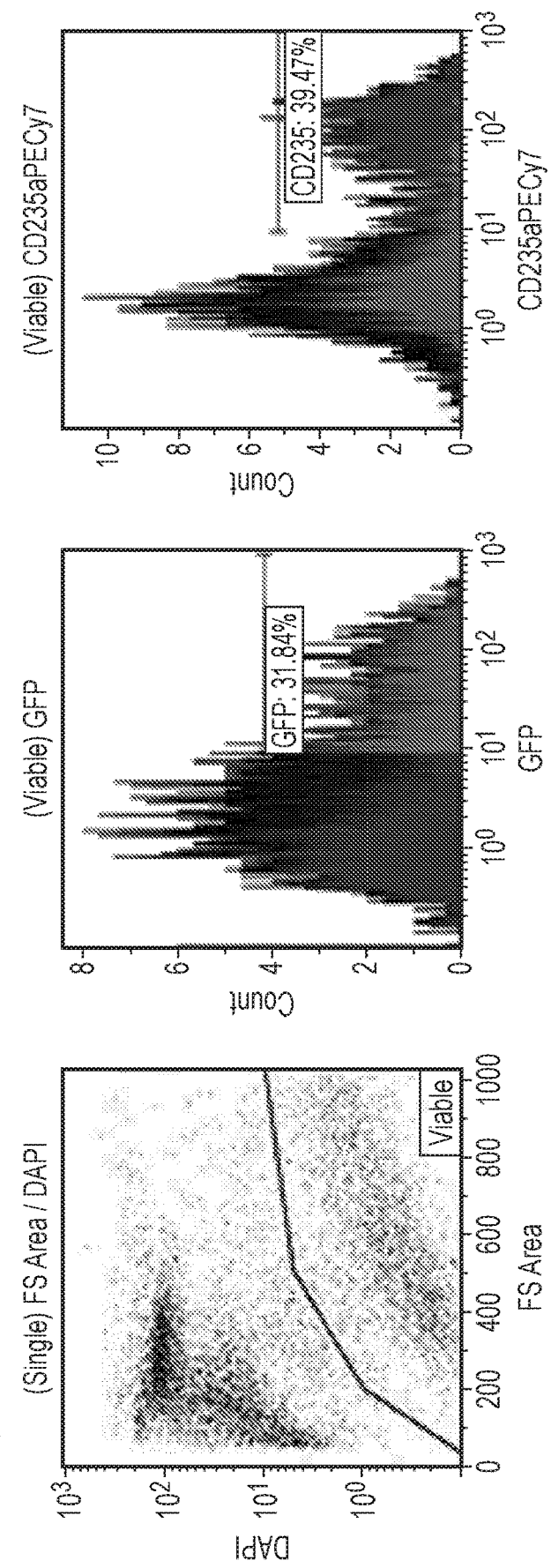
Figure 4:
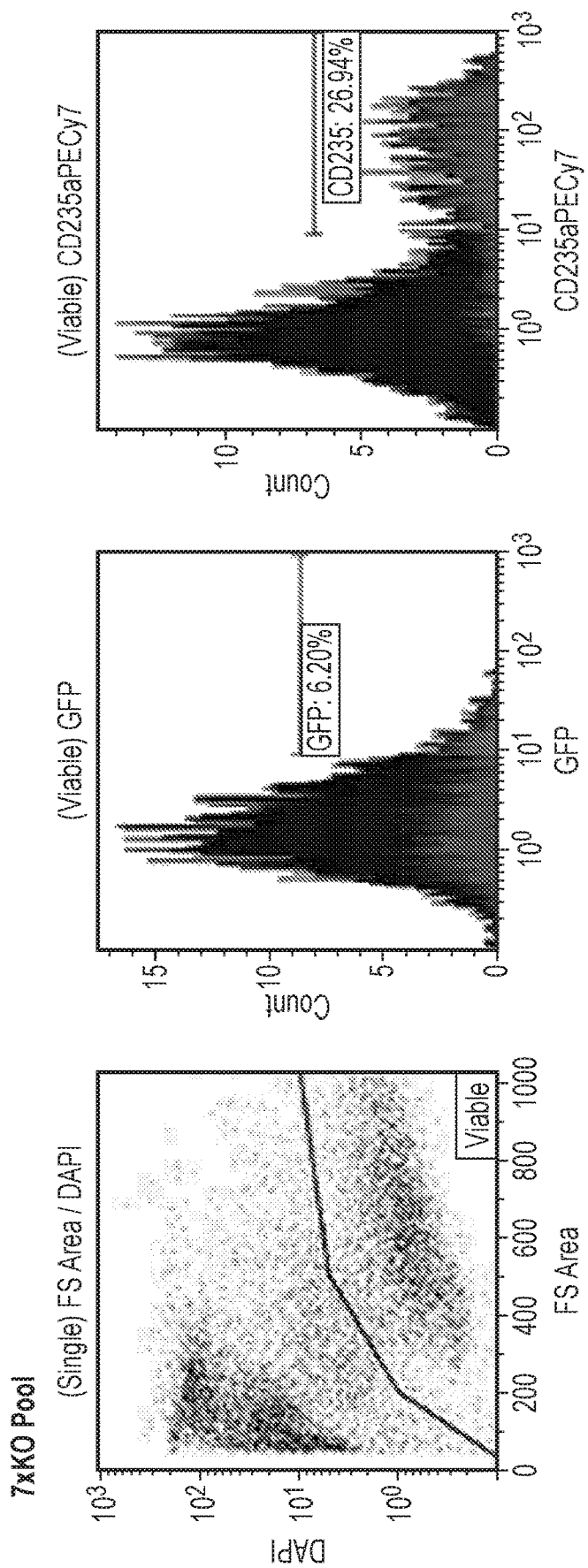
Figure 4:
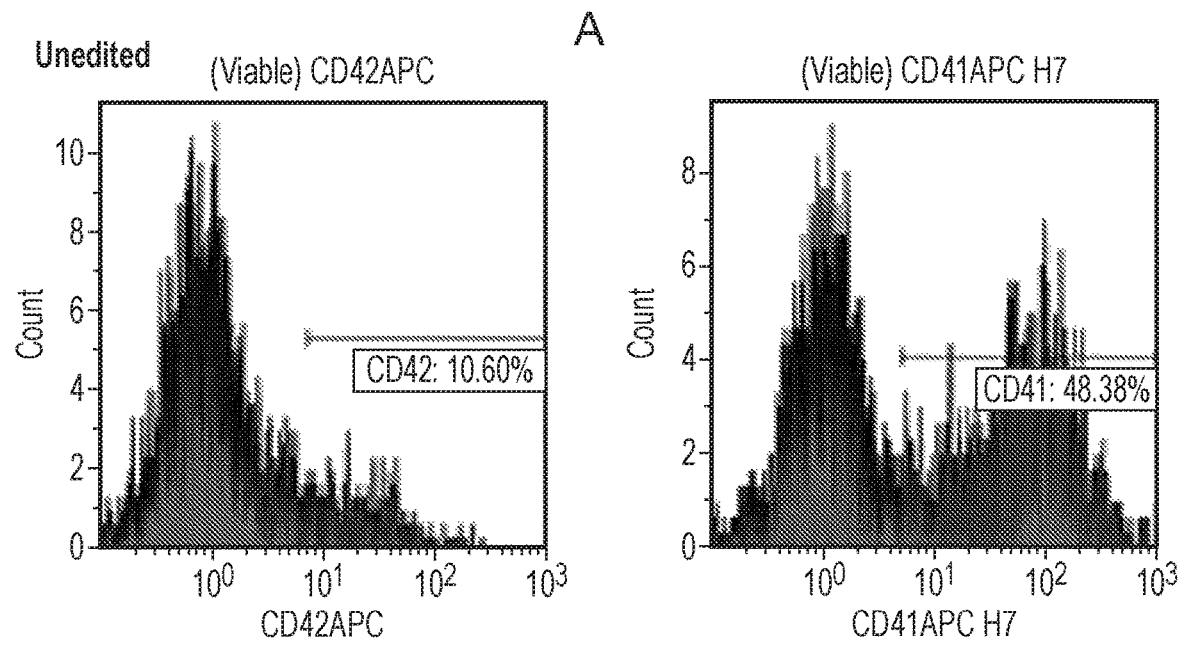
Figure 4:
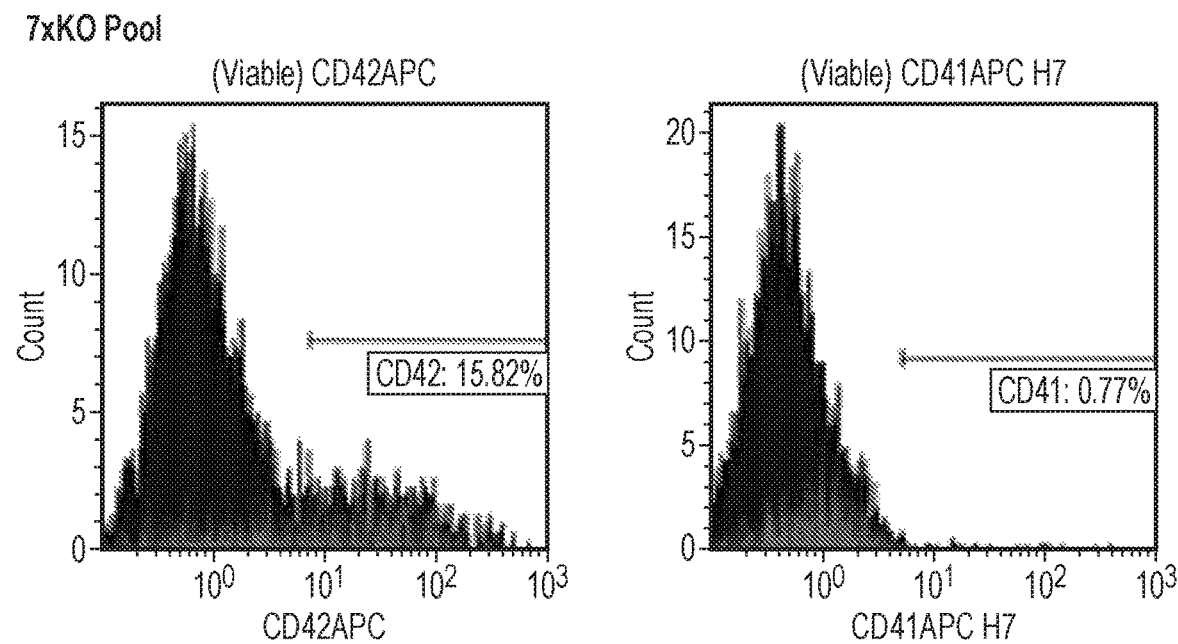
Figure 4:
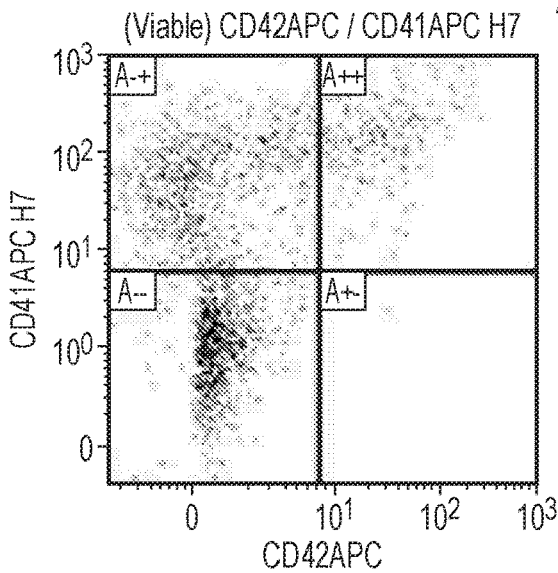
Figure 4:
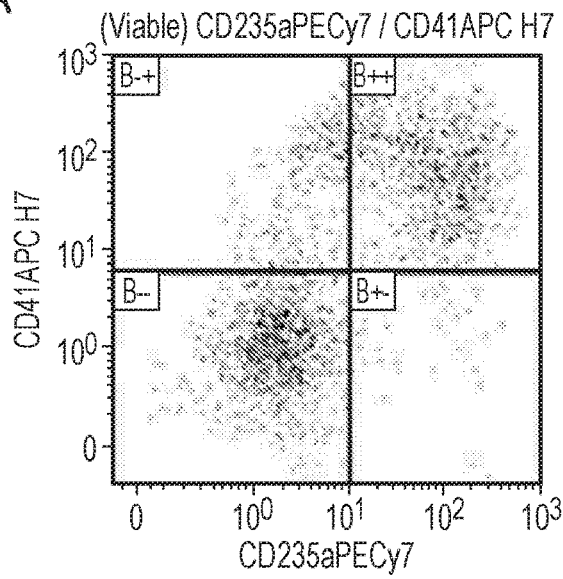
Figure 4:
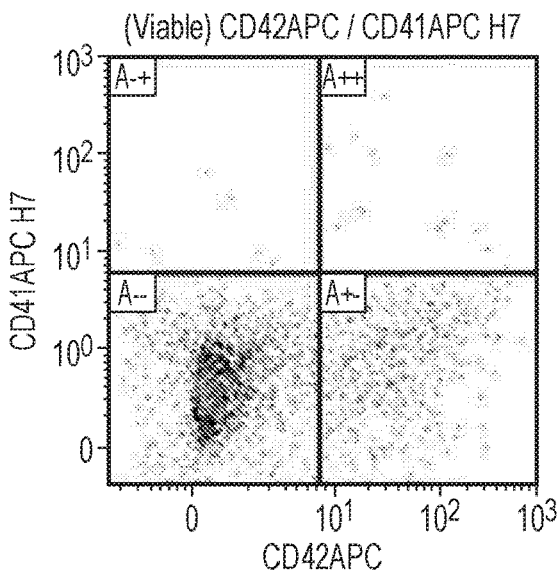
Figure 4:
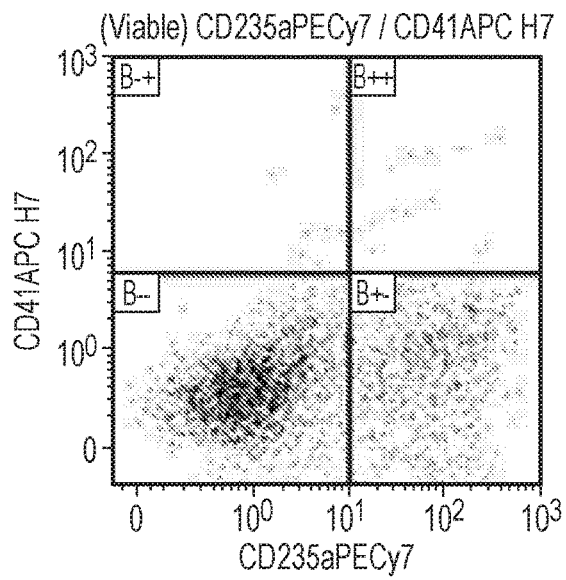
Figure 4:
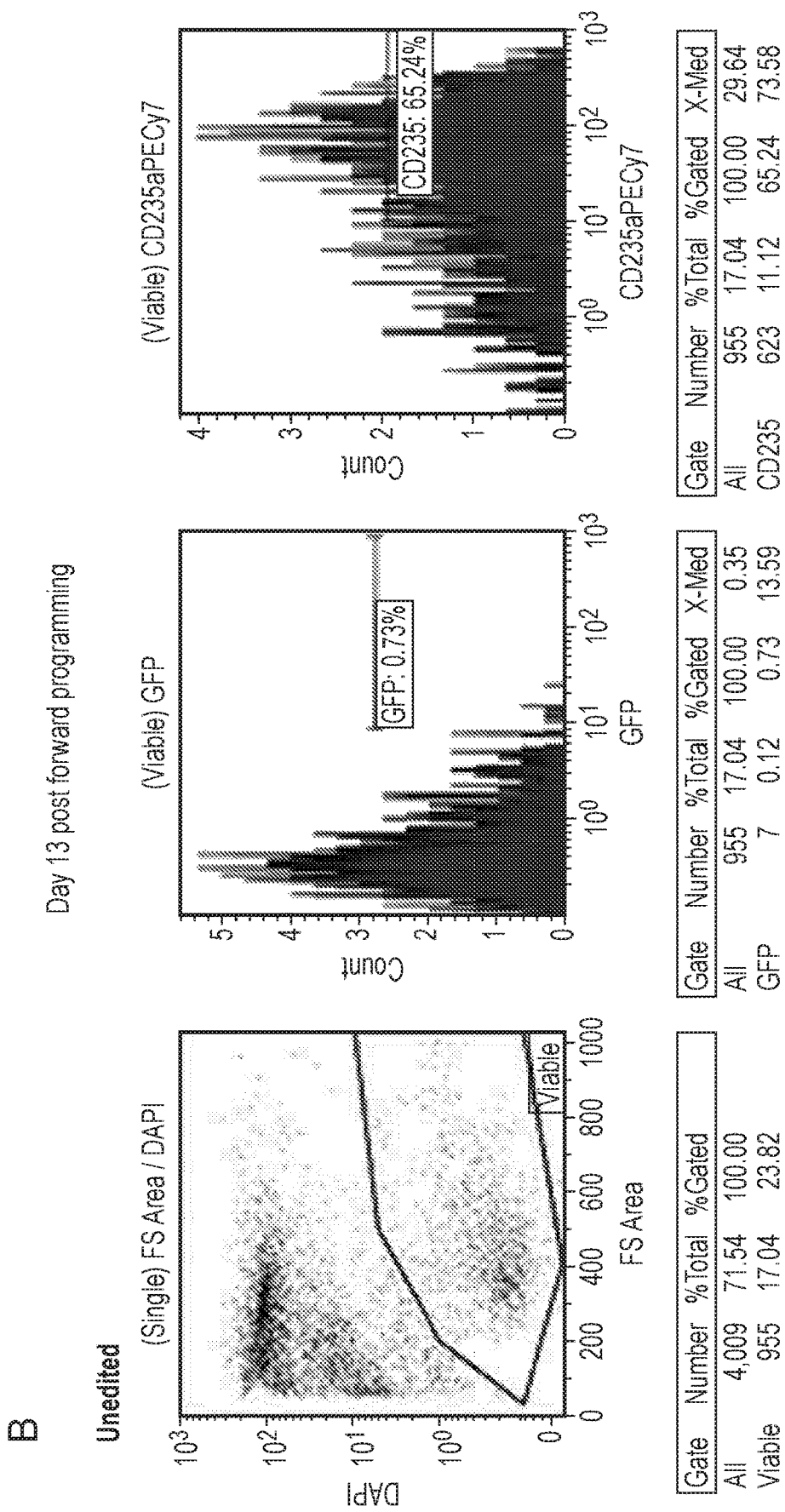
Figure 4:
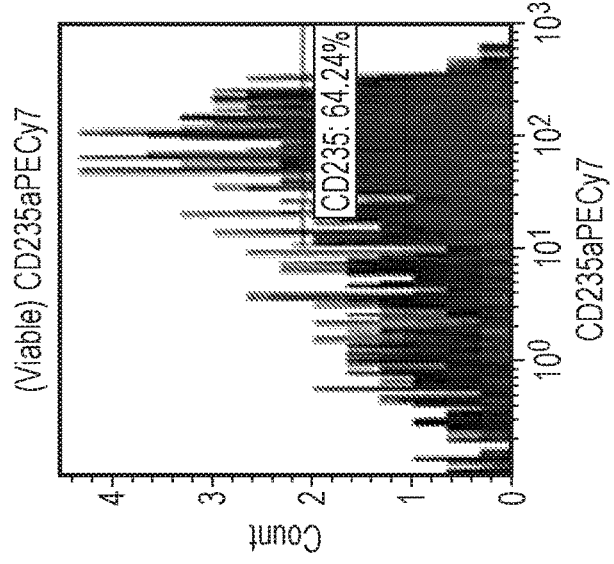
Figure 4:
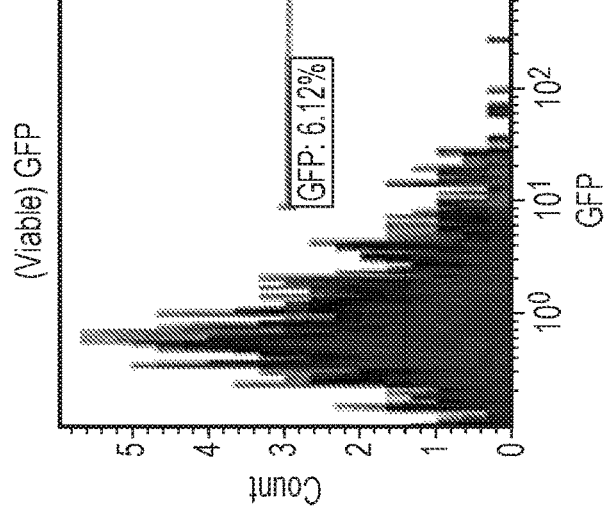
Figure 4:
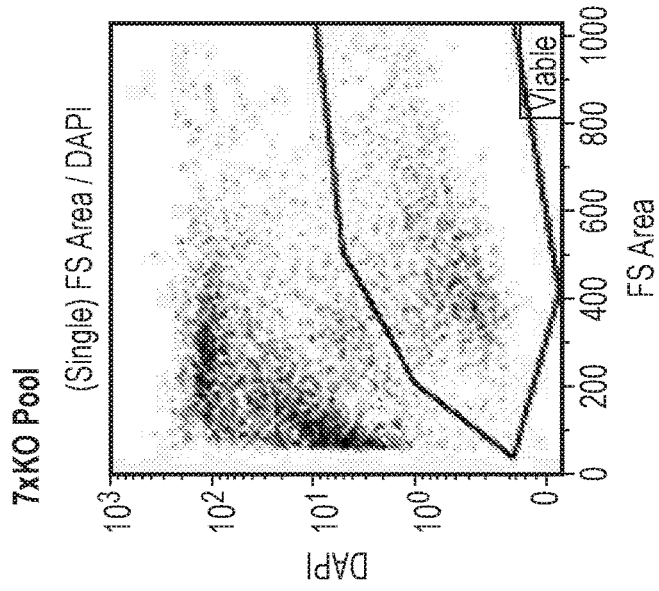
Figure 4:
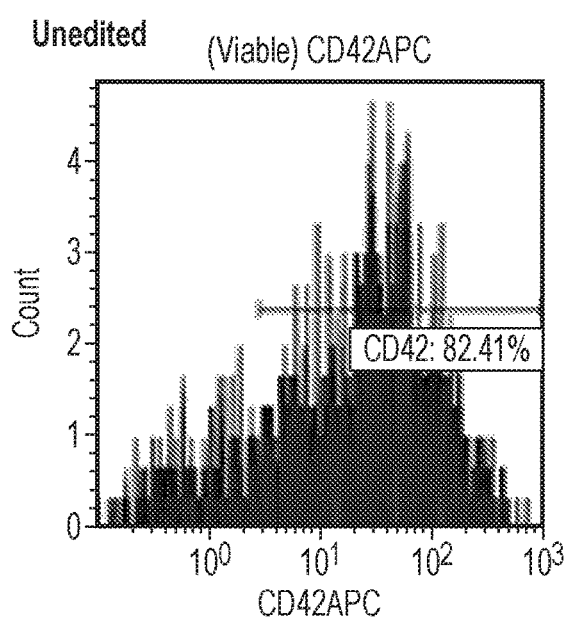
Figure 4:
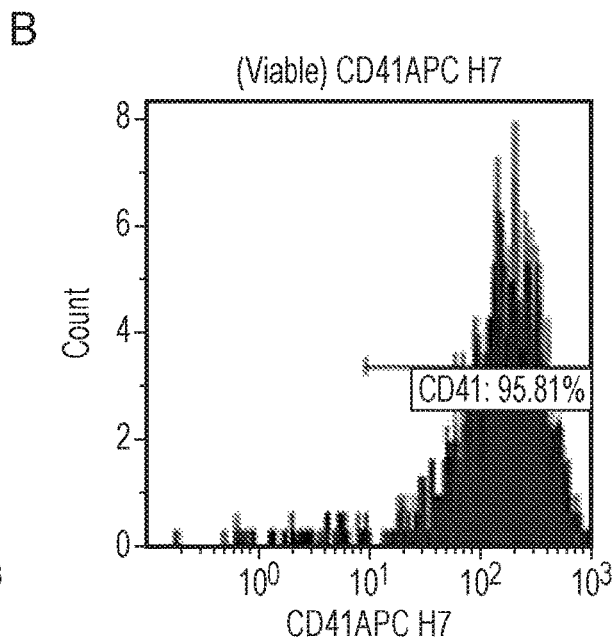
Figure 4:
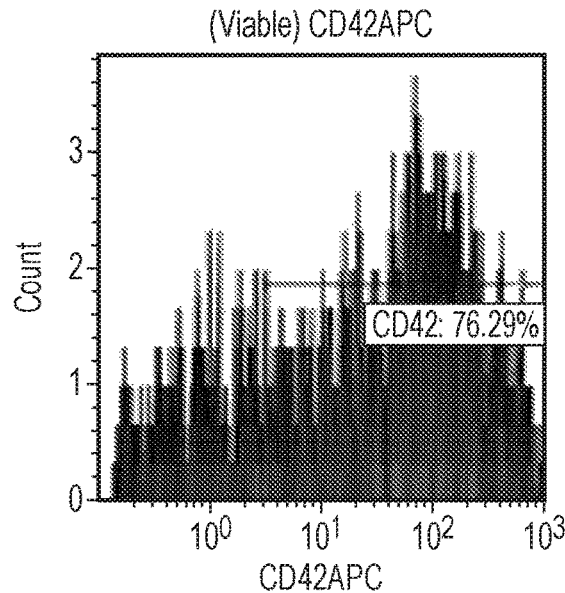
Figure 4:
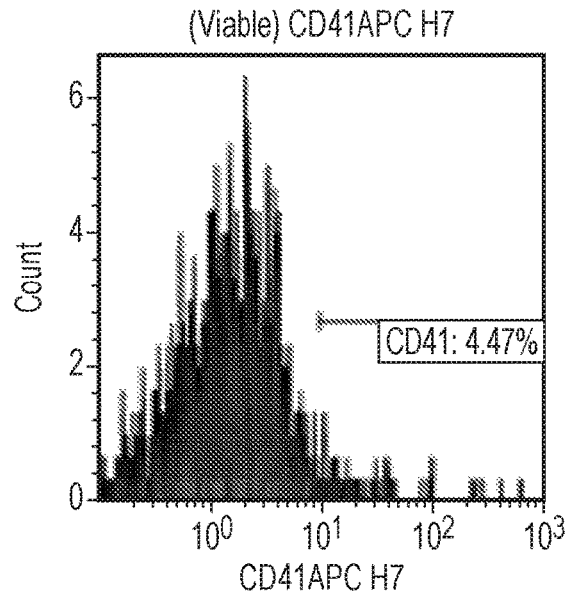
Figure 4:
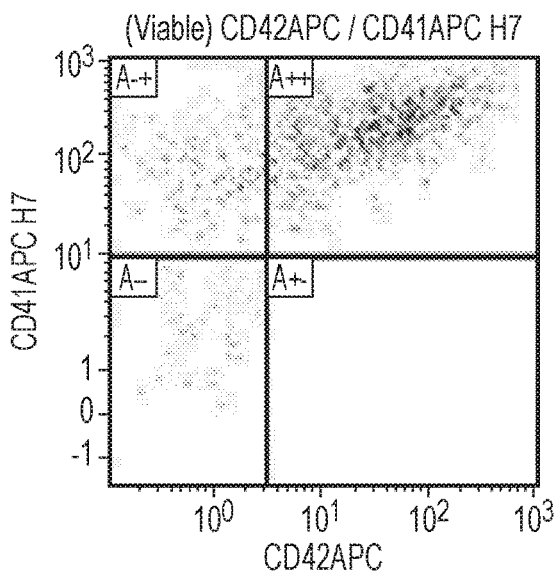
Figure 4:
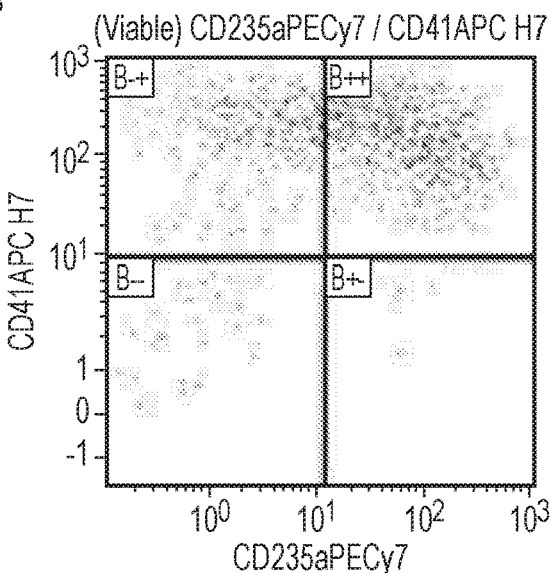
Figure 4:
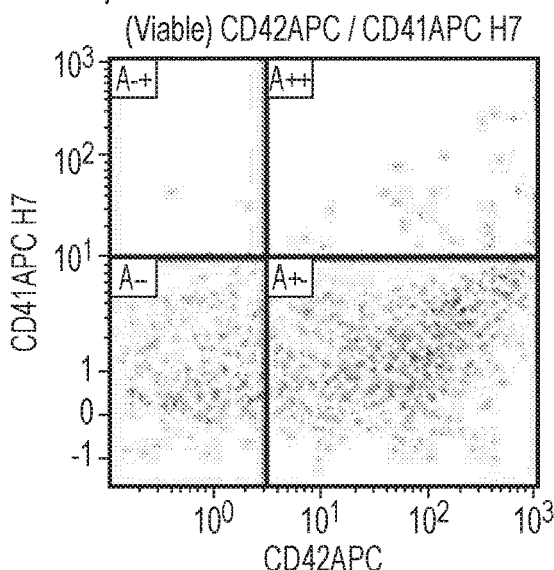
Figure 4:
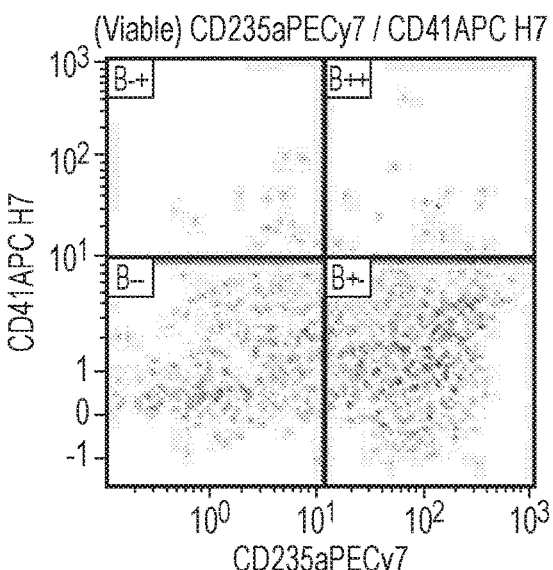

FIG. 2—Sequential editing process→7×KO. A) Schematic of sequential knock-out approach. B) Quantification of viable cell number during sequential KO approach. Viable cells identified based on exclusion of PI stain. C) Pooled knock-out efficiencies throughout sequential KO approach. At each Cas9 RNP nucleofection event, half the cells were taken for genomic DNA extraction and amplicons for all previous target sites were amplified and screened for their KO level using Synthego ICE.

FIG. 3—7×KO clone identification. A) Table showing Synthego ICE results for gene KOs within clones produced from a single cell sort of the 7×KO pool. B) Repetition of Synthego ICE analysis on amplicons generated from further expanded clones where results were absent in (A).

FIG. 4—7×KO pool of cells forward programs towards a megakaryocyte like phenotype. A) Flow cytometry based MK differentiation marker panel and viability analysis on 7×KO pool 10 days post forward programming induction using doxycycline. Performed in both unedited and 7×KO pool. B) As in (A), however 13 days post forward programming induction.

Figure 5:
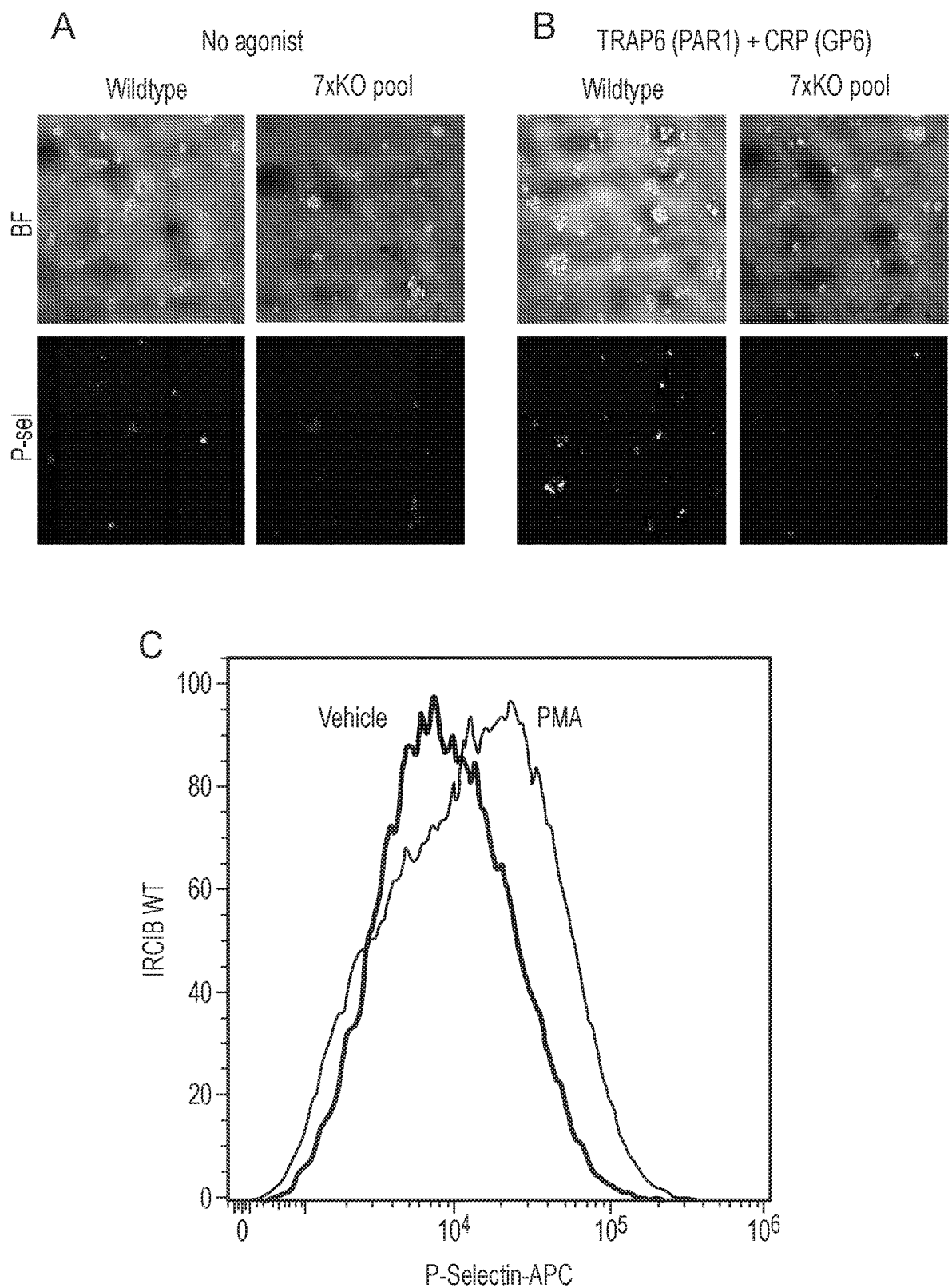
Figure 5:
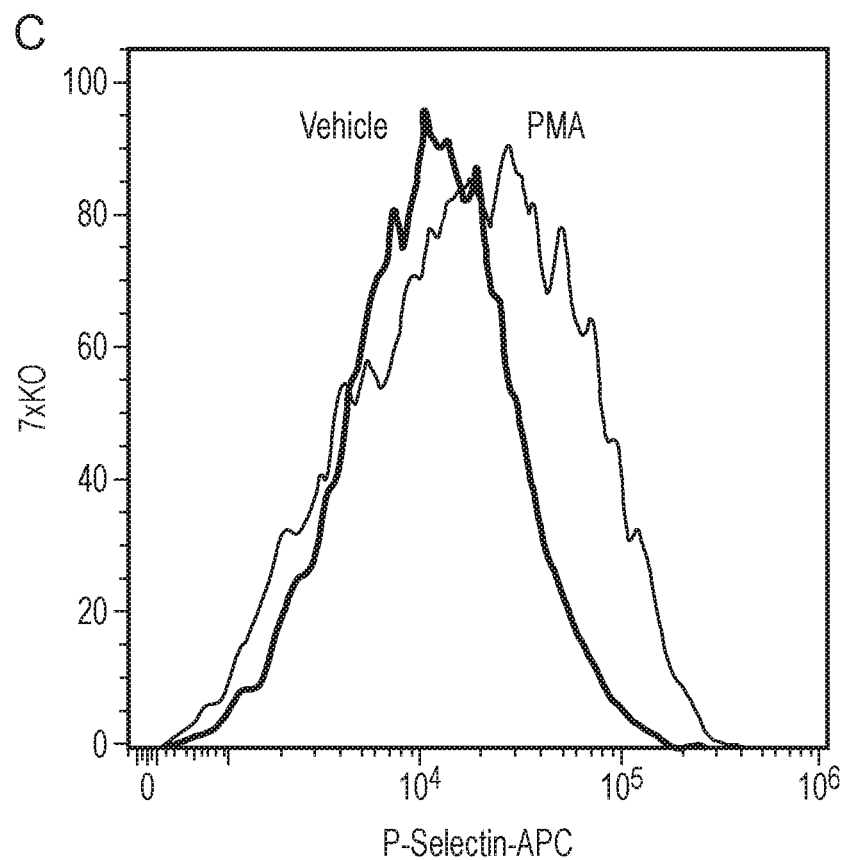
Figure 5:
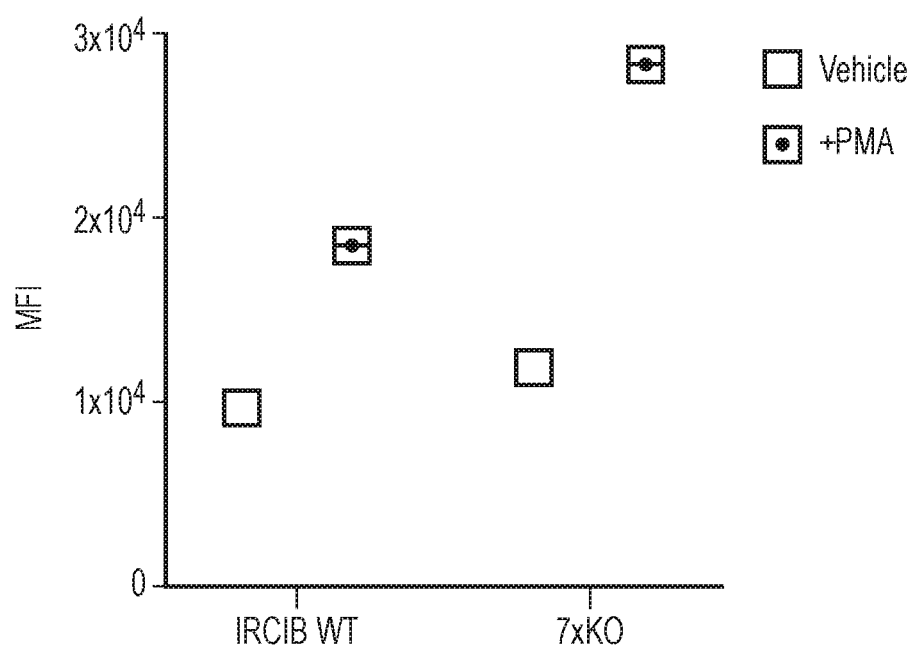
Figure 6:
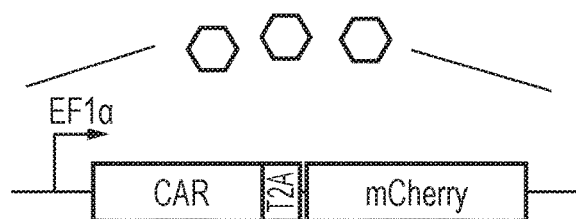
Figure 6:
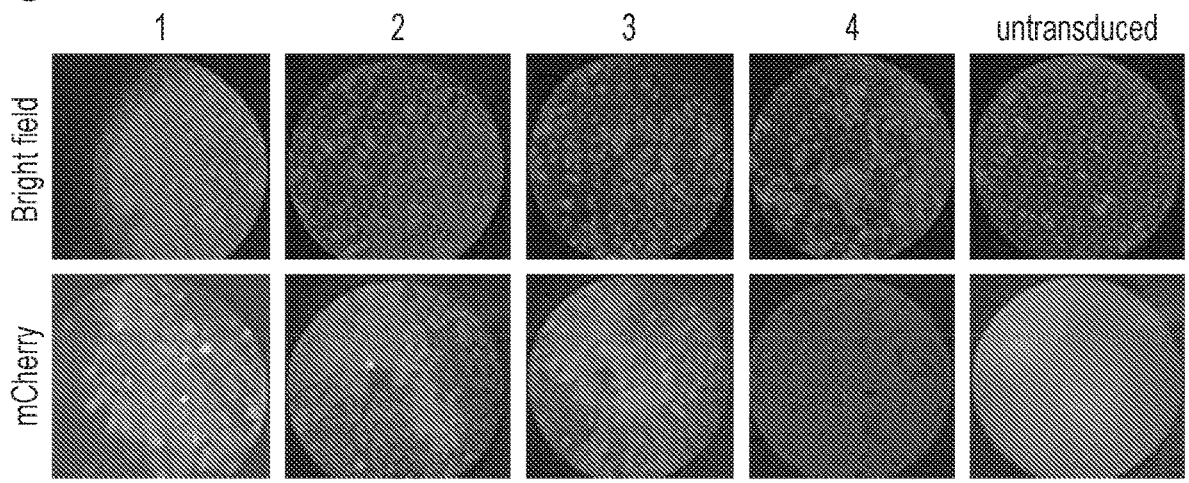
Figure 7:
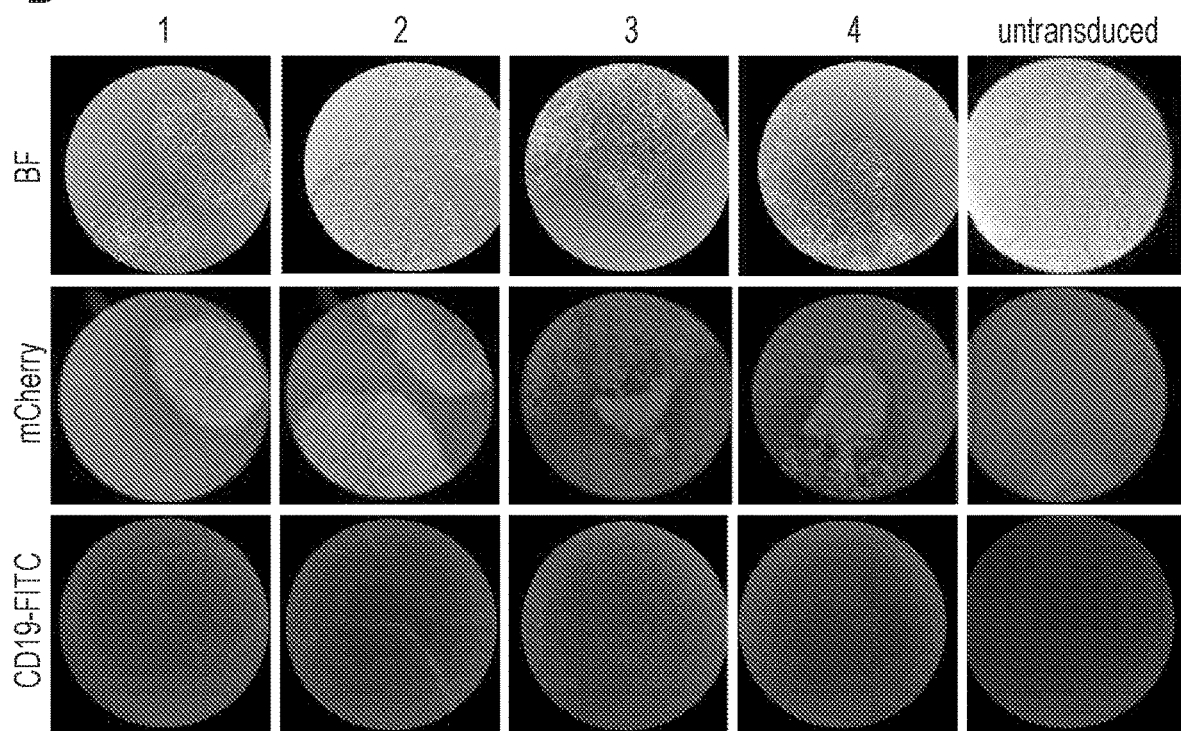

FIG. 5—7×KO pool of cells is not activated by standard agonist. A) Microscopy images of unedited MKs and 7×KO pools, stained for P-Selectin at day 13 post doxycycline addition, following fixation. B) As in (A), however after the addition of TRAP6 (10 uM) and CRP (10 ug/ml) for 30 minutes, followed by fixation. C) Flow cytometry assay of P-Selectin exposure in MKs stimulated with 300 ng/mL of PMA. Vehicle control or PMA was added to live MKs and histograms shown are of P-Selectin staining 7-10 minutes post agonist/vehicle addition. This assay was performed on a 7×KO clone (not pool) and done on day 15 post doxycycline addition.

FIG. 6—Receptor design and lentiviral transduction. A) CPR receptor design IDs. B) Schematic of CPR expression vectors packaged within in lentivirus. CPRs listed in A and mCherry expressed as a multicistronic transcript through the use of T2A sequence. Expression is driven by the EF1a promoter. C) Microscopy images of iPSCs transduced with lentivirus expressing CPR sequences in (A), 2 days post transduction FIG. 7—Receptor expression on iPSC cell surface. A) CPR receptor design IDs. B) mCherry expression and CPR surface localisation as assayed by CD19-FITC based staining for CPR expression. 10 days post transduction with lentivirus.

Figure 8:
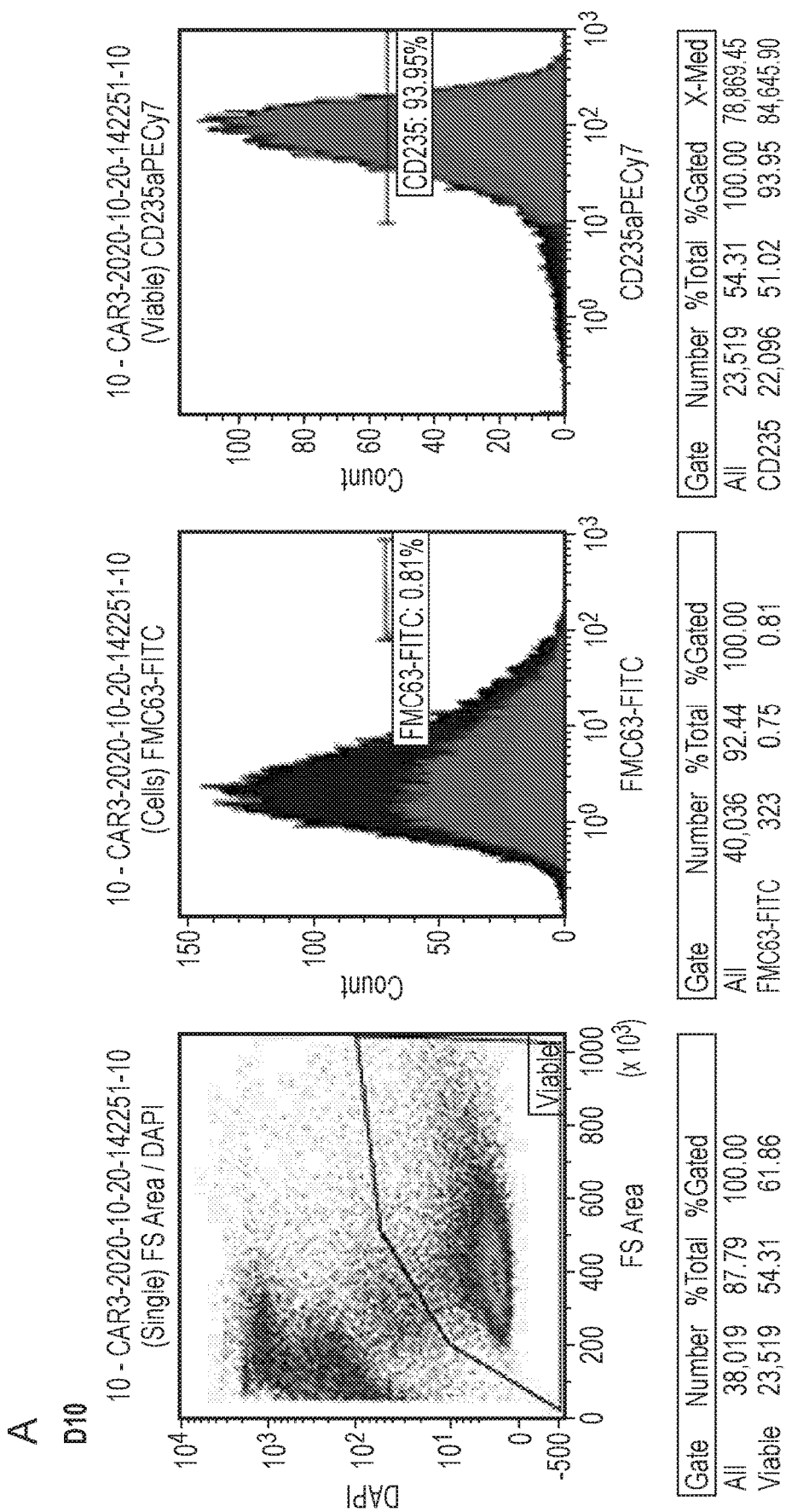
Figure 8:
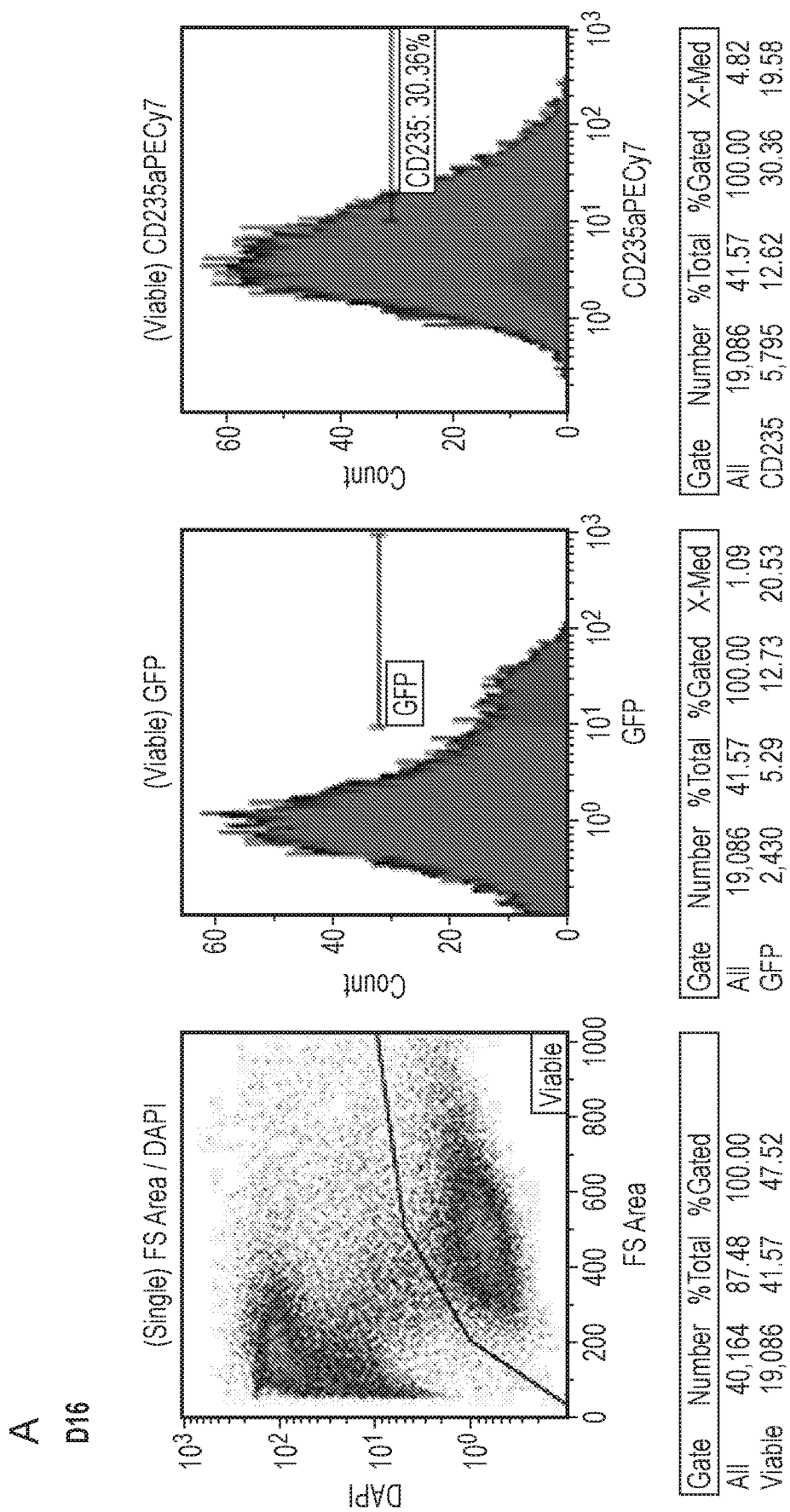
Figure 8:
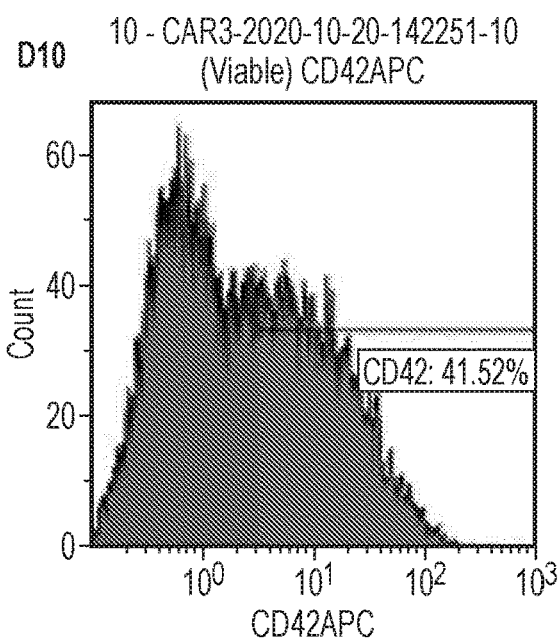
Figure 8:
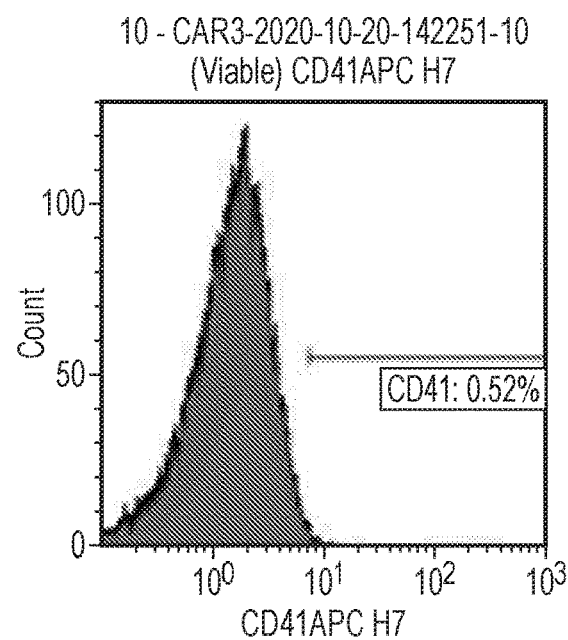
Figure 8:
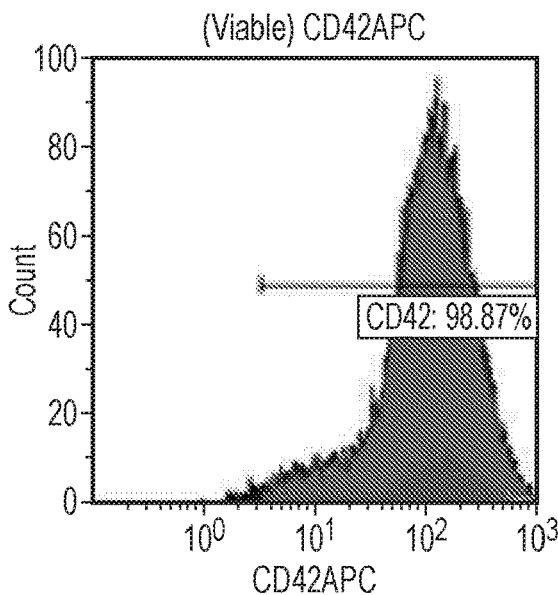
Figure 8:
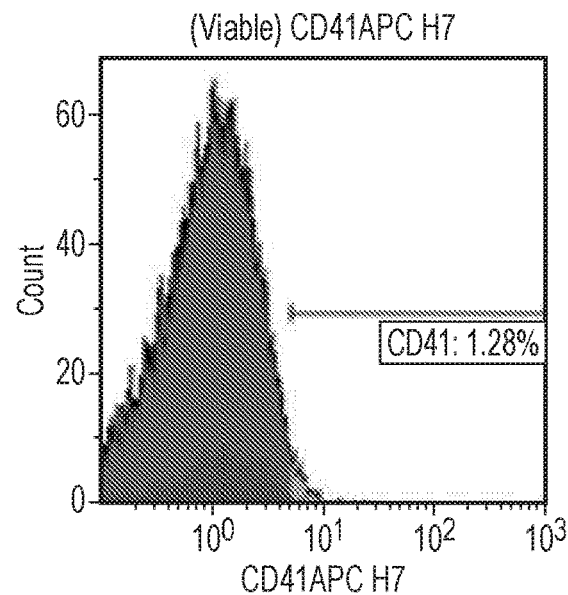
Figure 8:
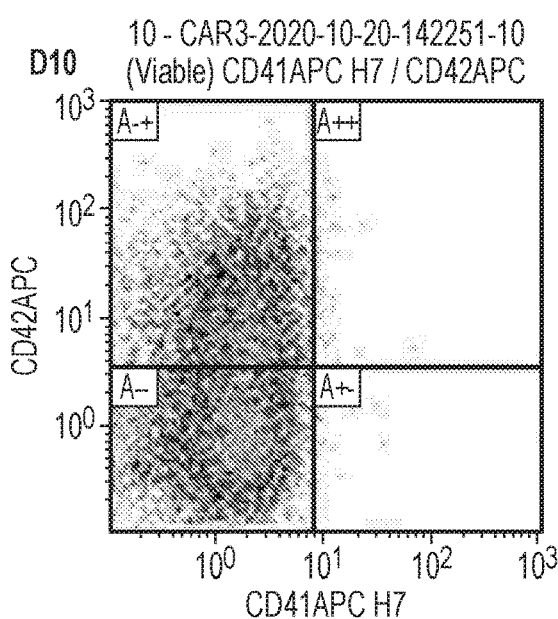
Figure 8:
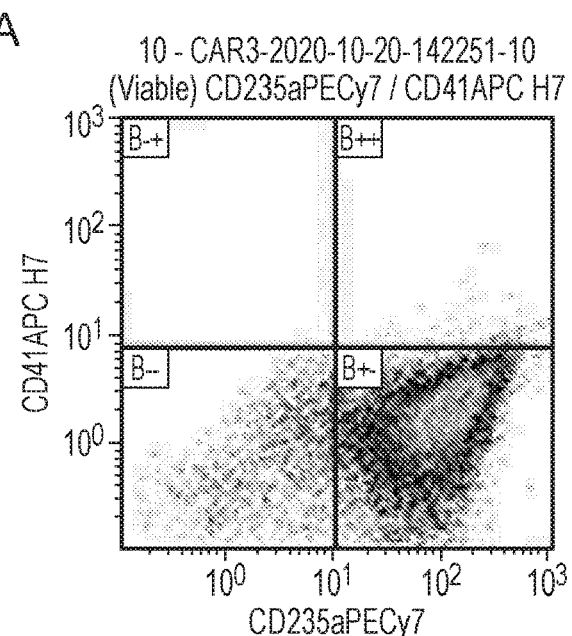
Figure 8:
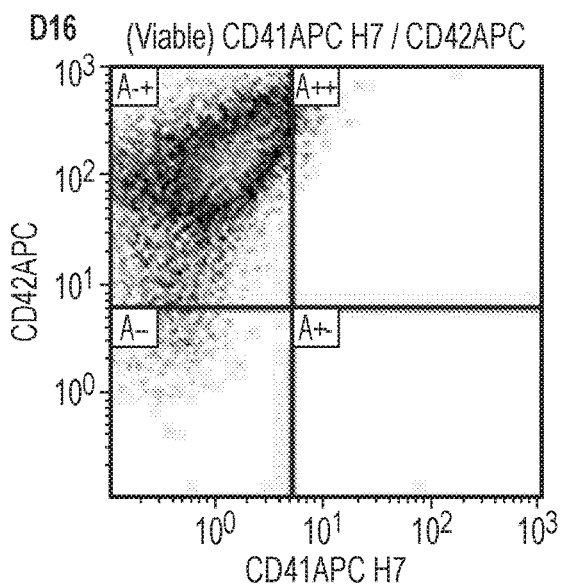
Figure 8:
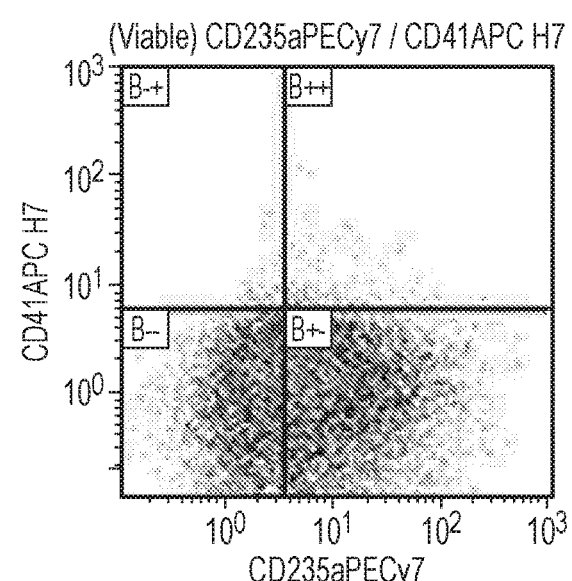
Figure 8:
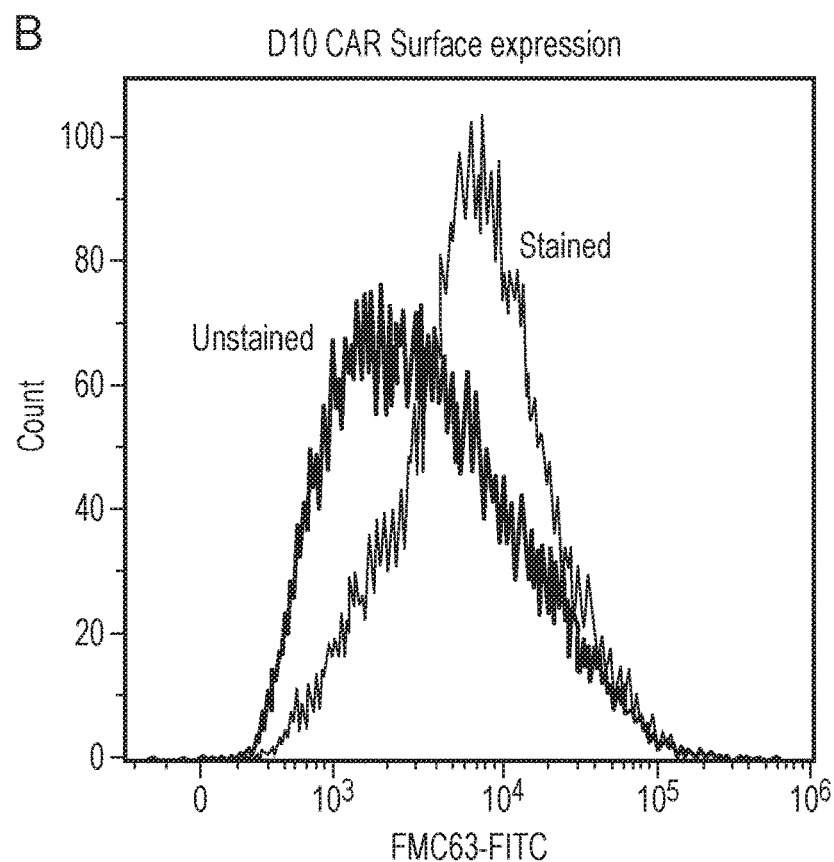

FIG. 8—Receptor expressing cells FoP and retain expression. A) Flow cytometry based MK differentiation marker panel and viability analysis on CPR3 expressing cells 10 and 16 days post forward programming induction using doxycycline. B) CPR3 surface expression quantified using FMC63-FITC staining of CPR3 expressing MKs and unstained MKs 10 days post doxycycline addition.

Figure 9:
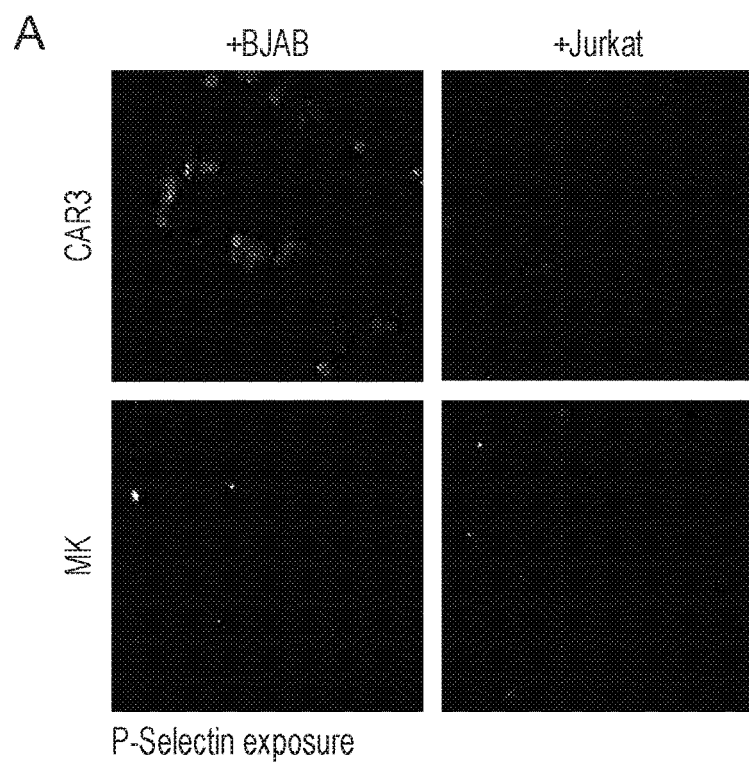
Figure 9:
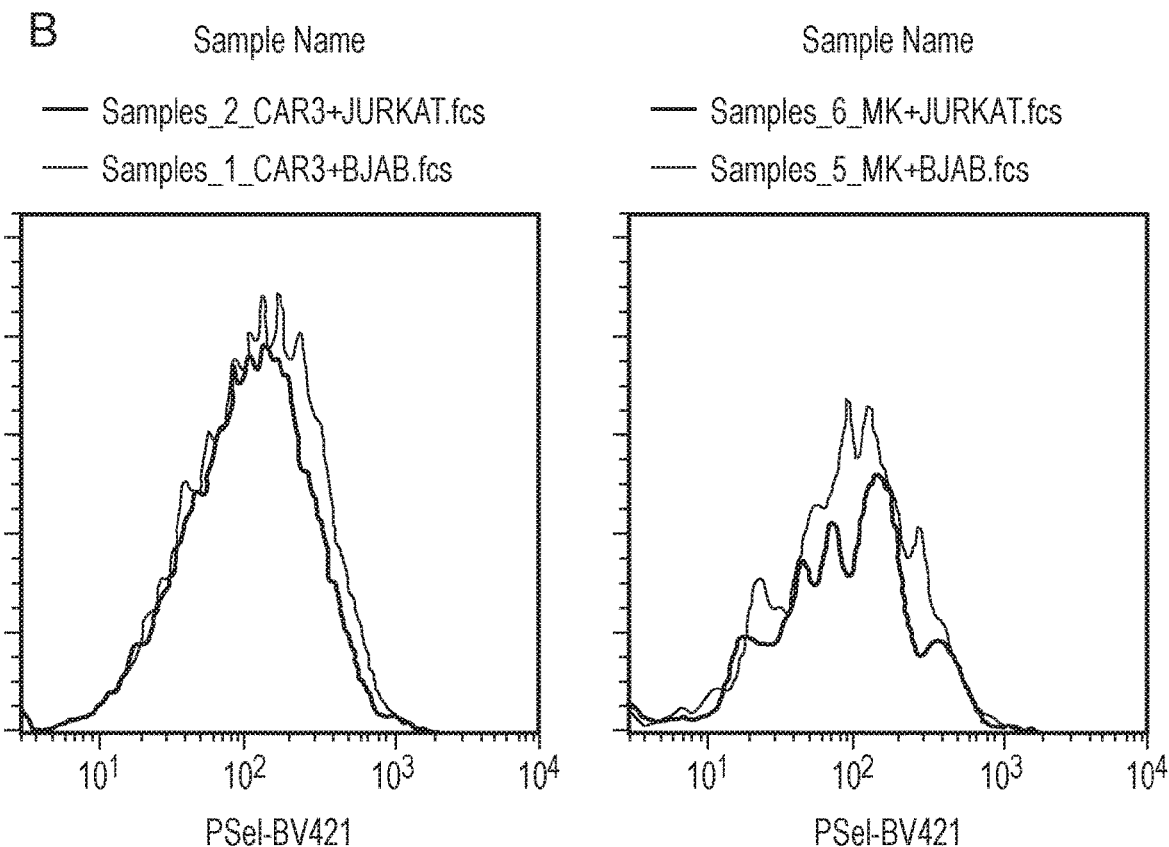
Figure 9:
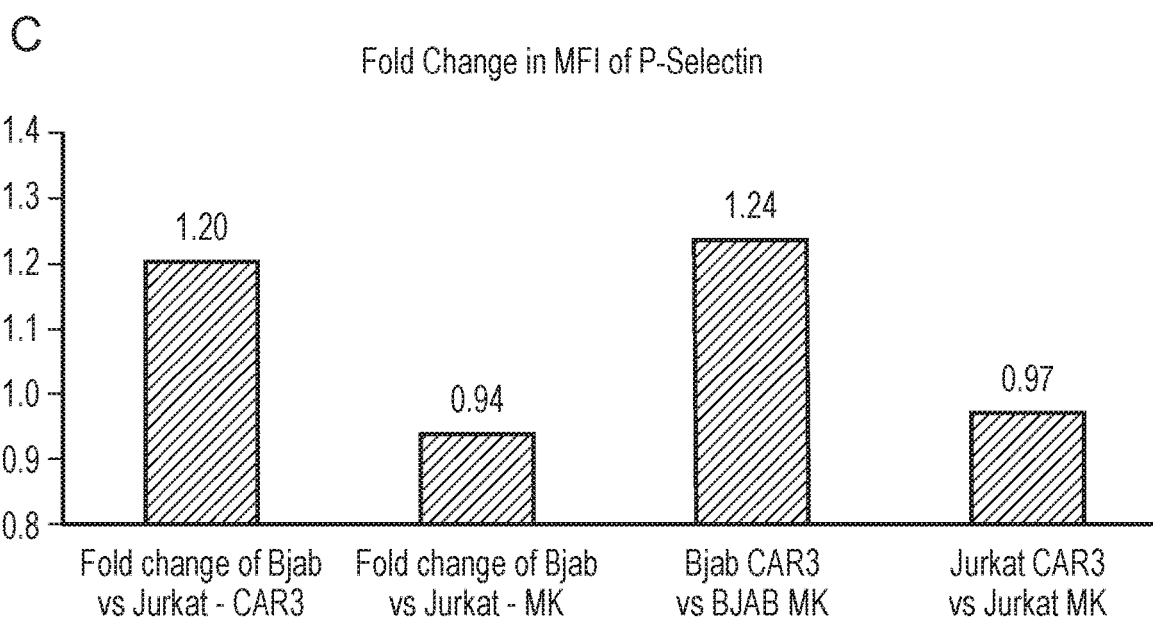

FIG. 9—Receptor expressing MKs activate/degranulate in response to CD19+ve cells. A) Microscopy images of P-Selectin staining on fixed MKs expressing CPR3 or untransduced controls following 30 minutes of incubation with either BJABs (CD19+ve B cells) or Jurkats (CD19 negative T cells). B) Flow cytometry quantification of P-Selectin staining of samples imaged in (A). C) MFI fold change of P-Selectin staining in indicated comparisons. MFI calculated following background subtraction, and performed within CD42 positive MK cell population.

Figure 10:
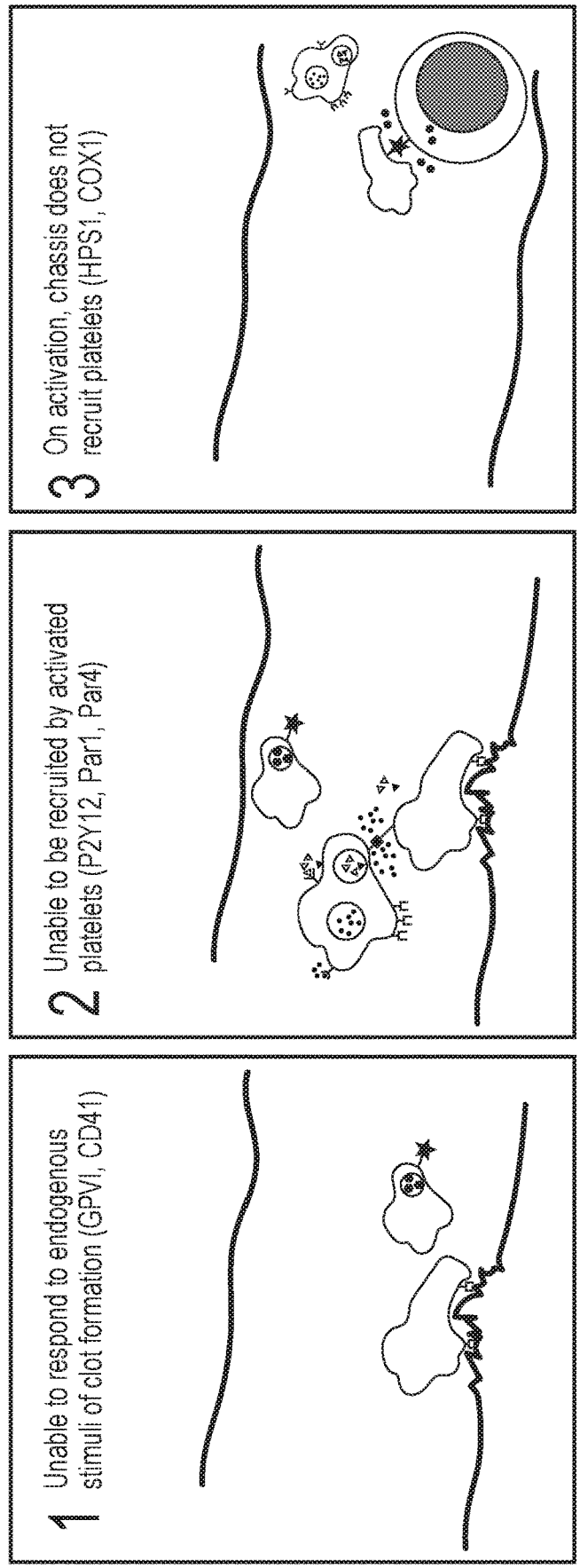

FIG. 10—schematic demonstrating the reduced thrombogenic potential of the platelets of the invention.

EXAMPLES

Example 1. Establishing Platelet Production in a Laboratory iPSC-iMKCL will be obtained from the Koji Eto Lab at Megakaryon Corporation (Kyoto office/Kyoto Lab: Kyoto Research Park, 93, Awatacho, Chudoji, Shimogyo-ku, Kyoto, 600-8815, JAPAN and the Tokyo office: 337 Bldg #1, The University of Tokyo Institute of Medical Science 4-6-1, Shirokanedai, Minato-ku, Tokyo, 108-8639, JAPAN, in addition to a VERMES™ bioreactor (Satake Multimix) to allow rapid, high-quality platelet production.

Alternatively, a megakaryocyte line of choice, chosen after consultation with key opinion leaders (KOLs) will be obtained and cultured. Back-up cell lines will be established and stored at −80° C. Platelet production may take place in a VERMES™ bioreactor, or in a shaking flask with the six factors identified Ito et al., Cell, 174(3): 636-648.e18, 2018, which is hereby incorporated by reference in its entirety. The method is hypothesized to yield about $2.4 \times 10^6$ platelets/ml in three days). A hybrid approach combining the techniques described herein also may be used. For example, Meg01 cells (ATCC® CRL-2021™ from Sigma Aldrich) may be combined with the six factors in a bioreactor with turbulence to result in less clinical translation.

An in vitro assay for CD62 (specifically displayed on platelets on activation) may be performed to ensure the platelets are active. For example, platelet CD62 will be measured using flow cytometry prior to activation. Adenosine diphosphate (ADP), thrombin, or collagen will be added to activate platelets, then percent of surface exposure of CD62 will be measured.

Example 2. Generating Non-Thrombogenic Platelets

Once the progenitor cell line is established, it can be edited before platelet production. Genes may be knocked out, such as genes that affect the thrombogenicity of a platelet. Cas9 may be introduced to the megakaryocytes using a retrovirus to assist the editing process. Then, guide RNA (gRNA) electroporation would be performed. A tracking of indels by decomposition (TIDE) analysis will be performed to confirm the knockout of desired regions.

The cloning efficiency of cells also will be measured to ensure the cells can be singly plated and grown up. In some embodiments of the invention described herein, the function of the edited platelets will be measured using in vitro assays of platelet function, for example, microfluidic chips are commercially available to test aggregation.

Then, the platelets will be moved to in vivo function testing. A mouse model as shown in Boulaftali et al. 2013, where endogenous mouse platelets can be depleted, may be used (See, Boulaftali et al. "Platelet ITAM signaling is critical for vascular integrity in inflammation". JCI, 2013, which is hereby incorporated by reference in its entirety). A line of CLEC-2 knock-out (KO) human platelets will be generated to act as a control line.

The non-thrombogenic platelets (CLEC-2 and vascular endothelial cadherin (ve)) will be combined with a dye or beta-gal (β-Gal). Each mouse is transfused with a mix of control (CLEC-2) human platelets and non-thrombogenic edited platelets. The mouse will be injured according to the protocol of an assay, such as hemoglobin (Hb) skin accumulation or tail vein bleeding time.

Any clot formed as a result of the assay will be observed for the presence of edited platelets. The mice will be treated with rhodocytin (a snake venom component that acts through CLEC-2) to trigger CLEC-2 dependent platelet aggregation of the edited platelets. Mice will be examined for the presence of a clot. If no clot is present, the edited platelets are truly non-thrombogenic.

Example 3. Generating CPR-Expressing Platelets

To test whether the edited platelets can be activated by an engineered stimulus using a CPR, CPRs were designed between known ITAM containing platelet receptors (GPVI, CLEC-2, and FCgR2A) and a model single chain antibody specific to an antigen (e.g. CD19). The construct will be introduced either as an additional copy or by knock-in to the endogenous platelet receptor locus to replace the cognate extracellular domain of the receptor. The CPR expressing platelets will be generated in vitro and exposed to a cell line expressing CD19 (e.g., NALM-6 cell line) and a control CD19 negative cell line (e.g., B16 melanoma cell line).

The ability of the CPR expressing platelets to subsequently activate in response to the presence of CD19 will be assayed in vitro through microscopy. In some embodiments, a gene (e.g., TRAIL) will be expressed to increase cytotoxicity by the engineered platelets.

Using a similar technique, the CPR may be engineered to include portions of known ITAM containing platelet receptors (GPVI, CLEC-2, and FCgR2A) and single chain MHC class 1 and MHC class 2 receptors. The variant of MHC receptor used depends on the model used, e.g. New York esophageal squamous cell carcinoma 1 (NY-ESO-1) from Astarte Biologics. The construct may be introduced as either an additional copy or by knock-in to the endogenous platelet receptor locus replacing its cognate extracellular domain. These CPR-expressing platelets will be produced in vitro, and a peptide antigen will be added to the sample. The CPR-expressing platelets will be exposed to a T-cell line responsive to peptide-MHC (or to a naïve batch of mixed T cells), and T cell response to exposure will be observed. The platelets will be loaded with different cytokine cocktails to determine whether the T cell response can be modified.

Example 5. Testing Non-Thrombogenic CPR-Expressing Platelets In Vivo

Non-thrombogenic platelets derived from a CD19 expressing melanoma cell line (or other melanoma cell line) will be engineered to contain CTLA4 and PD-1 antibodies either passively or through retroviral transduction. Immunocompetent mice will be treated with these platelets and checked for melanoma treatment.

Using the CD19 Nalm-6 B Cell leukemia model, TRAIL will be expressed in non-thrombogenic platelets. FASL and CD40L are already present, which synergize with TRAIL to induce B Cell leukaemia death. NOD scid gamma mice (NSG) mice having a tumor will be treated with the engineered platelets. The mice will be observed for a therapeutic benefit to validate the approach.

Alternatively, experimental autoimmune encephalomyelitis (EAE) may be induced in mice using previously described protocol (vaccinated with maltose binding protein (MBP)). Human platelets with mouse MHC and/or L8057 mouse cells with mouse MHC will be loaded with MBP peptide used for immunization. Further, platelets will be loaded with at least one of cytotoxic components (to kill off specific cells) and TGF-β and other anti-inflammatories. A well-defined clinical score system will be used to establish whether the above is an effective model system for testing the efficacy of non-thrombogenic CPR-expressing platelets in vivo.

Example 6—Materials and Methods for Example 7

CRISPR Guide Design
Guides were designed by identifying the first common exon of the target exon of a gene. This exon was used as input to the CRISPOR algorithm for guide selection. Four guides per target gene were chosen based on their distribution across the exon and their specificity score, listed in table 21.
Lentiviral iPSC Transduction
Replication deficient lentiviral particles containing CPR constructs and mCherry were produced by Flash Therapeutics. hiPSC lines were routinely transduced by 18-24 h single exposure to LVPs using multiplicity of infection of 100 in presence of 10 μg ml$^{-1}$ Protamine Sulfate (Sigma) in routine culture medium.
iPSC Cloning
HiPSCs were cloned by single cell sorting into 96 well plates. The day prior to sorting, iPSCs were treated with CloneR (Stem Cell Technologies). 96 well plates were coated with Biolaminin 521 LN (Biolamina). CloneR was kept in the media until day 2 post sorting. Colonies were harvested 15-20 days post sorting, by treating wells with ReLeSr and replating colonies into 24 well plates.
Flow Cytometry and Staining
Single-cell suspensions were stained for 20 min at room temperature using combinations of FITC-, PE-, PE-Cy7-, APC-, and APC-H7-conjugated antibodies. Background fluorescence were set against fluorochrome-matched isotype control antibodies and compensation matrices defined using single colour-stained cells.
CRISPR Editing—Screening
24 hours prior to nucleofection media was swapped for CloneR containing media. On the day of nucleofection, 1 μl of 61 pmol/μL of Alt-R HiFi Cas9 V3 (Integrated DNA Technologies) was mixed with 2 μl of 91.5 pmol/μL of sgRNA in TE (Synthego) (a 1:3 molar ratio) directly and incubated for at least 1 hour at room temperature. 100,000-500,000 HiPSCs per nucleofection were harvested with GCDR (Stem Cell Technologies). Harvested cells were spun down and resuspended in 20 µL nucleofection buffer P3 (Lonza). Cas9/gRNA mix was then added to the 20 µL cell/buffer P3 mix, then nucleofection was performed using 16-well Nucleocuvette Strip with 4D Nucleofector system (Lonza). Following nucleofection, 80 µL of media was added to the nucleocuvette well, and cells were replated into a single well of a 24 well plate, in CloneR containing media. Media was changed two days later for mTeSR Plus.

CRISPR Editing—Sequential 24 hours prior to nucleofection media was swapped for CloneR containing media. On the day of nucleofection, 5 µl of 61 pmol/µL of Alt-R HiFi Cas9 V3 (Integrated DNA Technologies) was mixed with 10 µl of 91.5 pmol/µL of sgRNA in TE (Synthego) (a 1:3 molar ratio) directly and incubated for at least 1 hour at room temperature. 1-2.5 million HiPSCs per nucleofection were harvested with GCDR (Stem Cell Technologies). Harvested cells were spun down and resuspended in 100 µL nucleofection buffer P3 (Lonza). Cas9/gRNA mix was then added to the 100 µL cell/buffer P3 mix, then nucleofection was performed using the 100 µL Nucleocuvette with 4D Nucleofector system (Lonza). Following nucleofection, 400 µL of media was added to the nucleocuvette well, and cells were replated into two wells of a 6 well plate and one well of a 24 well plate, in CloneR containing media. Media was changed two days later for mTeSR Plus. Cells were given 3-4 days total to recover, before the subsequent nucleofection was performed.

CRISPR KO Quantification

Genotyping was performed by first harvesting HiPSC cells using GCDR or ReLeSr. Genomic DNA was extracted using Kapa Express Extract Kit (Roche) following manufacturers instructions. Following genomic DNA extraction, the targeted genomic region was amplified using target locus specific primers (See table 2). PCR fragments were PCR purified and submitted for Sanger Sequencing (Source Bioscience). These sequences were then input into the ICE analysis software (Synthego) and thus editing efficiencies were quantified.

iPSC Cell Culture and Forward Programming to MK

The iPSC cell line RCIB-10 was forward programmed to megakaryocytes by the concurrent expression of TAL1, FLI1 and GATA1 from a doxycycline inducible promoter (see for example Dalby thesis, University of Cambridge "Forward programming of human pluripotent stem cells to a megakaryocyte-erythrocyte bi-potent progenitor population"; and Moreau 14 Sep. 2017 "Forward Programming Megakaryocytes from Human Pluripotent Stem Cells" BBTS Annual Conference Glasgow 2017). The parental RCIB-10 line was originally derived by episomal vector mediated expression of human OCT4, SOX2, KLF4 and MYC reprogramming factors from the donor cell line.

Cells were cultured under standard conditions with doxycycline for 10 days at which point the cells were harvested.

P-Selectin Based Activation Assay (CRP/TRAP-6/PMA)

To assay the activation of MKs in response to mixing with known agonists, 100,000-500,000 MKs were first harvested by centrifugation at 100G for 8 minutes and resuspended in 100 µL of Tyrode's buffer (134 mM NaCl, 12 mM NaHCO3, 2.9 mM KCl, 0.34 mM Na2HPO4, 1 mM MgCl2, 10 mM HEPES, pH 7.4) containing anti P-Selectin antibody (Biolegend, clone AK4, variable fluorophore at 1 µL/100 µL of cells). Where live cells were assayed by flow, this was performed by direct sampling from the tube without resuspension of cells. Agonists were subsequently added and incubated with MKs for 40 minutes, before fixation with 1% PFA for 15 minutes. Following PFA fixation, cells were resuspended in 300 µL Tyrode's buffer containing anti-CD42 antibody (1 µL/100 µL) was added to allow for mature MK identification. MKs were analysed either by imaging using confocal microscopy, or by flow cytometry. CRP (Cambcol) was added to cells at a concentration of 10 µg/ml, TRAP-6 (Abcam) at a concentration of 10 µM PMA (Sigma) at a concentration of 300 ng/mL. When cells were used as agonists (Jurkats, DSMZ cat no; ACC 282 and BJABs—B Cell lymphoma line, Ghevaert lab stock) they were added in 1:1 number vs. Mks.

TABLE 21 gRNA primer sequences:

| | HPS1 Exon 7 | |
|---|---|---|
| Name | Sequence | PAM sequence |
| grna1_HPS1_1r | GGGGTGAATCAGTCGCTCCA [SEQ ID NO: 56] | GGG |
| grna2_HPS1_2 | GTCAACACCAGCCCCGAGCG [SEQ ID NO: 57] | GGG |
| grna3_HPS1_3 | GCTGGAGCGGCACGTCATCC [SEQ ID NO: 58] | AGG |
| grna4_HPS1_4r | CTTGGAGTGCACGAGCAGGA [SEQ ID NO: 59] | AGG |
| | ITGA2B Exon 7 | |
| Name | Sequence | PAM sequence |
| grna5_ITGA2B_1r | CAGTAGCCGTCGAAGTACTC [SEQ ID NO: 60] | TGG |

TABLE 21-continued gRNA primer sequences:

| | | |
|---|---|---|
| grna6_ITGA2B_2 | ATTTTCTCGAGTTACCGCCC [SEQ ID NO: 61] | *AGG* |
| grna7_ITGA2B_3r | CTCGAGAAAATATCCGCAAC [SEQ ID NO: 62] | *TGG* |
| grna8_ITGA2B_3r | GGGAGGACACGTGCCACAAA [SEQ ID NO: 63] | *AGG* |

GP6
Exon 3

| Name | Sequence | PAM sequence |
|---|---|---|
| grna9_GP6_1 | GGGCGTGGACCTGTACCGCC [SEQ ID NO: 64] | *TGG* |
| grna10_GP6_2r | ACGAGCTCCAGCTGGTCGCT [SEQ ID NO: 65] | *GGG* |
| grna11_GP6_3r | CGGAGGTCCCTGGCACCGGA [SEQ ID NO: 66] | *GGG* |
| grna12_GP6_4 | CCAGTGACCCTCCGGTGCCA [SEQ ID NO: 67] | *GGG* |

Par1
Exon 2

| Name | Sequence | PAM sequence |
|---|---|---|
| grna13_Par1_1r | GGAGCTGGTCAAATATCCGG [SEQ ID NO: 68] | *AGG* |
| grna14_Par1_2r | TTCCTGAGAAGAAATGACCG [SEQ ID NO: 69] | *GGG* |
| grna15_Par1_3r | ACACTCCGGTGTACACAGAT [SEQ ID NO: 70] | *GGG* |
| grna16_Par1_4r | ACGATGGCCATGATGTTTAG [SEQ ID NO: 71] | *TGG* |

Par4
Exon 2

| Name | Sequence | PAM sequence |
|---|---|---|
| grna17_Par4_1r | ACTTGGCCTGGGTAGCCGCG [SEQ ID NO: 72] | *GGG* |
| grna18_Par4_2 | GGTGCCCGCCCTCTATGGGC [SEQ ID NO: 73] | *TGG* |
| grna19_Par4_3 | TGGTGGGGCTGCCGGCCAAT [SEQ ID NO: 74] | *GGG* |
| grna20_Par4_4r | AGCAGTGCCCGTGAGCTGTC [SEQ ID NO: 75] | *CGG* |

Cox1
Exon 7 3' and exon 8

| Name | Sequence | PAM sequence |
|---|---|---|
| grna21_Cox1_1 | ACTTCTGGCAAGATGGGTCC [SEQ ID NO: 76] | *TGG* |
| grna22_Cox1_2 | TCACCAAGGCCTTGGGCCAT [SEQ ID NO: 77] | *GGG* |
| grna23_Cox1_3r | TGTCTCCATAAATGTGGCCG [SEQ ID NO: 78] | *AGG* |

TABLE 21-continued gRNA primer sequences:

| grna24_Cox1_4 | AACTGCGGCTCTTTAAGGAT [SEQ ID NO: 79] | GGG |

P2Y12
Exon 3

| Name | Sequence | PAM sequence |
| --- | --- | --- |
| grna29_P2Y12_1r | GTAGTCTCTGGTGCACAGAC [SEQ ID NO: 80] | TGG |
| grna30_P2Y12_2r | GAAAGAAAATCCTCATCGCC [SEQ ID NO: 81] | AGG |
| grna31_P2Y12_3 | ATTCTTAGTGATGCCAAACT [SEQ ID NO: 82] | GGG |
| grna32_P2Y12_4r | GATCGATAGTTATCAGTCCC [SEQ ID NO: 83] | AGG |

B2M
Exon 2

| Name | Sequence | PAM sequence |
| --- | --- | --- |
| grna40_B2M_1r | AAGTCAACTTCAATGTCGGA [SEQ ID NO: 84] | TGG |
| grna41_B2M_2r | AGTCACATGGTTCACACGGC [SEQ ID NO: 85] | AGG |
| grna42_B2M_3 | ACTTGTCTTTCAGCAAGGAC [SEQ ID NO: 86] | TGG |
| grna43_B2M_4 | TCACGTCATCCAGCAGAGAA [SEQ ID NO: 87] | TGG |

TABLE 22 amplicon primers:

HPS1

Sequencing primers

| Roc01_sHPS1_F1 | F | ATCTGGTGCAGAGTCCAAGC [SEQ ID NO: 88] |
| --- | --- | --- |
| Roc01_sHPS1_R1 | R | TGGAGGAGGTGATTCTTGGC [SEQ ID NO: 89] |
| Product size: | 387 | |

ITGA2B

Sequencing primers

| Roc03_ITGA2B_F1 | F | GGCTCCTGGCGGCTATTATT [SEQ ID NO: 90] |
| --- | --- | --- |
| Roc04_ITGA2B_R1 | R | CTTAGGCGGTGGGTTGGC [SEQ ID NO: 91] |
| Product size: | 360 | |

ITGA2B

Sequencing primers

| Roc05_GP6_F1 | F | AGCAGCGGGGTCCAGG [SEQ ID NO: 92] |
| --- | --- | --- |
| Roc06_GP6_R1 | R | CGTGGCACCACCACCC [SEQ ID NO: 93] |
| Product size: | 462 | |

Par1

Sequencing primers

| Roc07_Par1_F1 | F | ACCCACTCCTCCTAGTAAGAAAACAT [SEQ ID NO: 93] |
| --- | --- | --- |
| Roc08_Par1_R1 | R | CAAACTGCCAATCACTGCCG [SEQ ID NO: 94] |
| Product size: | 541 | |

TABLE 22-continued amplicon primers:

Par4

Sequencing primers

| RocO9_Par4_F1 | F | ATGTCCAGCTGTTTCCCACC [SEQ ID NO: 95] |
|---|---|---|
| RocO10_Par4_R1 | R | GCAGGTGGTAGGCGATCC [SEQ ID NO: 96] |
| Product size: | 415 | |

Cox1

Sequencing primers

| RocO11_Cox1_F1 | F | CCAACCAGGGAAGAAGCAGT [SEQ ID NO: 97] |
|---|---|---|
| RocO12_Cox1_R1 | R | TGGCACAAGCTTCCCACTC [SEQ ID NO: 98] |
| Product size: | 514 | |

P2Y12

Sequencing primers

| RocO15_P2Y12_F1 | F | GAGGAGGCTGTGTCCAAAAA [SEQ ID NO: 99] |
|---|---|---|
| RocO16_P2Y12_R1 | R | GGCTGCCTGTTGGTCAGAAT [SEQ ID NO: 100] |
| Product size: | 607 | |

B2M

Sequencing primers

| RocO58_B2M_F1 | F | TGACACCAAGTTAGCCCCAA [SEQ ID NO: 101] |
|---|---|---|
| RocO59_B2M_R1 | R | GGGATGGGACTCATTCAGGG [SEQ ID NO: 102] |
| Product size: | 463 | |

TABLE 23

(Media recipes):

| Mesoderm medium | DMEM/F12, HEPES (Thermofisher | 500 ml |
|---|---|---|
| | 7.5% NaHCO3 (Thermofisher) | 3.6 ml |
| | 100x L-Ascorbic acid 2-phosphate sesquimagnesium salt hydrate (Sigma) | 5 ml |
| | Insulin-Transferrin-Selenium (ITS -G) 100x (but use as 50x) (Thermofisher) | 10 ml |
| MK medium | IMDM without phenol red | 500 ml |
| | 30% BSA (BioSera SA-296) | 8.4 ml |
| | Insulin-Transferrin-Selenium (ITS -G) 100x (Thermofisher) | 5 ml |

TABLE 23-continued (Media recipes):

| Beta Mercaptoethanol 55 mM | 500 µl |
|---|---|

Example 7

To generate a non-thrombogenic, iPSC derived platelet-like chassis, genes encoding key components of the endogenous thrombotic process must be deleted. In this instance, the genes targeted were Cox1, GPVI, HPS1, ITGA2B, P2Y12, Par1 and Par4. CRISPR/Cas9 mediated IN/DEL generation was chosen as the method for gene knock-out (KO). First, guides were designed to target Cas9 nuclease to the above mentioned targets (FIG. 1A). Four guides were designed per target, and nucleofected as complex with the Cas9 protein into iPSCs, and their gene editing efficiency within the pool measured by Sanger sequencing and TIDE or the Synthego ICE algorithm. High efficiency guides resulting in >80% KO of each target were identified in the guide screen (FIG. 1B). These guides generated reproducibly high editing efficiency (FIG. 1C).

To generate the non-thrombogenic chassis producing iPSC line, these KOs must all be introduced into the same cell. To achieve this, a sequential editing protocol was designed (FIG. 2A). In brief, Cas9 RNP complexes featuring the high efficiency guides identified previously were nucleofected into the same population of iPSCs sequentially, with 3-4 days rest between each nucleofection. This protocol did not produce an adverse effect on cell viability or growth throughout the ~3.5 week process (FIG. 2B). Gene KO was quantified for each target hit previously throughout the sequential nucleofection protocol. No gene KO dilution was observed (as might occur if the KO itself was detrimental), and surprisingly high gene editing efficiencies were observed for all targets (>94% for all targets except COX1) (FIG. 2C). Following the sequential KO protocol, single cells were sorted into a 96 well plate and allowed to grow up forming clonal colonies. These colonies were subsequently isolated and sequenced. Three 7×KO clones were identified (FIG. 3).

Given the number of megakaryocyte (MK) specific genes KO'd within these iPSCs, it remained unclear as to whether these iPSCs would still be able to differentiate into MK like cells. To understand this, iPSCs were forward programmed into MKs by doxycycline mediated induction of MK specific transcription factors GATA1, TAL1 and FLI1. Cell surface expression of known, well defined MK markers and viability was assayed during the forward programming process (FIGS. 4A and B). This study was performed in the pool of 7×KO MKs, but given the exceedingly high editing efficiencies within the pool it is likely >90% of cells feature at least 6 KOs. We observed no effect on forward programming efficiency or MK viability during the forward programming process. CD41 is ITGA2B, one of our target genes. Thus the lack of CD41 expression within the 7×KO population validated the protein level KO of this gene as predicted by our sequencing based approach.

To validate the non-thrombogenicity of our 7×KO MKs, and also their retained function, we studied their degranulation response to known platelet agonists. MKs contain the same core signal transduction machinery, plasma membranes and components as platelets (given platelets are fragments of MKs), and thus MKs were used here as a surrogate for actual platelets. It is expected that the results seen in MKs would translate directly to platelets. To assay for degranulation, cell surface P-Selectin exposure was used as a marker. P-Selectin is an alpha-granule membrane protein, and is not usually present on the platelet surface. Upon platelet activation, alpha-granules fuse with the plasma membrane and exocytose their contents (degranulation), and their membrane components mix with the plasma membrane. P-Selectin thus becomes exposed and detectable by fluorescent antibody mediated staining. Resting 7×KO MKs feature lower basal levels of P-Selectin exposure than unedited wildtype MKs (FIG. 5A). Upon stimulation with two classical platelet agonists, CRP and TRAP6 (which signal through GPVI and PAR1 respectively—both KO'd in the 7×KO pool), no increase in P-Selectin staining was observed in the 7×KO MK pool. This is in contrast to the unedited MKs, which increased their P-Selectin and also appeared began to form small aggregates of cells (FIG. 5B). Importantly, upon stimulation of the 7×KO MKs with PMA, an agonist that bypasses the signaling pathways removed within the 7×KO line, 7×KO MKs exposed P-Selectin as well if not better than unedited MKs (FIG. 5C). Taken together, these activation experiments and the cell surface marker experiments discussed previously demonstrate that deletion of our candidate non-thrombogenic genes in iPSCs does not perturb their ability to differentiate into MK like cells, and does not disrupt the ability of MKs to degranulate in response to non-deleted signal transduction mechanisms.

Platelets contain ITAM domain containing receptors—specifically CLEC2, FCERG and FCGR2A. CLEC2 is a type-II membrane protein, whilst FCERG and FCGR2A are type-I membrane proteins. Type-I membrane proteins are amenable to fusion with scFV antibody domains (and other N-terminal targeting mechanisms). Chimeric platelet receptors (CPRs) were thus designed as fusions between an scFV targeting the B cell antigen CD19 derived from the FMC63 antibody, a hinge domain, and the transmembrane and cytoplasmic domains of FCERG and FCGR2A. This yielded four potential receptor designs (FIG. 6A). These designs were inserted into lentiviral expression vectors as a multi-cistronic construct, with an mCherry fluorescent protein linked by a T2A peptide splitting sequence (FIG. 6B). Viral particles were transduced onto iPSCs, and transduction efficiency examined by mCherry expression. Notable mCherry expression was detected across all four lentiviral expression vectors, and was not present in the untransduced control (FIG. 6C).

To validate that the receptor itself was expressed and cell surface localised, virally transduced iPSCs were stained with recombinant CD19 fluorescently labelled with FITC. CD19-FITC should only label iPSCs if they express the anti-CD19 scFV on their cell surface, in the correct orientation. Notably, colonies positive for transduction (i.e. mCherry positive) were also positive for CD19-FITC, indicating that the designed CPRs fold and correctly localise to the plasma membrane of the cells expressing them (FIG. 7). A clonal high CPR3 expressing iPSC line was forward programmed into MKs. Expression of the CPR3 construct did not impact the ability for iPSCs to forward program, as all classical MK specific markers were expressed within these cells. MK viability was not impacted by CPR3 expression either (FIG. 8A). Note that CD41 is clonally KO'd within these cells, and thus the lack of its expression is expected. To validate that CPR3 was expressed and that this expression was maintained on the MK cell surface, CD19-FITC staining was conducted (FIG. 8B). CPR surface expression was observed, indicating MK differentiation did not silence the lentiviral expression construct, or somehow alter receptor localisation.

To study the functionality of the CPR, CPR3 expressing MKs and control untransduced MKs were mixed with a CD19 expressing B cell leukaemia line (BJABs) or CD19 negative T cell leukaemia line (Jurkats) and P-Selectin exposure was measured as before. Microscopy imaging of mixed cell populations demonstrated increased P-Selectin exposure specifically within CPR3 expressing MKs when mixed with the CD19+ve BJABs (FIG. 9A). This was result was confirmed quantitatively by FACS based measurement of P-Selectin exposure (FIGS. 9B and C). BJAB cells do not activate untransduced MKs, and CD19 negative Jurkats do not activate CPR3 expressing MKs. These results demonstrate that the CPR3 construct specifically stimulates MK degranulation in response to triggering by CD19 positive BJAB cells. Given that platelets are cytoplasmic fragments of MKs and the core signalling machinery is shared between them (given the shared cytoplasm), it is expected that these results should translate into platelets when produced from CPR3 expressing MKs. Additionally, given our observation that 7×KO MKs retain the ability to activate and degranulate in response to agonists that have not had their cognate receptors deleted, it is expected that CPR3 expression within a 7×KO line should trigger its degranulation upon mixing with CD19 positive cells. Given the swappable nature of the external CPR targeting domain, target specificity could be altered by swapping the anti-CD19 scFV for alternative targeting mechanisms, while retaining the same internal signalling domain that has been shown here to trigger MK degranulation on target engagement.

Example Embodiments

1. A chimeric platelet receptor (CPR) comprising:
(a) a first region encoded by a nucleic acid sequence selected from the group consisting of SEQ ID NO: 1-19, 24-47, and 52-55; and
(b) a second region selected from the group consisting of: (i) a linker or targeting domain encoded by a nucleic acid sequence selected from the group consisting of SEQ ID NO: 48-51; (ii) at least a portion of a protein selected from the group consisting of: myelin oligodendrocyte glycoprotein (MOG), glutamic acid decarboxylase 2 (GAD65), myelin associated glycoprotein (MAG), peripheral myelin protein 22 (PMP22), thyroid peroxidase (TPO), voltage-gated potassium channel (VGKC), proteolipid protein (PLP), acetylcholine receptor (AChR), tribbles pseudokinase 2 (TRIB2), N-methyl-D-aspartate (NMDA)-type glutamate receptor (GluR), glutamate decarboxylase 2 (GAD2), Armadillo repeat containing 9 (ARMC9), Cytochrome P450 Family 21 Subfamily A Member 2 (CYP21A2), calcium sensing receptor (CASR), nuclear autoantigenic sperm protein (NASP), insulin, thyroid stimulating hormone receptor (TSHR), thyroperoxidase, asioglycoprotein receptor, Cytochrome P450 Family 2 Subfamily D Member 6 (CYP2D6), lactoferrin (LF), tissue trans-glutaminase (TTG), H/K ATP-ase, Factor XIII (F8), beta2-glycoprotein I (Beta2-GPI), erythrocyte I/I, B2 integrin (ITGB2), granulocyte-colony stimulating factor (G-CSF), glycoprotein (GP) IIb/IIIa, collagen II (COLII), fibrinogen (FBG) βα, myeloperoxidase (MPO), cardiac myosin (CYO), proteinase 3 (PRTN3), trichohyalin (TCHH), bullous pemphigoid associated (BP), glycoprotein 1 (GPI), laminin-332 (LM332), transglutaminase (TGM), type VII collagen (COLVII), P80 Coilin (COIL), Desmoglein I (DSG1), Desmoglein III (DSG3), SRY-Box 10 (SOX10), small nuclear ribonucleoprotein U1 subunit (70SNRNP70), S-antigen (SAG), and Collagen alpha-3(IV) chain (α3(IV)NC1 collagen); (iii) at least a portion of an antibody selected from the group consisting of; 3F8, 8H9, Abagovomab, Abciximab, Abituzumab, Abrezekimab, Abrilumab, Actoxumab, Adalimumab, Adecatumumab, Atidortoxumab, Aducanumab, Afasevikumab, Afelimomab, Alacizumab pego, Alemtuzumab, Alirocumab, Altumomab pentetate, Amatuximab, Anatumomab mafenatox, Andecaliximab, Anetumab ravtansine, Anifrolumab, Anrukinzumab, Apolizumab, Aprutumab ixadotin, Arcitumomab, Ascrinvacumab, Aselizumab, Atezolizumab, Atinumab, Atorolimumab, Avelumab, Azintuxizumab vedotin, Bapineuzumab, Basiliximab, Bavituximab, BCD-100, Bectumomab, Begelomab, Belantamab mafodotin, Belimumab, Bemarituzumab, Benralizumab, Berlimatoxumab, Bermekimab, Bersanlimab, Bertilimumab, Besilesomab, Bevacizumab, Bezlotoxumab, Biciromab, Bimagrumab, Bimekizumab, Birtamimab, Bivatuzumab mertansine, Bleselumab, Blinatumomab, Blontuvetmab, Blosozumab, Bococizumab, Brazikumab, Brentuximab vedotin, Briakinumab, Brodalumab, Brolucizumab, Brontictuzumab, Burosumab, Cabiralizumab, Camidanlumab tesirine, Camrelizumab, Canakinumab, Cantuzumab mertansine, Cantuzumab ravtansine, Caplacizumab, Capromab pendetide, Carlumab, Carotuximab, Catumaxomab, cBR96-doxorubicin immunoconjugate, Cedelizumab, Cemiplimab, Cergutuzumab amunaleukin, Certolizumab pegol, Cetrelimab, Cetuximab, Cibisatamab, Cirmtuzumab, Citatuzumab bogatox, Cixutumumab, Clazakizumab, Clenoliximab, Clivatuzumab tetraxetan, Codrituzumab, Cofetuzumab pelidotin, Coltuximab ravtansine, Conatumumab, Concizumab, Cosfroviximab, Crenezumab, Crizanlizumab, Crotedumab, CR6261, Cusatuzumab, Dacetuzumab, Daclizumab, Dalotuzumab, Dapirolizumab pegol, Daratumumab, Dectrekumab, Demcizumab, Denintuzumab mafodotin, Denosumab, Depatuxizumab mafodotin, Derlotuximab biotin, Detumomab, Dezamizumab, Dinutuximab, Diridavumab, Domagrozumab, Dorlimomab aritox, Dostarlimab, Drozitumab, DS-8201, Duligotuzumab, Dupilumab, Durvalumab, Dusigitumab, Duvortuxizumab, Ecromeximab, Eculizumab, Edobacomab, Edrecolomab, Efalizumab, Efungumab, Eldelumab, Elezanumab, Elgemtumab, Elotuzumab, Elsilimomab, Emactuzumab, Emapalumab, Emibetuzumab, Emicizumab, Enapotamab vedotin, Enavatuzumab, Enfortumab vedotin, Enlimomab pegol, Enoblituzumab, Enokizumab, Enoticumab, Ensituximab, Epitumomab cituxetan, Epratuzumab, Eptinezumab, Erenumab, Erlizumab, Ertumaxomab, Etaracizumab, Etigilimab, Etrolizumab, Evinacumab, Evolocumab, Exbivirumab, Fanolesomab, Faralimomab, Faricimab, Farletuzumab, Fasinumab, FBTA05, Felvizumab, Fezakinumab, Fibatuzumab, Ficlatuzumab, Figitumumab, Firivumab, Flanvotumab, Fletikumab, Flotetuzumab, Fontolizumab, Foralumab, Foravirumab, Fremanezumab, Fresolimumab, Frovocimab, Frunevetmab, Fulranumab, Futuximab, Galcanezumab, Galiximab, Gancotamab, Ganitumab, Gantenerumab, Gatipotuzumab, Gavilimomab, Gedivumab, Gemtuzumab ozogamicin, Gevokizumab, Gilvetmab, Gimsilumab, Girentuximab, Glembatumumab vedotin, Golimumab, Gomiliximab, Gosuranemab, Guselkumab, Ianalumab, Ibalizumab, IBI308, Ibritumomab tiuxetan, Icrucumab, Idarucizumab, Ifabotuzumab, Igovomab, Iladatuzumab vedotin, IMAB362, Imalumab, Imaprelimab, Imciromab, Imgatuzumab, Inclacumab, Indatuximab ravtansine, Indusatumab vedotin, Inebilizumab, Infliximab, Intetumumab, Inolimomab, Inotuzumab ozogamicin, Ipilimumab, Iomab-B, Iratumumab, Isatuximab, Iscalimab, Istiratumab, Itolizumab, Ixekizumab, Keliximab, Labetuzumab, Lacnotuzumab, Ladiratuzumab vedotin, Lampalizumab, Lanadelumab, Landogrozumab, Laprituximab emtansine, Larcaviximab, Lebrikizumab, Lemalesomab, Lendalizumab, Lenvervimab, Lenzilumab, Lerdelimumab, Leronlimab, Lesofavumab, Letolizumab, Lexatumumab, Libivirumab, Lifastuzumab vedotin, Ligelizumab, Loncastuximab tesirine, Losatuxizumab vedotin, Lilotomab satetraxetan, Lintuzumab, Lirilumab, Lodelcizumab, Lokivetmab, Lorvotuzumab mertansine, Lucatumumab, Lulizumab pegol, Lumiliximab, Lumretuzumab, Lupartumab amadotin, Lutikizumab, Mapatumumab, Margetuximab, Marstacimab, Maslimomab, Mavrilimumab, Matuzumab, Mepolizumab, Metelimumab, Milatuzumab, Minretumomab, Mirikizumab, Mirvetuximab soravtansine, Mitumomab, Modotuximab, Mogamulizumab, Monalizumab, Morolimumab, Mosunetuzumab, Motavizumab, Moxetumomab pasudotox, Muromonab-CD3, Nacolomab tafenatox, Namilumab, Naptumomab estafenatox, Naratuximab emtansine, Narnatumab, Natalizumab, Navicixizumab, Navivumab, Naxitamab, Nebacumab, Necitumumab, Nemolizumab, NEOD001, Nerelimomab, Nesvacumab, Netakimab, Nimotuzumab, Nirsevimab, Nivolumab, Nofetumomab merpentan, Obiltoxaximab, Obinutuzumab, Ocaratuzumab, Ocrelizumab, Odulimomab, Ofatumumab, Olaratumab, Oleclumab, Olendalizumab, Olokizumab, Omalizumab, Omburtamab, OMS721, Onartuzumab, Ontuxizumab, Onvatilimab, Opicinumab, Oportuzumab monatox, Oregovomab, Orticumab, Otelixizumab, Otilimab, Otlertuzumab, Oxelumab, Ozanezumab, Ozoralizumab, Pagibaximab, Palivizumab, Pamrevlumab, Panitumumab, Pankomab, Panobacumab, Parsatuzumab, Pascolizumab, Pasotuxizumab, Pateclizumab, Patritumab, PDR001, Pembrolizumab, Pemtumomab, Perakizumab, Pertuzumab, Pexelizumab, Pidilizumab, Pinatuzumab vedotin, Pintumomab, Placulumab, Plozalizumab, Pogalizumab, Polatuzumab vedotin, Ponezumab, Porgaviximab, Prasinezumab, Prezalizumab, Priliximab, Pritoxaximab, Pritumumab, PRO 140, Quilizumab, Racotumomab, Radretumab, Rafivirumab, Ralpancizumab, Ramucirumab, Ranevetmab, Ranibizumab, Raxibacumab, Ravagalimab, Ravulizumab, Refanezumab, Regavirumab, Relatlimab, Remtolumab, Reslizumab, Rilotumumab, Rinucumab, Risankizumab, Rituximab, Rivabazumab pegol, Robatumumab, Rmab, Roledumab, Romilkimab, Romosozumab, Rontalizumab, Rosmantuzumab, Rovalpituzumab tesirine, Rovelizumab, Rozanolixizumab, Ruplizumab, SA237, Sacituzumab govitecan, Samalizumab, Samrotamab vedotin, Sarilumab, Satralizumab, Satumomab pendetide, Secukinumab, Selicrelumab, Seribantumab, Setoxaximab, Setrusumab, Sevirumab, Sibrotuzumab, SGN-CD19A, SHP647, Sifalimumab, Siltuximab, Simtuzumab, Siplizumab, Sirtratumab vedotin, Sirukumab, Sofituzumab vedotin, Solanezumab, Solitomab, Sonepcizumab, Sontuzumab, Spartalizumab, Stamulumab, Sulesomab, Suptavumab, Sutimlimab, Suvizumab, Suvratoxumab, Tabalumab, Tacatuzumab tetraxetan, Tadocizumab, Talacotuzumab, Talizumab, Tamtuvetmab, Tanezumab, Taplitumomab paptox, Tarextumab, Tavolimab, Tefibazumab, Telimomab aritox, Telisotuzumab vedotin, Tenatumomab, Teneliximab, Teplizumab, Tepoditamab, Teprotumumab, Tesidolumab, Tetulomab, Tezepelumab, TGN1412, Tibulizumab, Tildrakizumab, Tigatuzumab, Timigutuzumab, Timolumab, Tiragotumab, Tislelizumab, Tisotumab vedotin, TNX-650, Tocilizumab, Tomuzotuximab, Toralizumab, Tosatoxumab, Tositumomab, Tovetumab, Tralokinumab, Trastuzumab, Trastuzumab emtansine, TRBS07, Tregalizumab, Tremelimumab, Trevogrumab, Tucotuzumab celmoleukin, Tuvirumab, Ublituximab, Ulocuplumab, Urelumab, Urtoxazumab, Ustekinumab, Utomilumab, Vadastuximab talirine, Vanalimab, Vandortuzumab vedotin, Vantictumab, Vanucizumab, Vapaliximab, Varisacumab, Varlilumab, Vatelizumab, Vedolizumab, Veltuzumab, Vepalimomab, Vesencumab, Visilizumab, Vobarilizumab, Volociximab, Vonlerolizumab, Vopratelimab, Vorsetuzumab mafodotin, Votumumab, Vunakizumab, Xentuzumab, XMAB-5574, Zalutumumab, Zanolimumab, Zatuximab, Zenocutuzumab, Ziralimumab, Zolbetuximab, Zolimomab aritox; and (iv) a major histocompatibility complex (MHC) class 1 receptor or a major histocompatibility complex (MHC) class 2 receptor, wherein the MHC class 1 receptor is bound to a peptide derived from a tumor antigen, a neoantigen, or an autoantigen or the MHC class 2 receptor is bound to a peptide derived from a tumor antigen, a neoantigen, or an autoantigen.

2. The chimeric platelet receptor of embodiment 1, wherein the chimeric platelet receptor binds at least one antigen.

3. The chimeric platelet receptor of any one of embodiments 1 and 2, wherein the chimeric platelet receptor binds a tissue in the body of a subject.

4. The chimeric platelet receptor of any one of embodiments 1-3, wherein the chimeric platelet receptor is an ITIM-containing receptor.

5. The chimeric platelet receptor of any one of embodiments 1-4, wherein the chimeric platelet receptor is an ITAM-containing receptor.

6. A therapeutic delivery system comprising:
(a) an engineered platelet presenting the chimeric platelet receptor of any of embodiments 1-5; and
(b) at least one therapeutic agent selected from the group consisting of; a toxin, a protein, a small molecule drug, and a nucleic acid packaged within a vesicle inside the platelet.

7. The therapeutic delivery system of embodiment 6, wherein the engineered platelet is produced from an iPSC progenitor.

8. The therapeutic delivery system of any one of embodiments 6 and 7, wherein the nucleic acid is a mRNA, a miRNA, shRNA, and a clustered regularly interspaced short palindromic repeats (CRISPR) sequence.

9. The therapeutic delivery system of any one of embodiments 6-8, wherein the protein is selected from the group consisting of an antibody, an enzyme, a cytokine, and a CRISPR associated protein 9 (Cas9).

10. The therapeutic delivery system of embodiment 9, wherein the enzyme is a nuclease.

11. The therapeutic delivery system of embodiment 10, wherein the nuclease is a transcription activator-like effector nuclease (TALEN).

12. The therapeutic delivery system of embodiment 9, wherein the antibody binds a tumor antigen or a neoantigen.

13. The therapeutic delivery system of any one of embodiments 6-12, wherein the therapeutic agent is release from the platelet following activation of the platelet by an antigen recognized by the chimeric platelet receptor.

14. A method of treating a disease, disorder, or condition in a subject, the method comprising: administering to the subject the therapeutic delivery system of any of embodiments 6-13, wherein the chimeric receptor is specific to an antigen associated with the disease, disorder, or condition.

15. The method of embodiment 14, wherein the disease, disorder, or condition is selected from the group consisting of; a cancer, an autoimmunity, and an infection.

16. The method of any of embodiments 14 and 15, wherein the cancer is selected from the group consisting of: Acute granulocytic leukemia, Acute lymphocytic leukemia, Acute myelogenous leukemia, Adenocarcinoma, Adenosarcoma, Adrenal cancer, Adrenocortical carcinoma, Anal cancer, Anaplastic astrocytoma, Angiosarcoma, Appendix cancer, Astrocytoma, Basal cell carcinoma, B-Cell lymphoma), Bile duct cancer, Bladder cancer, Bone cancer, Bowel cancer, Brain cancer, Brain stem glioma, Brain tumor, Breast cancer, Carcinoid tumors, Cervical cancer, Cholangiocarcinoma, Chondrosarcoma, Chronic lymphocytic leukemia, Chronic myelogenous leukemia, Colon cancer, Colorectal cancer, Craniopharyngioma, Cutaneous lymphoma, Cutaneous melanoma, Diffuse astrocytoma, Ductal carcinoma in situ, Endometrial cancer, Ependymoma, Epithelioid sarcoma, Esophageal cancer, Ewing sarcoma, Extrahepatic bile duct cancer, Eye cancer, Fallopian tube cancer, Fibrosarcoma, Gallbladder cancer, Gastric cancer, Gastrointestinal cancer, Gastrointestinal carcinoid cancer, Gastrointestinal stromal tumors, General, Germ cell tumor, Glioblastoma multiforme, Glioma, Hairy cell leukemia, Head and neck cancer, Hemangioendothelioma, Hodgkin lymphoma, Hodgkin's disease, Hodgkin's lymphoma, Hypopharyngeal cancer, Infiltrating ductal carcinoma, Infiltrating lobular carcinoma, Inflammatory breast cancer, Intestinal Cancer, Intrahepatic bile duct cancer, Invasive/infiltrating breast cancer, Islet cell cancer, Jaw cancer, Kaposi sarcoma, Kidney cancer, Laryngeal cancer, Leiomyosarcoma, Leptomeningeal metastases, Leukemia, Lip cancer, Liposarcoma, Liver cancer, Lobular carcinoma in situ, Low-grade astrocytoma, Lung cancer, Lymph node cancer, Lymphoma, Male breast cancer, Medullary carcinoma, Medulloblastoma, Melanoma, Meningioma, Merkel cell carcinoma, Mesenchymal chondrosarcoma, Mesenchymous, Mesothelioma, Metastatic breast cancer, Metastatic melanoma, Metastatic squamous neck cancer, Mixed gliomas, Mouth cancer, Mucinous carcinoma, Mucosal melanoma, Multiple myeloma, Nasal cavity cancer, Nasopharyngeal cancer, Neck cancer, Neuroblastoma, Neuroendocrine tumors, Non-Hodgkin lymphoma, Non-Hodgkin's lymphoma, Non-small cell lung cancer, Oat cell cancer, Ocular cancer, Ocular melanoma, Oligodendroglioma, Oral cancer, Oral cavity cancer, Oropharyngeal cancer, Osteogenic sarcoma, Osteosarcoma, Ovarian cancer, Ovarian epithelial cancer, Ovarian germ cell tumor, Ovarian primary peritoneal carcinoma, Ovarian sex cord stromal tumor, Paget's disease, Pancreatic cancer, Papillary carcinoma, Paranasal sinus cancer, Parathyroid cancer, Pelvic cancer, Penile cancer, Peripheral nerve cancer, Peritoneal cancer, Pharyngeal cancer, Pheochromocytoma, Pilocytic astrocytoma, Pineal region tumor, Pineoblastoma, Pituitary gland cancer, Primary central nervous system lymphoma, Prostate cancer, Rectal cancer, Renal cell cancer, Renal pelvis cancer, Rhabdomyosarcoma, Salivary gland cancer, Sarcoma, Sarcoma, bone, Sarcoma, soft tissue, Sarcoma, uterine, Sinus cancer, Skin cancer, Small cell lung cancer, Small intestine cancer, Soft tissue sarcoma, Spinal cancer, Spinal column cancer, Spinal cord cancer, Spinal tumor, Squamous cell carcinoma, Stomach cancer, Synovial sarcoma, T-cell lymphoma), Testicular cancer, Throat cancer, Thymoma/thymic carcinoma, Thyroid cancer, Tongue cancer, Tonsil cancer, Transitional cell cancer, Transitional cell cancer, Transitional cell cancer, Triple-negative breast cancer, Tubal cancer, Tubular carcinoma, Ureteral cancer, Ureteral cancer, Urethral cancer, Uterine adenocarcinoma, Uterine cancer, Uterine sarcoma, Vaginal cancer, and Vulvar cancer.

17. The method of any of embodiments 14-16, further comprising incubating the engineered platelet with the at least one therapeutic agent selected from the group consisting of: a toxin, a protein, and a small molecule drug to produce the therapeutic delivery system.

18. The method of embodiment 17, wherein the nucleic acid is selected from the group consisting of: a mRNA, a miRNA, shRNA, and a clustered regularly interspaced short palindromic repeats (CRISPR) sequence.

19. The method of any one of embodiments 14-18, wherein the protein is selected from the group consisting of an antibody, an enzyme, and a CRISPR associated protein 9 (Cas9).

20. The method of embodiment 19, wherein the enzyme is a nuclease.

21. The method of embodiment 20, wherein the nuclease is a transcription activator-like effector nuclease (TALEN).

22. The method of any of embodiments 17-21, wherein incubating occurs prior to administering.

23. The method of any one of embodiments 14, 15, and 17-22, wherein the disease, disorder, or condition is an autoimmunity selected from the group consisting of: Autoimmune disseminated encephalomyelitis, Autoimmune inner ear disease, Batten disease/Neuronal Ceroid Lipofuscinoses, Chronic inflammatory demyelinating polyneuropathy, Encephalitis lethargica, Anti-basal ganglia, Guillain-Barré syndrome, Hashimoto's Encephalopathy, Anti-TPO, Isaac's syndrome/acquired neuromyotonia, Miller Fisher syndrome Morvan's syndrome, Multiple sclerosis, Myasthenia gravis, Narcolepsy PANDAS, Rasmussen's encephalitis, Stiff-person syndrome, Vogt-Koyanagi-Harada syndrome, Addison's disease, Autoimmune hypoparathyroidism, Autoimmune hypophysitis, Autoimmune oophoritis, Autoimmune orchitis, Autoimmune polyglandular syndrome I (APECED), Autoimmune polyglandular syndrome II, Autoimmune polyglandular syndrome III, Diabetes mellitus, type 1, Graves' disease, Hashimoto's autoimmune thyroiditis, Immunodysregulation, polyendocrinopathy, enteropathy, X-linked, Autoimmune hepatitis type 1, Autoimmune hepatitis type 2, Autoimmune pancreatitis, Coeliac disease, Crohn's disease, Pernicious anemia/atrophic gastritis, Primary biliary cirrhosis, Primary sclerosing cholangitis, Ulcerative colitis, Acquired hemophilia A, Antiphospholipid syndrome, Autoimmune hemolytic anemia, Autoimmune lymphoproliferative syndrome, Autoimmune neutropenia, Evans syndrome, Felty's syndrome, Immune thrombocytopenic purpura, Polymyositis/dermatomyositis, Relapsing polychondritis, Rheumatoid arthritis, Still's disease, Alopecia areata, Bullous pemphigoid, Cicatricial pemphigoid, Dermatitis herpetiformis, Discoid lupus erythematosus, Epidermolysis bullosa acquisita, Linear morphea, Pemphigus foliaceus, Pemphigus vulgaris, Vitiligo, Behçet disease, Churg-Strauss syndrome, Cogan's syndrome, CREST syndrome, Anti-fibrillarin, Essential mixed cryoglobulinemia, Mixed connective tissue disease, POEMS syndrome, Scleroderma, Sjögren's syndrome, Systemic lupus erythematosus, Erythema elevatum diutinum, Kawasaki disease, Microscopic polyangiitis, Polyarteritis nodosa, Rheumatic fever, Takayasu arteritis Temporal arteritis, Wegener's granulomatosis, HLA-B27-associated acute anterior uveitis, Sympathetic ophthalmia, and Goodpasture's disease.

24. An engineered platelet produced from a megakaryocyte comprising a mutation in the nucleic acid sequence resulting in disruption of a vesicle biogenesis pathway or a vesicle release pathway in the platelet, expression of a toxin, or deletion of a platelet receptor, mediator, or signal transduction protein compared to a platelet produced from a megakaryocyte without the mutation.

25. The engineered platelet of embodiment 24, wherein the megakaryocyte is differentiated from an iPSC progenitor or the megakaryocyte is immortalized.

26. The engineered platelet of any one of embodiments 24 and 25, wherein the mutation occurs in a gene encoding a component of the vesicle biogenesis pathway or a vesicle release pathway of the engineered platelet selected from the group consisting of: α-granules, dense granules, and large dense-core vesicle.

27. The engineered platelet of any one of embodiments 24-26, wherein the deletion is of at least one gene selected from the group consisting of; Rab27a (RAS oncogene), HPS (haptoglobin) genes, integrin AIIbB3, GPIb-IX-V (Glycoprotein Ib complexed with glycoprotein IX), Par1 (protease activated receptor 1), Par4 (protease activated receptor 4), P2Y 1 (purinergic receptor P2Y1), P2Y12 (purinergic receptor P2Y12), IP (PGI2R or prostaglandin 12 receptor), TP (TxA2R or Thromboxane A2 Receptor), TLR (toll-like receptor), GPVI, a2B1 (type 1 collagen receptor), GPIIbIIIA (Glycoprotein 11b Platelet Subunit Alpha), CLEC-2 (C-type lectinlike receptor 2), MyD88 (Myeloid Differentiation Primary Response 88), Galphaq (G-protein alpha pathway q), LIMK1 (LIM Domain Kinase 1), vWF (von Willebrand), Fibrinogen, PDGF (platelet derived growth factor), VEGF (vascular endothelial growth factor), Factor V, Factor VIII, Factor XI, Factor XIII, PF4 (platelet factor 4), NAP2 (Nucleosome Assembly Protein 2), Prothrombin, High Molecular Weight Kininogens, Plasminogen activator inhibitor 1, a2-antiplasmin, plasminogen, P-Selectin, CXCL4 (C-X-C motif chemokine ligand 4), CXCL7 (C-X-C motif chemokine ligand 7), FGF (fibroblast growth factor), EGF (elongation growth factor), HGF (hepatocyte growth factor), IGF (insulin-like growth factor), Angipoetin, Thromboxane synthase, PAF (platelet activating factor), cPLA2a, Thromospondin, CD40L, SgIII (Secretogranin III), Endostatin, TGF-β (transforming growth factor beta), Talin1, Kindlins, and ANO6 (Anoctamin 6).

28. The engineered platelet of any one of embodiments 24-27, wherein the deletion is a knock-out of a gene encoding a pro-thrombotic factor.

29. The engineered platelet of embodiment 24, wherein the gene is a β2 microglobulin gene, wherein the deletion results in endogenous MHC class 1 disruption and the generation of a non-immunogenic platelet.

30. The engineered platelet of any one of embodiments 24-29, wherein the mutation reduces the thrombogenic potential of the engineered platelet compared to a platelet produced from a megakaryocyte without the mutation.

31. A method of reducing activity in the immune system of a subject, the method comprising:
(a) administering to the subject an engineered platelet presenting at least one receptor expressing a major histocompatibility complex (MHC) molecule bound to a peptide derived from a tumor antigen, a neoantigen, or an autoantigen; and at least a portion of a domain from an ITAM receptor.

32. The method of embodiment 31, wherein the receptor expresses an MHC class I molecule.

33. The method of embodiment 31, wherein the receptor expresses an MHC class II molecule.

34. The method of any one of embodiments 31-33, wherein the MHC molecule stimulates an immune response to an antigen.

35. The method of embodiment 34, wherein the antigen is associated with at least one disease, disorder, or condition selected from the group consisting of: a cancer, an autoimmunity, and an infection.

36. A method of in vitro production of platelets, the method comprising:

a) transfecting a plurality of induced pluripotent stem cell (iPSC) progenitors with an expression system, wherein the expression system is induced by an agent not found in an iPSC;

b) establishing a megakaryocyte progenitor cell line by contacting the expression system with the agent to expand megakaryocytes;

c) engineering the megakaryocyte to have at least one mutation selected from the group consisting of: insertion of a nucleic sequence encoding a chimeric platelet receptor of any one of embodiments 1-5, insertion of a nucleic acid sequence encoding a toxin, and deletion of a nucleic acid sequence encoding a platelet receptor; and d) removing the agent from the expression system to induce differentiation of the megakaryocytes into platelets.

37. The method of platelet production of embodiment 36, wherein the mutation results in platelets with less immunogenicity compared to platelets from human donors.

38. The method of platelet production of embodiment 37, wherein the platelet does not function analogously to platelets derived from a human donor.

39. The method of platelet production of any one of embodiments 36-38, wherein the deletion prevents release of cargo in the vesicles of the engineered platelets in response to endogenous platelet activation signals.

40. The method of platelet production of any of embodiments 36-39, wherein the toxin is attached to an α-granule localization signal.

41. The method of platelet production of embodiment 40, wherein the α-granule localization signal directs the toxin to uptake into α-granule vesicles of the engineered platelet.

42. The method of platelet production of any one of embodiments 36-38, further comprising contacting the platelets with at least one selected from the group consisting of: a toxin, and a small molecule drug under conditions to facilitate absorption by the platelet.

43. The method of platelet production of any one of embodiments 36-42, wherein the expression system further comprises a platelet-specific promotors.

44. A method of in vivo gene editing or gene therapy in a subject, the method comprising:

(a) administering to the subject an engineered platelet comprising a chimeric platelet receptor of any one of embodiments 1-5 specific to a tissue to be edited, wherein the engineered platelet is cloaking an adenovirus loaded with genome engineering machinery; and (b) releasing the genome engineering machinery at the tissue.

45. The method of embodiment 44, wherein the genome engineering machinery is a CRISPR/Cas gene editing system.

46. A use of the therapeutic delivery system of any of embodiments 6-13, wherein the chimeric receptor is specific to an antigen associated with the disease, disorder, or condition in treating a disease, disorder, or condition in a subject.

47. The use of embodiment 46, wherein the disease, disorder, or condition is selected from the group consisting of: a cancer, an autoimmunity, and an infection.

48. The use of embodiment 47, wherein the cancer is selected from the group consisting of: Acute granulocytic leukemia, Acute lymphocytic leukemia, Acute myelogenous leukemia, Adenocarcinoma, Adenosarcoma, Adrenal cancer, Adrenocortical carcinoma, Anal cancer, Anaplastic astrocytoma, Angiosarcoma, Appendix cancer, Astrocytoma, Basal cell carcinoma, B-Cell lymphoma), Bile duct cancer, Bladder cancer, Bone cancer, Bowel cancer, Brain cancer, Brain stem glioma, Brain tumor, Breast cancer, Carcinoid tumors, Cervical cancer, Cholangiocarcinoma, Chondrosarcoma, Chronic lymphocytic leukemia, Chronic myelogenous leukemia, Colon cancer, Colorectal cancer, Craniopharyngioma, Cutaneous lymphoma, Cutaneous melanoma, Diffuse astrocytoma, Ductal carcinoma in situ, Endometrial cancer, Ependymoma, Epithelioid sarcoma, Esophageal cancer, Ewing sarcoma, Extrahepatic bile duct cancer, Eye cancer, Fallopian tube cancer, Fibrosarcoma, Gallbladder cancer, Gastric cancer, Gastrointestinal cancer, Gastrointestinal carcinoid cancer, Gastrointestinal stromal tumors, General, Germ cell tumor, Glioblastoma multiforme, Glioma, Hairy cell leukemia, Head and neck cancer, Hemangioendothelioma, Hodgkin lymphoma, Hodgkin's disease, Hodgkin's lymphoma, Hypopharyngeal cancer, Infiltrating ductal carcinoma, Infiltrating lobular carcinoma, Inflammatory breast cancer, Intestinal Cancer, Intrahepatic bile duct cancer, Invasive/infiltrating breast cancer, Islet cell cancer, Jaw cancer, Kaposi sarcoma, Kidney cancer, Laryngeal cancer, Leiomyosarcoma, Leptomeningeal metastases, Leukemia, Lip cancer, Liposarcoma, Liver cancer, Lobular carcinoma in situ, Low-grade astrocytoma, Lung cancer, Lymph node cancer, Lymphoma, Male breast cancer, Medullary carcinoma, Medulloblastoma, Melanoma, Meningioma, Merkel cell carcinoma, Mesenchymal chondrosarcoma, Mesenchymous, Mesothelioma, Metastatic breast cancer, Metastatic melanoma, Metastatic squamous neck cancer, Mixed gliomas, Mouth cancer, Mucinous carcinoma, Mucosal melanoma, Multiple myeloma, Nasal cavity cancer, Nasopharyngeal cancer, Neck cancer, Neuroblastoma, Neuroendocrine tumors, Non-Hodgkin lymphoma, Non-Hodgkin's lymphoma, Non-small cell lung cancer, Oat cell cancer, Ocular cancer, Ocular melanoma, Oligodendroglioma, Oral cancer, Oral cavity cancer, Oropharyngeal cancer, Osteogenic sarcoma, Osteosarcoma, Ovarian cancer, Ovarian epithelial cancer, Ovarian germ cell tumor, Ovarian primary peritoneal carcinoma, Ovarian sex cord stromal tumor, Paget's disease, Pancreatic cancer, Papillary carcinoma, Paranasal sinus cancer, Parathyroid cancer, Pelvic cancer, Penile cancer, Peripheral nerve cancer, Peritoneal cancer, Pharyngeal cancer, Pheochromocytoma, Pilocytic astrocytoma, Pineal region tumor, Pineoblastoma, Pituitary gland cancer, Primary central nervous system lymphoma, Prostate cancer, Rectal cancer, Renal cell cancer, Renal pelvis cancer, Rhabdomyosarcoma, Salivary gland cancer, Sarcoma, Sarcoma, bone, Sarcoma, soft tissue, Sarcoma, uterine, Sinus cancer, Skin cancer, Small cell lung cancer, Small intestine cancer, Soft tissue sarcoma, Spinal cancer, Spinal column cancer, Spinal cord cancer, Spinal tumor, Squamous cell carcinoma, Stomach cancer, Synovial sarcoma, T-cell lymphoma), Testicular cancer, Throat cancer, Thymoma/thymic carcinoma, Thyroid cancer, Tongue cancer, Tonsil cancer, Transitional cell cancer, Transitional cell cancer, Transitional cell cancer, Triple-negative breast cancer, Tubal cancer, Tubular carcinoma, Ureteral cancer, Ureteral cancer, Urethral cancer, Uterine adenocarcinoma, Uterine cancer, Uterine sarcoma, Vaginal cancer, and Vulvar cancer.

49. The use of any one of embodiments 47 and 48, wherein the disease, disorder, or condition is an autoimmunity selected from the group consisting of: Autoimmune disseminated encephalomyelitis, Autoimmune inner ear disease, Batten disease/Neuronal Ceroid Lipofuscinoses, Chronic inflammatory demyelinating polyneuropathy, Encephalitis lethargica, Anti-basal ganglia, Guillain-Barré syndrome, Hashimoto's Encephalopathy, Anti-TPO, Isaac's syndrome/acquired neuromyotonia, Miller Fisher syndrome Morvan's syndrome, Multiple sclerosis, Myasthenia gravis, Narcolepsy PANDAS, Rasmussen's encephalitis, Stiff-person syndrome, Vogt-Koyanagi-Harada syndrome, Addison's disease, Autoimmune hypoparathyroidism, Autoimmune hypophysitis, Autoimmune oophoritis, Autoimmune orchitis, Autoimmune polyglandular syndrome I (APECED), Autoimmune polyglandular syndrome II, Autoimmune polyglandular syndrome III, Diabetes mellitus, type 1, Graves' disease, Hashimoto's autoimmune thyroiditis, Immunodysregulation, polyendocrinopathy, enteropathy, X-linked, Autoimmune hepatitis type 1, Autoimmune hepatitis type 2, Autoimmune pancreatitis, Coeliac disease, Crohn's disease, Pernicious anemia/atrophic gastritis, Primary biliary cirrhosis, Primary sclerosing cholangitis, Ulcerative colitis, Acquired hemophilia A, Antiphospholipid syndrome, Autoimmune hemolytic anemia, Autoimmune lymphoproliferative syndrome, Autoimmune neutropenia, Evans syndrome, Felty's syndrome, Immune thrombocytopenic purpura, Polymyositis/dermatomyositis, Relapsing polychondritis, Rheumatoid arthritis, Still's disease, Alopecia areata, Bullous pemphigoid, Cicatricial pemphigoid, Dermatitis herpetiformis, Discoid lupus erythematosus, Epidermolysis bullosa acquisita, Linear morphea, Pemphigus foliaceus, Pemphigus vulgaris, Vitiligo, Behçet disease, Churg-Strauss syndrome, Cogan's syndrome, CREST syndrome, Anti-fibrillarin, Essential mixed cryoglobulinemia, Mixed connective tissue disease, POEMS syndrome, Scleroderma, Sjögren's syndrome, Systemic lupus erythematosus, Erythema elevatum diutinum, Kawasaki disease, Microscopic polyangiitis, Polyarteritis nodosa, Rheumatic fever, Takayasu arteritis Temporal arteritis, Wegener's granulomatosis, HLA-B27-associated acute anterior uveitis, Sympathetic ophthalmia, and Goodpasture's disease.

50. A chimeric platelet receptor comprising:
(a) a first region comprising at least a portion of a domain of an ITAM receptor; and
b) a second region comprising region selected from the group consisting of: (i) a linker or targeting domain encoded by a nucleic acid sequence selected from the group consisting of SEQ ID NO: 48-51; (ii) at least a portion of a protein selected from the group consisting of: myelin oligodendrocyte glycoprotein (MOG), glutamic acid decarboxylase 2 (GAD65), myelin associated glycoprotein (MAG), peripheral myelin protein 22 (PMP22), thyroid peroxidase (TPO), voltage-gated potassium channel (VGKC), proteolipid protein (PLP), acetylcholine receptor (AChR), tribbles pseudokinase 2 (TRIB2), N-methyl-D-aspartate (NMDA)-type glutamate receptor (GluR), glutamate decarboxylase 2 (GAD2), Armadillo repeat containing 9 (ARMC9), Cytochrome P450 Family 21 Subfamily A Member 2 (CYP21 A2), calcium sensing receptor (CASR), nuclear autoantigenic sperm protein (NASP), insulin, thyroid stimulating hormone receptor (TSHR), thyroperoxidase, asioglycoprotein receptor, Cytochrome P450 Family 2 Subfamily D Member 6 (CYP2D6), lactoferrin (LF), tissue trans-glutaminase (TTG), H/K ATP-ase, Factor XIII (F8), beta2-glycoprotein I (Beta2-GPI), erythrocyte I/I, B2 integrin (ITGB2), granulocyte-colony stimulating factor (G-CSF), glycoprotein (GP) IIb/IIa, collagen II (COLII), fibrinogen (FBG) pia, myeloperoxidase (MPO), cardiac myosin (CYO), proteinase 3 (PRTN3), trichohyalin (TCHH), bullous pemphigoid associated (BP), glycoprotein 1 (GPI), laminin-332 (LM332), transglutaminase (TGM), type VII collagen (COLVII), P80 Coilin (COIL), Desmoglein I (DSG1), Desmoglein III (DSG3), SRY-Box 10 (SOX10), small nuclear ribonucleoprotein U1 subunit (70SNRNP70), S-antigen (SAG), and Collagen alpha-3(IV) chain (α3(IV) NC1 collagen); (iii) at least a portion of an antibody selected from the group consisting of; 3F8, 8H9, Abagovomab, Abciximab, Abituzumab, Abrezekimab, Abrilumab, Actoxumab, Adalimumab, Adecatumumab, Atidortoxumab, Aducanumab, Afasevikumab, Afelimomab, Alacizumab pego, Alemtuzumab, Alirocumab, Altumomab pentetate, Amatuximab, Anatumomab mafenatox, Andecaliximab, Anetumab ravtansine, Anifrolumab, Anrukinzumab, Apolizumab, Aprutumab ixadotin, Arcitumomab, Ascrinvacumab, Aselizumab, Atezolizumab, Atinumab, Atorolimumab, Avelumab, Azintuxizumab vedotin, Bapineuzumab, Basiliximab, Bavituximab, BCD-100, Bectumomab, Begelomab, Belantamab mafodotin, Belimumab, Bemarituzumab, Benralizumab, Berlimatoxumab, Bermekimab, Bersanlimab, Bertilimumab, Besilesomab, Bevacizumab, Bezlotoxumab, Biciromab, Bimagrumab, Bimekizumab, Birtamimab, Bivatuzumab mertansine, Bleselumab, Blinatumomab, Blontuvetmab, Blosozumab, Bococizumab, Brazikumab, Brentuximab vedotin, Briakinumab, Brodalumab, Brolucizumab, Brontictuzumab, Burosumab, Cabiralizumab, Camidanlumab tesirine, Camrelizumab, Canakinumab, Cantuzumab mertansine, Cantuzumab ravtansine, Caplacizumab, Capromab pendetide, Carlumab, Carotuximab, Catumaxomab, cBR96-doxorubicin immunoconjugate, Cedelizumab, Cemiplimab, Cergutuzumab amunaleukin, Certolizumab pegol, Cetrelimab, Cetuximab, Cibisatamab, Cirmtuzumab, Citatuzumab bogatox, Cixutumumab, Clazakizumab, Clenoliximab, Clivatuzumab tetraxetan, Codrituzumab, Cofetuzumab pelidotin, Coltuximab ravtansine, Conatumumab, Concizumab, Cosfroviximab, Crenezumab, Crizanlizumab, Crotedumab, CR6261, Cusatuzumab, Dacetuzumab, Daclizumab, Dalotuzumab, Dapirolizumab pegol, Daratumumab, Dectrekumab, Demcizumab, Denintuzumab mafodotin, Denosumab, Depatuxizumab mafodotin, Derlotuximab biotin, Detumomab, Dezamizumab, Dinutuximab, Diridavumab, Domagrozumab, Dorlimomab aritox, Dostarlimab, Drozitumab, DS-8201, Duligotuzumab, Dupilumab, Durvalumab, Dusigitumab, Duvortuxizumab, Ecromeximab, Eculizumab, Edobacomab, Edrecolomab, Efalizumab, Efungumab, Eldelumab, Elezanumab, Elgemtumab, Elotuzumab, Elsilimomab, Emactuzumab, Emapalumab, Emibetuzumab, Emicizumab, Enapotamab vedotin, Enavatuzumab, Enfortumab vedotin, Enlimomab pegol, Enoblituzumab, Enokizumab, Enoticumab, Ensituximab, Epitumomab cituxetan, Epratuzumab, Eptinezumab, Erenumab, Erlizumab, Ertumaxomab, Etaracizumab, Etigilimab, Etrolizumab, Evinacumab, Evolocumab, Exbivirumab, Fanolesomab, Faralimomab, Faricimab, Farletuzumab, Fasinumab, FBTA05, Felvizumab, Fezakinumab, Fibatuzumab, Ficlatuzumab, Figitumumab, Firivumab, Flanvotumab, Fletikumab, Flotetuzumab, Fontolizumab, Foralumab, Foravirumab, Fremanezumab, Fresolimumab, Frovocimab, Frunevetmab, Fulranumab, Futuximab, Galcanezumab, Galiximab, Gancotamab, Ganitumab, Gantenerumab, Gatipotuzumab, Gavilimomab, Gedivumab, Gemtuzumab ozogamicin, Gevokizumab, Gilvetmab, Gimsilumab, Girentuximab, Glembatumumab vedotin, Golimumab, Gomiliximab, Gosuranemab, Guselkumab, Ianalumab, Ibalizumab, IBI308, Ibritumomab tiuxetan, Icrucumab, Idarucizumab, Ifabotuzumab, Igovomab, Iladatuzumab vedotin, IMAB362, Imalumab, Imaprelimab, Imciromab, Imgatuzumab, Inclacumab, Indatuximab ravtansine, Indusatumab vedotin, Inebilizumab, Infliximab, Intetumumab, Inolimomab, Inotuzumab ozogamicin, Ipilimumab, Iomab-B, Iratumumab, Isatuximab, Iscalimab, Istiratumab, Itolizumab, Ixekizumab, Keliximab, Labetuzumab, Lacnotuzumab, Ladiratuzumab vedotin, Lampalizumab, Lanadelumab, Landogrozumab, Laprituximab emtansine, Larcaviximab, Lebrikizumab, Lemalesomab, Lendalizumab, Lenvervimab, Lenzilumab, Lerdelimumab, Leronlimab, Lesofavumab, Letolizumab, Lexatumumab, Libivirumab, Lifastuzumab vedotin, Ligelizumab, Loncastuximab tesirine, Losatuxizumab vedotin, Lilotomab satetraxetan, Lintuzumab, Lirilumab, Lodelcizumab, Lokivetmab, Lorvotuzumab mertansine, Lucatumumab, Lulizumab pegol, Lumiliximab, Lumretuzumab, Lupartumab amadotin, Lutikizumab, Mapatumumab, Margetuximab, Marstacimab, Maslimomab, Mavrilimumab, Matuzumab, Mepolizumab, Metelimumab, Milatuzumab, Minretumomab, Mirikizumab, Mirvetuximab soravtansine, Mitumomab, Modotuximab, Mogamulizumab, Monalizumab, Morolimumab, Mosunetuzumab, Motavizumab, Moxetumomab pasudotox, Muromonab-CD3, Nacolomab tafenatox, Namilumab, Naptumomab estafenatox, Naratuximab emtansine, Narnatumab, Natalizumab, Navicixizumab, Navivumab, Naxitamab, Nebacumab, Necitumumab, Nemolizumab, NEOD001, Nerelimomab, Nesvacumab, Netakimab, Nimotuzumab, Nirsevimab, Nivolumab, Nofetumomab merpentan, Obiltoxaximab, Obinutuzumab, Ocaratuzumab, Ocrelizumab, Odulimomab, Ofatumumab, Olaratumab, Oleclumab, Olendalizumab, Olokizumab, Omalizumab, Omburtamab, OMS721, Onartuzumab, Ontuxizumab, Onvatilimab, Opicinumab, Oportuzumab monatox, Oregovomab, Orticumab, Otelixizumab, Otilimab, Otlertuzumab, Oxelumab, Ozanezumab, Ozoralizumab, Pagibaximab, Palivizumab, Pamrevlumab, Panitumumab, Pankomab, Panobacumab, Parsatuzumab, Pascolizumab, Pasotuxizumab, Pateclizumab, Patritumab, PDR001, Pembrolizumab, Pemtumomab, Perakizumab, Pertuzumab, Pexelizumab, Pidilizumab, Pinatuzumab vedotin, Pintumomab, Placulumab, Plozalizumab, Pogalizumab, Polatuzumab vedotin, Ponezumab, Porgaviximab, Prasinezumab, Prezalizumab, Priliximab, Pritoxaximab, Pritumumab, PRO 140, Quilizumab, Racotumomab, Radretumab, Rafivirumab, Ralpancizumab, Ramucirumab, Ranevetmab, Ranibizumab, Raxibacumab, Ravagalimab, Ravulizumab, Refanezumab, Regavirumab, Relatlimab, Remtolumab, Reslizumab, Rilotumumab, Rinucumab, Risankizumab, Rituximab, Rivabazumab pegol, Robatumumab, Rmab, Roledumab, Romilkimab, Romosozumab, Rontalizumab, Rosmantuzumab, Rovalpituzumab tesirine, Rovelizumab, Rozanolixizumab, Ruplizumab, SA237, Sacituzumab govitecan, Samalizumab, Samrotamab vedotin, Sarilumab, Satralizumab, Satumomab pendetide, Secukinumab, Selicrelumab, Seribantumab, Setoxaximab, Setrusumab, Sevirumab, Sibrotuzumab, SGN-CD19A, SHP647, Sifalimumab, Siltuximab, Simtuzumab, Siplizumab, Sirtratumab vedotin, Sirukumab, Sofituzumab vedotin, Solanezumab, Solitomab, Sonepcizumab, Sontuzumab, Spartalizumab, Stamulumab, Sulesomab, Suptavumab, Sutimlimab, Suvizumab, Suvratoxumab, Tabalumab, Tacatuzumab tetraxetan, Tadocizumab, Talacotuzumab, Talizumab, Tamtuvetmab, Tanezumab, Taplitumomab paptox, Tarextumab, Tavolimab, Tefibazumab, Telimomab aritox, Telisotuzumab vedotin, Tenatumomab, Teneliximab, Teplizumab, Tepoditamab, Teprotumumab, Tesidolumab, Tetulomab, Tezepelumab, TGN1412, Tibulizumab, Tildrakizumab, Tigatuzumab, Timigutuzumab, Timolumab, Tiragotumab, Tislelizumab, Tisotumab vedotin, TNX-650, Tocilizumab, Tomuzotuximab, Toralizumab, Tosatoxumab, Tositumomab, Tovetumab, Tralokinumab, Trastuzumab, Trastuzumab emtansine, TRBS07, Tregalizumab, Tremelimumab, Trevogrumab, Tucotuzumab celmoleukin, Tuvirumab, Ublituximab, Ulocuplumab, Urelumab, Urtoxazumab, Ustekinumab, Utomilumab, Vadastuximab talirine, Vanalimab, Vandortuzumab vedotin, Vantictumab, Vanucizumab, Vapaliximab, Varisacumab, Varlilumab, Vatelizumab, Vedolizumab, Veltuzumab, Vepalimomab, Vesencumab, Visilizumab, Vobarilizumab, Volociximab, Vonlerolizumab, Vopratelimab, Vorsetuzumab mafodotin, Votumumab, Vunakizumab, Xentuzumab, XMAB-5574, Zalutumumab, Zanolimumab, Zatuximab, Zenocutuzumab, Ziralimumab, Zolbetuximab, Zolimomab aritox; and (iv) a major histocompatibility complex (MHC) class 1 receptor or a major histocompatibility complex (MHC) class 2 receptor, wherein the MHC class 1 receptor is bound to a peptide derived from a tumor antigen, a neoantigen, or an autoantigen or the MHC class 2 receptor is bound to a peptide derived from a tumor antigen, a neoantigen, or an autoantigen.

51. A therapeutic delivery system comprising:
(a) an engineered platelet presenting the chimeric platelet receptor of any of embodiments 1-5 or 50, wherein the engineered platelet has been produced through genetic modification of a progenitor megakaryocyte to be non-thrombogenic and non-immunogenic; and
(b) at least one therapeutic agent selected from the group consisting of: a toxin, a protein, a small molecule drug, and a nucleic acid packaged within a vesicle inside the platelet.
  i) wherein the therapeutic agent is the nucleic acid or the protein, loading occurs through expression in a progenitor megakaryocyte, or
  ii) wherein the therapeutic agent is loaded by incubation of the engineered platelet with the therapeutic agent.

The invention claimed is:

1. An engineered megakaryocyte or megakaryocyte progenitor cell line that produces platelets with reduced thrombogenic potential, comprising a disruption of or deletion of at least two genes encoding:
   (a) a protein involved in recognition of primary stimuli of thrombus formation selected from the group consisting of: GPIb/V/IX, GPVI (GP6), ITGA2B, CLEC2, integrins $\alpha_{IIb}\beta_3$, $\alpha_2\beta_1$, $\alpha_5\beta_1$ and/or $\alpha_6\beta_1$;
   (b) a protein involved in recognition of secondary mediators of thrombus formation selected from the group consisting of Par1, Par4, P2Y12, GPIb/V/IX, the Thromboxane receptor (TBXA2R), P2Y1, P2X1 and/or integrin $\alpha_{IIb}\beta_3$; and/or
   (c) a protein involved in the release of secondary mediators of thrombus formation selected from the group consisting of Cox1, HPS and/or thromboxane-A synthase (TBXAS1).

2. The engineered megakaryocyte or megakaryocyte progenitor cell line of claim 1 comprising a disruption or deletion of:
   (a) a gene expressing GPVI or ITGA2B;
   (b) a gene expressing Par1, Par4 or P2Y12; and
   (c) a gene expressing Cox1 or HPS.

3. The engineered megakaryocyte or megakaryocyte progenitor cell line of claim 1 wherein GPVI, ITGA2B, Par1, Par4, P2Y12, Cox1 and HPS genes are disrupted or deleted.

4. The engineered megakaryocyte or megakaryocyte progenitor cell line of claim 1 that produces platelets that exhibit (a) reduced clotting potential, (b) reduced recruitment by other activated platelets, and/or (c) reduced ability to recruit other platelets.

5. The engineered megakaryocyte or megakaryocyte progenitor cell line of claim 2 that produces platelets that exhibit (a) reduced clotting potential, (b) reduced recruitment by other activated platelets, and/or (c) reduced ability to recruit other platelets.

6. The engineered megakaryocyte or megakaryocyte progenitor cell line thereof of claim 1, wherein the disruption of said gene expression comprises contacting the megakaryocyte or megakaryocyte progenitor cell line with a gene-specific RNA interference construct (RNAi), small interfering RNA (siRNA), microRNA (miRNA), or short hairpin RNA (shRNA), thereby disrupting said gene expression.

7. The engineered megakaryocyte or megakaryocyte progenitor cell line thereof of claim 1 comprising a mutation or deletion of at least a fragment of said gene that disrupts said gene expression.

8. The megakaryocyte or megakaryocyte progenitor cell line of claim 1 further comprising a mutation or deletion in a gene encoding β2 microglobulin that reduces immunogenicity of platelets generated from the megakaryocyte or megakaryocyte progenitor cell line.

9. The megakaryocyte or megakaryocyte progenitor cell line of claim 1 further comprising a mutation or deletion in a gene encoding an MHC I protein, wherein the megakaryocyte or megakaryocyte progenitor cell line produces platelets with reduced immunogenicity.

10. The megakaryocyte or megakaryocyte progenitor cell line of claim 1 further comprising a heterologous nucleic acid encoding a therapeutic agent that is a protein, peptide or RNA.

11. The megakaryocyte or megakaryocyte progenitor cell line of claim 10 wherein the nucleic acid encoding the therapeutic agent further comprises a platelet-specific promoter.

12. The megakaryocyte or megakaryocyte progenitor cell line of claim 10 wherein the nucleic acid encoding the therapeutic agent further comprises an α-granule localization signal.

13. An engineered megakaryocyte or megakaryocyte progenitor cell line of claim 1 further comprising a mutation, deletion and/or insertion of a platelet receptor.

14. A method of using the megakaryocyte or megakaryocyte progenitor cell line of claim 1 to produce platelets with reduced thrombogenic potential, comprising culturing the megakaryocyte or megakaryocyte progenitor cell line under conditions that generate platelets, and collecting the platelets.

15. The method of claim 14 further comprising incubating the platelets with one or more diagnostic or therapeutic agents to load the platelets with the diagnostic or therapeutic agents.

* * * * *

SEQUENCE LISTING

<160> NUMBER OF SEQ ID NOS: 103

<210> SEQ ID NO 1
<211> LENGTH: 261
<212> TYPE: DNA
<213> ORGANISM: Homo sapiens

<400> SEQUENCE: 1

```
atgattccag cagtggtctt gctcttactc cttttggttg aacaagcagc ggccctggga      60
gagcctcagc tctgctatat cctggatgcc atcctgtttc tgtatggaat tgtcctcacc     120
ctcctctact gtcgactgaa gatccaagtg cgaaaggcag ctataaccag ctatgagaaa     180
tcagatggtg tttacacggg cctgagcacc aggaaccagg agacttacga gactctgaag     240
```

```
catgagaaac caccacagta g                                              261

<210> SEQ ID NO 2
<211> LENGTH: 54
<212> TYPE: DNA
<213> ORGANISM: Homo sapiens

<400> SEQUENCE: 2
atgattccag cagtggtctt gctcttactc cttttggttg aacaagcagc ggcc          54

<210> SEQ ID NO 3
<211> LENGTH: 15
<212> TYPE: DNA
<213> ORGANISM: Homo sapiens

<400> SEQUENCE: 3
ctgggagagc ctcag                                                     15

<210> SEQ ID NO 4
<211> LENGTH: 63
<212> TYPE: DNA
<213> ORGANISM: Homo sapiens

<400> SEQUENCE: 4
ctctgctata tcctggatgc catcctgttt ctgtatggaa ttgtcctcac cctcctctac    60
tgt                                                                  63

<210> SEQ ID NO 5
<211> LENGTH: 126
<212> TYPE: DNA
<213> ORGANISM: Homo sapiens

<400> SEQUENCE: 5
cgactgaaga tccaagtgcg aaaggcagct ataaccagct atgagaaatc agatggtgtt    60
tacacgggcc tgagcaccag gaaccaggag acttacgaga ctctgaagca tgagaaacca   120
ccacag                                                              126

<210> SEQ ID NO 6
<211> LENGTH: 690
<212> TYPE: DNA
<213> ORGANISM: Homo sapiens

<400> SEQUENCE: 6
atgcaggatg aagatggata catcacctta aatattaaaa ctcggaaacc agctctcatc    60
tccgttggct ctgcatcctc ctcctggtgg cgtgtgatgg ctttgattct gctgatcctg   120
tgcgtgggga tggttgtcgg gctggtggct ctgggatttg gtctgtcat gcagcgcaat    180 tacctacaag gtgagaatga aaatcgcaca ggaactctgc aacaattagc aaagcgcttc   240
tgtcaatatg tggtaaaaca atcagaacta aagggcactt tcaaaggtca taatgcagc    300 ccctgtgaca caaactggag atattatgga gatagctgct atgggttctt caggcacaac   360
ttaacatggg aagagagtaa gcagtactgc actgacatga atgctactct cctgaagatt   420
gacaaccgga acattgtgga gtacatcaaa gccaggactc atttaattcg ttgggtcgga   480
ttatctcgcc agaagtcgaa tgaggtctgg aagtgggagg atggctcggt tatctcagaa   540
aatatgtttg agttttttgga agatggaaaa ggaaatatga attgtgctta ttttcataat   600
gggaaaatgc accctacctt ctgtgagaac aaacattatt taatgtgtga gaggaaggct   660
ggcatgacca aggtggacca actaccttaa                                    690
```

<210> SEQ ID NO 7
<211> LENGTH: 99
<212> TYPE: DNA
<213> ORGANISM: Homo sapiens

<400> SEQUENCE: 7

```
atgcaggatg aagatggata catcacctta aatattaaaa ctcggaaacc agctctcatc      60
tccgttggct ctgcatcctc ctcctggtgg cgtgtgatg                             99
```

<210> SEQ ID NO 8
<211> LENGTH: 63
<212> TYPE: DNA
<213> ORGANISM: Homo sapiens

<400> SEQUENCE: 8

```
gctttgattc tgctgatcct gtgcgtgggg atggttgtcg ggctggtggc tctggggatt      60
tgg                                                                    63
```

<210> SEQ ID NO 9
<211> LENGTH: 525
<212> TYPE: DNA
<213> ORGANISM: Homo sapiens

<400> SEQUENCE: 9

```
tctgtcatgc agcgcaatta cctacaaggt gagaatgaaa atcgcacagg aactctgcaa      60
caattagcaa agcgcttctg tcaatatgtg gtaaaacaat cagaactaaa gggcactttc     120
aaaggtcata atgcagccc ctgtgacaca aactggagat attatggaga tagctgctat      180
gggttcttca ggcacaactt aacatgggaa gagagtaagc agtactgcac tgacatgaat     240
gctactctcc tgaagattga caaccggaac attgtggagt acatcaaagc caggactcat     300
ttaattcgtt gggtcggatt atctcgccag aagtcgaatg aggtctggaa gtgggaggat     360
ggctcggtta tctcagaaaa tatgtttgag tttttggaag atggaaaagg aaatatgaat     420
tgtgcttatt ttcataatgg gaaaatgcac cctaccttct gtgagaacaa acattattta     480
atgtgtgaga ggaaggctgg catgaccaag gtggaccaac tacct                     525
```

<210> SEQ ID NO 10
<211> LENGTH: 954
<212> TYPE: DNA
<213> ORGANISM: Homo sapiens

<400> SEQUENCE: 10

```
atgactatgg agacccaaat gtctcagaat gtatgtccca gaaacctgtg gctgcttcaa      60
ccattgacag ttttgctgct gctggcttct gcagacagtc aagctgcagc tcccccaaag     120
gctgtgctga acttgagcc cccgtggatc aacgtgctcc aggaggactc tgtgactctg     180
acatgccagg gggctcgcag ccctgagagc gactccattc agtggttcca caatgggaat     240
ctcattccca cccacacgca gcccagctac aggttcaagg ccaacaacaa tgacagcggg     300
gagtacacgt gccagactgg ccagaccagc ctcagcgacc ctgtgcatct gactgtgctt     360
tccgaatggc tggtgctcca gaccctcac ctggagttcc aggagggaga aaccatcatg     420
ctgaggtgcc acagctggaa ggacaagcct ctggtcaagg tcacattctt ccagaatgga     480
aaatcccaga aattctccca tttggatccc accttctcca tcccacagc aaaccacagt     540 cacagtggtg attaccactg cacaggaaac ataggctaca cgctgttctc atccaagcct     600
```

```
gtgaccatca ctgtccaagt gcccagcatg ggcagctctt caccaatggg gatcattgtg    660
gctgtggtca ttgcgactgc tgtagcagcc attgttgctg ctgtagtggc cttgatctac    720
tgcaggaaaa agcggatttc agccaattcc actgatcctg tgaaggctgc ccaatttgag    780
ccacctggac gtcaaatgat tgccatcaga aagagacaac ttgaagaaac caacaatgac    840
tatgaaacag ctgacggcgg ctacatgact ctgaacccca gggcacctac tgacgatgat    900
aaaaacatct acctgactct tcctcccaac gaccatgtca acagtaataa ctaa          954
```

<210> SEQ ID NO 11
<211> LENGTH: 99
<212> TYPE: DNA
<213> ORGANISM: Homo sapiens

<400> SEQUENCE: 11

```
atgactatgg agacccaaat gtctcagaat gtatgtccca gaaacctgtg gctgcttcaa     60
ccattgacag ttttgctgct gctggcttct gcagacagt                            99
```

<210> SEQ ID NO 12
<211> LENGTH: 552
<212> TYPE: DNA
<213> ORGANISM: Homo sapiens

<400> SEQUENCE: 12

```
caagctgcag ctcccccaaa ggctgtgctg aaacttgagc ccccgtggat caacgtgctc     60
caggaggact ctgtgactct gacatgccag ggggctcgca gccctgagag cgactccatt    120
cagtggttcc acaatgggaa tctcattccc acccacgc agcccagcta caggttcaag      180
gccaacaaca tgacagcgg ggagtacacg tgccagactg ccagaccag cctcagcgac      240 cctgtgcatc tgactgtgct ttccgaatgg ctggtgctcc agacccctca cctggagttc    300
caggagggag aaaccatcat gctgaggtgc cacagctgga aggacaagcc tctggtcaag    360
gtcacattct tccagaatgg aaaatcccag aaattctccc atttggatcc caccttctcc    420
atcccacaag caaaccacag tcacagtggt gattaccact gcacaggaaa cataggctac    480
acgctgttct catccaagcc tgtgaccatc actgtccaag tgcccagcat gggcagctct    540
tcaccaatgg gg                                                         552
```

<210> SEQ ID NO 13
<211> LENGTH: 69
<212> TYPE: DNA
<213> ORGANISM: Homo sapiens

<400> SEQUENCE: 13

```
atcattgtgg ctgtggtcat tgcgactgct gtagcagcca ttgttgctgc tgtagtggcc     60
ttgatctac                                                             69
```

<210> SEQ ID NO 14
<211> LENGTH: 231
<212> TYPE: DNA
<213> ORGANISM: Homo sapiens

<400> SEQUENCE: 14

```
tgcaggaaaa agcggatttc agccaattcc actgatcctg tgaaggctgc ccaatttgag     60
ccacctggac gtcaaatgat tgccatcaga aagagacaac ttgaagaaac caacaatgac    120
tatgaaacag ctgacggcgg ctacatgact ctgaacccca gggcacctac tgacgatgat    180
aaaaacatct acctgactct tcctcccaac gaccatgtca acagtaataa c             231
```

```
<210> SEQ ID NO 15
<211> LENGTH: 1020
<212> TYPE: DNA
<213> ORGANISM: Homo sapiens

<400> SEQUENCE: 15
atgtctccat ccccgaccgc cctcttctgt cttgggctgt gtctggggcg tgtgccagcg      60
cagagtggac cgctccccaa gccctccctc caggctctgc ccagctccct ggtgcccctg     120
gagaagccag tgaccctccg gtgccaggga cctccgggcg tggacctgta ccgcctggag     180
aagctgagtt ccagcaggta ccaggatcag gcagtcctct tcatcccggc catgaagaga     240
agtctggctg gacgctaccg ctgctcctac cagaacggaa gcctctggtc cctgcccagc     300
gaccagctgg agtcgttgc cacgggagtt tttgccaaac cctcgctctc agcccagccc     360
ggcccggcgg tgtcgtcagg aggggacgta accctacagt gtcagactcg gtatggcttt     420
gaccaatttg ctctgtacaa ggaaggggac cctgcgccct acaagaatcc cgagagatgg     480
tacagggcta gttttcccat catcacggtg accgccgccc acagcggaac ctaccgatgc     540
tacagcttct ccagcaggga cccatacctg tggtcagccc ccagcgaccc cctggagctt     600
gtggtcacag gaacctctgt gacccccagc cggttaccaa cagaaccacc ttccccggta     660
gcagaattct cagaagccac cgctgaactg accgtctcat tcacaaacga agtcttcaca     720
actgagactt ctaggagtat caccgccagt ccaaaggagt cagactctcc agctggtcct     780
gcccgccagt actacaccaa gggcaacctg gtccggatat gcctcgggc tgtgatccta     840
ataatcctgg cggggtttct ggcagaggac tggcacagcc ggaggaagcg cctgcggcac     900
aggggcaggg ctgtgcagag gccgcttccg ccctcccgc ccctcccgct gacccggaaa     960
tcaaacgggg gtcaggatgg aggccgacag gatgttcaca gccgcgggtt atgttcatga    1020

<210> SEQ ID NO 16
<211> LENGTH: 60
<212> TYPE: DNA
<213> ORGANISM: Homo sapiens

<400> SEQUENCE: 16
atgtctccat ccccgaccgc cctcttctgt cttgggctgt gtctggggcg tgtgccagcg      60

<210> SEQ ID NO 17
<211> LENGTH: 741
<212> TYPE: DNA
<213> ORGANISM: Homo sapiens

<400> SEQUENCE: 17
cagagtggac cgctccccaa gccctccctc caggctctgc ccagctccct ggtgcccctg      60
gagaagccag tgaccctccg gtgccaggga cctccgggcg tggacctgta ccgcctggag     120
aagctgagtt ccagcaggta ccaggatcag gcagtcctct tcatcccggc catgaagaga     180
agtctggctg gacgctaccg ctgctcctac cagaacggaa gcctctggtc cctgcccagc     240
gaccagctgg agtcgttgc cacgggagtt tttgccaaac cctcgctctc agcccagccc     300
ggcccggcgg tgtcgtcagg aggggacgta accctacagt gtcagactcg gtatggcttt     360
gaccaatttg ctctgtacaa ggaaggggac cctgcgccct acaagaatcc cgagagatgg     420
tacagggcta gttttcccat catcacggtg accgccgccc acagcggaac ctaccgatgc     480
tacagcttct ccagcaggga cccatacctg tggtcagccc ccagcgaccc cctggagctt     540
```

```
gtggtcacag gaacctctgt gacccccagc cggttaccaa cagaaccacc ttccccggta    600
gcagaattct cagaagccac cgctgaactg accgtctcat tcacaaacga agtcttcaca    660
actgagactt ctaggagtat caccgccagt ccaaaggagt cagactctcc agctggtcct    720
gcccgccagt actacaccaa g                                              741

<210> SEQ ID NO 18
<211> LENGTH: 63
<212> TYPE: DNA
<213> ORGANISM: Homo sapiens

<400> SEQUENCE: 18
ggcaacctgg tccggatatg cctcggggct gtgatcctaa taatcctggc ggggtttctg     60
gca                                                                  63

<210> SEQ ID NO 19
<211> LENGTH: 153
<212> TYPE: DNA
<213> ORGANISM: Homo sapiens

<400> SEQUENCE: 19
gaggactggc acagccggag gaagcgcctg cggcacaggg gcagggctgt gcagaggccg     60
cttccgcccc tcccgcccct cccgctgacc cggaaatcaa acgggggtca ggatggaggc    120
cgacaggatg ttcacagccg cgggttatgt tca                                 153

<210> SEQ ID NO 20
<211> LENGTH: 1032
<212> TYPE: DNA
<213> ORGANISM: Artificial Sequence
<220> FEATURE:
<223> OTHER INFORMATION: Description of Artificial Sequence: Chimeric
      ITAM receptor

<400> SEQUENCE: 20
atgattccag cagtggtctt gctcttactc cttttggttg aacaagcagc ggccgacatc     60
cagatgaccc agaccaccag cagcctgagc gccagcctgg gcgacagagt gaccatcagc    120
tgcagagcca gccaggacat cagcaagtac ctgaactggt accagcagaa gcccgacggc    180
accgtgaagc tgctgatcta ccacaccagc agactgcaca cggcgtgccc cagcagattc    240
agcggcagcg gcagcggcac cgactacagc ctgaccatca gcaacctgga gcaggaggac    300
atcgccacct acttctgcca gcagggcaac accctgccct acaccttcgg cggcggcacc    360
aagctggaga tcaccggcag caccagcggc agcggcaagc ccggcagcgg cgagggcagc    420
accaagggcg aggtgaagct gcaggagagc ggccccggcc tggtggcccc agccagagc     480 ctgagcgtga cctgcaccgt gagcggcgtg agcctgcccg actacggcgt gagctggatc    540
agacagcccc ccagaaaggg cctggagtgg ctgggcgtga tctggggcag cgagaccacc    600
tactacaaca gcgccctgaa gagcagactg accatcatca aggacaacag caagagccag    660
gtgttcctga agatgaacag cctgcagacc gacgacaccg ccatctacta ctgcgccaag    720
cactactact acggcggcag ctacgccatg gactactggg gccagggcac cagcgtgacc    780
gtgagcagcg aatctaagta cggaccgccc tgccccccct tgccctctgg gagagcctcag   840 ctctgctata tcctggatgc catcctgttt ctgtatggaa ttgtcctcac cctcctctac    900
tgtcgactga gatccaagt gcgaaaggca gctataacca gctatgagaa atcagatggt     960
gtttacacgg gcctgagcac caggaaccag gagacttacg agactctgaa gcatgagaaa   1020
```
ccaccacagt ag                                                       1032

<210> SEQ ID NO 21
<211> LENGTH: 951
<212> TYPE: DNA
<213> ORGANISM: Artificial Sequence
<220> FEATURE:
<223> OTHER INFORMATION: Description of Artificial Sequence: Chimeric
      ITAM receptor

<400> SEQUENCE: 21
atgcaggatg aagatggata catcacctta aatattaaaa ctcggaaacc agctctcatc     60
tccgttggct ctgcatcctc ctcctggtgg cgtgtgatgg ctttgattct gctgatcctg    120
tgcgtgggga tggttgtcgg gctggtggct ctggggattt ggtctgtcat gcagcgcgaa    180
tctaagtacg gaccgccctg ccccccttgc cctgacatcc agatgaccca gaccaccagc    240
agcctgagcg ccagcctggg cgacagagtg accatcagct gcagagccag ccaggacatc    300
agcaagtacc tgaactggta ccagcagaag cccgacggca ccgtgaagct gctgatctac    360
cacaccagca gactgcacag cggcgtgccc agcagattca gcggcagcgg cagcggcacc    420
gactacagcc tgaccatcag caacctggag caggaggaca tcgccaccta cttctgccag    480
cagggcaaca ccctgcccta ccttcggc ggcggcacca agctggagat caccggcagc      540
accagcggca gcggcaagcc cggcagcggc gagggcagca ccaagggcga ggtgaagctg    600
caggagagcg gccccggcct ggtggccccc agccagagcc tgagcgtgac ctgcaccgtg    660
agcggcgtga gcctgcccga ctacggcgtg agctggatca gcagccccc cagaaagggc    720
ctggagtggc tgggcgtgat ctggggcagc gagaccacct actacaacag cgccctgaag    780
agcagactga ccatcatcaa ggacaacagc aagagccagg tgttcctgaa gatgaacagc    840
ctgcagaccg acgacaccgc catctactac tgcgccaagc actactacta cggcggcagc    900
tacgccatgg actactgggg ccagggcacc agcgtgaccg tgagcagcta a             951

<210> SEQ ID NO 22
<211> LENGTH: 1188
<212> TYPE: DNA
<213> ORGANISM: Artificial Sequence
<220> FEATURE:
<223> OTHER INFORMATION: Description of Artificial Sequence: Chimeric
      ITAM receptor

<400> SEQUENCE: 22
atgactatgg agacccaaat gtctcagaat gtatgtccca gaaacctgtg gctgcttcaa     60
ccattgacag ttttgctgct gctggcttct gcagacagtg acatccagat gacccagacc    120
accagcagcc tgagcgccag cctgggcgac agagtgacca tcagctgcag agccagccag    180
gacatcagca agtacctgaa ctggtaccag cagaagcccg acggcaccgt gaagctgctg    240
atctaccaca ccagcagact gcacagcggc gtgcccagca gattcagcgg cagcggcagc    300
ggcaccgact acagcctgac catcagcaac ctggagcagg aggacatcgc cacctacttc    360
tgccagcagg gcaacaccct gccctacacc ttcggcggcg gcaccaagct ggagatcacc    420
ggcagcacca gcggcagcgg caagcccggc agcggcgagg gcagcaccaa gggcgaggtg    480
aagctgcagg agagcggccc cggcctggtg gcccccagcc agagcctgag cgtgacctgc    540
accgtgagcg gcgtgagcct gcccgactac ggcgtgagct ggatcagaca gccccccaga    600
aagggcctgg agtggctggg cgtgatctgg ggcagcgaga ccacctacta caacagcgcc    660
ctgaagagca gactgaccat catcaaggac aacagcaaga gccaggtgtt cctgaagatg    720

```
aacagcctgc agaccgacga caccgccatc tactactgcg ccaagcacta ctactacggc    780
ggcagctacg ccatggacta ctggggccag ggcaccagct gaccgtgag cagcgaatct    840 aagtacggac cgccctgccc cccttgccct tcttcaccaa tggggatcat tgtggctgtg    900
gtcattgcga ctgctgtagc agccattgtt gctgctgtag tggccttgat ctactgcagg    960
aaaaagcgga tttcagccaa ttccactgat cctgtgaagg ctgcccaatt tgagccacct   1020
ggacgtcaaa tgattgccat cagaaagaga caacttgaag aaaccaacaa tgactatgaa   1080
acagctgacg gcggctacat gactctgaac cccagggcac ctactgacga tgataaaaac   1140
atctacctga ctcttcctcc caacgaccat gtcaacagta taactaa               1188
```

<210> SEQ ID NO 23
<211> LENGTH: 1065
<212> TYPE: DNA
<213> ORGANISM: Artificial Sequence
<220> FEATURE:
<223> OTHER INFORMATION: Description of Artificial Sequence: Chimeric
      ITAM receptor

<400> SEQUENCE: 23

```
atgtctccat ccccgaccgc cctcttctgt cttgggctgt gtctggggcg tgtgccagcg     60
gacatccaga tgacccagac caccagcagc ctgagcgcca gcctgggcga cagagtgacc    120
atcagctgca gagccagcca ggacatcagc aagtacctga actggtacca gcagaagccc    180
gacggcaccg tgaagctgct gatctaccac accagcagac tgcacagcgg cgtgcccagc    240
agattcagcg gcagcggcag cggcaccgac tacagcctga ccatcagcaa cctggagcag    300
gaggacatcg ccacctactt ctgccagcag ggcaacaccc tgccctacac cttcggcggc    360
ggcaccaagc tggagatcac cggcagcacc agcggcagcg gcaagcccgg cagcggcgag    420
ggcagcacca agggcgaggt gaagctgcag gagagcggcc ccggcctggt ggcccccagc    480
cagagcctga gcgtgacctg caccgtgagc ggcgtgagcc tgcccgacta cggcgtgagc    540
tggatcagac agcccccag aaagggcctg gagtggctgg gcgtgatctg gggcagcgag    600
accacctact acaacagcgc cctgaagagc agactgacca tcatcaagga caacagcaag    660
agccaggtgt tcctgaagat gaacagcctg cagaccgacg acaccgccat ctactactgc    720
gccaagcact actactacgg cggcagctac gccatggact actggggcca gggcaccagc    780
gtgaccgtga gcagcgaatc taagtacgga ccgccctgcc cccttgccc tcagtactac    840 accaagggca acctggtccg gatatgcctc ggggctgtga tcctaataat cctggcgggg    900
tttctggcag aggactggca cagccggagg aagcgcctgc ggcacagggg cagggctgtg    960
cagaggccgc ttccgcccct cccgcccctc ccgctgaccc ggaaatcaaa cggggggtcag   1020 gatggaggcc gacaggatgt tcacagccgc gggttatgtt catga                   1065
```

<210> SEQ ID NO 24
<211> LENGTH: 1581
<212> TYPE: DNA
<213> ORGANISM: Homo sapiens

<400> SEQUENCE: 24

```
atggggcacc tctcagcccc acttcacaga gtgcgtgtac cctggcaggg gcttctgctc     60
acagcctcac ttctaacctt ctggaacccg cccaccactg cccagctcac tactgaatcc    120
atgccattca atgttgcaga ggggaaggag gttcttctcc ttgtccacaa tctgccccag    180 caacttttg gctacagctg gtacaaaggg gaaagagtgg atggcaaccg tcaaattgta    240
```

-continued

```
ggatatgcaa taggaactca acaagctacc ccagggcccg caaacagcgg tcgagagaca      300 atataccccca atgcatccct gctgatccag aacgtcaccc agaatgacac aggattctac      360
accctacaag tcataaagtc agatcttgtg aatgaagaag caactggaca gttccatgta      420
tacccggagc tgcccaagcc ctccatctcc agcaacaact ccaaccctgt ggaggacaag      480
gatgctgtgg ccttcacctg tgaacctgag actcaggaca caacctacct gtggtggata      540
aacaatcaga gcctcccggt cagtcccagg ctgcagctgt ccaatggcaa caggaccctc      600
actctactca gtgtcacaag gaatgacaca ggaccctatg agtgtgaaat acagaaccca      660
gtgagtgcga accgcagtga cccagtcacc ttgaatgtca cctatggccc ggacaccccc      720
accatttccc cttcagacac ctattaccgt ccaggggcaa acctcagcct ctcctgctat      780
gcagcctcta acccacctgc acagtactcc tggcttatca atggaacatt ccagcaaagc      840
acacaagagc tctttatccc taacatcact gtgaataata gtggatccta tacctgccac      900
gccaataact cagtcactgg ctgcaacagg accacagtca agacgatcat agtcactgag      960
ctaagtccag tagtagcaaa gccccaaatc aaagccagca agaccacagt cacaggagat     1020
aaggactctg tgaacctgac ctgctccaca atgacactg gaatctccat ccgttggttc     1080
ttcaaaaacc agagtctccc gtcctcggag aggatgaagc tgtcccaggg caacaccacc     1140
ctcagcataa accctgtcaa gagggaggat gctgggacgt attggtgtga ggtcttcaac     1200
ccaatcagta agaaccaaag cgaccccatc atgctgaacg taaactataa tgctctacca     1260
caagaaaatg gcctctcacc tggggccatt gctggcattg tgattggagt agtggccctg     1320
gttgctctga tagcagtagc cctggcatgt tttctgcatt tcgggaagac cggcagggca     1380
agcgaccagc gtgatctcac agagcacaaa ccctcagtct ccaaccacac tcaggaccac     1440
tccaatgacc cacctaacaa gatgaatgaa gttacttatt ctaccctgaa ctttgaagcc     1500
cagcaaccca cacaaccaac ttcagcctcc ccatccctaa cagccacaga ataaatttat     1560
tcagaagtaa aaaagcagta a                                               1581
```

<210> SEQ ID NO 25
<211> LENGTH: 102
<212> TYPE: DNA
<213> ORGANISM: Homo sapiens

<400> SEQUENCE: 25

```
atggggcacc tctcagcccc acttcacaga gtgcgtgtac cctggcaggg gcttctgctc       60
acagcctcac ttctaaccctt ctggaacccg cccaccactg cc                        102
```

<210> SEQ ID NO 26
<211> LENGTH: 1182
<212> TYPE: DNA
<213> ORGANISM: Homo sapiens

<400> SEQUENCE: 26

```
cagctcacta ctgaatccat gccattcaat gttgcagagg ggaaggaggt tcttctcctt       60
gtccacaatc tgccccagca acttttttggc tacagctggt acaaagggga aagagtggat      120
ggcaaccgtc aaattgtagg atatgcaata ggaactcaac aagctacccc agggcccgca      180
aacagcggtc gagagacaat ataccccaat gcatccctgc tgatccagaa cgtcacccag      240
aatgacacag gattctacac cctacaagtc ataaagtcag atcttgtgaa tgaagaagca      300
actggacagt tccatgtata cccggagctg cccaagccct ccatctccag caacaactcc      360
```

```
aaccctgtgg aggacaagga tgctgtggcc ttcacctgtg aacctgagac tcaggacaca    420
acctacctgt ggtggataaa caatcagagc ctcccggtca gtcccaggct gcagctgtcc    480
aatggcaaca ggaccctcac tctactcagt gtcacaagga atgacacagg accctatgag    540
tgtgaaatac agaacccagt gagtgcgaac cgcagtgacc cagtcacctt gaatgtcacc    600
tatggcccgg acacccccac catttcccct tcagacacct attaccgtcc aggggcaaac    660
ctcagcctct cctgctatgc agcctctaac ccacctgcac agtactcctg gcttatcaat    720
ggaacattcc agcaaagcac acaagagctc tttatcccta acatcactgt gaataatagt    780
ggatcctata cctgccacgc caataactca gtcactggct gcaacaggac cacagtcaag    840
acgatcatag tcactgagct aagtccagta gtagcaaagc cccaaatcaa agccagcaag    900
accacagtca caggagataa ggactctgtg aacctgacct gctccacaaa tgacactgga    960
atctccatcc gttggttctt caaaaaccag agtctcccgt cctcggagag gatgaagctg   1020
tcccagggca acaccaccct cagcataaac cctgtcaaga gggaggatgc tgggacgtat   1080
tggtgtgagg tcttcaaccc aatcagtaag aaccaaagcg accccatcat gctgaacgta   1140
aactataatg ctctaccaca agaaaatggc ctctcacctg gg                      1182

<210> SEQ ID NO 27
<211> LENGTH: 72
<212> TYPE: DNA
<213> ORGANISM: Homo sapiens

<400> SEQUENCE: 27
gccattgctg gcattgtgat tggagtagtg gccctggttg ctctgatagc agtagccctg     60
gcatgttttc tg                                                        72

<210> SEQ ID NO 28
<211> LENGTH: 222
<212> TYPE: DNA
<213> ORGANISM: Homo sapiens

<400> SEQUENCE: 28
catttcggga agaccggcag ggcaagcgac cagcgtgatc tcacagagca caaaccctca     60
gtctccaacc acactcagga ccactccaat gacccaccta acaagatgaa tgaagttact    120
tattctaccc tgaactttga agcccagcaa cccacacaac caacttcagc ctccccatcc    180
ctaacagcca cagaaataat ttattcagaa gtaaaaaagc ag                       222

<210> SEQ ID NO 29
<211> LENGTH: 726
<212> TYPE: DNA
<213> ORGANISM: Homo sapiens

<400> SEQUENCE: 29
atggctgtgt ttctgcagct gctaccgctg ctgctctcga gggcccaagg gaaccctggg     60
gcttctctgg acggccgccc tgggaccgg gtgaatctct cctgcggagg agtctctcat    120
cccatccgct gggtctgggc acccagcttc ccggcctgca agggcctgtc caaaggacgc    180
cgaccgatcc tgtgggcctc ttcgagcggg acccccaccg tgcctcccct ccagcctttc    240
gtcggccgcc tacgctccct ggactctggt atccggcggc tggagctcct cttgagcgcg    300
ggggactcgg gcacttttttt ctgcaagggc cgccacgagg acgagagccg tacagtgctt    360
cacgtgctgg ggacaggac ctattgcaag gcccccgggc taccccatgg gtccgtgtat    420
ccccagctcc tgatcccgct gctgggcgct gggttggtgc tcggactggg agctttgggc    480
```

```
ctggtctggt ggctgcacag gcgcctgccc ccgcaaccga ttcgaccact ccctagattt    540
gctccacttg tgaaaaccga gccccagagg ccagtaaagg aggaagagcc caagattcca    600
ggggacctgg accaggaacc gagcctgctc tatgcggatc tggaccatct agccctcagc    660
aggccccgcc ggctgtccac agcggaccct gctgatgcct ccaccatcta tgcagttgta    720
gtttga                                                              726
```

<210> SEQ ID NO 30
<211> LENGTH: 51
<212> TYPE: DNA
<213> ORGANISM: Homo sapiens

<400> SEQUENCE: 30

```
atggctgtgt ttctgcagct gctaccgctg ctgctctcga gggcccaagg g              51
```

<210> SEQ ID NO 31
<211> LENGTH: 375
<212> TYPE: DNA
<213> ORGANISM: Homo sapiens

<400> SEQUENCE: 31

```
aaccctgggg cttctctgga cggccgccct ggggaccggg tgaatctctc ctgcggagga    60
gtctctcatc ccatccgctg ggtctgggca cccagcttcc cggcctgcaa gggcctgtcc    120
aaaggacgcc gaccgatcct gtgggcctct tcgagcggga cccccaccgt gcctcccctc    180
cagccttccg tcggccgcct acgctccctg gactctggta tccggcggct ggagctcctc    240
ttgagcgcgg gggactcggg cacttttttc tgcaagggcc gccacgagga cgagagccgt    300
acagtgcttc acgtgctggg ggacaggacc tattgcaagg ccccgggcc tacccatggg    360 tccgtgtatc cccag                                                    375
```

<210> SEQ ID NO 32
<211> LENGTH: 63
<212> TYPE: DNA
<213> ORGANISM: Homo sapiens

<400> SEQUENCE: 32

```
ctcctgatcc cgctgctggg cgctgggttg gtgctcggac tgggagcttt gggcctggtc    60
tgg                                                                 63
```

<210> SEQ ID NO 33
<211> LENGTH: 234
<212> TYPE: DNA
<213> ORGANISM: Homo sapiens

<400> SEQUENCE: 33

```
tggctgcaca ggcgcctgcc cccgcaaccg attcgaccac tccctagatt tgctccactt    60
gtgaaaaccg agccccagag gccagtaaag gaggaagagc caagattcc aggggacctg    120 gaccaggaac cgagcctgct ctatgcggat ctggaccatc tagccctcag caggccccgc    180
cggctgtcca cagcggaccc tgctgatgcc tccaccatct atgcagttgt agtt         234
```

<210> SEQ ID NO 34
<211> LENGTH: 1797
<212> TYPE: DNA
<213> ORGANISM: Homo sapiens

<400> SEQUENCE: 34

```
atgacccca tcgtcacagt cctgatctgt ctcgggctga gtctgggccc caggacccac    60
gtgcagacag ggaccattcc caagcccacc ctgtgggctg agccagactc tgtgatcacc   120
caggggagtc ccgtcaccct cagttgtcag gggagccttg aagcccagga gtaccgtcta   180
tatagggaga aaaaatcagc atcttggatt acacggatac gaccagagct tgtgaagaac   240
ggccagttcc acatcccatc catcacctgg gaacacacag gcgatatgg ctgtcagtat    300
tacagccgcg ctcggtggtc tgagctcagt gaccccctgg tgctggtgat gacaggagcc   360
tacccaaaac ccaccctctc agcccagccc agccctgtgg tgacctcagg aggaagggtg   420
accctccagt gtgagtcaca ggtggcattt ggcggcttca ttctgtgtaa ggaaggagaa   480
gaagaacacc cacaatgcct gaactcccag ccccatgccc gtgggtcgtc ccgcgccatc   540
ttctccgtgg gccccgtgag cccgaatcgc aggtggtcgc acaggtgcta tggttatgac   600
ttgaactctc cctatgtgtg gtcttcaccc agtgatctcc tggagctcct ggtcccaggt   660
gtttctaaga agccatcact ctcagtgcag ccgggtcctg tcgtggcccc tggggaaagc   720
ctgaccctcc agtgtgtctc tgatgtcggc tatgacagat ttgttctgta caaggagggg   780
gaacgtgacc ttcgccagct ccctggccgg cagcccagg ctgggctctc ccaggccaac    840
ttcacccctgg gccctgtgag ccgctcctac ggggccagt acagatgcta cggtgcacac   900
aacctctcct ctgagtgctc ggccccagc gacccctgg acatcctgat cacaggacag     960
atccgtggca caccttcat ctcagtgcag ccaggcccca cagtggcctc aggagagaac   1020
gtgaccctgc tgtgtcagtc atggcggcag ttccacactt tccttctgac caaggcggga  1080
gcagctgatg ccccactccg tctaagatca atacacgaat atcctaagta ccaggctgaa  1140
ttccccatga gtcctgtgac ctcagcccac gcggggacct acaggtgcta cggctcactc  1200
aactccgacc cctacctgct gtctcacccc agtgagcccc tggagctcgt ggtctcagga  1260
ccctccatgg gttccagccc cccacccacc ggtcccatct ccacacctgc aggccctgag  1320
gaccagcccc tcacccccac tgggtcggat cccaaagtg gtctgggaag gcacctgggg   1380
gttgtgatcg gcatcttggt ggccgtcgtc ctactgctcc tcctcctcct cctcctcttc  1440
ctcatcctcc gacatcgacg tcagggcaaa cactggacat cgacccagag aaaggctgat  1500
ttccaacatc ctgcagggg tgtggggcca gagcccacag acagaggcct gcagtggagg  1560
tccagcccag ctgccgacgc ccaggaagaa aacctctatg ctgccgtgaa ggacacacag  1620
cctgaagatg gggtggagat ggacactcgg gctgctgcat ctgaagcccc caggatgtg   1680
acctacgccc agctgcacag cttgacccct agacggaagg caactgagcc tcctccatcc  1740
caggaagggg aacctccagc tgagcccagc atctacgcca ccctggccat ccactag    1797
```

<210> SEQ ID NO 35
<211> LENGTH: 63
<212> TYPE: DNA
<213> ORGANISM: Homo sapiens

<400> SEQUENCE: 35

```
atgacccca tcgtcacagt cctgatctgt ctcgggctga gtctgggccc caggacccac    60
gtg                                                                 63
```

<210> SEQ ID NO 36
<211> LENGTH: 1320
<212> TYPE: DNA
<213> ORGANISM: Homo sapiens

<400> SEQUENCE: 36

```
cagacaggga ccattcccaa gcccaccctg tgggctgagc cagactctgt gatcacccag    60
gggagtcccg tcaccctcag ttgtcagggg agccttgaag cccaggagta ccgtctatat   120
agggagaaaa aatcagcatc ttggattaca cggatacgac cagagcttgt gaagaacggc   180
cagttccaca tcccatccat cacctgggaa cacacagggc gatatggctg tcagtattac   240
agccgcgctc ggtggtctga gctcagtgac cccctggtgc tggtgatgac aggagcctac   300
ccaaaaccca ccctctcagc ccagcccagc cctgtggtga cctcaggagg aagggtgacc   360
ctccagtgtg agtcacaggt ggcatttggc ggcttcattc tgtgtaagga aggagaagaa   420
gaacacccac aatgcctgaa ctcccagccc catgcccgtg ggtcgtcccg cgccatcttc   480
tccgtgggcc ccgtgagccc gaatcgcagg tggtcgcaca ggtgctatgg ttatgacttg   540
aactctccct atgtgtggtc ttcacccagt gatctcctgg agctcctggt cccaggtgtt   600
tctaagaagc catcactctc agtgcagccg ggtcctgtcg tggcccctgg ggaaagcctg   660
accctccagt gtgtctctga tgtcggctat gacagatttg ttctgtacaa ggaggggaa    720 cgtgaccttc gccagctccc tggccggcag ccccaggctg ggctctccca ggccaacttc   780 accctggggcc ctgtgagccg ctcctacggg gccagtaca gatgctacgg tgcacacaac    840
ctctcctctg agtgctcggc ccccagcgac ccctggaca tcctgatcac aggacagatc    900
cgtggcacac ccttcatctc agtgcagcca ggcccacag tggcctcagg agagaacgtg    960
accctgctgt gtcagtcatg gcggcagttc cacactttcc ttctgaccaa ggcgggagca  1020
gctgatgccc cactccgtct aagatcaata cacgaatatc ctaagtacca ggctgaattc  1080
cccatgagtc ctgtgacctc agcccacgcg gggacctaca ggtgctacgg ctcactcaac  1140 tccgaccct acctgctgtc tcaccccagt gagcccctgg agctcgtggt ctcaggaccc  1200 tccatggtt ccagcccccc acccaccggt cccatctcca cacctgcagg ccctgaggac  1260
cagcccctca cccccactgg gtcggatccc caaagtggtc tgggaaggca cctgggggtt  1320
```

<210> SEQ ID NO 37
<211> LENGTH: 63
<212> TYPE: DNA
<213> ORGANISM: Homo sapiens

<400> SEQUENCE: 37

```
gtgatcggca tcttggtggc cgtcgtccta ctgctcctcc tcctcctcct cctcttcctc    60
atc                                                                  63
```

<210> SEQ ID NO 38
<211> LENGTH: 2217
<212> TYPE: DNA
<213> ORGANISM: Homo sapiens

<400> SEQUENCE: 38

```
atgcagccga ggtgggccca aggggccacg atgtggcttg gagtcctgct gacccttctg    60
ctctgttcaa gccttgaggg tcaagaaaac tctttcacaa tcaacagtgt tgacatgaag   120
agcctgccgg actggacggt gcaaaatggg aagaacctga ccctgcagtg cttcgcggat   180
gtcagcacca cctctcacgt caagcctcag caccagatgc tgttctataa ggatgacgtg   240 ctgtttttaca acatctcctc catgaagagc acagagagtt attttattcc tgaagtccgg   300
atctatgact cagggacata taatgtact gtgattgtga caacaaaga gaaaaccact   360 gcagagtacc aggtgttggt ggaaggagtg cccagtccca gggtgacact ggacaagaaa   420
```

```
gaggccatcc aagtgggat cgtgagggtc aactgttctg tcccagagga aaaggcccca    480
atacacttca caattgaaaa acttgaacta aatgaaaaaa tggtcaagct gaaaagagag    540
aagaattctc gagaccagaa ttttgtgata ctggaattcc ccgttgagga acaggaccgc    600
gttttatcct tccgatgtca agctaggatc atttctggga tccatatgca gacctcagaa    660
tctaccaaga gtgaactggt caccgtgacg gaatccttct ctacacccaa gttccacatc    720
agccccaccg gaatgatcat ggaaggagct cagctccaca ttaagtgcac cattcaagtg    780
actcacctgg cccaggagtt tccagaaatc ataattcaga aggacaaggc gattgtggcc    840
cacaacagac atggcaacaa ggctgtgtac tcagtcatgg ccatggtgga gcacagtggc    900
aactacacgt gcaaagtgga gtccagccgc atatccaagg tcagcagcat cgtggtcaac    960
ataacagaac tattttccaa gcccgaactg gaatcttcct tcacacatct ggaccaaggt   1020
gaaagactga acctgtcctg ctccatccca ggagcacctc cagccaactt caccatccag   1080
aaggaagata cgattgtgtc acagactcaa gatttcacca agatagcctc aaagtcggac   1140
agtgggacgt atatctgcac tgcaggtatt gacaaagtgg tcaagaaaag caacacagtc   1200
cagatagtcg tatgtgaaat gctctcccag cccaggattt cttatgatgc ccagtttgag   1260
gtcataaaag gacagaccat cgaagtccgt tgcgaatcga tcagtggaac tttgcctatt   1320
tcttaccaac tttaaaaac aagtaaagtt ttggagaata gtaccaagaa ctcaaatgat   1380
cctgcggtat tcaaagacaa ccccactgaa gacgtcgaat accagtgtgt tgcagataat   1440
tgccattccc atgccaaaat gttaagtgag gttctgaggg tgaaggtgat agccccggtg   1500
gatgaggtcc agatttctat cctgtcaagt aaggtggtgg agtctggaga ggacattgtg   1560
ctgcaatgtg ctgtgaatga aggatctggt cccatcacct ataagttta cagagaaaaa   1620 gagggcaaac ccttctatca aatgacctca aatgccaccc aggcattttg gaccaagcag   1680
aaggctagca aggaacagga gggagagtat tactgcacag ccttcaacag agccaaccac   1740
gcctccagtg tccccagaag caaaatactg acagtcagag tcattcttgc cccatggaag   1800
aaaggactta ttgcagtggt tatcatcgga gtgatcattg ctctcttgat cattgcggcc   1860
aaatgttatt ttctgaggaa agccaaggcc aagcagatgc cagtggaaat gtccaggcca   1920
gcagtaccac ttctgaactc caacaacgag aaaatgtcag atcccaatat ggaagctaac   1980
agtcattacg gtcacaatga cgatgtcaga aaccatgcaa tgaaaccaat aaatgataat   2040
aaagagcctc tgaactcaga cgtgcagtac acggaagttc aagtgtcctc agctgagtct   2100
cacaaagatc taggaaagaa ggacacagag acagtgtaca gtgaagtccg gaaagctgtc   2160
cctgatgccg tggaaagcag atactctaga acggaaggct cccttgatgg aacttag     2217
```

<210> SEQ ID NO 39
<211> LENGTH: 81
<212> TYPE: DNA
<213> ORGANISM: Homo sapiens

<400> SEQUENCE: 39

```
atgcagccga ggtgggccca aggggccacg atgtggcttg gagtcctgct gacccttctg     60
ctctgttcaa gccttgaggg t                                              81
```

<210> SEQ ID NO 40
<211> LENGTH: 1722
<212> TYPE: DNA
<213> ORGANISM: Homo sapiens

<400> SEQUENCE: 40

```
caagaaaact ctttcacaat caacagtgtt gacatgaaga gcctgccgga ctggacggtg      60
caaaatggga agaacctgac cctgcagtgc ttcgcggatg tcagcaccac ctctcacgtc     120
aagcctcagc accagatgct gttctataag gatgacgtgc tgttttacaa catctcctcc     180
atgaagagca cagagagtta ttttattcct gaagtccgga tctatgactc agggacatat     240
aaatgtactg tgattgtgaa caacaaagag aaaccactg cagagtacca ggtgttggtg      300
gaaggagtgc ccagtcccag ggtgacactg gacaagaaag aggccatcca aggtgggatc     360
gtgagggtca actgttctgt cccagaggaa aaggccccaa tacacttcac aattgaaaaa     420
cttgaactaa atgaaaaaat ggtcaagctg aaaagagaga gaattctcg agaccagaat      480 tttgtgatac tggaattccc cgttgaggaa caggaccgcg ttttatcctt ccgatgtcaa     540
gctaggatca tttctgggat ccatatgcag acctcagaat ctaccaagag tgaactggtc     600
accgtgacgg aatccttctc tacacccaag ttccacatca gccccaccgg aatgatcatg     660
gaaggagctc agctccacat taagtgcacc attcaagtga ctcacctggc ccaggagttt     720
ccagaaatca taattcagaa ggacaaggcg attgtggccc acaacagaca tggcaacaag     780
gctgtgtact cagtcatggc catggtggag cacagtggca actacacgtg caaagtggag     840
tccagccgca tatccaaggt cagcagcatc gtggtcaaca taacagaact atttttccaag    900 cccgaactgg aatcttcctt cacacatctg gaccaaggtg aaagactgaa cctgtcctgc     960
tccatcccag gagcacctcc agccaacttc accatccaga aggaagatac gattgtgtca    1020
cagactcaag atttccaccaa gatagcctca agtcggaca gtgggacgta tatctgcact    1080
gcaggtattg acaaagtggt caagaaaagc aacacagtcc agatagtcgt atgtgaaatg    1140
ctctcccagc ccaggatttc ttatgatgcc cagtttgagg tcataaaagg acagaccatc    1200
gaagtccgtt gcgaatcgat cagtggaact ttgcctattt cttaccaact tttaaaaaca    1260
agtaaagttt tggagaatag taccaagaac tcaaatgatc ctgcggtatt caaagacaac    1320
cccactgaag acgtcgaata ccagtgtgtt gcagataatt gccattccca tgccaaaatg    1380
ttaagtgagg ttctgagggt gaaggtgata gccccggtgg atgaggtcca gatttctatc    1440
ctgtcaagta aggtggtgga gtctggagag gacattgtgc tgcaatgtgc tgtgaatgaa    1500
ggatctggtc ccatcaccta taagttttac agagaaaaag agggcaaacc cttctatcaa    1560
atgacctcaa atgccaccca ggcattttgg accaagcaga aggctagcaa ggaacaggag    1620
ggagagtatt actgcacagc cttcaacaga gccaaccacg cctccagtgt ccccagaagc    1680
aaaatactga cagtcagagt cattcttgcc ccatggaaga aa                       1722
```

<210> SEQ ID NO 41
<211> LENGTH: 57
<212> TYPE: DNA
<213> ORGANISM: Homo sapiens

<400> SEQUENCE: 41

```
ggacttattg cagtggttat catcggagtg atcattgctc tcttgatcat tgcggcc        57
```

<210> SEQ ID NO 42
<211> LENGTH: 354
<212> TYPE: DNA
<213> ORGANISM: Homo sapiens

<400> SEQUENCE: 42

```
aaatgttatt ttctgaggaa agccaaggcc aagcagatgc cagtggaaat gtccaggcca      60
```

| | | |
|---|---|---|
| gcagtaccac | ttctgaactc caacaacgag aaaatgtcag atcccaatat ggaagctaac | 120 |
| agtcattacg | gtcacaatga cgatgtcaga accatgcaa tgaaaccaat aaatgataat | 180 |
| aaagagcctc | tgaactcaga cgtgcagtac acggaagttc aagtgtcctc agctgagtct | 240 |
| cacaaagatc | taggaaagaa ggacacagag acagtgtaca gtgaagtccg gaaagctgtc | 300 |
| cctgatgccg | tggaaagcag atactctaga acggaaggct cccttgatgg aact | 354 |

<210> SEQ ID NO 43
<211> LENGTH: 936
<212> TYPE: DNA
<213> ORGANISM: Homo sapiens

<400> SEQUENCE: 43

| | | |
|---|---|---|
| atgggcctca | ccctgctctt gctgctgctc ctgggactag aaggtcaggg catagttggc | 60 |
| agcctccctg | aggtgctgca ggcacccgtg ggaagctcca ttctggtgca gtgccactac | 120 |
| aggctccagg | atgtcaaagc tcagaaggtg tggtgccggt tcttgccgga ggggtgccag | 180 |
| cccctggtgt | cctcagctgt ggatcgcaga gctccagcgg gcaggcgtac gtttctcaca | 240 |
| gacctgggtg | ggggcctgct gcaggtggaa atggttaccc tgcaggaaga ggatgctggc | 300 |
| gagtatggct | gcatggtgga tggggccagg gggccccaga ttttgcacag agtctctctg | 360 |
| aacatactgc | ccccagagga agaagaagag acccataaga ttggcagtct ggctgagaac | 420 |
| gcattctcag | accctgcagg cagtgccaac cctttggaac ccagccagga tgagaagagc | 480 |
| atcccccttga | tctggggtgc tgtgctcctg gtaggtctgc tggtggcagc ggtggtgctg | 540 |
| tttgctgtga | tggccaagag gaaacaaggg acaggcttg gtgtctgtgg ccgattcctg | 600 |
| agcagcagag | tttcaggcat gaatccctcc tcagtggtcc accacgtcag tgactctgga | 660 |
| ccggctgctg | aattgcccttt ggatgtacca cacattaggc ttgactcacc accttcattt | 720 |
| gacaatacca | cctacaccag cctacctctt gattccccat caggaaaacc ttcactccca | 780 |
| gctccatcct | cattgccccc tctacctcct aaggtcctgg tctgctccaa gcctgtgaca | 840 |
| tatgccacag | taatcttccc gggagggaac aagggtggag ggacctcgtg tgggccagcc | 900 |
| cagaatccac | ctaacaatca gactccatcc agctaa | 936 |

<210> SEQ ID NO 44
<211> LENGTH: 45
<212> TYPE: DNA
<213> ORGANISM: Homo sapiens

<400> SEQUENCE: 44

| | | |
|---|---|---|
| atgggcctca | ccctgctctt gctgctgctc ctgggactag aaggt | 45 |

<210> SEQ ID NO 45
<211> LENGTH: 441
<212> TYPE: DNA
<213> ORGANISM: Homo sapiens

<400> SEQUENCE: 45

| | | |
|---|---|---|
| cagggcatag | ttggcagcct ccctgaggtg ctgcaggcac ccgtgggaag ctccattctg | 60 |
| gtgcagtgcc | actacaggct ccaggatgtc aaagctcaga aggtgtggtg ccggttcttg | 120 |
| ccggaggggt | gccagcccct ggtgtcctca gctgtggatc gcagagctcc agcgggcagg | 180 |
| cgtacgtttc | tcacagacct gggtgggggc ctgctgcagg tggaaatggt taccctgcag | 240 |
| gaagaggatg | ctggcgagta tggctgcatg gtggatgggg ccgggggcc ccagattttg | 300 |
| cacagagtct | ctctgaacat actgccccca gaggaagaag aagagaccca taagattggc | 360 |

```
agtctggctg agaacgcatt ctcagaccct gcaggcagtg ccaacccttt ggaacccagc    420
caggatgaga agagcatccc c                                              441

<210> SEQ ID NO 46
<211> LENGTH: 63
<212> TYPE: DNA
<213> ORGANISM: Homo sapiens

<400> SEQUENCE: 46
ttgatctggg gtgctgtgct cctggtaggt ctgctggtgg cagcggtggt gctgtttgct    60
gtg                                                                  63

<210> SEQ ID NO 47
<211> LENGTH: 384
<212> TYPE: DNA
<213> ORGANISM: Homo sapiens

<400> SEQUENCE: 47
atggccaaga ggaaacaagg gaacaggctt ggtgtctgtg gccgattcct gagcagcaga    60
gtttcaggca tgaatccctc ctcagtggtc caccacgtca gtgactctgg accggctgct    120
gaattgcctt tggatgtacc acacattagg cttgactcac caccttcatt tgacaatacc    180
acctacacca gcctacctct tgattcccca tcaggaaaac cttcactccc agctccatcc    240
tcattgcccc ctctacctcc taaggtcctg gtctgctcca agcctgtgac atatgccaca    300
gtaatcttcc cggagggaa caagggtgga gggacctcgt gtgggccagc ccagaatcca    360
cctaacaatc agactccatc cagc                                          384

<210> SEQ ID NO 48
<211> LENGTH: 360
<212> TYPE: DNA
<213> ORGANISM: Homo sapiens

<400> SEQUENCE: 48
gaggtgaagc tgcaggagag cggccccggc ctggtggccc ccagccagag cctgagcgtg    60
acctgcaccg tgagcggcgt gagcctgccc gactacggcg tgagctggat cagacagccc    120
cccagaaagg gcctggagtg gctgggcgtg atctggggca gcgagaccac ctactacaac    180
agcgccctga gagcagact gaccatcatc aaggacaaca gcaagagcca ggtgttcctg    240
aagatgaaca gcctgcagac cgacgacacc gccatctact actgcgccaa gcactactac    300
tacggcggca gctacgccat ggactactgg ggccagggca ccagcgtgac cgtgagcagc    360

<210> SEQ ID NO 49
<211> LENGTH: 54
<212> TYPE: DNA
<213> ORGANISM: Homo sapiens

<400> SEQUENCE: 49
ggcagcacca gcggcagcgg caagcccggc agcggcgagg gcagcaccaa gggc          54

<210> SEQ ID NO 50
<211> LENGTH: 321
<212> TYPE: DNA
<213> ORGANISM: Homo sapiens

<400> SEQUENCE: 50
gacatccaga tgacccagac caccagcagc ctgagcgcca gcctgggcga cagagtgacc    60
```

```
atcagctgca gagccagcca ggacatcagc aagtacctga actggtacca gcagaagccc    120
gacggcaccg tgaagctgct gatctaccac accagcagac tgcacagcgg cgtgcccagc    180
agattcagcg gcagcggcag cggcaccgac tacagcctga ccatcagcaa cctggagcag    240
gaggacatcg ccacctactt ctgccagcag ggcaacaccc tgccctacac cttcggcggc    300
ggcaccaagc tggagatcac c                                              321

<210> SEQ ID NO 51
<211> LENGTH: 36
<212> TYPE: DNA
<213> ORGANISM: Homo sapiens

<400> SEQUENCE: 51
gaatctaagt acggaccgcc ctgccccct tgccct                                36

<210> SEQ ID NO 52
<211> LENGTH: 348
<212> TYPE: DNA
<213> ORGANISM: Homo sapiens

<400> SEQUENCE: 52
ctccgacatc gacgtcaggg caaacactgg acatcgaccc agagaaaggc tgatttccaa     60
catcctgcag gggctgtggg gccagagccc acagacagag gcctgcagtg gaggtccagc    120
ccagctgccg acgcccagga agaaaacctc tatgctgccg tgaaggacac acagcctgaa    180
gatggggtgg agatggacac tcgggctgct gcatctgaag ccccccagga tgtgacctac    240
gcccagctgc acagcttgac cctcagacgg aaggcaactg agcctcctcc atcccaggaa    300
agggaacctc cagctgagcc cagcatctac gccaccctgg ccatccac                 348

<210> SEQ ID NO 53
<211> LENGTH: 15
<212> TYPE: DNA
<213> ORGANISM: Homo sapiens

<400> SEQUENCE: 53
tctgtcatgc agcgc                                                      15

<210> SEQ ID NO 54
<211> LENGTH: 15
<212> TYPE: DNA
<213> ORGANISM: Homo sapiens

<400> SEQUENCE: 54
tcttcaccaa tgggg                                                      15

<210> SEQ ID NO 55
<211> LENGTH: 15
<212> TYPE: DNA
<213> ORGANISM: Homo sapiens

<400> SEQUENCE: 55
cagtactaca ccaag                                                      15

<210> SEQ ID NO 56
<211> LENGTH: 20
<212> TYPE: DNA
<213> ORGANISM: Artificial Sequence
<220> FEATURE:
<223> OTHER INFORMATION: grna1_HPS1_1r

<400> SEQUENCE: 56
``` gggtgaatc agtcgctcca                                                20

<210> SEQ ID NO 57
<211> LENGTH: 20
<212> TYPE: DNA
<213> ORGANISM: Artificial Sequence
<220> FEATURE:
<223> OTHER INFORMATION: grna2_HPS1_2

<400> SEQUENCE: 57
gtcaacacca gccccgagcg                                                20

<210> SEQ ID NO 58
<211> LENGTH: 20
<212> TYPE: DNA
<213> ORGANISM: Artificial Sequence
<220> FEATURE:
<223> OTHER INFORMATION: grna3_HPS1_3

<400> SEQUENCE: 58
gctggagcgg cacgtcatcc                                                20

<210> SEQ ID NO 59
<211> LENGTH: 20
<212> TYPE: DNA
<213> ORGANISM: Artificial Sequence
<220> FEATURE:
<223> OTHER INFORMATION: grna4_HPS1_4r

<400> SEQUENCE: 59
cttggagtgc acgagcagga                                                20

<210> SEQ ID NO 60
<211> LENGTH: 20
<212> TYPE: DNA
<213> ORGANISM: Artificial Sequence
<220> FEATURE:
<223> OTHER INFORMATION: grna5_ITGA2B_1r

<400> SEQUENCE: 60
cagtagccgt cgaagtactc                                                20

<210> SEQ ID NO 61
<211> LENGTH: 20
<212> TYPE: DNA
<213> ORGANISM: Artificial Sequence
<220> FEATURE:
<223> OTHER INFORMATION: grna6_ITGA2B_2

<400> SEQUENCE: 61
attttctcga gttaccgccc                                                20

<210> SEQ ID NO 62
<211> LENGTH: 20
<212> TYPE: DNA
<213> ORGANISM: Artificial Sequence
<220> FEATURE:
<223> OTHER INFORMATION: grna7_ITGA2B_3r

<400> SEQUENCE: 62
ctcgagaaaa tatccgcaac                                                20

<210> SEQ ID NO 63
<211> LENGTH: 20
<212> TYPE: DNA

```
<213> ORGANISM: Artificial Sequence
<220> FEATURE:
<223> OTHER INFORMATION: grna8_ITGA2B_4r

<400> SEQUENCE: 63
gggaggacac gtgccacaaa                                              20

<210> SEQ ID NO 64
<211> LENGTH: 20
<212> TYPE: DNA
<213> ORGANISM: Artificial Sequence
<220> FEATURE:
<223> OTHER INFORMATION: grna9_GP6_1

<400> SEQUENCE: 64
gggcgtggac ctgtaccgcc                                              20

<210> SEQ ID NO 65
<211> LENGTH: 20
<212> TYPE: DNA
<213> ORGANISM: Artificial Sequence
<220> FEATURE:
<223> OTHER INFORMATION: grna10_GP6_2r

<400> SEQUENCE: 65
acgagctcca gctggtcgct                                              20

<210> SEQ ID NO 66
<211> LENGTH: 20
<212> TYPE: DNA
<213> ORGANISM: Artificial Sequence
<220> FEATURE:
<223> OTHER INFORMATION: grna11_GP6_3r

<400> SEQUENCE: 66
cggaggtccc tggcaccgga                                              20

<210> SEQ ID NO 67
<211> LENGTH: 20
<212> TYPE: DNA
<213> ORGANISM: Artificial Sequence
<220> FEATURE:
<223> OTHER INFORMATION: grna12_GP6_4

<400> SEQUENCE: 67
ccagtgaccc tccggtgcca                                              20

<210> SEQ ID NO 68
<211> LENGTH: 20
<212> TYPE: DNA
<213> ORGANISM: Artificial Sequence
<220> FEATURE:
<223> OTHER INFORMATION: grna13_Par1_1r

<400> SEQUENCE: 68
ggagctggtc aaatatccgg                                              20

<210> SEQ ID NO 69
<211> LENGTH: 20
<212> TYPE: DNA
<213> ORGANISM: Artificial Sequence
<220> FEATURE:
<223> OTHER INFORMATION: grna14_Par1_2r

<400> SEQUENCE: 69
ttcctgagaa gaaatgaccg                                              20
```

<210> SEQ ID NO 70
<211> LENGTH: 20
<212> TYPE: DNA
<213> ORGANISM: Artificial Sequence
<220> FEATURE:
<223> OTHER INFORMATION: grna15_Par1_3r

<400> SEQUENCE: 70
acactccggt gtacacagat                                               20

<210> SEQ ID NO 71
<211> LENGTH: 20
<212> TYPE: DNA
<213> ORGANISM: Artificial Sequence
<220> FEATURE:
<223> OTHER INFORMATION: grna16_Par1_4r

<400> SEQUENCE: 71
acgatggcca tgatgtttag                                               20

<210> SEQ ID NO 72
<211> LENGTH: 20
<212> TYPE: DNA
<213> ORGANISM: Artificial Sequence
<220> FEATURE:
<223> OTHER INFORMATION: grna17_Par4_1r

<400> SEQUENCE: 72
acttggcctg ggtagccgcg                                               20

<210> SEQ ID NO 73
<211> LENGTH: 20
<212> TYPE: DNA
<213> ORGANISM: Artificial Sequence
<220> FEATURE:
<223> OTHER INFORMATION: grna18_Par4_2

<400> SEQUENCE: 73
ggtgcccgcc ctctatgggc                                               20

<210> SEQ ID NO 74
<211> LENGTH: 20
<212> TYPE: DNA
<213> ORGANISM: Artificial Sequence
<220> FEATURE:
<223> OTHER INFORMATION: grna19_Par4_3

<400> SEQUENCE: 74
tggtggggct gccggccaat                                               20

<210> SEQ ID NO 75
<211> LENGTH: 20
<212> TYPE: DNA
<213> ORGANISM: Artificial Sequence
<220> FEATURE:
<223> OTHER INFORMATION: grna20_Par4_4r

<400> SEQUENCE: 75
agcagtgccc gtgagctgtc                                               20

<210> SEQ ID NO 76
<211> LENGTH: 20
<212> TYPE: DNA
<213> ORGANISM: Artificial Sequence
<220> FEATURE:

<223> OTHER INFORMATION: grna21_Cox1_1

<400> SEQUENCE: 76
acttctggca agatgggtcc                                               20

<210> SEQ ID NO 77
<211> LENGTH: 20
<212> TYPE: DNA
<213> ORGANISM: Artificial Sequence
<220> FEATURE:
<223> OTHER INFORMATION: grna22_Cox1_2

<400> SEQUENCE: 77
tcaccaaggc cttgggccat                                               20

<210> SEQ ID NO 78
<211> LENGTH: 20
<212> TYPE: DNA
<213> ORGANISM: Artificial Sequence
<220> FEATURE:
<223> OTHER INFORMATION: grna23_Cox1_3r

<400> SEQUENCE: 78
tgtctccata aatgtggccg                                               20

<210> SEQ ID NO 79
<211> LENGTH: 20
<212> TYPE: DNA
<213> ORGANISM: Artificial Sequence
<220> FEATURE:
<223> OTHER INFORMATION: grna24_Cox1_4

<400> SEQUENCE: 79
aactgcggct ctttaaggat                                               20

<210> SEQ ID NO 80
<211> LENGTH: 20
<212> TYPE: DNA
<213> ORGANISM: Artificial Sequence
<220> FEATURE:
<223> OTHER INFORMATION: grna29_P2Y12_1r

<400> SEQUENCE: 80
gtagtctctg gtgcacagac                                               20

<210> SEQ ID NO 81
<211> LENGTH: 20
<212> TYPE: DNA
<213> ORGANISM: Artificial Sequence
<220> FEATURE:
<223> OTHER INFORMATION: grna30_P2Y12_2r

<400> SEQUENCE: 81
gaaagaaaat cctcatcgcc                                               20

<210> SEQ ID NO 82
<211> LENGTH: 20
<212> TYPE: DNA
<213> ORGANISM: Artificial Sequence
<220> FEATURE:
<223> OTHER INFORMATION: grna31_P2Y12_3

<400> SEQUENCE: 82
attcttagtg atgccaaact                                               20

```
<210> SEQ ID NO 83
<211> LENGTH: 20
<212> TYPE: DNA
<213> ORGANISM: Artificial Sequence
<220> FEATURE:
<223> OTHER INFORMATION: grna32_P2Y12_4r

<400> SEQUENCE: 83
gatcgatagt tatcagtccc                                                     20

<210> SEQ ID NO 84
<211> LENGTH: 20
<212> TYPE: DNA
<213> ORGANISM: Artificial Sequence
<220> FEATURE:
<223> OTHER INFORMATION: grna40_B2M_1r

<400> SEQUENCE: 84
aagtcaactt caatgtcgga                                                     20

<210> SEQ ID NO 85
<211> LENGTH: 20
<212> TYPE: DNA
<213> ORGANISM: Artificial Sequence
<220> FEATURE:
<223> OTHER INFORMATION: grna41_B2M_2r

<400> SEQUENCE: 85
agtcacatgg ttcacacggc                                                     20

<210> SEQ ID NO 86
<211> LENGTH: 20
<212> TYPE: DNA
<213> ORGANISM: Artificial Sequence
<220> FEATURE:
<223> OTHER INFORMATION: grna42_B2M_3

<400> SEQUENCE: 86
acttgtcttt cagcaaggac                                                     20

<210> SEQ ID NO 87
<211> LENGTH: 20
<212> TYPE: DNA
<213> ORGANISM: Artificial Sequence
<220> FEATURE:
<223> OTHER INFORMATION: grna43_B2M_4

<400> SEQUENCE: 87
tcacgtcatc cagcagagaa                                                     20

<210> SEQ ID NO 88
<211> LENGTH: 20
<212> TYPE: DNA
<213> ORGANISM: Artificial Sequence
<220> FEATURE:
<223> OTHER INFORMATION: RocO1_sHPS1_F1

<400> SEQUENCE: 88
atctggtgca gagtccaagc                                                     20

<210> SEQ ID NO 89
<211> LENGTH: 20
<212> TYPE: DNA
<213> ORGANISM: Artificial Sequence
<220> FEATURE:
<223> OTHER INFORMATION: RocO2_sHPS1_R1
```

<400> SEQUENCE: 89
tggaggaggt gattcttggc                                                    20

<210> SEQ ID NO 90
<211> LENGTH: 20
<212> TYPE: DNA
<213> ORGANISM: Artificial Sequence
<220> FEATURE:
<223> OTHER INFORMATION: RocO3_ITGA2B_F1

<400> SEQUENCE: 90
ggctcctggc ggctattatt                                                    20

<210> SEQ ID NO 91
<211> LENGTH: 18
<212> TYPE: DNA
<213> ORGANISM: Artificial Sequence
<220> FEATURE:
<223> OTHER INFORMATION: RocO4_ITGA2B_R1

<400> SEQUENCE: 91
cttaggcggt gggttggc                                                      18

<210> SEQ ID NO 92
<211> LENGTH: 16
<212> TYPE: DNA
<213> ORGANISM: Artificial Sequence
<220> FEATURE:
<223> OTHER INFORMATION: RocO5_GP6_F1

<400> SEQUENCE: 92
agcagcgggg tccagg                                                        16

<210> SEQ ID NO 93
<211> LENGTH: 16
<212> TYPE: DNA
<213> ORGANISM: Artificial Sequence
<220> FEATURE:
<223> OTHER INFORMATION: RocO6_GP6_R1

<400> SEQUENCE: 93
cgtggcacca ccaccc                                                        16

<210> SEQ ID NO 94
<211> LENGTH: 25
<212> TYPE: DNA
<213> ORGANISM: Artificial Sequence
<220> FEATURE:
<223> OTHER INFORMATION: RocO7_Par1_F1

<400> SEQUENCE: 94
acccactctc ctagtaagaa aacat                                              25

<210> SEQ ID NO 95
<211> LENGTH: 20
<212> TYPE: DNA
<213> ORGANISM: Artificial Sequence
<220> FEATURE:
<223> OTHER INFORMATION: RocO8_Par1_R1

<400> SEQUENCE: 95
caaactgcca atcactgccg                                                    20

<210> SEQ ID NO 96
<211> LENGTH: 20

```
<212> TYPE: DNA
<213> ORGANISM: Artificial Sequence
<220> FEATURE:
<223> OTHER INFORMATION: Roc09_Par4_F1

<400> SEQUENCE: 96
atgtccagct gtttcccacc                                              20

<210> SEQ ID NO 97
<211> LENGTH: 18
<212> TYPE: DNA
<213> ORGANISM: Artificial Sequence
<220> FEATURE:
<223> OTHER INFORMATION: Roc010_Par4_R1

<400> SEQUENCE: 97
gcaggtggta ggcgatcc                                                18

<210> SEQ ID NO 98
<211> LENGTH: 20
<212> TYPE: DNA
<213> ORGANISM: Artificial Sequence
<220> FEATURE:
<223> OTHER INFORMATION: Roc011_Cox1_F1

<400> SEQUENCE: 98
ccaaccaggg aagaagcagt                                              20

<210> SEQ ID NO 99
<211> LENGTH: 19
<212> TYPE: DNA
<213> ORGANISM: Artificial Sequence
<220> FEATURE:
<223> OTHER INFORMATION: Roc012_Cox1_R1

<400> SEQUENCE: 99
tggcacaagc ttcccactc                                               19

<210> SEQ ID NO 100
<211> LENGTH: 20
<212> TYPE: DNA
<213> ORGANISM: Artificial Sequence
<220> FEATURE:
<223> OTHER INFORMATION: Roc015_P2Y12_F1

<400> SEQUENCE: 100
gaggaggctg tgtccaaaaa                                              20

<210> SEQ ID NO 101
<211> LENGTH: 20
<212> TYPE: DNA
<213> ORGANISM: Artificial Sequence
<220> FEATURE:
<223> OTHER INFORMATION: Roc016_P2Y12_R1

<400> SEQUENCE: 101
ggctgcctgt tggtcagaat                                              20

<210> SEQ ID NO 102
<211> LENGTH: 20
<212> TYPE: DNA
<213> ORGANISM: Artificial Sequence
<220> FEATURE:
<223> OTHER INFORMATION: Roc058_B2M_F1

<400> SEQUENCE: 102
```

```
tgacaccaag ttagccccaa                                               20

<210> SEQ ID NO 103
<211> LENGTH: 20
<212> TYPE: DNA
<213> ORGANISM: Artificial Sequence
<220> FEATURE:
<223> OTHER INFORMATION: Roc059_B2M_R1

<400> SEQUENCE: 103
gggatgggac tcattcaggg                                               20
```